United States Patent
Christensen, IV et al.

(10) Patent No.: US 9,242,929 B2
(45) Date of Patent: Jan. 26, 2016

(54) COMPOUNDS AS DIACYLGLYCEROL ACYLTRANSFERASE INHIBITORS

(75) Inventors: Siegfried Benjamin Christensen, IV, Collegeville, PA (US); Rowena Christensen, legal representative, King of Prussia, PA (US); Donghui Qin, King of Prussia Pa, PA (US); Hemant Joshi, King of Prussia, PA (US); Raghuram S. Tangirala, King of Prussia, PA (US)

(73) Assignee: GlaxoSmithKline Intellectual Property (No.2) Limited, Brentford, Middlesex (GB)

( * ) Notice: Subject to any disclaimer, the term of this patent is extended or adjusted under 35 U.S.C. 154(b) by 0 days.

(21) Appl. No.: 14/118,913

(22) PCT Filed: May 18, 2012

(86) PCT No.: PCT/US2012/038520
§ 371 (c)(1),
(2), (4) Date: Dec. 4, 2014

(87) PCT Pub. No.: WO2012/162127
PCT Pub. Date: Nov. 29, 2012

(65) Prior Publication Data
US 2015/0307445 A1    Oct. 29, 2015

Related U.S. Application Data

(60) Provisional application No. 61/495,049, filed on Jun. 9, 2011.

(30) Foreign Application Priority Data

May 20, 2011 (IN) ............................ 1451/DEL/2011

(51) Int. Cl.
| C07C 275/42 | (2006.01) |
| C07D 217/26 | (2006.01) |
| C07D 239/42 | (2006.01) |
| C07D 213/75 | (2006.01) |
| C07D 241/20 | (2006.01) |
| C07D 237/20 | (2006.01) |
| A61K 31/17 | (2006.01) |
| A61K 31/4418 | (2006.01) |
| A61K 31/444 | (2006.01) |
| A61K 31/472 | (2006.01) |
| A61K 31/4965 | (2006.01) |

(52) U.S. Cl.
CPC ............ *C07C 275/42* (2013.01); *C07D 213/75* (2013.01); *C07D 217/26* (2013.01); *C07D 237/20* (2013.01); *C07D 239/42* (2013.01); *C07D 241/20* (2013.01)

(58) Field of Classification Search
None
See application file for complete search history.

(56) References Cited

U.S. PATENT DOCUMENTS

2007/0249620 A1    10/2007   Kurata et al.
2010/0041590 A1    2/2010    Bouillot
2011/0245247 A1    10/2011   Braje et al.

FOREIGN PATENT DOCUMENTS

| WO | WO 2007/126957 A2 | 11/2007 |
| WO | WO 2009/126861 A2 | 10/2009 |
| WO | WO 2011/024932 A1 | 3/2011 |
| WO | WO 2011/080718 A1 | 7/2011 |

OTHER PUBLICATIONS

Zhao, et al. J. Med. Chem., 51: 380-383 (2008).
Curtin, et al. *Bioorganic & Medicinal Chemistry Letters*, 14: 4505-4509 (2004).

*Primary Examiner* — Zinna Northington Davis
(74) *Attorney, Agent, or Firm* — Duke M. Fitch; Edward R. Gimmi; William R. Majarian

(57) ABSTRACT

This invention relates to novel compounds which are inhibitors of acyl coenzymeA: diacylglycerol acyltransferase 1 (DGAT-1), to pharmaceutical compositions containing them, to processes for their preparation, and to their use in therapy for the prevention or treatment of diseases related to DGAT-1 dysfunction or where modulation of DGAT-1 activity may have therapeutic benefit including but not limited to obesity, obesity related disorders, hypertriglyceridemia, hyperlipoproteinemia, chylomicronemia, dyslipidemia, non-alcoholic steatohepatitis, diabetes, insulin resistance, metabolic syndrome, hepatitis C virus infection and acne or other skin disorders.

19 Claims, No Drawings

COMPOUNDS AS DIACYLGLYCEROL ACYLTRANSFERASE INHIBITORS

CONTINUING DATA

This application is a 371 of PCT/US2012/038520 filed May 18, 2012 which claims benefit of 61/495,049 filed Jun. 9, 2011.

FIELD OF INVENTION

This invention relates to novel compounds which are inhibitors of acyl coenzymeA: diacylglycerol acyltransferase 1 (DGAT-1), to pharmaceutical compositions containing them, to processes for their preparation, and to their use in therapy for the prevention or treatment of diseases related to DGAT-1 dysfunction or where modulation of DGAT-1 activity may have therapeutic benefit including but not limited to obesity, obesity related disorders, hypertriglyceridemia, hyperlipoproteinemia, chylomicronemia, dyslipidemia, non-alcoholic steatohepatitis, diabetes, insulin resistance, metabolic syndrome, hepatitis C virus infection and acne or other skin disorders.

BACKGROUND OF THE INVENTION

Obesity is a medical condition that is reaching epidemic proportions among humans in a number of countries throughout the world. It is a condition that is also associated with or induces other diseases or conditions that disrupt life activities and lifestyles. Obesity is recognized as a serious risk factor for other diseases and conditions such as diabetes, hypertension, and arteriosclerosis. It is also known that increased body weight due to obesity can place a burden on joints, such as knee joints, causing arthritis, pain, and stiffness.

Because overeating and obesity have become such a problem in the general population, many individuals are now interested in losing weight, reducing weight, and maintaining a healthy body weight and desirable lifestyle. One approach to treating obesity is to reduce food intake and/or hyperlipidemia. It has been suggested that molecules which are developed to prevent the accumulation of triglyceride would not only reduce obesity but also have the additional beneficial effect of reducing insulin resistance, a primary factor contributing to the development of diabetes.

Acyl coenzymeA:diacylglycerol acyltransferase 1 (DGAT-1) is one of two known DGAT enzymes that catalyze the final step in mammalian triglyceride synthesis. DGAT-1 is an enzyme that is implicated in the development of both diabetes and insulin resistance. Studies of DGAT-1 deficient mice show that DGAT-1 deficiency protects against insulin resistance and obesity, see Chen, H. C. et al., *J Clin Invest.*, 109(8), 1049-1055 (2002). Therefore, inhibitors of DGAT-1 should be useful for the treatment of metabolic disorders, e.g. obesity, Type 2 diabetes, and insulin resistance syndrome (or metabolic syndrome) and other associated or related diseases and conditions.

SUMMARY OF THE INVENTION

This invention relates to compounds for Formula (I):

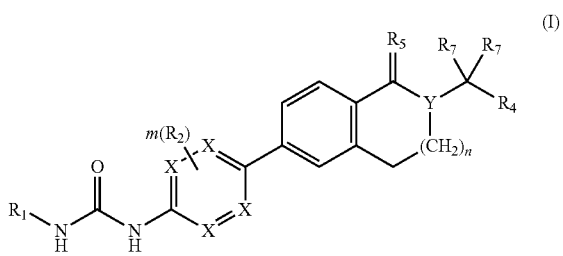

wherein
$R_1$ is $C_1$-$C_6$alkyl, $C_3$-$C_7$cycloalkyl, aryl or heteroaryl, wherein said aryl and heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;
$R_2$ is selected from the group consisting of H, $C_1$-$C_6$alkyl, alkoxy, cyano, halo, urea, amide, hydroxyl, oxo, and nitro;
$R_4$ is $CH_2COOH$, COOH, ester, or amide;
$R_5$ is hydrogen, hydroxyl, or oxo;
each $R_7$ is independently H or $C_1$-$C_3$alkyl;
each X is independently C or N, provided that at least two X's are C;
Y is N or $CR_3$, wherein $R_3$ is H, $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;
m is 0-3;
n is 0-1, provided that when n is 0, Y is $CR_3$;
or a pharmaceutically acceptable salt thereof.

This invention also relates to a pharmaceutical composition comprising a compound of Formula (I) and a pharmaceutically acceptable carrier.

This invention also relates to a method of treating obesity comprising administering to a human in need thereof an effective amount of a compound of Formula (I) or a pharmaceutically acceptable salt thereof in a pharmaceutical composition.

DETAIL DESCRIPTION OF THE INVENTION

This invention relates to compounds of the Formula (I) as defined above.

This invention also relates to compounds of Formula (I)(A)

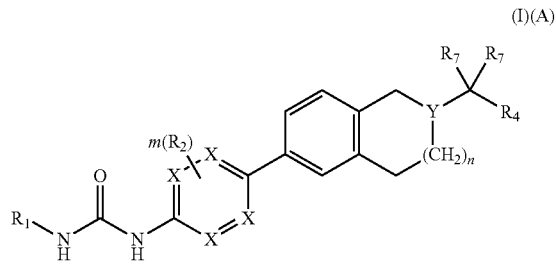

wherein $R_1$ is $C_1$-$C_6$alkyl, $C_3$-$C_7$cycloalkyl, aryl or heteroaryl, wherein said aryl or heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;

$R_2$ is selected from the group consisting of H, $C_1$-$C_6$alkyl, alkoxy, cyano, halo, urea, amide, hydroxyl, oxo, and nitro;

$R_4$ is $CH_2COOH$, COOH, ester, or amide;

each $R_7$ is independently H or $C_1$-$C_3$alkyl;

each X is independently C or N, provided that at least two X's are C;

Y is N or $CR_3$, wherein $R_3$ is H, $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;

m is 0-3;

n is 0-1, provided that when n is 0, Y is $CR_3$;

or a pharmaceutically acceptable salt thereof.

This invention also relates to compounds of Formula (I)(B),

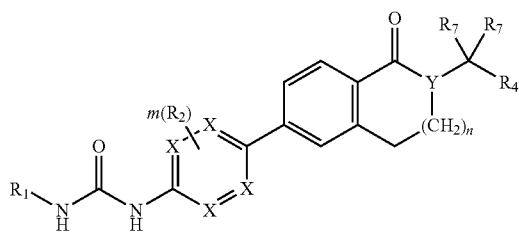

(I)(B)

wherein $R_1$ is $C_1$-$C_6$alkyl, $C_3$-$C_7$cycloalkyl, aryl or heteroaryl, wherein said aryl or heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;

$R_2$ is selected from the group consisting of H, $C_1$-$C_6$alkyl, alkoxy, cyano, halo, urea, amide, hydroxyl, oxo, and nitro;

$R_4$ is $CH_2COOH$, COOH, ester, or amide;

each $R_7$ is independently H or $C_1$-$C_3$alkyl;

each X is independently C or N, provided that at least two X's are C;

Y is N or $CR_3$, wherein $R_3$ is H, $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;

m is 0-3;

n is 0-1, provided that when n is 0, Y is $CR_3$;

or a pharmaceutically acceptable salt thereof.

This invention also relates to compounds of Formula (I)(C):

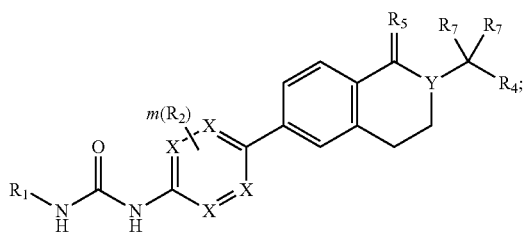

(I)(C)

wherein $R_1$ is $C_1$-$C_6$alkyl, $C_3$-$C_7$cycloalkyl, aryl or heteroaryl, wherein said aryl or heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;

$R_2$ is selected from the group consisting of H, $C_1$-$C_6$alkyl, alkoxy, cyano, halo, urea, amide, hydroxyl, oxo, and nitro;

$R_4$ is $CH_2COOH$, COOH, ester, or amide;

$R_5$ is hydrogen, hydroxyl, or oxo;

each $R_7$ is independently H or $C_1$-$C_3$alkyl;

each X is independently C or N, provided that at least two X's are C;

Y is N or $CR_3$, wherein $R_3$ is H, $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;

m is 0-3;

or a pharmaceutically acceptable salt thereof.

This invention also relates to compounds of Formula (I)(D):

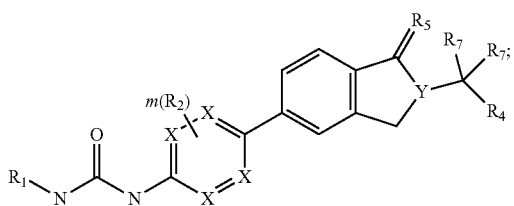

(I)(D)

wherein $R_1$ is $C_1$-$C_6$alkyl, $C_3$-$C_7$cycloalkyl, aryl or heteroaryl, wherein said aryl or heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;

$R_2$ is selected from the group consisting of H, $C_1$-$C_6$alkyl, alkoxy, cyano, halo, urea, amide, hydroxyl, oxo, and nitro;

$R_4$ is $CH_2COOH$, COOH, ester, or amide;

$R_5$ is hydrogen, hydroxyl, or oxo;

each $R_7$ is independently H or $C_1$-$C_3$alkyl;

each X is independently C or N, provided that at least two X's are C;

Y is $CR_3$, wherein $R_3$ is H, $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;

m is 0-3;

or a pharmaceutically acceptable salt thereof.

This invention also relates to compounds of Formula (I)(E):

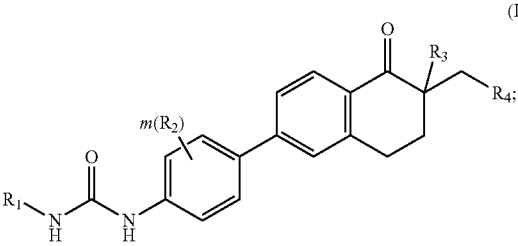

(I)(E)

wherein $R_1$ is $C_1$-$C_6$alkyl, $C_3$-$C_7$cycloalkyl, aryl or heteroaryl, wherein said aryl or heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;
$R_2$ is selected from the group consisting of H, $C_1$-$C_6$alkyl, alkoxy, cyano, halo, urea, amide, hydroxyl, oxo, and nitro;
$R_4$ is $CH_2COOH$, COOH, ester, or amide;
$R_3$ is $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;
m is 0-3;
or a pharmaceutically acceptable salt thereof.

This invention also relates to compounds of Formula (I) (F):

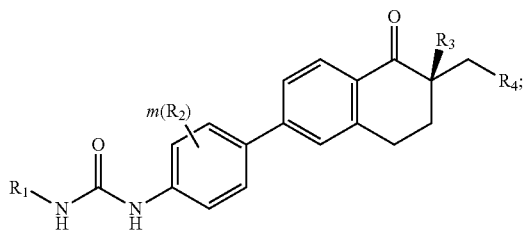

(I)(F)

wherein $R_1$ is $C_1$-$C_6$alkyl, $C_3$-$C_7$cycloalkyl, aryl or heteroaryl, wherein said aryl or heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;
$R_2$ is selected from the group consisting of H, $C_1$-$C_6$alkyl, alkoxy, cyano, halo, urea, amide, hydroxyl, oxo, and nitro;
$R_4$ is $CH_2COOH$, COOH, ester, or amide;
$R_3$ is $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;
m is 0-3;
or a pharmaceutically acceptable salt thereof.

This invention also relates to compounds of Formula (I) (G):

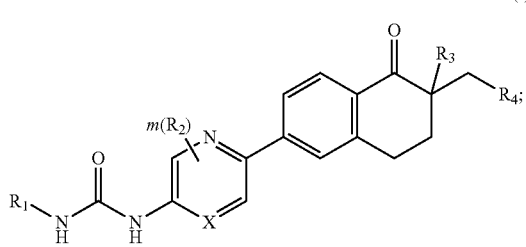

(I)(G)

wherein $R_1$ is $C_1$-$C_6$alkyl, $C_3$-$C_7$cycloalkyl, aryl or heteroaryl, wherein said aryl or heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;
$R_2$ is selected from the group consisting of H, $C_1$-$C_6$alkyl, alkoxy, cyano, halo, urea, amide, hydroxyl, oxo, and nitro;
$R_4$ is $CH_2COOH$, COOH, ester, or amide;
X is independently C or N;
$R_3$ is H, $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;
m is 0-2;
or a pharmaceutically acceptable salt thereof.

This invention also relates to compounds of Formula (I) (H):

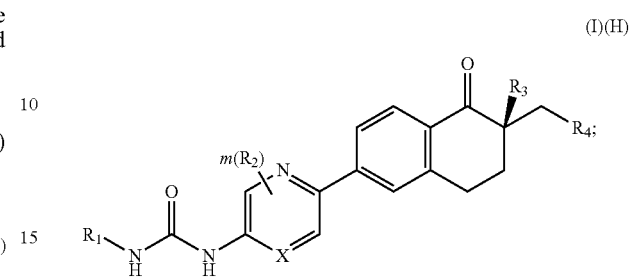

(I)(H)

wherein $R_1$ is $C_1$-$C_6$alkyl, $C_3$-$C_7$cycloalkyl, aryl or heteroaryl, wherein said aryl or heteroaryl may be substituted with one to three groups selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;
$R_2$ is selected from the group consisting of H, $C_1$-$C_6$alkyl, alkoxy, cyano, halo, urea, amide, hydroxyl, oxo, and nitro;
$R_4$ is $CH_2COOH$, COOH, ester, or amide;
X is independently C or N;
$R_3$ is H, $C_1$-$C_6$alkyl, hydroxyl, halo, or alkoxy, wherein said $C_1$-$C_6$alkyl may be further substituted with one to three groups selected from halo, hydroxyl, alkoxy, COOH, and ester;
m is 0-2;
or a pharmaceutically acceptable salt thereof.

This invention relates to compounds for Formula (I)(K):

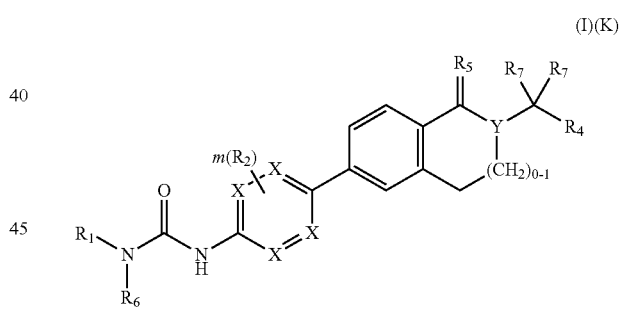

(I)(K)

wherein $R_1$ is $C_3$-$C_7$cycloalkyl, aryl or heteroaryl, which may be substituted with one to three groups selected from the group consisting of: acyl, $C_1$-$C_6$alkyl, alkylsulfonyl, alkoxy, alkoxycarbonyl, cyano, halogen, urea, amide, hydroxyl, $SF_5$, oxo, and nitro,
and $R_6$ is H or $C_1$-$C_3$alkyl,
or $R_1$ and $R_6$ together with the N they are attached to form a mono- or bicyclic ring which may contain 0-3 hetero atoms and may be substituted with one to three halogen, $C_1$-$C_3$alkyl, or alkoxy,
$R_2$ is selected from the group consisting of: H, $C_1$-$C_6$alkyl, alkoxy, cyano, halogen, urea, amide, hydroxyl, oxo, and nitro,
$R_4$ is $CH_2COOH$, COOH, ester, or amide,
$R_5$ is hydrogen, hydroxyl, or oxo,
each $R_7$ is independently H or $C_1$-$C_3$alkyl,
each X is independently C or N, provided that at least two X's are C, Y is N or $CR_3$, wherein $R_3$ is H, $C_1$-$C_6$alkyl, hydroxyl, halogen, or alkoxy, wherein said $C_1$-$C_6$alkyl may be further substituted with one to three groups selected from: halogen, hydroxyl, alkoxy, carboxylic acid, and ester, m is 0-3;

or a pharmaceutically acceptable salt thereof.

This invention also relates to compounds of Formula (I), wherein $R_5$ is hydroxyl, or a pharmaceutically acceptable salt thereof.

This invention also relates to compounds of Formula (I), (I)(A), (I)(B), (I)(C), (I)(D), (I)(G) or (I)(H), wherein X's are C, or a pharmaceutically acceptable salt thereof.

This invention also relates to compounds of Formula (I), (I)(A), (I)(B), (I)(C) or (I)(D), wherein X is independently C or N, and two X's are N, or a pharmaceutically acceptable salt thereof.

This invention also relates to compounds of Formula (I), (I)(A), (I)(B), (I)(C), (I)(D), (IE), (I)(F), (I)(G) or (I)(H), wherein $R_1$ is phenyl which may be substituted with one to three groups selected from the group consisting of methyl, ethyl, $OCF_3$, —$OCF_2H$, trifluoromethyl, methoxy, ethoxy, cyano, Cl or F, or a pharmaceutically acceptable salt thereof.

This invention also relates to compounds of Formula (I), (I)(A), (I)(B), (I)(C), (I)(D), (IE), (I)(F), (I)(G) or (I)(H), wherein $R_1$ is $C_1$-$C_6$alkyl, or a pharmaceutically acceptable salt thereof.

This invention also relates to compounds of Formula (I), (I)(A), (I)(B), (I)(C), (I)(D), (IE), (I)(F), (I)(G) or (I)(H), wherein $R_2$ is $C_1$-$C_3$alkyl, F, Cl, or CN, or a pharmaceutically acceptable salt thereof.

This invention also relates to compounds of Formula (I), (I)(A), (I)(B), (I)(C), (I)(D), (IE), or (I)(F), (I)(G) or (I)(H), wherein Y is $CR_3$, wherein $R_3$ is H, $C_1$-$C_6$alkyl, hydroxyl, halo, or alkoxy, or a pharmaceutically acceptable salt thereof.

This invention also relates to compounds of Formula (I), (I)(A), (I)(B), (I)(C) or (I)(D), wherein Y is $CR_3$, wherein $R_3$ is methyl, $CH_2CF_3$, $CH_2OCH_3$ or ethyl, or a pharmaceutically acceptable salt thereof.

This invention also relates to compounds of Formula (I), (I)(A), (I)(B), (I)(C) or (I)(D), wherein Y is N, or a pharmaceutically acceptable salt thereof.

This invention also relates to compounds of Formula (I), (I)(A), (I)(B), (I)(C), (I)(D), (I)(E), (I)(F), (I)(G) or (I)(H), wherein m is 0.

This invention also relates to compounds of Formula (I), (I)(A), (I)(B), (I)(C), (I)(D), (IE), (I)(F), (I)(G) or (I)(H), wherein $R_4$ is $CH_2COOH$ or COOH, or a pharmaceutically acceptable salt thereof.

This invention also relates to compounds of Formula (I), (I)(A), (I)(B), (I)(C) or (I)(D), wherein Y is $CR_3$, wherein $R_3$ is H, methyl, ethyl, propyl, isopropyl, hydroxyl, halo, alkoxymethyl, hydroxyl alkyl or alkoxy, or a pharmaceutically acceptable salt thereof.

This invention also relates to compounds that are exemplified in the Experimental section.

Specific compounds of this invention include:

2-{1-oxo-6-[4-({[3-(trifluoromethyl)phenyl]carbamoyl}amino)phenyl]-1,2,3,4-tetrahydroisoquinolin-2-yl}acetic acid;

2-{1-oxo-6-[4-({[4-(trifluoromethyl)phenyl]carbamoyl}amino)phenyl]-1,2,3,4-tetrahydroisoquinolin-2-yl}acetic acid;

2-[6-(4-{[(3-methylphenyl)carbamoyl]amino}phenyl)-1-oxo-1,2,3,4-tetrahydroisoquinolin-2-yl]acetic acid;

2-{1-oxo-6-[4-({[4-(trifluoromethoxy)phenyl]carbamoyl}amino)phenyl]-1,2,3,4-tetrahydroisoquinolin-2-yl}acetic acid;

2-{6-[4-({[3-methyl-5-(trifluoromethyl)phenyl]carbamoyl}amino)phenyl]-1-oxo-1,2,3,4-tetrahydroisoquinolin-2-yl}acetic acid;

3-{1-oxo-6-[4-({[3-(trifluoromethyl)phenyl]carbamoyl}amino)phenyl]-1,2,3,4-tetrahydroisoquinolin-2-yl}propanoic acid;

3-{1-oxo-6-[4-({[4-(trifluoromethyl)phenyl]carbamoyl}amino)phenyl]-1,2,3,4-tetrahydroisoquinolin-2-yl}propanoic acid;

3-[6-(4-{[(2-methoxy-5-methylphenyl)carbamoyl]amino}phenyl)-1-oxo-1,2,3,4-tetrahydroisoquinolin-2-yl]propanoic acid;

2-{[6-(4-{[(2-methoxy-5-methylphenyl)carbamoyl]amino}phenyl)-1-oxo-1,2,3,4-tetrahydroisoquinolin-2-yl]methyl}pentanedioic acid;

2-(6-{4-[(phenylcarbamoyl)amino]phenyl}-1,2,3,4-tetrahydronaphthalen-2-yl)acetic acid;

2-{6-[2-({[3-(trifluoromethyl)phenyl]carbamoyl}amino)pyrimidin-5-yl]-1,2,3,4-tetrahydronaphthalen-2-yl}acetic acid;

2-[6-(2-{[(3-methylphenyl)carbamoyl]amino}pyrimidin-5-yl)-1,2,3,4-tetrahydronaphthalen-2-yl]acetic acid;

2-{6-[4-({[3-(trifluoromethyl)phenyl]carbamoyl}amino)phenyl]-1,2,3,4-tetrahydronaphthalen-2-yl}acetic acid;

2-{6-[4-({[3,5-bis(trifluoromethyl)phenyl]carbamoyl}amino)phenyl]-1,2,3,4-tetrahydronaphthalen-2-yl}acetic acid;

2-[6-(4-{[(3-fluorophenyl)carbamoyl]amino}phenyl)-1,2,3,4-tetrahydronaphthalen-2-yl]acetic acid;

2-[6-(4-{[(4-fluorophenyl)carbamoyl]amino}phenyl)-1,2,3,4-tetrahydronaphthalen-2-yl]acetic acid;

2-[6-(4-{[(3-cyanophenyl)carbamoyl]amino}phenyl)-1,2,3,4-tetrahydronaphthalen-2-yl]acetic acid;

2-[6-(4-{[(3-nitrophenyl)carbamoyl]amino}phenyl)-1,2,3,4-tetrahydronaphthalen-2-yl]acetic acid;

2-{6-[4-({[2-(trifluoromethoxy)phenyl]carbamoyl}amino)phenyl]-1,2,3,4-tetrahydronaphthalen-2-yl}acetic acid;

2-{6-[4-({[4-fluoro-3-(trifluoromethyl)phenyl]carbamoyl}amino)phenyl]-1,2,3,4-tetrahydronaphthalen-2-yl}acetic acid;

2-{6-[4-({[3-(trifluoromethoxy)phenyl]carbamoyl}amino)phenyl]-1,2,3,4-tetrahydronaphthalen-2-yl}acetic acid;

2-{6-[4-({[3-(pentafluoro$\lambda^6$-sulfanyl)phenyl]carbamoyl}amino)phenyl]-1,2,3,4-tetrahydronaphthalen-2-yl}acetic acid;

2-{6-[4-({[2-(trifluoromethyl)phenyl]carbamoyl}amino)phenyl]-1,2,3,4-tetrahydronaphthalen-2-yl}acetic acid;

2-[6-(4-{[(3-methylphenyl)carbamoyl]amino}phenyl)-1,2,3,4-tetrahydronaphthalen-2-yl]acetic acid;

2-[6-(4-{[(2-methoxy-5-methylphenyl)carbamoyl]amino}phenyl)-1,2,3,4-tetrahydronaphthalen-2-yl]acetic acid;

2-{6-[4-({[4-(trifluoromethyl)phenyl]carbamoyl}amino)phenyl]-1,2,3,4-tetrahydronaphthalen-2-yl}acetic acid;

2-[6-(4-{[(4-methylphenyl)carbamoyl]amino}phenyl)-1,2,3,4-tetrahydronaphthalen-2-yl]acetic acid;

2-[6-(4-{[(3-methoxyphenyl)carbamoyl]amino}phenyl)-1,2,3,4-tetrahydronaphthalen-2-yl]acetic acid;

2-[6-(4-{[(3-chlorophenyl)carbamoyl]amino}phenyl)-1,2,3,4-tetrahydronaphthalen-2-yl]acetic acid;

2-{6-[4-({[3-(difluoromethoxy)phenyl]carbamoyl}amino)phenyl]-1,2,3,4-tetrahydronaphthalen-2-yl}acetic acid;

rel-2-[(2R)-6-[4-({[3-(trifluoromethyl)phenyl]carbamoyl}amino)phenyl]-1,2,3,4-tetrahydronaphthalen-2-yl]acetic acid (enantiomer-1);

rel-2-[(2R)-6-[4-({[3-(trifluoromethyl)phenyl]
carbamoyl}amino)phenyl]-1,2,3,4-tetrahydronaphthalen-
2-yl]acetic acid (enantiomer-2);
2-{6-[3-fluoro-4-({[3-(trifluoromethyl)phenyl]
carbamoyl}amino)phenyl]-1,2,3,4-tetrahydronaphthalen-
2-yl}acetic acid;
2-{6-[3-fluoro-4-({[4-fluoro-3-(trifluoromethyl)phenyl]
carbamoyl}amino)phenyl]-1,2,3,4-tetrahydronaphthalen-
2-yl}acetic acid;
2-[6-(3-fluoro-4-{[(3-methylphenyl)carbamoyl]
amino}phenyl)-1,2,3,4-tetrahydronaphthalen-2-yl]acetic
acid;
2-[6-(4-{[(3,5-dimethylphenyl)carbamoyl]amino}phenyl)-
1,2,3,4-tetrahydronaphthalen-2-yl]acetic acid;
2-{6-[5-({[3-(trifluoromethyl)phenyl]carbamoyl}amino)py-
ridin-2-yl]-1,2,3,4-tetrahydronaphthalen-2-yl}acetic acid;
2-{6-[5-({[3-(trifluoromethyl)phenyl]carbamoyl}amino)
pyrazin-2-yl]-1,2,3,4-tetrahydronaphthalen-2-yl}acetic
acid;
2-{6-(5-{[(3-chlorophenyl)carbamoyl]amino}pyrazin-2-yl)-
1,2,3,4-tetrahydronaphthalen-2-yl]acetic acid;
2-{2-hydroxy-6-[4-({[3-(trifluoromethyl)phenyl]
carbamoyl}amino)phenyl]-1,2,3,4-tetrahydronaphthalen-
2-yl}acetic acid;
2-{2-hydroxy-6-[4-({[4-(trifluoromethyl)phenyl]
carbamoyl}amino)phenyl]-1,2,3,4-tetrahydronaphthalen-
2-yl}acetic acid;
2-{2-ethyl-1-oxo-5-[4-({[3-(trifluoromethyl)phenyl]
carbamoyl}amino)phenyl]-2,3-dihydro-1H-inden-2-
yl}acetic acid;
2-{1-oxo-5-[4-({[3-(trifluoromethyl)phenyl]
carbamoyl}amino)phenyl]-2,3-dihydro-1H-inden-2-
yl}acetic acid;
2-{1-oxo-5-[4-({[4-(trifluoromethyl)phenyl]
carbamoyl}amino)phenyl]-2,3-dihydro-1H-inden-2-
yl}acetic acid;
2-[5-(4-{[(3-methylphenyl)carbamoyl]amino}phenyl)-1-
oxo-2,3-dihydro-1H-inden-2-yl]acetic acid;
2-[5-(4-{[(3-chlorophenyl)carbamoyl]amino}phenyl)-2-
ethyl-1-oxo-2,3-dihydro-1H-inden-2-yl]acetic acid;
2-{1-oxo-6-[4-({[3-(trifluoromethyl)phenyl]
carbamoyl}amino)phenyl]-1,2,3,4-tetrahydronaphthalen-
2-yl}acetic acid;
2-{1-oxo-6-[4-({[4-(trifluoromethyl)phenyl]
carbamoyl}amino)phenyl]-1,2,3,4-tetrahydronaphthalen-
2-yl}acetic acid;
2-{1-oxo-6-[4-({[2-(trifluoromethyl)phenyl]
carbamoyl}amino)phenyl]-1,2,3,4-tetrahydronaphthalen-
2-yl}acetic acid;
2-[6-(4-{[(3-methylphenyl)carbamoyl]amino}phenyl)-1-
oxo-1,2,3,4-tetrahydronaphthalen-2-yl]acetic acid;
2-[6-(4-{[(2-methoxy-5-methylphenyl)carbamoyl]
amino}phenyl)-1-oxo-1,2,3,4-tetrahydronaphthalen-2-yl]
acetic acid;
2-[6-(4-{[(4-methylphenyl)carbamoyl]amino}phenyl)-1-
oxo-1,2,3,4-tetrahydronaphthalen-2-yl]acetic acid;
2-(1-oxo-6-{4-[(phenylcarbamoyl)amino]phenyl}-1,2,3,4-
tetrahydronaphthalen-2-yl)acetic acid;
2-{1-oxo-6-[4-({[2-(trifluoromethoxy)phenyl]
carbamoyl}amino)phenyl]-1,2,3,4-tetrahydronaphthalen-
2-yl}acetic acid;
2-{6-[3-fluoro-4-({[3-(trifluoromethyl)phenyl]
carbamoyl}amino)phenyl]-1-oxo-1,2,3,4-tetrahy-
dronaphthalen-2-yl}acetic acid;
2-[6-(3-fluoro-4-{[(3-methylphenyl)carbamoyl]
amino}phenyl)-1-oxo-1,2,3,4-tetrahydronaphthalen-2-yl]
acetic acid;
2-(6-{3-fluoro-4-[(phenylcarbamoyl)amino]phenyl}-1-oxo-
1,2,3,4-tetrahydronaphthalen-2-yl)acetic acid;
2-[6-(3-fluoro-4-{[(3-fluorophenyl)carbamoyl]
amino}phenyl)-1-oxo-1,2,3,4-tetrahydronaphthalen-2-yl]
acetic acid;
2-[6-(4-{[(3-chlorophenyl)carbamoyl]amino}-3-fluorophe-
nyl)-1-oxo-1,2,3,4-tetrahydronaphthalen-2-yl]acetic acid;
2-[6-(3-fluoro-4-{[(3-methoxyphenyl)carbamoyl]
amino}phenyl)-1-oxo-1,2,3,4-tetrahydronaphthalen-2-yl]
acetic acid;
2-[6-(4-{[(3,5-dimethylphenyl)carbamoyl]amino}-3-fluo-
rophenyl)-1-oxo-1,2,3,4-tetrahydronaphthalen-2-yl]ace-
tic acid;
2-[6-(3-fluoro-4-{[(2-fluoro-5-methylphenyl)carbamoyl]
amino}phenyl)-1-oxo-1,2,3,4-tetrahydronaphthalen-2-yl]
acetic acid;
2-[6-(4-{[(3-cyanophenyl)carbamoyl]amino}-3-fluorophe-
nyl)-1-oxo-1,2,3,4-tetrahydronaphthalen-2-yl]acetic acid;
2-{6-[2-fluoro-4-({[3-(trifluoromethyl)phenyl]
carbamoyl}amino)phenyl]-1-oxo-1,2,3,4-tetrahy-
dronaphthalen-2-yl}acetic acid;
2-[6-(2-fluoro-4-{[(2-methoxy-5-methylphenyl)carbamoyl]
amino}phenyl)-1-oxo-1,2,3,4-tetrahydronaphthalen-2-yl]
acetic acid;
2-(6-{2-fluoro-4-[(phenylcarbamoyl)amino]phenyl}-1-oxo-
1,2,3,4-tetrahydronaphthalen-2-yl)acetic acid;
2-{1-oxo-6-[5-({[3-(trifluoromethyl)phenyl]
carbamoyl}amino)pyrimidin-2-yl]-1,2,3,4-tetrahy-
dronaphthalen-2-yl}acetic acid;
2-{1-hydroxy-6-[4-({[3-(trifluoromethyl)phenyl]
carbamoyl}amino)phenyl]-1,2,3,4-tetrahydronaphthalen-
2-yl}acetic acid;
3-{1-oxo-6-[4-({[3-(trifluoromethyl)phenyl]
carbamoyl}amino)phenyl]-1,2,3,4-tetrahydronaphthalen-
2-yl}propanoic acid;
3-(1-oxo-6-{4-[(phenylcarbamoyl)amino]phenyl}-1,2,3,4-
tetrahydronaphthalen-2-yl)propanoic acid;
3-[6-(4-{[(2-methoxy-5-methylphenyl)carbamoyl]
amino}phenyl)-1-oxo-1,2,3,4-tetrahydronaphthalen-2-yl]
propanoic acid;
3-[6-(4-{[(3-methylphenyl)carbamoyl]amino}phenyl)-1-
oxo-1,2,3,4-tetrahydronaphthalen-2-yl]propanoic acid;
3-{6-[3-fluoro-4-({[3-(trifluoromethyl)phenyl]
carbamoyl}amino)phenyl]-1-oxo-1,2,3,4-tetrahy-
dronaphthalen-2-yl}propanoic acid;
3-[6-(3-fluoro-4-{[(3-methylphenyl)carbamoyl]
amino}phenyl)-1-oxo-1,2,3,4-tetrahydronaphthalen-2-yl]
propanoic acid;
3-[6-(4-{[(3-chlorophenyl)carbamoyl]amino}-3-fluorophe-
nyl)-1-oxo-1,2,3,4-tetrahydronaphthalen-2-yl]propanoic
acid;
2-methyl-2-{1-oxo-6-[4-({[3-(trifluoromethyl)phenyl]
carbamoyl}amino)phenyl]-1,2,3,4-tetrahydronaphthalen-
2-yl}propanoic acid;
2-methyl-2-(1-oxo-6-{4-[(phenylcarbamoyl)amino]phe-
nyl}-1,2,3,4-tetrahydronaphthalen-2-yl)propanoic acid;
2-[6-(4-{[(3-chlorophenyl)carbamoyl]amino}phenyl)-1-
oxo-1,2,3,4-tetrahydronaphthalen-2-yl]-2-methylpro-
panoic acid;
2-{2-methyl-1-oxo-6-[4-({[3-(trifluoromethyl)phenyl]
carbamoyl}amino)phenyl]-1,2,3,4-tetrahydronaphthalen-
2-yl}acetic acid;
2-[2-methyl-6-(4-{[(3-methylphenyl)carbamoyl]
amino}phenyl)-1-oxo-1,2,3,4-tetrahydronaphthalen-2-yl]
acetic acid;

2-[6-(4-{[(3-chlorophenyl)carbamoyl]amino}phenyl)-2-methyl-1-oxo-1,2,3,4-tetrahydronaphthalen-2-yl]acetic acid;

2-{2-methyl-1-oxo-6-{4-[(phenylcarbamoyl)amino]phenyl}-1,2,3,4-tetrahydronaphthalen-2-yl)acetic acid;

2-[6-(4-{[(3-methoxyphenyl)carbamoyl]amino}phenyl)-2-methyl-1-oxo-1,2,3,4-tetrahydronaphthalen-2-yl]acetic acid;

2-[6-(4-{[(3-fluorophenyl)carbamoyl]amino}phenyl)-2-methyl-1-oxo-1,2,3,4-tetrahydronaphthalen-2-yl]acetic acid;

2-[6-(2-fluoro-4-{[(3-methylphenyl)carbamoyl]amino}phenyl)-2-methyl-1-oxo-1,2,3,4-tetrahydronaphthalen-2-yl]acetic acid;

2-[6-(2-chloro-4-{[(3-chlorophenyl)carbamoyl]amino}phenyl)-2-methyl-1-oxo-1,2,3,4-tetrahydronaphthalen-2-yl]acetic acid;

rel-2-[(2R)-2-methyl-1-oxo-6-[4-({[3-(trifluoromethyl)phenyl]carbamoyl}amino)phenyl]-1,2,3,4-tetrahydronaphthalen-2-yl]acetic acid (enantiomer-1);

rel-2-[(2R)-2-methyl-1-oxo-6-[4-({[3-(trifluoromethyl)phenyl]carbamoyl}amino)phenyl]-1,2,3,4-tetrahydronaphthalen-2-yl]acetic acid (enantiomer-2);

2-{6-[3-fluoro-4-({[3-(trifluoromethyl)phenyl]carbamoyl}amino)phenyl]-2-methyl-1-oxo-1,2,3,4-tetrahydronaphthalen-2-yl}acetic acid;

2-[6-(4-{[(3-chlorophenyl)carbamoyl]amino}-3-fluorophenyl)-2-methyl-1-oxo-1,2,3,4-tetrahydronaphthalen-2-yl]acetic acid;

2-(6-{3-fluoro-4-[(phenylcarbamoyl)amino]phenyl}-2-methyl-1-oxo-1,2,3,4-tetrahydronaphthalen-2-yl)acetic acid;

2-[6-(3-fluoro-4-{[(3-fluorophenyl)carbamoyl]amino}phenyl)-2-methyl-1-oxo-1,2,3,4-tetrahydronaphthalen-2-yl]acetic acid;

2-[6-(3-fluoro-4-{[(3-methoxyphenyl)carbamoyl]amino}phenyl)-2-methyl-1-oxo-1,2,3,4-tetrahydronaphthalen-2-yl]acetic acid;

2-{6-[3-chloro-4-({[3-(trifluoromethyl)phenyl]carbamoyl}amino)phenyl]-2-methyl-1-oxo-1,2,3,4-tetrahydronaphthalen-2-yl}acetic acid;

2-[6-(4-{[(3-chlorophenyl)carbamoyl]amino}-2,5-difluorophenyl)-2-methyl-1-oxo-1,2,3,4-tetrahydronaphthalen-2-yl]acetic acid;

2-(6-{2,5-difluoro-4-[(phenylcarbamoyl)amino]phenyl}-2-methyl-1-oxo-1,2,3,4-tetrahydronaphthalen-2-yl)acetic acid;

2-[6-(4-{[(3-chlorophenyl)carbamoyl]amino}-2-methylphenyl)-2-methyl-1-oxo-1,2,3,4-tetrahydronaphthalen-2-yl]acetic acid;

2-(2-methyl-6-{2-methyl-4-[(phenylcarbamoyl)amino]phenyl}-1-oxo-1,2,3,4-tetrahydronaphthalen-2-yl)acetic acid;

2-[2-methyl-6-(2-methyl-4-{[(3-methylphenyl)carbamoyl]amino}phenyl)-1-oxo-1,2,3,4-tetrahydronaphthalen-2-yl]acetic acid;

2-{2-methyl-6-[2-methyl-4-({[3-(trifluoromethyl)phenyl]carbamoyl}amino)phenyl]-1-oxo-1,2,3,4-tetrahydronaphthalen-2-yl}acetic acid;

2-{2-methyl-6-[2-methyl-4-({[4-(trifluoromethyl)phenyl]carbamoyl}amino)phenyl]-1-oxo-1,2,3,4-tetrahydronaphthalen-2-yl}acetic acid;

2-[6-(4-{[(4-chlorophenyl)carbamoyl]amino}-2-methylphenyl)-2-methyl-1-oxo-1,2,3,4-tetrahydronaphthalen-2-yl]acetic acid;

2-{6-[2-fluoro-4-({[3-(trifluoromethyl)phenyl]carbamoyl}amino)phenyl]-2-methyl-1-oxo-1,2,3,4-tetrahydronaphthalen-2-yl}acetic acid;

2-[6-(4-{[(3-chlorophenyl)carbamoyl]amino}-2-fluorophenyl)-2-methyl-1-oxo-1,2,3,4-tetrahydronaphthalen-2-yl]acetic acid;

2-{6-[2-chloro-4-({[3-(trifluoromethyl)phenyl]carbamoyl}amino)phenyl]-2-methyl-1-oxo-1,2,3,4-tetrahydronaphthalen-2-yl}acetic acid;

2-(6-{2-chloro-4-[(phenylcarbamoyl)amino]phenyl}-2-methyl-1-oxo-1,2,3,4-tetrahydronaphthalen-2-yl)acetic acid;

2-(6-{2-cyano-4-[(phenylcarbamoyl)amino]phenyl}-2-methyl-1-oxo-1,2,3,4-tetrahydronaphthalen-2-yl)acetic acid;

2-[6-(5-{[(3-chlorophenyl)carbamoyl]amino}pyridin-2-yl)-2-methyl-1-oxo-1,2,3,4-tetrahydronaphthalen-2-yl]acetic acid;

2-{2-methyl-1-oxo-6-[5-({[3-(trifluoromethyl)phenyl]carbamoyl}amino)pyridin-2-yl]-1,2,3,4-tetrahydronaphthalen-2-yl}acetic acid;

2-(2-methyl-1-oxo-6-{5-[(phenylcarbamoyl)amino]pyridin-2-yl}-1,2,3,4-tetrahydronaphthalen-2-yl)acetic acid;

2-{2-methyl-1-oxo-6-[5-({[3-(trifluoromethyl)phenyl]carbamoyl}amino)pyrazin-2-yl]-1,2,3,4-tetrahydronaphthalen-2-yl}acetic acid;

2-[6-(5-{[(3-chlorophenyl)carbamoyl]amino}pyrazin-2-yl)-2-methyl-1-oxo-1,2,3,4-tetrahydronaphthalen-2-yl]acetic acid;

2-(2-methyl-1-oxo-6-{5-[(phenylcarbamoyl)amino]pyrimidin-2-yl}-1,2,3,4-tetrahydronaphthalen-2-yl)acetic acid;

2-{2-methyl-1-oxo-6-[5-({[3-(trifluoromethyl)phenyl]carbamoyl}amino)pyrimidin-2-yl]-1,2,3,4-tetrahydronaphthalen-2-yl}acetic acid;

2-{2-ethyl-1-oxo-6-[4-({[3-(trifluoromethyl)phenyl]carbamoyl}amino)phenyl]-1,2,3,4-tetrahydronaphthalen-2-yl}acetic acid;

2-{2-ethyl-1-oxo-6-[4-({[4-(trifluoromethyl)phenyl]carbamoyl}amino)phenyl]-1,2,3,4-tetrahydronaphthalen-2-yl}acetic acid;

2-{2-ethyl-1-oxo-6-[4-({[2-(trifluoromethyl)phenyl]carbamoyl}amino)phenyl]-1,2,3,4-tetrahydronaphthalen-2-yl}acetic acid;

2-(2-ethyl-1-oxo-6-{4-[(phenylcarbamoyl)amino]phenyl}-1,2,3,4-tetrahydronaphthalen-2-yl)acetic acid;

2-[6-(4-{[(3-chlorophenyl)carbamoyl]amino}phenyl)-2-ethyl-1-oxo-1,2,3,4-tetrahydronaphthalen-2-yl]acetic acid;

2-[2-ethyl-6-(4-{[(3-methoxyphenyl)carbamoyl]amino}phenyl)-1-oxo-1,2,3,4-tetrahydronaphthalen-2-yl]acetic acid;

2-(6-{4-[(cyclohexylcarbamoyl)amino]phenyl}-2-ethyl-1-oxo-1,2,3,4-tetrahydronaphthalen-2-yl)acetic acid;

2-[2-ethyl-6-(4-{[(3-methylphenyl)carbamoyl]amino}phenyl)-1-oxo-1,2,3,4-tetrahydronaphthalen-2-yl]acetic acid;

2-[2-ethyl-6-(4-{[(4-methoxyphenyl)carbamoyl]amino}phenyl)-1-oxo-1,2,3,4-tetrahydronaphthalen-2-yl]acetic acid;

2-[6-(4-{[(4-chlorophenyl)carbamoyl]amino}phenyl)-2-ethyl-1-oxo-1,2,3,4-tetrahydronaphthalen-2-yl]acetic acid;

2-[2-ethyl-6-(4-{[(4-methylphenyl)carbamoyl]amino}phenyl)-1-oxo-1,2,3,4-tetrahydronaphthalen-2-yl]acetic acid;

2-[2-ethyl-6-(4-{[(3-fluorophenyl)carbamoyl]amino}phenyl)-1-oxo-1,2,3,4-tetrahydronaphthalen-2-yl]acetic acid;

2-[6-(4-{[(3,5-dimethylphenyl)carbamoyl]amino}phenyl)-2-ethyl-1-oxo-1,2,3,4-tetrahydronaphthalen-2-yl]acetic acid;

2-[2-ethyl-6-(4-{[(2-methoxy-5-methylphenyl)carbamoyl] amino}phenyl)-1-oxo-1,2,3,4-tetrahydronaphthalen-2-yl] acetic acid;

2-[(2S)-2-ethyl-1-oxo-6-[4-({[3-(trifluoromethyl)phenyl] carbamoyl}amino)phenyl]-1,2,3,4-tetrahydronaphthalen-2-yl]acetic acid;

2-[(2R)-2-ethyl-1-oxo-6-[4-({[3-(trifluoromethyl)phenyl] carbamoyl}amino)phenyl]-1,2,3,4-tetrahydronaphthalen-2-yl]acetic acid;

rel-2-[(2R)-6-(4-{[(4-chlorophenyl)carbamoyl] amino}phenyl)-2-ethyl-1-oxo-1,2,3,4-tetrahydronaphthalen-2-yl]acetic acid (enantiomer-1);

rel-2-[(2R)-6-(4-{[(4-chlorophenyl)carbamoyl] amino}phenyl)-2-ethyl-1-oxo-1,2,3,4-tetrahydronaphthalen-2-yl]acetic acid (enantiomer-2);

2-[6-(2-chloro-4-{[(3-methoxyphenyl)carbamoyl] amino}phenyl)-2-ethyl-1-oxo-1,2,3,4-tetrahydronaphthalen-2-yl]acetic acid;

2-[6-(2-chloro-4-{[(4-chlorophenyl)carbamoyl] amino}phenyl)-2-ethyl-1-oxo-1,2,3,4-tetrahydronaphthalen-2-yl]acetic acid;

2-{6-[2-chloro-4-({[4-(trifluoromethyl)phenyl] carbamoyl}amino)phenyl]-2-ethyl-1-oxo-1,2,3,4-tetrahydronaphthalen-2-yl}acetic acid;

2-[6-(2-chloro-4-{[(2-methoxy-5-methylphenyl)carbamoyl] amino}phenyl)-2-ethyl-1-oxo-1,2,3,4-tetrahydronaphthalen-2-yl]acetic acid;

2-[6-(2-chloro-4-{[(3,5-dimethylphenyl)carbamoyl] amino}phenyl)-2-ethyl-1-oxo-1,2,3,4-tetrahydronaphthalen-2-yl]acetic acid;

2-{6-[2-chloro-4-({[3-(trifluoromethyl)phenyl] carbamoyl}amino)phenyl]-2-ethyl-1-oxo-1,2,3,4-tetrahydronaphthalen-2-yl}acetic acid;

2-[6-(2-chloro-4-{[(3-chlorophenyl)carbamoyl] amino}phenyl)-2-ethyl-1-oxo-1,2,3,4-tetrahydronaphthalen-2-yl]acetic acid;

2-(6-{2-chloro-4-[(phenylcarbamoyl)amino]phenyl}-2-ethyl-1-oxo-1,2,3,4-tetrahydronaphthalen-2-yl)acetic acid;

2-(2-ethyl-6-{3-fluoro-4-[(phenylcarbamoyl)amino]phenyl}-1-oxo-1,2,3,4-tetrahydronaphthalen-2-yl)acetic acid;

2-(6-{4-[(cyclohexylcarbamoyl)amino]-3-fluorophenyl}-2-ethyl-1-oxo-1,2,3,4-tetrahydronaphthalen-2-yl)acetic acid;

2-{2-ethyl-6-[3-fluoro-4-({[3-(trifluoromethyl)phenyl] carbamoyl}amino)phenyl]-1-oxo-1,2,3,4-tetrahydronaphthalen-2-yl}acetic acid;

2-[6-(4-{[(3-chlorophenyl)carbamoyl]amino}-3-fluorophenyl)-2-ethyl-1-oxo-1,2,3,4-tetrahydronaphthalen-2-yl] acetic acid;

2-[2-ethyl-6-(3-fluoro-4-{[(3-fluorophenyl)carbamoyl] amino}phenyl)-1-oxo-1,2,3,4-tetrahydronaphthalen-2-yl] acetic acid;

2-[6-(4-{[(4-chlorophenyl)carbamoyl]amino}-3-fluorophenyl)-2-ethyl-1-oxo-1,2,3,4-tetrahydronaphthalen-2-yl] acetic acid;

2-[6-(4-{[(3,5-dimethylphenyl)carbamoyl]amino}-3-fluorophenyl)-2-ethyl-1-oxo-1,2,3,4-tetrahydronaphthalen-2-yl]acetic acid;

2-[2-ethyl-6-(3-fluoro-4-{[(2-methoxy-5-methylphenyl)carbamoyl]amino}phenyl)-1-oxo-1,2,3,4-tetrahydronaphthalen-2-yl]acetic acid;

2-{2-ethyl-1-oxo-6-[5-({[3-(trifluoromethyl)phenyl] carbamoyl}amino)pyridin-2-yl]-1,2,3,4-tetrahydronaphthalen-2-yl}acetic acid;

2-[6-(5-{[(3-chlorophenyl)carbamoyl]amino}pyridin-2-yl)-2-ethyl-1-oxo-1,2,3,4-tetrahydronaphthalen-2-yl]acetic acid;

2-(2-ethyl-1-oxo-6-{5-[(phenylcarbamoyl)amino]pyridin-2-yl}-1,2,3,4-tetrahydronaphthalen-2-yl)acetic acid;

2-[6-(5-{[(3,5-dimethylphenyl)carbamoyl]amino}pyridin-2-yl)-2-ethyl-1-oxo-1,2,3,4-tetrahydronaphthalen-2-yl] acetic acid;

2-[2-ethyl-6-(5-{[(2-methoxy-5-methylphenyl)carbamoyl] amino}pyridin-2-yl)-1-oxo-1,2,3,4-tetrahydronaphthalen-2-yl]acetic acid;

2-(2-ethyl-1-oxo-6-{5-[(phenylcarbamoyl)amino]pyrazin-2-yl}-1,2,3,4-tetrahydronaphthalen-2-yl)acetic acid;

2-{2-ethyl-1-oxo-6-[5-({[3-(trifluoromethyl)phenyl] carbamoyl}amino)pyrazin-2-yl]-1,2,3,4-tetrahydronaphthalen-2-yl}acetic acid;

2-[6-(5-{[(3-chlorophenyl)carbamoyl]amino}pyrazin-2-yl)-2-ethyl-1-oxo-1,2,3,4-tetrahydronaphthalen-2-yl]acetic acid;

2-[6-(5-{[(3,5-dimethylphenyl)carbamoyl]amino}pyrazin-2-yl)-2-ethyl-1-oxo-1,2,3,4-tetrahydronaphthalen-2-yl] acetic acid;

2-[2-ethyl-6-(5-{[(2-methoxy-5-methylphenyl)carbamoyl] amino}pyrazin-2-yl)-1-oxo-1,2,3,4-tetrahydronaphthalen-2-yl]acetic acid;

2-{2-ethyl-1-oxo-6-[6-({[3-(trifluoromethyl)phenyl] carbamoyl}amino)pyridazin-3-yl]-1,2,3,4-tetrahydronaphthalen-2-yl}acetic acid;

2-[6-(6-{[(3-chlorophenyl)carbamoyl]amino}pyridazin-3-yl)-2-ethyl-1-oxo-1,2,3,4-tetrahydronaphthalen-2-yl]acetic acid;

2-{2-ethyl-1-oxo-6-[6-({[3-(trifluoromethyl)phenyl] carbamoyl}amino)pyridin-3-yl]-1,2,3,4-tetrahydronaphthalen-2-yl}acetic acid;

2-[6-(6-{[(3-chlorophenyl)carbamoyl]amino}pyridin-3-yl)-2-ethyl-1-oxo-1,2,3,4-tetrahydronaphthalen-2-yl]acetic acid;

2-(2-ethyl-1-oxo-6-{6-[(phenylcarbamoyl)amino]pyridin-3-yl}-1,2,3,4-tetrahydronaphthalen-2-yl)acetic acid;

2-[(2S)-6-(5-{[(3-chlorophenyl)carbamoyl]amino}pyridin-2-yl)-2-ethyl-1-oxo-1,2,3,4-tetrahydronaphthalen-2-yl] acetic acid;

2-[(2R)-6-(5-{[(3-chlorophenyl)carbamoyl]amino}pyridin-2-yl)-2-ethyl-1-oxo-1,2,3,4-tetrahydronaphthalen-2-yl] acetic acid;

rel-2-[(2R)-2-ethyl-1-oxo-6-[5-({[3-(trifluoromethyl)phenyl]carbamoyl}amino)pyrazin-2-yl]-1,2,3,4-tetrahydronaphthalen-2-yl]acetic acid (enantiomer-1);

rel-2-[(2R)-2-ethyl-1-oxo-6-[5-({[3-(trifluoromethyl)phenyl]carbamoyl}amino)pyrazin-2-yl]-1,2,3,4-tetrahydronaphthalen-2-yl]acetic acid (enantiomer-2);

2-(1-oxo-6-{4-[(phenylcarbamoyl)amino]phenyl}-2-propyl-1,2,3,4-tetrahydronaphthalen-2-yl)acetic acid;

2-{1-oxo-2-propyl-6-[4-({[3-(trifluoromethyl)phenyl] carbamoyl}amino)phenyl]-1,2,3,4-tetrahydronaphthalen-2-yl}acetic acid;

2-[6-(4-{[(3-chlorophenyl)carbamoyl]amino}phenyl)-1-oxo-2-propyl-1,2,3,4-tetrahydronaphthalen-2-yl]acetic acid;

2-{1-oxo-2-propyl-6-[5-({[3-(trifluoromethyl)phenyl] carbamoyl}amino)pyridin-2-yl]-1,2,3,4-tetrahydronaphthalen-2-yl}acetic acid;

2-[6-(5-{[(3-chlorophenyl)carbamoyl]amino}pyridin-2-yl)-1-oxo-2-propyl-1,2,3,4-tetrahydronaphthalen-2-yl]acetic acid;

rel-2-[(1R,2S)-2-ethyl-1-hydroxy-6-[4-({[3-(trifluoromethyl)phenyl]carbamoyl}amino)phenyl]-1,2,3,4-tetrahydronaphthalen-2-yl]acetic acid;

rel-2-[(1R,2S)-2-ethyl-1-hydroxy-6-[4-({[3-(trifluoromethyl)phenyl]carbamoyl}amino)phenyl]-1,2,3,4-tetrahydronaphthalen-2-yl]acetic acid;

(2S)-3-methyl-2-(2-{1-oxo-6-[4-({[3-(trifluoromethyl)phenyl]carbamoyl}amino)phenyl]-1,2,3,4-tetrahydronaphthalen-2-yl}acetamido)butanoic acid;

2-(2-{1-oxo-6-[4-({[3-(trifluoromethyl)phenyl]carbamoyl}amino)phenyl]-1,2,3,4-tetrahydronaphthalen-2-yl}acetamido)acetic acid;

(2S)-3-methyl-2-(2-{6-[4-({[3-(trifluoromethyl)phenyl]carbamoyl}amino)phenyl]-1,2,3,4-tetrahydronaphthalen-2-yl}acetamido)butanoic acid;

(2S)-3-methyl-2-(2-{6-[4-({[3-(trifluoromethyl)phenyl]carbamoyl}amino)phenyl]-1,2,3,4-tetrahydronaphthalen-2-yl}acetamido)pentanoic acid;

(2S)-2-{2-[6-(3-fluoro-4-{[(3-methylphenyl)carbamoyl]amino}phenyl)-1,2,3,4-tetrahydronaphthalen-2-yl]acetamido}-3-methylbutanoic acid;

(2S)-2-{2-[6-(3-fluoro-4-{[(3-methylphenyl)carbamoyl]amino}phenyl)-1,2,3,4-tetrahydronaphthalen-2-yl]acetamido}-3-methylpentanoic acid;

2-{2-[6-(3-fluoro-4-{[(3-methylphenyl)carbamoyl]amino}phenyl)-1-oxo-1,2,3,4-tetrahydronaphthalen-2-yl]acetamido}acetic acid;

2-{2-fluoro-1-oxo-6-[4-({[3-(trifluoromethyl)phenyl]carbamoyl}amino)phenyl]-1,2,3,4-tetrahydronaphthalen-2-yl}acetic acid;

2-[6-(4-{[(3-chlorophenyl)carbamoyl]amino}phenyl)-2-fluoro-1-oxo-1,2,3,4-tetrahydronaphthalen-2-yl]acetic acid;

2-(2-fluoro-1-oxo-6-{4-[(phenylcarbamoyl)amino]phenyl}-1,2,3,4-tetrahydronaphthalen-2-yl)acetic acid;

2-{2-hydroxy-1-oxo-6-[4-({[3-(trifluoromethyl)phenyl]carbamoyl}amino)phenyl]-1,2,3,4-tetrahydronaphthalen-2-yl}acetic acid;

2-[6-(4-{[(3-chlorophenyl)carbamoyl]amino}phenyl)-2-hydroxy-1-oxo-1,2,3,4-tetrahydronaphthalen-2-yl]acetic acid;

2-[6-(4-{[(2-fluorophenyl)carbamoyl]amino}phenyl)-2-hydroxy-1-oxo-1,2,3,4-tetrahydronaphthalen-2-yl]acetic acid;

2-[6-(4-{[(4-chlorophenyl)carbamoyl]amino}phenyl)-2-hydroxy-1-oxo-1,2,3,4-tetrahydronaphthalen-2-yl]acetic acid;

2-[2-hydroxy-6-(4-{[(3-methylphenyl)carbamoyl]amino}phenyl)-1-oxo-1,2,3,4-tetrahydronaphthalen-2-yl]acetic acid;

2-(2-methoxy-1-oxo-6-{4-[(phenylcarbamoyl)amino]phenyl}-1,2,3,4-tetrahydronaphthalen-2-yl)acetic acid;

2-{2-methoxy-1-oxo-6-[4-({[3-(trifluoromethyl)phenyl]carbamoyl}amino)phenyl]-1,2,3,4-tetrahydronaphthalen-2-yl}acetic acid;

2-[6-(4-{[(3-chlorophenyl)carbamoyl]amino}phenyl)-2-methoxy-1-oxo-1,2,3,4-tetrahydronaphthalen-2-yl]acetic acid;

2-[6-(4-{[(4-chlorophenyl)carbamoyl]amino}phenyl)-2-methoxy-1-oxo-1,2,3,4-tetrahydronaphthalen-2-yl]acetic acid;

rel-2-[(2R)-6-(4-{[(4-chlorophenyl)carbamoyl]amino}phenyl)-2-methoxy-1-oxo-1,2,3,4-tetrahydronaphthalen-2-yl]acetic acid (enantiomer-2);

rel-2-[(2R)-6-(4-{[(4-chlorophenyl)carbamoyl]amino}phenyl)-2-methoxy-1-oxo-1,2,3,4-tetrahydronaphthalen-2-yl]acetic acid (enantiomer-1);

2-[6-(4-{[(3,5-dimethylphenyl)carbamoyl]amino}phenyl)-2-methoxy-1-oxo-1,2,3,4-tetrahydronaphthalen-2-yl]acetic acid;

2-[2-(methoxymethyl)-1-oxo-6-[4-({[3-(trifluoromethyl)phenyl]carbamoyl}amino)phenyl]-1,2,3,4-tetrahydronaphthalen-2-yl]acetic acid;

2-[6-(4-{[(3-chlorophenyl)carbamoyl]amino}-3-fluorophenyl)-2-(hydroxymethyl)-1-oxo-1,2,3,4-tetrahydronaphthalen-2-yl]acetic acid;

2-[2-(hydroxymethyl)-1-oxo-6-[4-({[3-(trifluoromethyl)phenyl]carbamoyl}amino)phenyl]-1,2,3,4-tetrahydronaphthalen-2-yl]acetic acid;

2-[2-(hydroxymethyl)-6-(4-{[(3-methylphenyl)carbamoyl]amino}phenyl)-1-oxo-1,2,3,4-tetrahydronaphthalen-2-yl]acetic acid;

2-(1-oxo-6-{4-[(phenylcarbamoyl)amino]phenyl}-2-(2,2,2-trifluoroethyl)-1,2,3,4-tetrahydronaphthalen-2-yl)acetic acid;

2-(1-hydroxy-6-{4-[(phenylcarbamoyl)amino]phenyl}-2-(2,2,2-trifluoroethyl)-1,2,3,4-tetrahydronaphthalen-2-yl)acetic acid;

2-[6-(4-{[(3,5-dimethylphenyl)carbamoyl]amino}phenyl)-1-oxo-2-(2,2,2-trifluoroethyl)-1,2,3,4-tetrahydronaphthalen-2-yl]acetic acid;

2-[6-(4-{[(3-methoxyphenyl)carbamoyl]amino}phenyl)-1-oxo-2-(2,2,2-trifluoroethyl)-1,2,3,4-tetrahydronaphthalen-2-yl]acetic acid;

2-[6-(4-{[(3-chlorophenyl)carbamoyl]amino}phenyl)-1-oxo-2-(2,2,2-trifluoroethyl)-1,2,3,4-tetrahydronaphthalen-2-yl]acetic acid;

2-[6-(4-{[(3-chlorophenyl)carbamoyl]amino}phenyl)-1-hydroxy-2-(2,2,2-trifluoroethyl)-1,2,3,4-tetrahydronaphthalen-2-yl]acetic acid;

2-[6-(4-{[(2-methoxy-5-methylphenyl)carbamoyl]amino}phenyl)-1-oxo-2-(2,2,2-trifluoroethyl)-1,2,3,4-tetrahydronaphthalen-2-yl]acetic acid;

2-{2-ethyl-1-hydroxy-6-[5-({[3-(trifluoromethyl)phenyl]carbamoyl}amino)pyridin-2-yl]-1,2,3,4-tetrahydronaphthalen-2-yl}acetic acid;

2-{2-ethyl-1-hydroxy-6-[5-({[3-(trifluoromethyl)phenyl]carbamoyl}amino)pyrazin-2-yl]-1,2,3,4-tetrahydronaphthalen-2-yl}acetic acid;

2-[2-(methoxymethyl)-1-oxo-6-{4-[(phenylcarbamoyl)amino]phenyl}-1,2,3,4-tetrahydronaphthalen-2-yl]acetic acid;

2-[6-(4-{[(3-chlorophenyl)carbamoyl]amino}phenyl)-2-(methoxymethyl)-1-oxo-1,2,3,4-tetrahydronaphthalen-2-yl]acetic acid;

rel-2-[(2R)-6-(2-chloro-4-{[(3-chlorophenyl)carbamoyl]amino}phenyl)-2-methyl-1-oxo-1,2,3,4-tetrahydronaphthalen-2-yl]acetic acid;

rel-2-[(2R)-6-(2-chloro-4-{[(3-chlorophenyl)carbamoyl]amino}phenyl)-2-ethyl-1-oxo-1,2,3,4-tetrahydronaphthalen-2-yl]acetic acid;

rel-2-[(2R)-6-(4-{[(3-chlorophenyl)carbamoyl]amino}phenyl)-1-oxo-2-(2,2,2-trifluoroethyl)-1,2,3,4-tetrahydronaphthalen-2-yl]acetic acid;

rel-2-[(2R)-6-(5-{[(3,4-difluorophenyl)carbamoyl]amino}pyrazin-2-yl)-1-oxo-2-(2,2,2-trifluoroethyl)-1,2,3,4-tetrahydronaphthalen-2-yl]acetic acid;

rel-2-[(2R)-6-{5-[(cyclohexylcarbamoyl)amino]pyrazin-2-yl}-1-oxo-2-(2,2,2-trifluoroethyl)-1,2,3,4-tetrahydronaphthalen-2-yl]acetic acid;

2-[(2S)-6-(4-{[(3,4-difluorophenyl)carbamoyl]amino}phenyl)-2-ethyl-1-oxo-1,2,3,4-tetrahydronaphthalen-2-yl]acetic acid;

rel-2-[(2R)-6-[2-chloro-4-({[3-(trifluoromethyl)phenyl] carbamoyl}amino)phenyl]-2-ethyl-1-oxo-1,2,3,4-tetrahydronaphthalen-2-yl]acetic acid;

rel-2-[(2R)-1-oxo-6-(5-{[(pentan-3-yl)carbamoyl] amino}pyrazin-2-yl)-2-(2,2,2-trifluoroethyl)-1,2,3,4-tetrahydronaphthalen-2-yl]acetic acid;

rel-2-[(2R)-6-(5-{[(4-ethylphenyl)carbamoyl] amino}pyrazin-2-yl)-1-oxo-2-(2,2,2-trifluoroethyl)-1,2,3, 4-tetrahydronaphthalen-2-yl]acetic acid;

rel-2-[(2R)-6-{4-[(butylcarbamoyl)amino]phenyl}-1-oxo-2-(2,2,2-trifluoroethyl)-1,2,3,4-tetrahydronaphthalen-2-yl] acetic acid;

rel-2-[(2R)-1-oxo-2-(2,2,2-trifluoroethyl)-6-[4-({[3-(trifluoromethyl)phenyl]carbamoyl}amino)phenyl]-1,2,3,4-tetrahydronaphthalen-2-yl]acetic acid;

rel-2-[(2R)-6-(5-{[(3-chlorophenyl)carbamoyl] amino}pyrazin-2-yl)-1-oxo-2-(2,2,2-trifluoroethyl)-1,2,3, 4-tetrahydronaphthalen-2-yl]acetic acid;

rel-2-[(2R)-6-(4-{[(3,5-dichlorophenyl)carbamoyl] amino}phenyl)-1-oxo-2-(2,2,2-trifluoroethyl)-1,2,3,4-tetrahydronaphthalen-2-yl]acetic acid;

rel-2-[(2R)-6-(4-{[(4-ethylphenyl)carbamoyl] amino}phenyl)-1-oxo-2-(2,2,2-trifluoroethyl)-1,2,3,4-tetrahydronaphthalen-2-yl]acetic acid;

rel-2-[(2R)-6-{4-[(cyclohexylcarbamoyl)amino]phenyl}-1-oxo-2-(2,2,2-trifluoroethyl)-1,2,3,4-tetrahydronaphthalen-2-yl]acetic acid;

rel-2-[(2R)-6-(2-chloro-4-{[(3-chlorophenyl)carbamoyl] amino}phenyl)-1-oxo-2-(2,2,2-trifluoroethyl)-1,2,3,4-tetrahydronaphthalen-2-yl]acetic acid;

rel-2-[(2R)-2-methoxy-1-oxo-6-[4-({[3-(trifluoromethyl) phenyl]carbamoyl}amino)phenyl]-1,2,3,4-tetrahydronaphthalen-2-yl]acetic acid;

rel-2-[(2R)-6-(4-{[(3-chlorophenyl)carbamoyl] amino}phenyl)-2-methoxy-1-oxo-1,2,3,4-tetrahydronaphthalen-2-yl]acetic acid;

rel-2-[(2R)-6-{5-[(cyclobutylcarbamoyl)amino]pyrazin-2-yl}-1-oxo-2-(2,2,2-trifluoroethyl)-1,2,3,4-tetrahydronaphthalen-2-yl]acetic acid;

or a pharmaceutically acceptable salt thereof.

A person of ordinary skills in the art recognizes that compounds of the present invention may have alternative names when different naming software is used.

The following exemplified compounds have alternative chemical names as illustrated in table below.

| Example # | Chemical Name | Alternative Chemical Names |
|---|---|---|
| 1 | 2-{1-oxo-6-[4-({[3-(trifluoromethyl)phenyl]carbamoyl}amino)phenyl]-1,2,3,4-tetrahydroisoquinolin-2-yl}acetic acid | 2-(1-Oxo-6-(4-(3-(3-(trifluoromethyl)phenyl)ureido)phenyl)-3,4-dihydroisoquinolin-2(1H)-yl)acetic acid |
| 10 | 2-(6-{4-[(phenylcarbamoyl)amino]phenyl}-1,2,3,4-tetrahydronaphthalen-2-yl)acetic acid | 2-(6-(4-(3-Phenylureido)phenyl)-1,2,3,4-tetrahydronaphthalen-2-yl)acetic acid |
| 40 | 2-{2-hydroxy-6-[4-({[3-(trifluoromethyl)phenyl]carbamoyl}amino)phenyl]-1,2,3,4-tetrahydronaphthalen-2-yl}acetic acid | 2-(2-Hydroxy-6-(4-(3-(3-(trifluoromethyl)phenyl)ureido)phenyl)-1,2,3,4-tetrahydronaphthalen-2-yl)acetic acid |
| 42 | 2-{2-ethyl-1-oxo-5-[4-({[3-(trifluoromethyl)phenyl]carbamoyl}amino)phenyl]-2,3-dihydro-1H-inden-2-yl}acetic acid | 2-(2-ethyl-1-oxo-5-(4-(3-(3-(trifluoromethyl)phenyl)ureido)phenyl)-2,3-dihydro-1H-inden-2-yl) acetic acid |
| 47 | 2-{1-oxo-6-[4-({[3-(trifluoromethyl)phenyl]carbamoyl}amino)phenyl]-1,2,3,4-tetrahydronaphthalen-2-yl}acetic acid | 2-(1-Oxo-6-(4-(3-(3-(trifluoromethyl)phenyl)ureido)phenyl)-1,2,3,4-tetrahydronaphthalen-2-yl)acetic acid |
| 68 | 2-{1-hydroxy-6-[4-({[3-(trifluoromethyl)phenyl]carbamoyl}amino)phenyl]-1,2,3,4-tetrahydronaphthalen-2-yl}acetic acid | 2-(1-hydroxy-6-(4-(3-(3-(trifluoromethyl)phenyl)ureido)phenyl)-1,2,3,4-tetrahydronaphthalen-2-yl)acetic acid |
| 69 | 3-{1-oxo-6-[4-({[3-(trifluoromethyl)phenyl]carbamoyl}amino)phenyl]-1,2,3,4-tetrahydronaphthalen-2-yl}propanoic acid | 3-(1-oxo-6-(4-(3-(3-(trifluoromethyl)phenyl)ureido)phenyl)-1,2,3,4-tetrahydronaphthalen-2-yl)propanoic acid |
| 76 | 2-methyl-2-{1-oxo-6-[4-({[3-(trifluoromethyl)phenyl]carbamoyl}amino)phenyl]-1,2,3,4-tetrahydronaphthalen-2-yl}propanoic acid | 2-Methyl-2-(1-oxo-6-(4-(3-(3-(trifluoromethyl) phenyl) ureido) phenyl)-1,2,3,4-tetrahydro naphthalen-2-yl) propanoic acid |
| 79 | 2-{2-methyl-1-oxo-6-[4-({[3-(trifluoromethyl)phenyl]carbamoyl}amino)phenyl]-1,2,3,4-tetrahydronaphthalen-2-yl}acetic acid | 2-(2-Methyl-1-oxo-6-(4-(3-(3-(trifluoromethyl)phenyl)ureido)phenyl)-1,2,3,4-tetrahydronaphthalen-2-yl)acetic acid |
| 115 | 2-{2-ethyl-1-oxo-6-[4-({[3-(trifluoromethyl)phenyl]carbamoyl}amino)phenyl]-1,2,3,4-tetrahydronaphthalen-2-yl}acetic acid | 2-(2-Ethyl-1-oxo-6-(4-(3-phenylureido)phenyl)-1,2,3,4-tetrahydronaphthalen-2-yl)acetic acid |
| 116 | 2-{2-ethyl-1-oxo-6-[4-({[4-(trifluoromethyl)phenyl]carbamoyl}amino)phenyl]-1,2,3,4-tetrahydronaphthalen-2-yl}acetic acid | 2-(2-Ethyl-1-oxo-6-(4-(3-(4-(trifluoromethyl)phenyl)ureido)phenyl)-1,2,3,4-tetrahydronaphthalen-2-yl)acetic acid |
| 129 | 2-[(2S)-2-ethyl-1-oxo-6-[4-({[3-(trifluoromethyl)phenyl]carbamoyl}amino)phenyl]-1,2,3,4-tetrahydronaphthalen-2-yl]acetic acid | (S)-2-(2-Ethyl-1-oxo-6-(4-(3-phenylureido)phenyl)-1,2,3,4-tetrahydronaphthalen-2-yl)acetic acid |

-continued

| Example # | Chemical Name | Alternative Chemical Names |
|---|---|---|
| 173 | rel-2-[(1R,2S)-2-ethyl-1-hydroxy-6-[4-({[3-(trifluoromethyl)phenyl]carbamoyl}amino)phenyl]-1,2,3,4-tetrahydronaphthalen-2-yl]acetic acid | 2-((2S)-2-Ethyl-1-hydroxy-6-(4-(3-(3-(trifluoromethyl)phenyl)ureido)phenyl)-1,2,3,4-tetrahydronaphthalen-2-yl)acetic acid |
| 175 | (2S)-3-methyl-2-(2-{1-oxo-6-[4-({[3-(trifluoromethyl)phenyl]carbamoyl}amino)phenyl]-1,2,3,4-tetrahydronaphthalen-2-yl}acetamido)butanoic acid | (2S)-3-Methyl-2-(2-(1-oxo-6-(4-(3-(3-(trifluoromethyl)phenyl)ureido)phenyl)-1,2,3,4-tetrahydronaphthalen-2-yl)acetamido)butanoic acid |
| 182 | 2-{2-fluoro-1-oxo-6-[4-({[3-(trifluoromethyl)phenyl]carbamoyl}amino)phenyl]-1,2,3,4-tetrahydronaphthalen-2-yl}acetic acid | 2-(2-Fluoro-1-oxo-6-(4-(3-(3-(trifluoromethyl)phenyl)ureido)phenyl)-1,2,3,4-tetrahydronaphthalen-2-yl)acetic acid |
| 185 | 2-{2-hydroxy-1-oxo-6-[4-({[3-(trifluoromethyl)phenyl]carbamoyl}amino)phenyl]-1,2,3,4-tetrahydronaphthalen-2-yl}acetic acid | 2-(2-Hydroxy-1-oxo-6-(4-(3-(3-(trifluoromethyl)phenyl)ureido)phenyl)-1,2,3,4-tetrahydronaphthalen-2-yl)acetic acid |
| 190 | 2-(2-methoxy-1-oxo-6-{4-[(phenylcarbamoyl)amino]phenyl}-1,2,3,4-tetrahydronaphthalen-2-yl)acetic acid | 2-(2-Methoxy-1-oxo-6-(4-(3-phenylureido)phenyl)-1,2,3,4-tetrahydronaphthalen-2-yl)acetic acid |
| 197 | 2-[2-(methoxymethyl)-1-oxo-6-[4-({[3-(trifluoromethyl)phenyl]carbamoyl}amino)phenyl]-1,2,3,4-tetrahydronaphthalen-2-yl]acetic acid | 2-(2-(Methoxymethyl)-1-oxo-6-(4-(3-(3-(trifluoromethyl)phenyl)ureido)phenyl)-1,2,3,4-tetrahydronaphthalen-2-yl)acetic acid |
| 198 | 2-[6-(4-{[(3-chlorophenyl)carbamoyl]amino}-3-fluorophenyl)-2-(hydroxymethyl)-1-oxo-1,2,3,4-tetrahydronaphthalen-2-yl]acetic acid | 2-(6-(4-(3-(3-Chlorophenyl)ureido)-3-fluorophenyl)-2-(hydroxymethyl)-1-oxo-1,2,3,4-tetrahydronaphthalen-2-yl)acetic acid |
| 201 | 2-(1-oxo-6-{4-[(phenylcarbamoyl)amino]phenyl}-2-(2,2,2-trifluoroethyl)-1,2,3,4-tetrahydronaphthalen-2-yl)acetic acid | 2-(1-Oxo-6-(4-(3-phenylureido)phenyl)-2-(2,2,2-trifluoroethyl)-1,2,3,4-tetrahydronaphthalen-2-yl)acetic acid |
| 212 | rel-2-[(2R)-6-(2-chloro-4-{[(3-chlorophenyl)carbamoyl]amino}phenyl)-2-methyl-1-oxo-1,2,3,4-tetrahydronaphthalen-2-yl]acetic acid | 2-(6-(2-Chloro-4-(3-(3-chlorophenyl)ureido)phenyl)-2-methyl-1-oxo-1,2,3,4-tetrahydronaphthalen-2-yl)acetic acid: |
| 213 | rel-2-[(2R)-6-(2-chloro-4-{[(3-chlorophenyl)carbamoyl]amino}phenyl)-2-ethyl-1-oxo-1,2,3,4-tetrahydronaphthalen-2-yl]acetic acid | 2-(6-(2-chloro-4-(3-(3-chlorophenyl)ureido)phenyl)-2-ethyl-1-oxo-1,2,3,4-tetrahydronaphthalen-2-yl)acetic acid |
| 214 | rel-2-[(2R)-6-(4-{[(3-chlorophenyl)carbamoyl]amino}phenyl)-1-oxo-2-(2,2,2-trifluoroethyl)-1,2,3,4-tetrahydronaphthalen-2-yl] acetic acid | 2-(6-(4-(3-(3-Chlorophenyl)ureido)phenyl)-1-oxo-2-(2,2,2-trifluoroethyl)-1,2,3,4-tetrahydronaphthalen-2-yl)acetic acid |
| 215 | rel-2-[(2R)-6-(5-{[(3,4-difluorophenyl)carbamoyl]amino}pyrazin-2-yl)-1-oxo-2-(2,2,2-trifluoroethyl)-1,2,3,4-tetrahydronaphthalen-2-yl]acetic acid | 2-(6-(5-(3-(3,4-Difluorophenyl)ureido)pyrazin-2-yl)-1-oxo-2-(2,2,2-trifluoroethyl)-1,2,3,4-tetrahydronaphthalen-2-yl)acetic acid |
| 216 | rel-2-[(2R)-6-{5-[(cyclohexylcarbamoyl)amino]pyrazin-2-yl}-1-oxo-2-(2,2,2-trifluoroethyl)-1,2,3,4-tetrahydronaphthalen-2-yl]acetic acid | 2-(6-(5-(3-cyclohexylureido)pyrazin-2-yl)-1-oxo-2-(2,2,2-trifluoroethyl)-1,2,3,4-tetrahydronaphthalen-2-yl)acetic acid |
| 217 | 2-[(2S)-6-(4-{[(3,4-difluorophenyl)carbamoyl]amino}phenyl)-2-ethyl-1-oxo-1,2,3,4-tetrahydronaphthalen-2-yl]acetic acid | (S)-2-(6-(4-(3-(3,4-Difluorophenyl)ureido)phenyl)-2-ethyl-1-oxo-1,2,3,4-tetrahydronaphthalen-2-yl)acetic acid |

This invention also relates to compounds of Formula (I), (I)(A), (I)(B), (I)(C), (I)(D), (I)(E), (I)(F), (I)(G), (I)(H), (I)(K) or any of the exemplified compounds, or their pharmaceutically acceptable salts thereof, for use as a medicament. This invention also relates to compounds of Formula (I), (I)(A), (I)(B), (I)(C), (I)(D), (IE), (I)(F), (I)(G), (I)(H), (I)(K), or any of the exemplified compounds, or their pharmaceutically acceptable salts thereof, for use in the treatment of obesity.

This invention also relates to compounds of Formula (I), (I)(A), (I)(B), (I)(C), (I)(D), (IE), (I)(F), (I)(G), (I)(H), (I)(K), or any of the exemplified compounds, or their pharmaceutically acceptable salts thereof, in the manufacture of a medicament for the treatment of obesity.

Typically, but not absolutely, the salts of the present invention are pharmaceutically acceptable salts. Salts encompassed within the term "pharmaceutically acceptable salts" refer to non-toxic salts of the compounds of this invention. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl) amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and 125I isotopes are particularly useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

DEFINITIONS

Terms are used within their accepted meanings. The following definitions are meant to clarify, but not limit, the terms defined.

As used herein, unless defined otherwise, the term "alkyl" (or "alkylene") refers to a straight or branched chain alkyl, preferably having from one to twelve carbon atoms, which may be unsubstituted or substituted, saturated or unsaturated with multiple degrees of substitution, preferably one, two or three, included within the present invention. Suitable substituents are selected from the group consisting of halo, amino, substituted amino, cyano, hydroxyl, alkoxy, ester, carboxylic acid and alkylthio. Examples of "alkyl" as used herein include, but are not limited to, methyl, trifluoromethyl, ethyl, propyl, isopropyl, isobutyl, n-butyl, t-butyl, isopentyl, n-pentyl, and the like, as well as substituted versions thereof.

As used herein, unless defined otherwise, the term "cycloalkyl" refers to an unsubstituted or substituted mono- or polycyclic non-aromatic saturated ring, which optionally includes an alkylene linker through which the cycloalkyl may be attached. Exemplary "cycloalkyl" groups include, but are not limited to, cyclopropyl, cyclobutyl, cyclopentyl, cyclohexyl, cycloheptyl, and the like, as well as unsubstituted and substituted versions thereof.

As used herein, unless defined otherwise, the term "alkoxy" refers to the group —OR$^a$, where R$^a$ is $C_1$-$C_4$alkyl or cycloalkyl as defined above.

As used herein, the term "amide" refers to the group —C(O)NR$^c$R$^d$, wherein R$^c$ and R$^d$ are each independently H, $C_1$-$C_6$alkyl, or $C_3$-$C_6$cycloalkyl, or R$^c$ is the remaining portion of a natural or un-natural amino acid.

As used herein, the term "heterocycle" or "heterocyclyl" refers to unsubstituted and substituted mono- or polycyclic non-aromatic ring system containing one or more heteroatoms. Preferred heteroatoms include N, O, and S, including N-oxides, sulfur oxides, and dioxides. Preferably the ring is three to eight-membered and is either fully saturated or has one or more degrees of unsaturation. Multiple degrees of substitution are included within the present definition. Examples of "heterocyclic" groups include, but are not limited to tetrahydrofuranyl, pyranyl, 1,4-dioxanyl, 1,3-dioxanyl, piperidinyl, pyrrolidinyl, morpholinyl, azetidinyl, piperazinyl, pyrrolidinonyl, piperazinonyl, pyrazolidinyl, and their various tautomers.

As used herein, the term "aryl", unless otherwise defined, is meant aromatic, hydrocarbon, ring system. The ring system may be monocyclic or fused polycyclic (e.g., bicyclic, tricyclic, etc.), substituted or unsubstituted. In various embodiments, the monocyclic aryl ring is C5-C10, or C5-C7, or C5-C6, where these carbon numbers refer to the number of carbon atoms that form the ring system. A C6 ring system, i.e. a phenyl ring, is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group. Suitable substituents for aryl are described below in the definition of "optionally substituted".

As used herein, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene. Suitable substituents for heteroaryl are described below in the definition of "optionally substituted".

As used herein, the term "cyano" refers to the group —CN.

As used herein, the term "acyl" refers to the group —C(O)R$^b$, where R$^b$ is alkyl, cycloalkyl, or heterocyclyl, as each is defined herein.

As used herein, the term "ester" refers to the group —C(O)OR$^e$, where R$^e$ is $C_1$-$C_6$alkyl, or $C_3$-$C_6$cycloalkyl.

As used herein, the term "urea" refers to the group —NR$^c$C(O)NR$^d$, wherein R$^c$ and R$^d$ are each independently H, $C_1$-$C_6$alkyl, or $C_3$-$C_6$cycloalkyl.

As used herein, the term "optionally" means that the subsequently described event(s) may or may not occur, and includes both event(s) that occur and event(s) that do not occur.

As used herein, unless otherwise defined, the phrase "optionally substituted" or variations thereof denote an optional substitution, including multiple degrees of substitution, with one or more substituent group, preferably one, two or three. The phrase should not be interpreted as duplicative of the substitutions herein described and depicted. Exemplary optional substituent groups include acyl, $C_1$-$C_6$alkyl, alkylsulfonyl, alkoxy, alkoxycarbonyl, cyano, halo, urea, amide, hydroxyl, oxo, and nitro.

Pharmaceutical Compositions

The invention further provides a pharmaceutical composition (also referred to as pharmaceutical formulation) comprising a compound of Formula I or pharmaceutically acceptable salt, thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula I or salt thereof with at least one excipient.

Pharmaceutical compositions may be in unit dose form containing a predetermined amount of active ingredient per unit dose. Such a unit may contain a therapeutically effective dose of the compound of Formula I or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

The present invention provides a method of treatment in a mammal, especially a human, suffering from obesity, diabetes, hypertension, depression, anxiety, drug addiction, substance addiction, or a combination thereof. Such treatment comprises the step of administering a therapeutically effective amount of a compound of Formula I or salt thereof to said mammal, particularly a human. Treatment can also comprise the step of administering a therapeutically effective amount of a pharmaceutical composition containing a compound of Formula I or salt thereof to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts thereof, may be administered as the raw chemical. Additionally, the active ingredient may be presented as a pharmaceutical composition.

While it is possible that, for use in therapy, a therapeutically effective amount of a compound of Formula I or salt thereof may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula I or salt thereof will be given for the treatment in the range of about 0.1 to 100 mg/kg body weight of recipient (patient, mammal) per day and more usually in the range of 0.1 to 10 mg/kg body weight per day. Acceptable daily dosages may be from about 1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula I per se. Similar dosages should be appropriate for treatment (including prophylaxis) of the other conditions referred herein for treatment. In general, determination of appropriate dosing can be readily arrived at by one skilled in medicine or the pharmacy art.

Additionally, the present invention comprises a compound of Formula I or salt thereof or a pharmaceutical composition thereof with at least one other anti-obesity drug and/or at least one anti-diabetes drug. Such anti-obesity drugs can include, for example, Metformin (or glucophage), CB1 receptor antagonists, GLP-1 agonists, opioid antagonists, and neurotransmitter reuptake inhibitors. When a compound of the invention is employed in combination with another anti-obesity drug or anti-diabetes drug, it is to be appreciated by those skilled in the art that the dose of each compound or drug of the combination may differ from that when the drug or compound is used alone. Appropriate doses will be readily appreciated and determined by those skilled in the art. The appropriate dose of the compound of Formula I or salt thereof and the other therapeutically active agent(s) and the relative timings of administration will be selected in order to achieve the desired combined therapeutic effect, and are with the expertise and discretion of the attending doctor or clinician.

Compounds Preparation

Generic Synthesis Schemes

The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The synthesis of the compounds of the general Formula (I) and pharmaceutically acceptable derivatives and salts thereof may be accomplished as outlined below in Schemes 1-15 by those skilled in the art. In the following description, the groups are as defined above for compounds of Formula (I) unless otherwise indicated. Starting materials are commercially available or are made from commercially available starting materials using methods known to those skilled in the art.

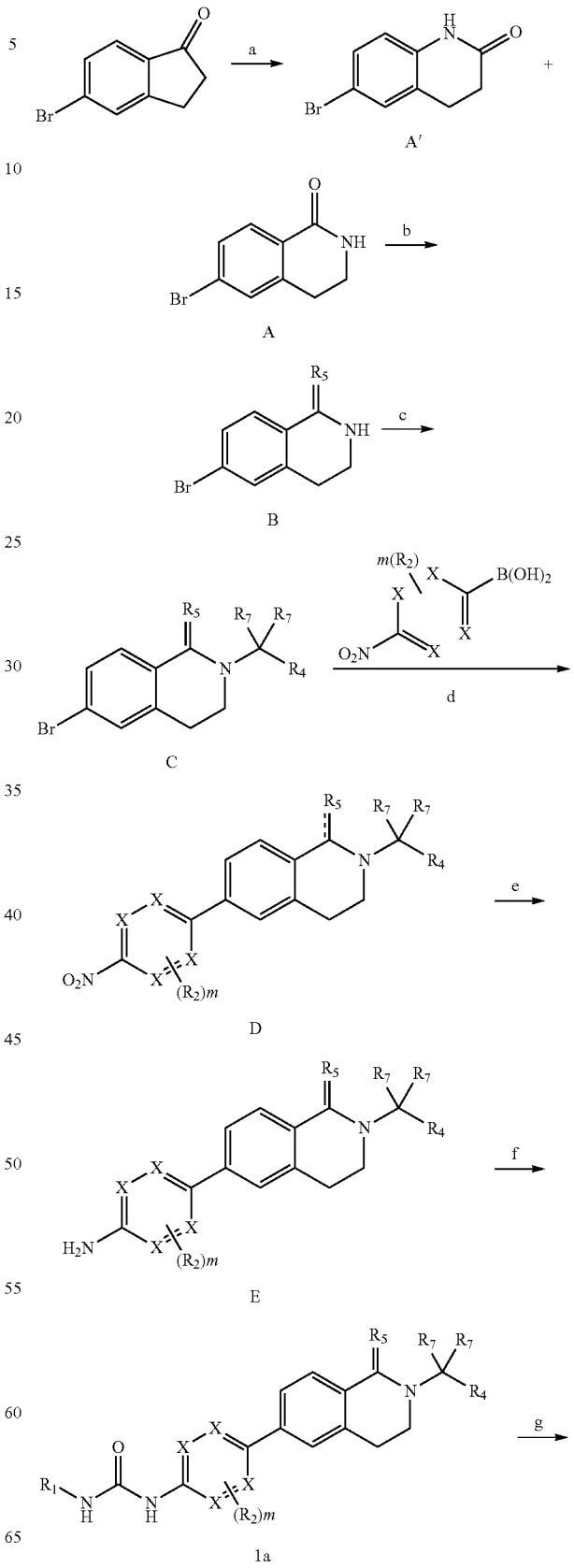

-continued

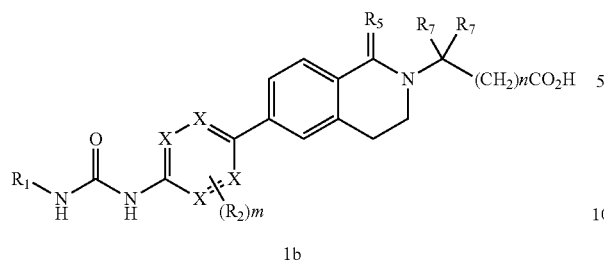

1b

Reagents and conditions: a) NaN₃, MeSO₃H, CH₂Cl₂, RT; b) BH₃:SMe₂, THF, 60° C.; c) X—C(R₇)(R₇)R₄, Et₃N, CH₂Cl₂, RT; d) Pd(PPh₃)₄, Cs₂CO₃, Dioxane-H₂O, 80° C.; e) 10% Pd/C, EtOH, H₂, RT; f) R₁NCO, Et₃N, THF, RT; g) LiOH, THF—H₂O, RT.

Compounds of Formula (I) may be prepared as illustrated in Scheme 1. Intermediate A can be obtained by rearrangement reaction of 5-bromo-1-indanone with NaN₃ in MeSO₃H in solvents such as CH₂Cl₂. Reduction of intermediate A with reducing agent such as BH₃:SMe₂ in solvents such as THF affords intermediate B (R₅=H) which can be alkylated using appropriately substituted alkyl halide (X—C(R₇)(R₇)R₄) and base such as Et₃N under standard conditions known to those skills in the art to form C. Intermediate A can also be alkylated directly with appropriately substituted alkyl halide under similar conditions to form intermediate C where R₅ is oxo. Palladium-catalyzed Suzuki coupling of intermediate C with appropriately substituted boronic acid or ester in the presence of base such as Cs₂CO₃ under standard conditions affords intermediate D. Reduction of nitro functional group in D under standard hydrogenation reduction condition provides aniline intermediate E. Coupling of E with appropriately substituted isocyanate affords urea compounds of Formula (I) (1a where R₅ is H). In compound 1a where R₄ is —CH₂C(O)OR$^e$ or —C(O)OR$^e$, hydrolysis of the ester group with base such as LiOH provides another compound of Formula (I)(1b) where R₄ is —CH₂C(O)OH or —C(O)OH respectively.

Scheme 2.

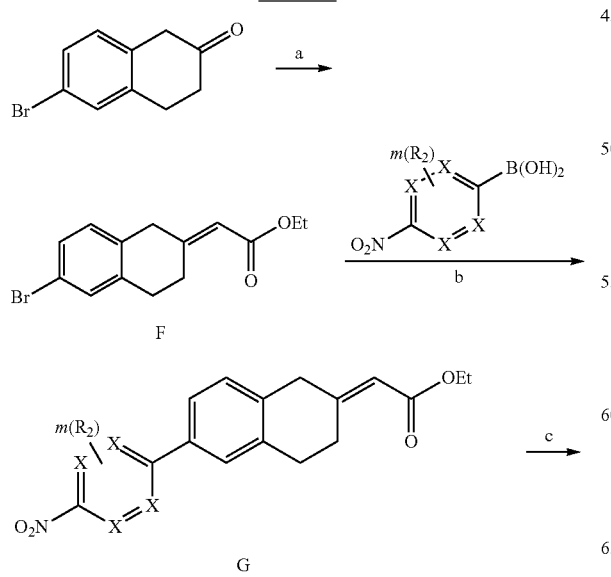

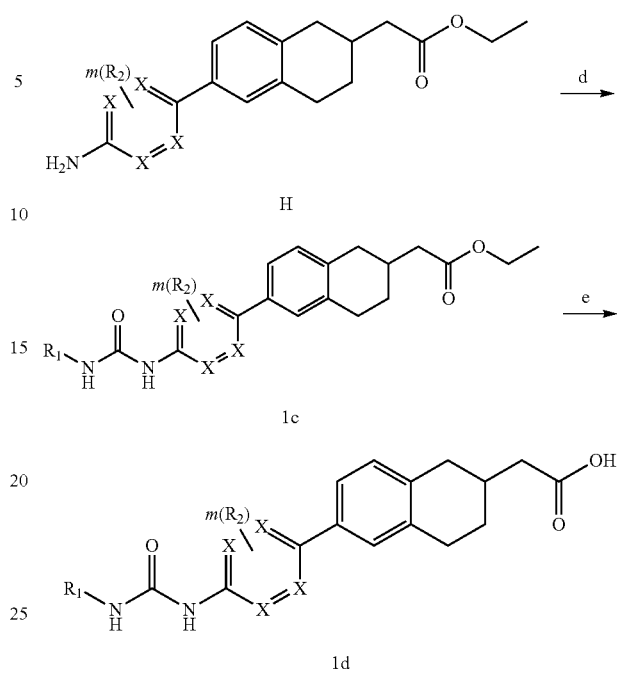

Reagents and conditions: a) Ph₃P═CHCO₂Et, NaH, DMF, RT; b) Pd(PPh₃)₄, Cs₂CO₃, Dioxane-H₂O, 80° C.; c) Pd/C, MeOH, H₂, RT; d) R₁NCO, Et₃N, THF, RT; e) LiOH, THF—H₂O, RT.

Compounds of Formula (I) may be prepared as illustrated in Scheme 2. Intermediate F can be prepared from 6-bromo-2-tetralone using standard Wittig reaction conditions such as Ph₃P═CHCO₂Et with base such as NaH in solvent such as DMF. Palladium catalyzed Suzuki coupling of F with appropriately substituted boronic acid/ester in the presence of base such as Cs₂CO₃ affords nitro intermediate G. Standard hydrogenation reduction reaction converts G to aniline H which can be coupled with appropriately substituted isocyanate (R₁NCO) to form compound of Formula (I) (1c). The ester in 1c can be further hydrolyzed under basic conditions such as LiOH in THF—H₂O to another compound of Formula (I) (1d).

Scheme 3.

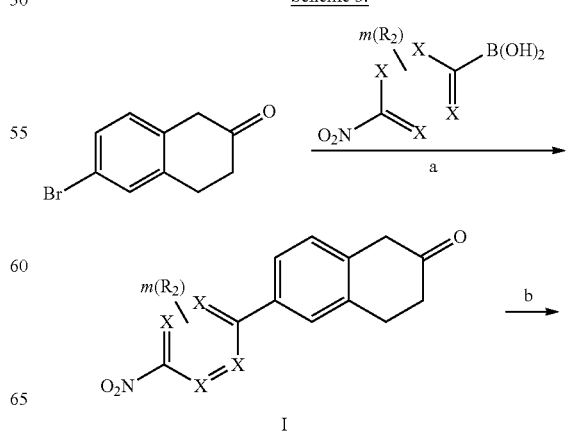

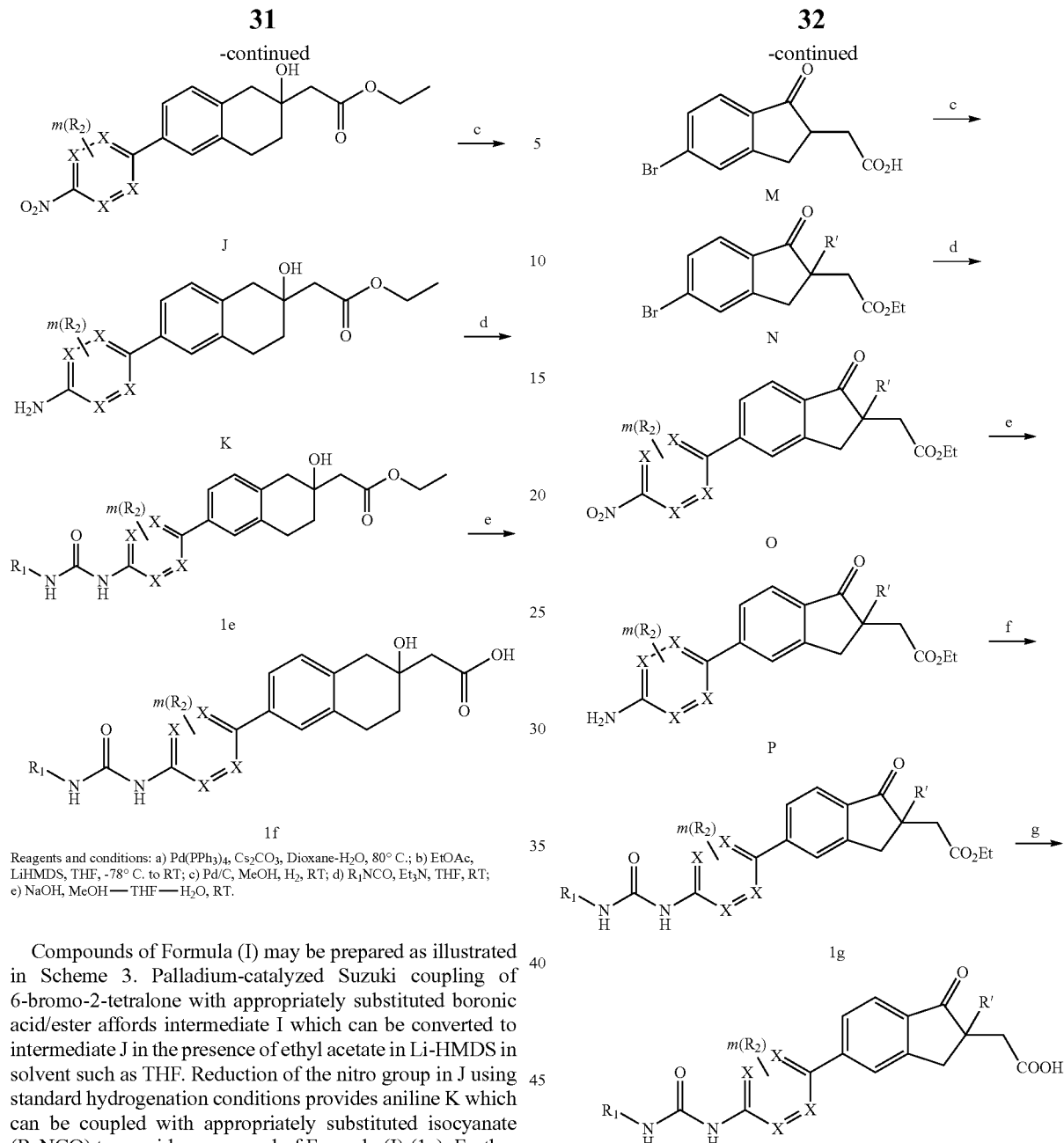

Reagents and conditions: a) Pd(PPh₃)₄, Cs₂CO₃, Dioxane-H₂O, 80° C.; b) EtOAc, LiHMDS, THF, -78° C. to RT; c) Pd/C, MeOH, H₂, RT; d) R₁NCO, Et₃N, THF, RT; e) NaOH, MeOH—THF—H₂O, RT.

Compounds of Formula (I) may be prepared as illustrated in Scheme 3. Palladium-catalyzed Suzuki coupling of 6-bromo-2-tetralone with appropriately substituted boronic acid/ester affords intermediate I which can be converted to intermediate J in the presence of ethyl acetate in Li-HMDS in solvent such as THF. Reduction of the nitro group in J using standard hydrogenation conditions provides aniline K which can be coupled with appropriately substituted isocyanate (R₁NCO) to provide compound of Formula (I) (1e). Further hydrolysis of the ester group in 1e with base such as NaOH in solvent such as MeOH-THF—H₂O affords another compound of Formula (I) (1f).

Reagents and conditions: a) CO(OMe)₂, NaH, THF, 75° C.; b) BrCH₂COOEt, THF, 75° C.; c) NaH, R'—X, DMF, RT; d) substituted boronic acid/ester, Pd(PPh₃)₄, Cs₂CO₃, Dioxane-H₂O, 80° C.; e) Fe/NH₄Cl, EtOH—H₂O, 85° C.; f) R₁NCO, Et₃N, THF, RT; g) LiOH, Dioxane-H₂O, RT.

Compounds of Formula (I) may be prepared as illustrated in Scheme 4. 5-Bromo indanone can be converted to intermediate L in the presence of NaH and dimethyl carbonate. Intermediate L can be converted to intermediate M with ethyl bromo acetate followed by decarboxylation conditions. Alkylation of M with appropriately substituted alkylating agent such as alkyl halide (eg R'—X wherein R' can be substituted C₁-C₃alkyl, and X can be halo such as iodo) provides intermediate N which can be converted to compounds of Formula (I) (1 g, 1 h) using Suzuki coupling, nitro reduction, urea formation, and/or subsequent hydrolysis conditions as described in Scheme 1-2. Intermediate M can also undergo similar chemical transformation (Suzuki coupling, nitro Scheme 4.

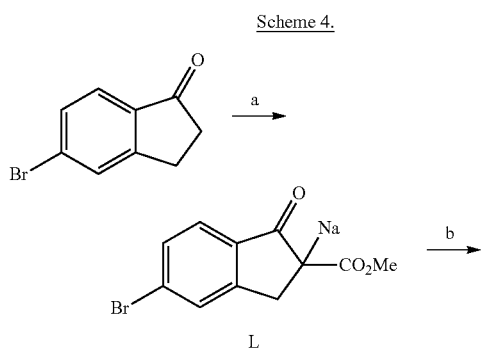

reduction, urea formation, and/or subsequent hydrolysis condition) to form compounds of Formula (I) (1 g, 1 h) where R' is H.

Scheme 5.

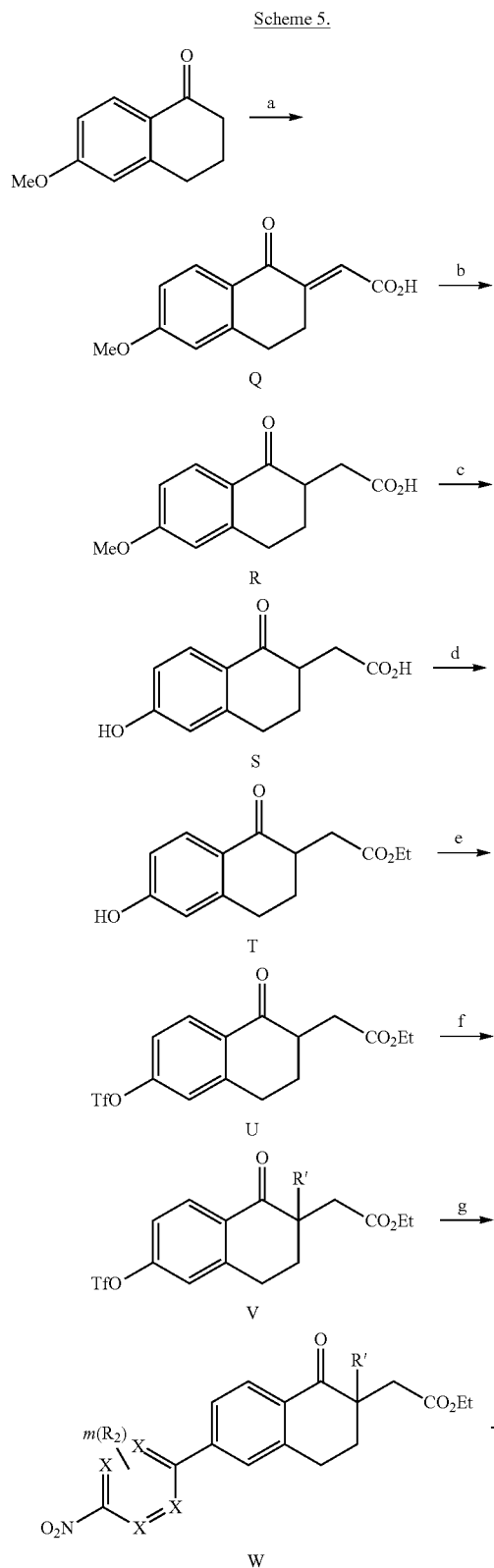

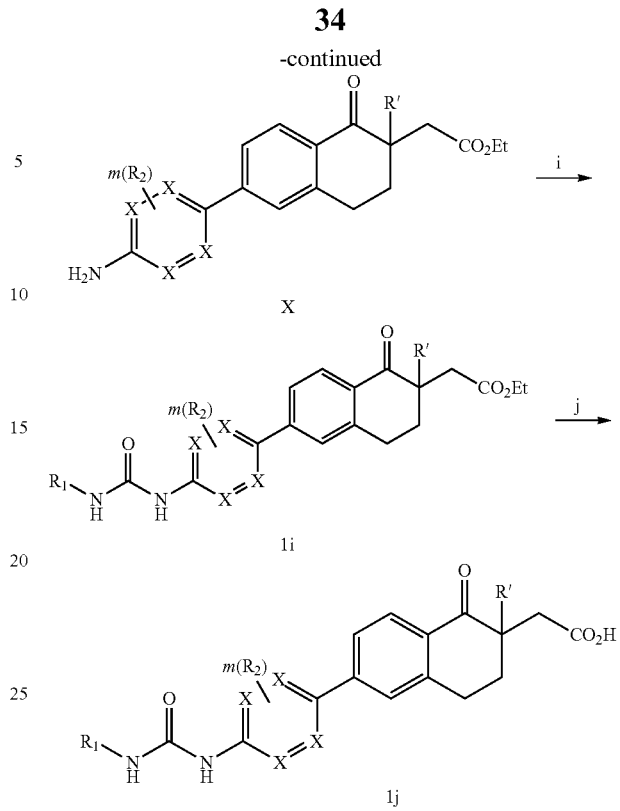

Reagents and conditions: a) Glyoxalic acid, H₂SO₄, diglyme, 85° C.; b) Zn, AcOH, 80° C.; c) Aq. HBr, 100° C.; d) MeSO₃H, EtOH, RT; e) Tf₂O, CH₂Cl₂, Et₃N, RT; f) R'—X, NaH, DMF, RT; g) Substituted boronic acid/ester, Pd(PPh₃)₄, Cs₂CO₃, Dioxane-H₂O, 80° C.; h) Pd/C, H₂, EtOH, RT; i) R₁NCO, Et₃N, THF, RT; j) LiOH, EtOH—H₂O, RT.

Compounds of Formula (I) may be prepared as illustrated in Scheme 5. 6-Methoxytetralone can be converted to intermediate Q using glyoxalic acid followed by sulphuric acid in diglyme under heating condition. Reduction of the olefin in the presence of reducing condition such as Zn in AcOH affords intermediate R which can be demethylated using aqueous HBr to provide phenol compound S. Esterification of S under standard conditions provides ester T where phenol functional group can be protected as triflate U using triflate anhydride under basic conditions. Alkylation of U with appropriately substituted alkyl halide (R'—X) such as methyl iodide, ethyl iodide, propyl iodide or trifluoroethyl iodide provides intermediate V which can be converted to compounds of Formula (I) (1i, 1j) using Suzuki coupling, nitro reduction, urea formation, and/or subsequent hydrolysis conditions as described in Scheme 1-2. Intermediate U can also undergo similar chemical transformation (Suzuki coupling, nitro reduction, urea formation, and/or subsequent hydrolysis condition) to form compounds of Formula (I) (1i, 1j) where R' is H.

Scheme 6.

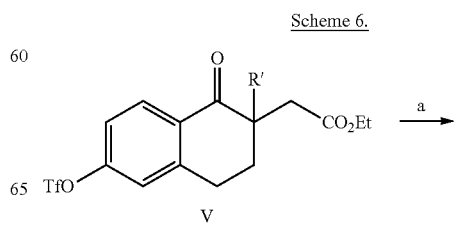

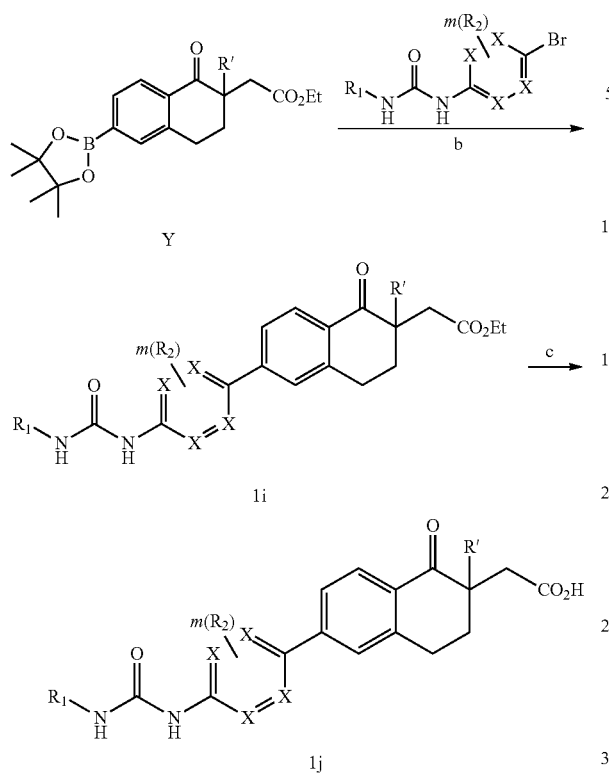

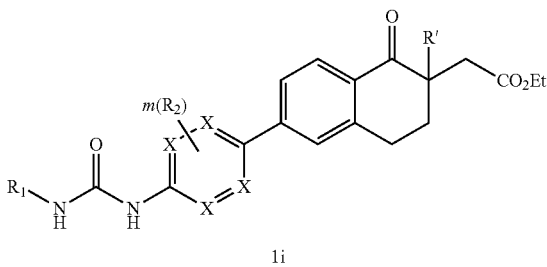

Reagents and conditions: a) 4,4,4′,4′,5,5,5′,5′-octamethyl-2,2′-bi(1,3,2-dioxaborolane, PdCl₂(dppf), KOAc, Dioxane, 100° C.; b) Pd(PPh₃)₄, Cs₂CO₃, Dioxane-H₂O, 80° C.; c) LiOH, EtOH—H₂O, RT.

Alternatively compounds of Formula (I) may be prepared as illustrated in Scheme 6. Intermediate V can be converted to boronic ester which can then undergo Palladium catalyzed Suzuki reaction with the appropriately substituted aryl or heteroaryl halide to form compounds of Formula (I) (1i). Appropriately substituted aryl or heteroaryl halides can be prepared using reaction conditions known to those skilled in the art, eg, by coupling of appropriately substituted amines with appropriately substituted isocyanates. 1i can be subsequently converted to another compounds of Formula (I) (1j) by standard hydrolysis conditions.

Scheme 7.

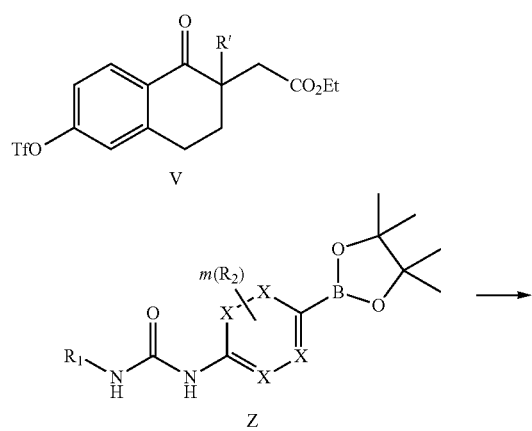

Alternatively compounds of Formula (I) may be prepared as illustrated in Scheme 7 by reversing the coupling partners as in Scheme 6. Intermediate V can be coupled with appropriately substituted boronic ester Z to form compounds of Formula (I) (1i) using palladium-catalyzed Suzuki coupling conditions. Appropriately substituted boronic ester Z can be prepared using reaction conditions known to those skilled in the art, eg, by converting the appropriately substituted aryl or heteroaryl halides to boronic esters using bis-pinacolato diborance in the presence of KOAc and catalytic amount of PdCl₂ (dppf) in solvent such as DMF under heated conditions.

Scheme 8.

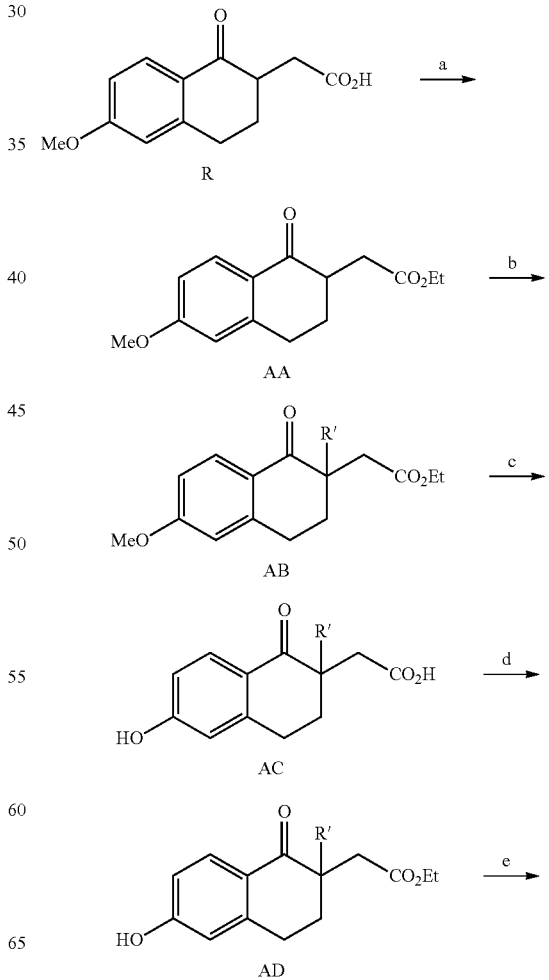

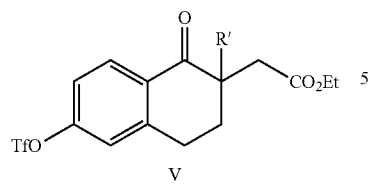

Reagents and conditions: a) MeSO₃H, EtOH, RT; b) R'—X, NaH, DMF, RT; c) Aq. HBr, 100° C.; d) MeSO₃H, EtOH, RT; e) Tf₂O, CH₂Cl₂, Et₃N, RT.

Intermediate V may also be prepared as illustrated in Scheme 8. Esterification of R provides ester AA which can be alkylated with appropriately substituted alkyl halide (R'—X) such as MeI, EtI and trifluoroethyl iodide to give intermediate AB. Demethylation of AB provides phenol AC which can be esterified to afford AD. Phenol group can then be protected as triflate to form intermediate V. Intermediate V can be converted to compounds of Formula (I) using Schemes 5-7 described above.

Enantiomeric enriched compounds may be obtained by chiral separation of appropriate intermediates or compounds of Formula (I). For example, for the racemic mixture of compounds 1i, pure enantiomers may be separated on the chiral column using chiral columns such as CHIRAL PAKIA (4.6× 250 mm) 5μ and appropriate mobile phases to give enantiomeric enriched compounds of 1i. The enantiomeric enriched compounds of 1i can then undergo additional chemical transformation such as ester hydrolysis to provide enantiomeric enriched compounds of 1j.

Scheme 9.

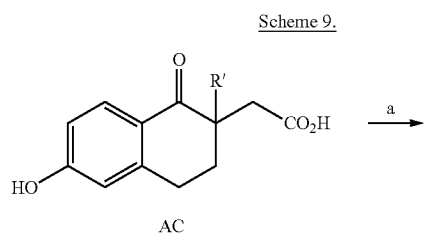

Reagents and conditions: a) Cinchonidine, IPA-H₂O, 80° C.-RT, 24 h then 6N HCl.

Alternatively, enantiomeric enriched compounds may be obtained by chemical resolution of racemic mixture of compounds. For example, as shown in Scheme 9, racemic intermediate AC can be resolved to enantiomeric pure AC using cinchonidine in the presence of solvents such as IPA-H₂O. The enantiomeric enriched intermediate AC can then converted to enantiomeric enriched compounds of Formula (I) (1i, 1j) using reactions similarly to those described in Schemes 5-8.

Scheme 10.

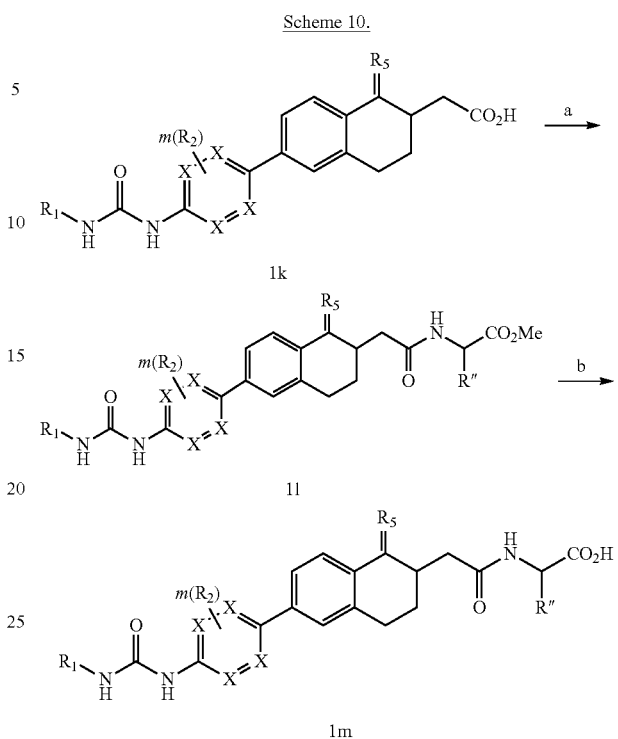

Reagents and conditions: a) HATU, THF, amino acid methyl ester (NH₂—CH(R″)CO₂Me), RT; b) LiOH, THF—H₂O, RT.

Compound of Formula (I) may be converted to another compound of Formula (I) using chemical transformation known to those skilled in the art. For example, as shown in Scheme 10, compound of Formula (I) (1k) can be coupled with methyl ester of amino acid (NH₂—CH(R″)CO₂Me) under coupling conditions known to those skilled in the art to another compound of formula I (1l) which can then be hydrolyzed to form compound of Formula (I) (1m).

Scheme 11.

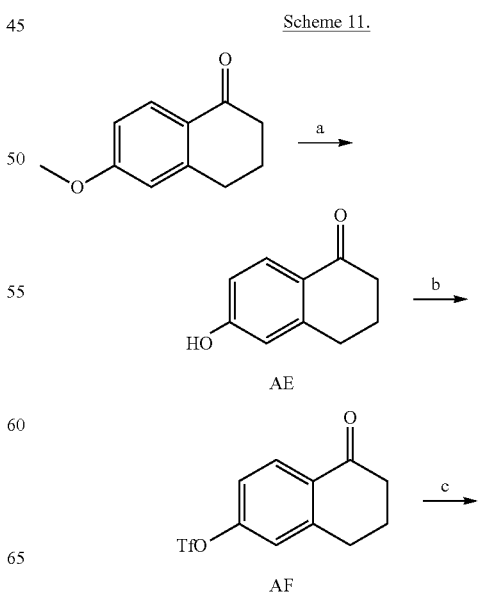

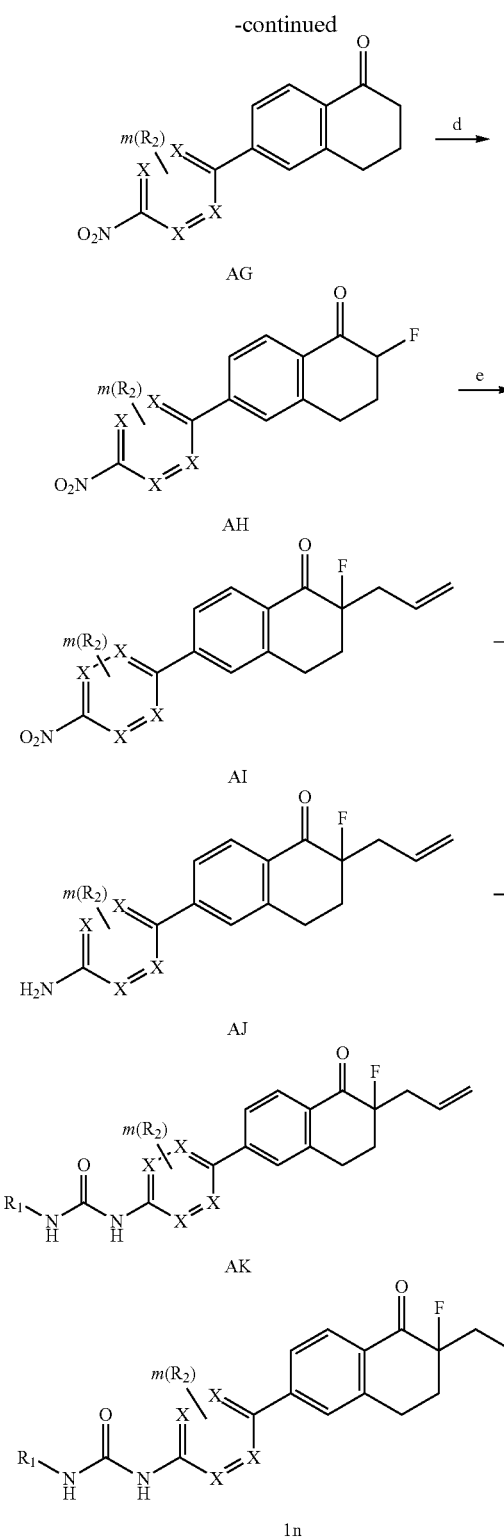

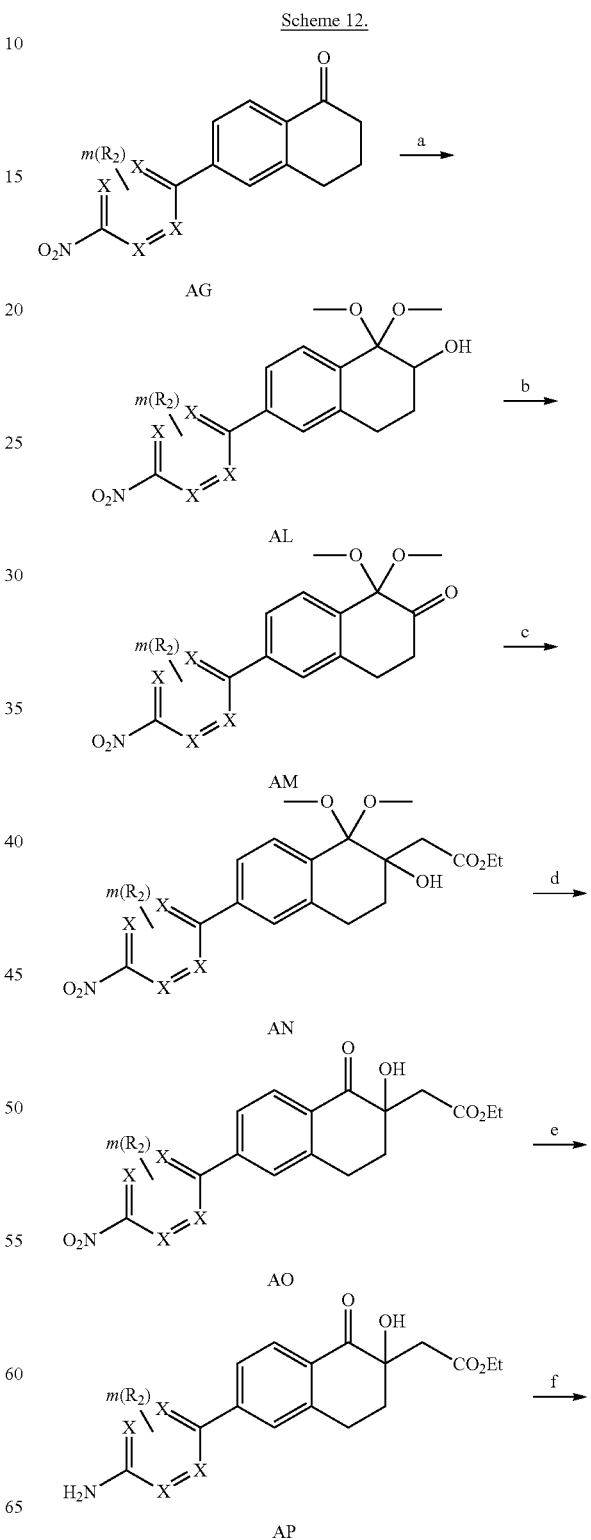

which can be fluorinated to give AH. Alkylation with allyl bromide provides AI which can be reduced by hydrogenation conditions to provide AJ. Coupling of AJ with appropriately substituted isocyanate affords AK. Oxidation of AK with oxidizing agents such as KMnO$_4$ and NaIO$_4$ in solvents such as acetone-water provides compound of Formula (I) (1n).

Scheme 12.

Reagents and conditions: a) Aq HBr Reflux; b) Tf$_2$O, DMAP, Py, RT; c) Substituted aryl/heteroaryl boronic acid or ester, Pd(PPh$_3$)$_4$, Cs$_2$CO$_3$, Dioxane-H$_2$O, 80° C.; d) select Fluor, MeOH, 80° C.; e) Allyl bromide, TBAI, KOH, RT; f) Fe/NH$_4$Cl, EtOH, H$_2$O, Reflux; g) R$_1$NCO, Et$_3$N, THF, RT; h) KMnO$_4$, NaIO$_4$, acetone-H$_2$O, RT.

Compounds of Formula (I) may be prepared as illustrated in Scheme 11. 6-Methoxy-1-tetralone can be demethylated to give phenol AE which is then protected as triflate AF. Palladium catalyzed Suzuki coupling of AF with appropriately substituted aryl/heteroaryl boronic acid or ester affords AG

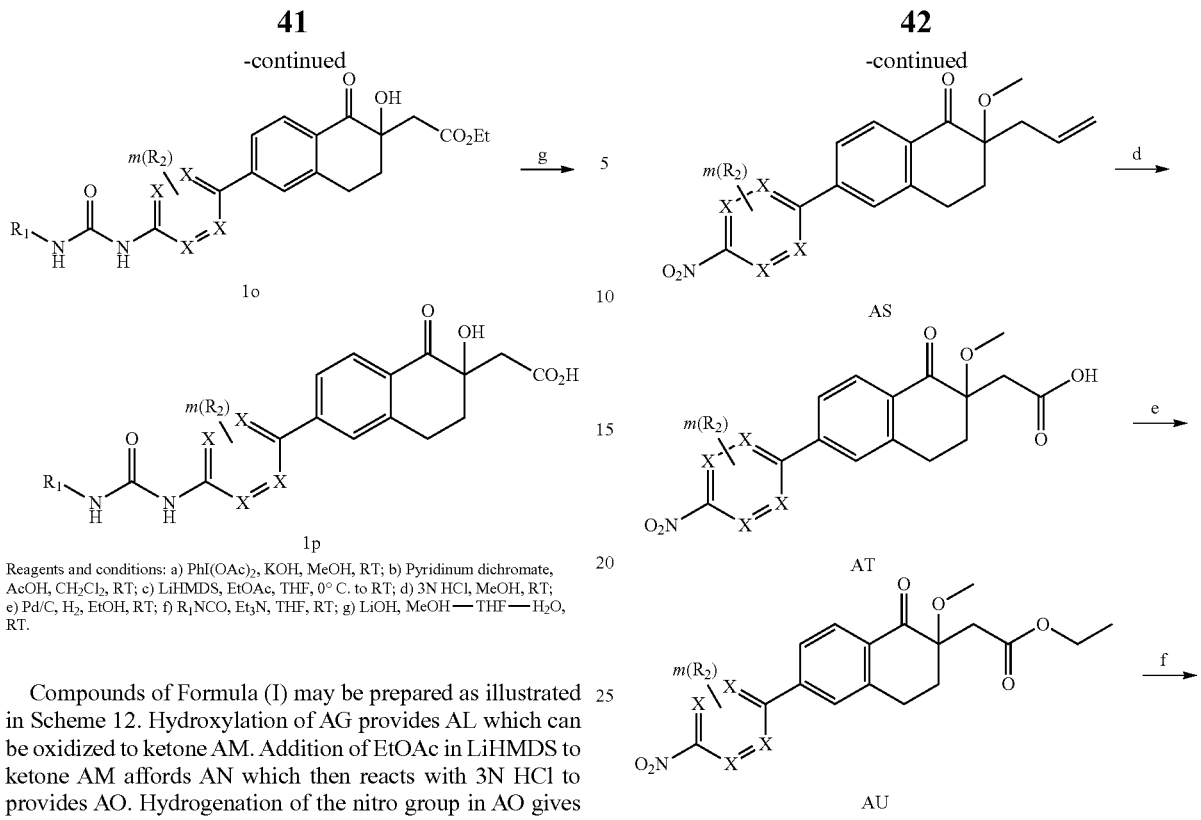

Reagents and conditions: a) PhI(OAc)₂, KOH, MeOH, RT; b) Pyridinum dichromate, AcOH, CH₂Cl₂, RT; c) LiHMDS, EtOAc, THF, 0° C. to RT; d) 3N HCl, MeOH, RT; e) Pd/C, H₂, EtOH, RT; f) R₁NCO, Et₃N, THF, RT; g) LiOH, MeOH—THF—H₂O, RT.

Compounds of Formula (I) may be prepared as illustrated in Scheme 12. Hydroxylation of AG provides AL which can be oxidized to ketone AM. Addition of EtOAc in LiHMDS to ketone AM affords AN which then reacts with 3N HCl to provides AO. Hydrogenation of the nitro group in AO gives aniline AP which can react with appropriately substituted isocyanate to provide urea compound of Formula (I) (1o). Hydrolysis of 1o provides another compound of Formula (I) (1p).

Scheme 13.

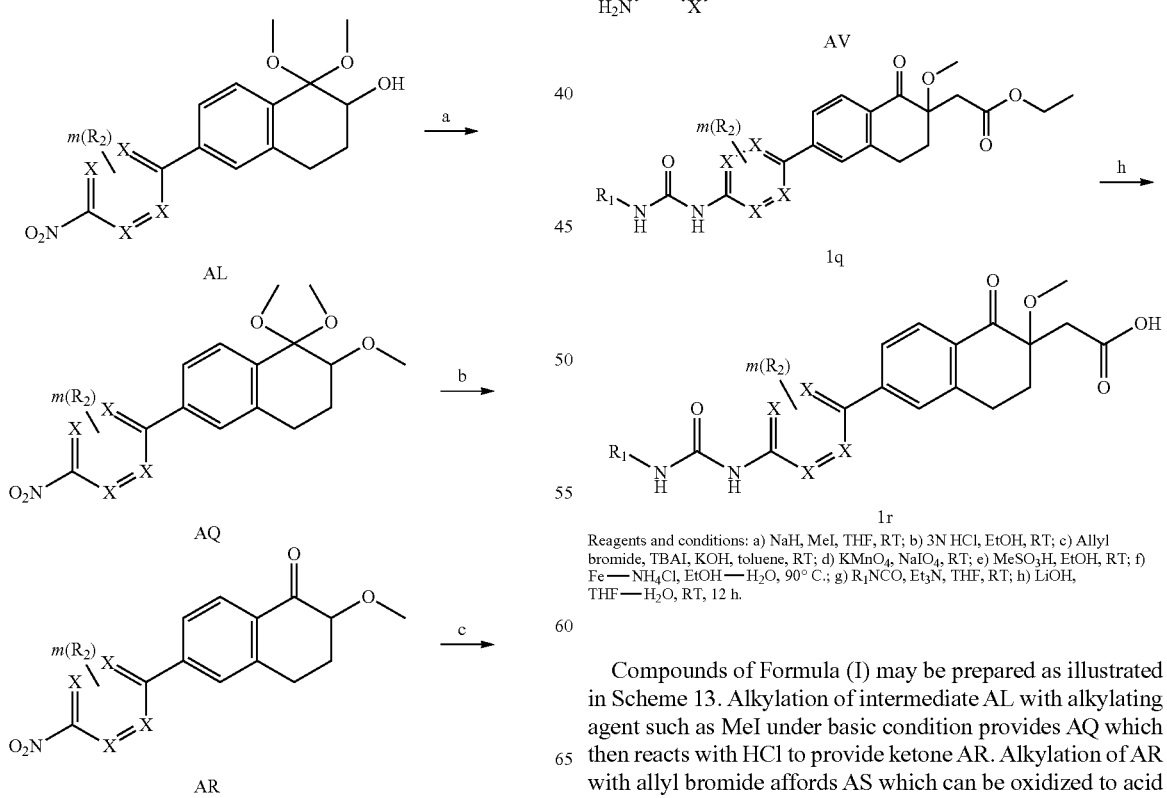

Reagents and conditions: a) NaH, MeI, THF, RT; b) 3N HCl, EtOH, RT; c) Allyl bromide, TBAI, KOH, toluene, RT; d) KMnO₄, NaIO₄, RT; e) MeSO₃H, EtOH, RT; f) Fe—NH₄Cl, EtOH—H₂O, 90° C.; g) R₁NCO, Et₃N, THF, RT; h) LiOH, THF—H₂O, RT, 12 h.

Compounds of Formula (I) may be prepared as illustrated in Scheme 13. Alkylation of intermediate AL with alkylating agent such as MeI under basic condition provides AQ which then reacts with HCl to provide ketone AR. Alkylation of AR with allyl bromide affords AS which can be oxidized to acid AT. Esterification of AT provides AU which then undergoes reduction and urea formation to form compound of Formula (I) (1q). Subsequent hydrolysis of 1q provides another compound of Formula (I) (1r).

Scheme 14.

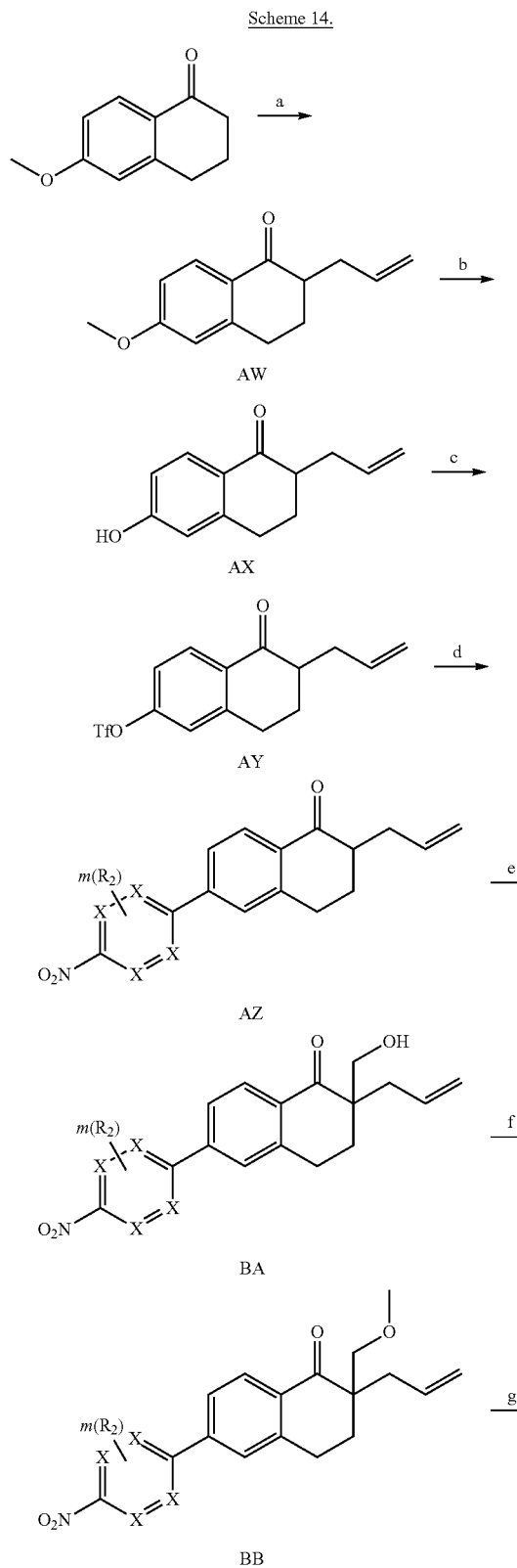

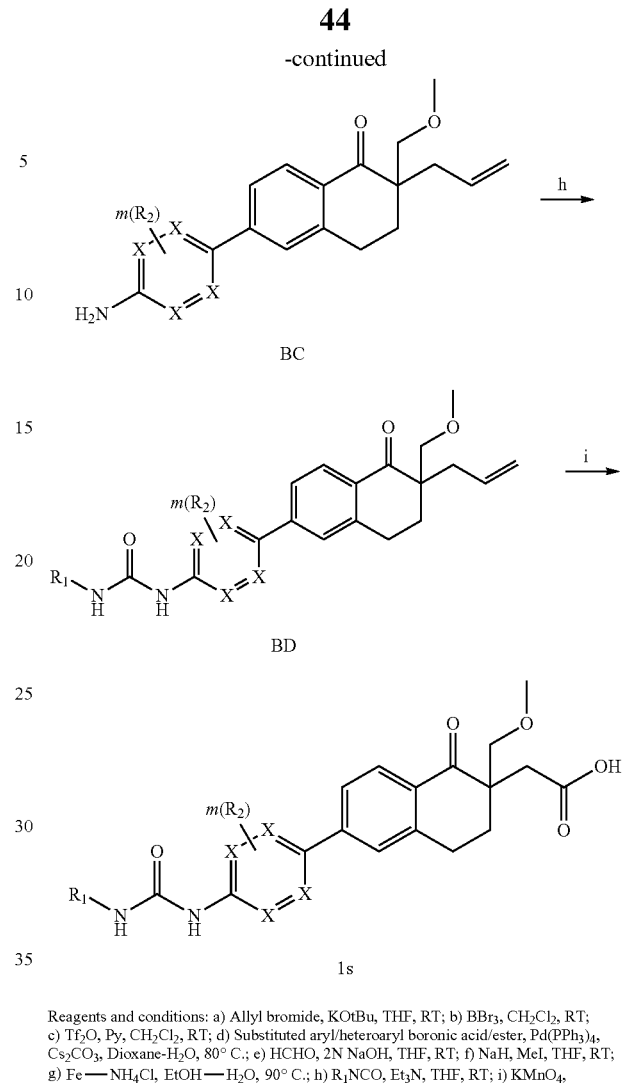

Reagents and conditions: a) Allyl bromide, KOtBu, THF, RT; b) BBr₃, CH₂Cl₂, RT; c) Tf₂O, Py, CH₂Cl₂, RT; d) Substituted aryl/heteroaryl boronic acid/ester, Pd(PPh₃)₄, Cs₂CO₃, Dioxane-H₂O, 80° C.; e) HCHO, 2N NaOH, THF, RT; f) NaH, MeI, THF, RT; g) Fe—NH₄Cl, EtOH—H₂O, 90° C.; h) R₁NCO, Et₃N, THF, RT; i) KMnO₄, NaIO₄, Acetone-H₂O, RT.

Compounds of Formula (I) may be prepared as illustrated in Scheme 14. Alkylation of 6-methoxy-1-tetralone with allyl bromide under basic condition affords AW. Demethylation of AW gives phenol AX which forms triflate AY using standard conditions known to those skilled in the art. Suzuki coupling of AY with appropriately substituted boronic acid or ester provides nitro intermediate AZ which then reacts with formaldehyde to form alcohol BA. Alkylation of alcohol with alkylating agent such as methyl iodide provides BB. Hydrogenation of the nitro group in BB affords aniline BC which can then react with appropriately substituted isocyanate to form urea compound BD. Oxidation of the olefin in BC provides compound of Formula (I) (1s).

Scheme 15.

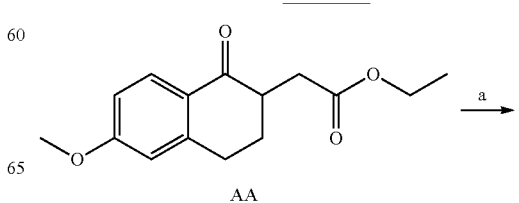

-continued

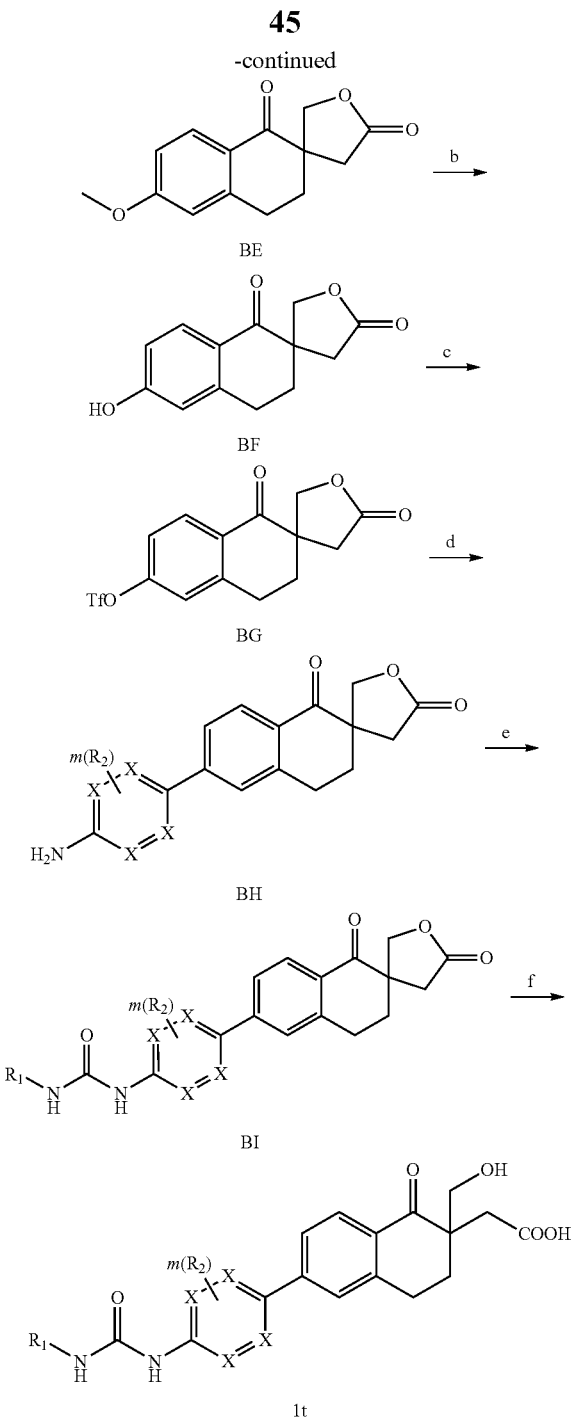

Regents and conditons: a) HCHO, 2N NaOH, THF, RT; b) Aq HBr, 100° C.; c) Tf$_2$O, Py, CH$_2$Cl$_2$, RT; d) Pd(PPh$_3$)$_4$, Cs$_2$CO$_3$, Dioxane-H$_2$O, 80° C.; e) R$_1$NCO, Et$_3$N, THF, RT; f) LiOH, THF—H$_2$O, RT;

Compounds of Formula (I) may be prepared as illustrated in Scheme 15. Cyclic ester BE can be formed from intermediate AA using formaldehyde in NaOH and THF as solvent. Demethylation of BE with aqueous HBr affords phenol BF which can be converted to triflate BG using triflate anhydride and pyridine. Suzuki coupling of BG with appropriately substituted boronic acid or ester affords aniline BH. Coupling of BH with appropriately substituted isocyanate provides urea BI which can be hydrolyzed to form compound of Formula I (1t).

Scheme 16.

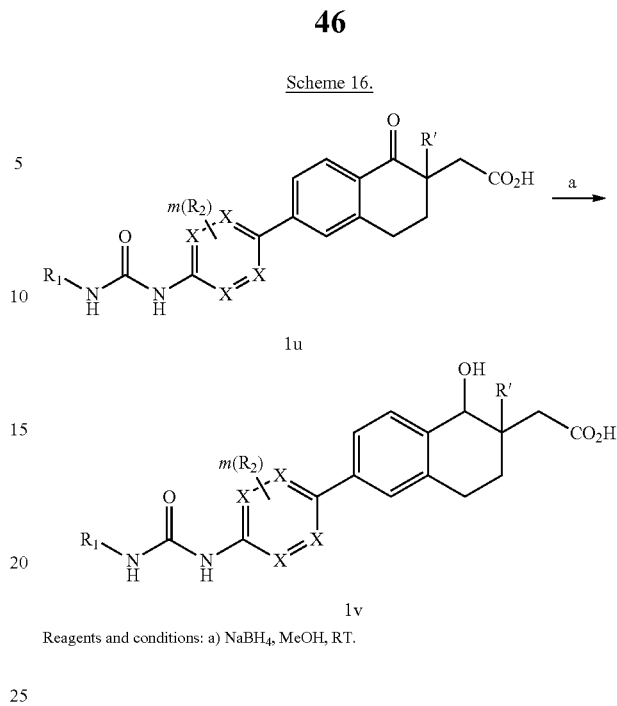

Reagents and conditions: a) NaBH$_4$, MeOH, RT.

Compound of Formula (I) may be converted to another compound of Formula (I). For example, as illustrated in Scheme 16, compound of Formula I (1u) can be reduced under standard reduction conditions known to those skilled in the art to alcohol as in compound 1v.

EXPERIMENTALS

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention. Unless otherwise noted, reagents are commercially available or are prepared according to procedures in the literature. The symbols and conventions used in the descriptions of processes, schemes, and examples are consistent with those used in the contemporary scientific literature, for example, the Journal of the American Chemical Society or the Journal of Biological Chemistry.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiples), br (broad).

Flash column chromatography was performed on silica gel.

The naming programs used are ACDLABs 11.0 Namebatch, ACD IUPAC or Chem Draw.

Abbreviations
BH$_3$:SMe$_2$ borane:dimethyl sulfide
CH$_2$Cl$_2$ dichloromethane
CHCl$_3$ chloroform
Cs$_2$CO$_3$ cesium carbonate
DMAP 4-(dimethylamino)pyridine
DMF N,N-dimethylformamide
DMSO dimethylsulfoxide Et₃N triethylamine
EtOAc ethyl acetate
EtOH ethanol
Fe iron
h hour(s)
H₂ hydrogen gas
H₂O water
HATU O-(7-azabenzotriazol-1-yl)-N,N,N',N'-tetramethyluronium hexafluorophosphate
HBr hydrobromic acid
HCl hydrochloric acid
KOH potassium hydroxide
KMnO4 potassium permanganate
LiHMDS lithium hexamethyldisilazide
LiOH lithium hydroxide
NaH sodium hydride
NaIO₄ sodium periodate
NaN₃ sodium azide
NH₄Cl ammonium chloride
MeI methyl iodide
MeOH methanol
MeSO₃H methane sulfonic acid
Pd/C palladium on carbon
Pd(PPh₃)₄ tetrakis(triphenylphosphine)palladium(0)
Py pyridine
rt room temperature
TBAI tetrabutyl ammonium iodide
THF tetrahydrofuran
Tf₂O triflate anhydride Example-1

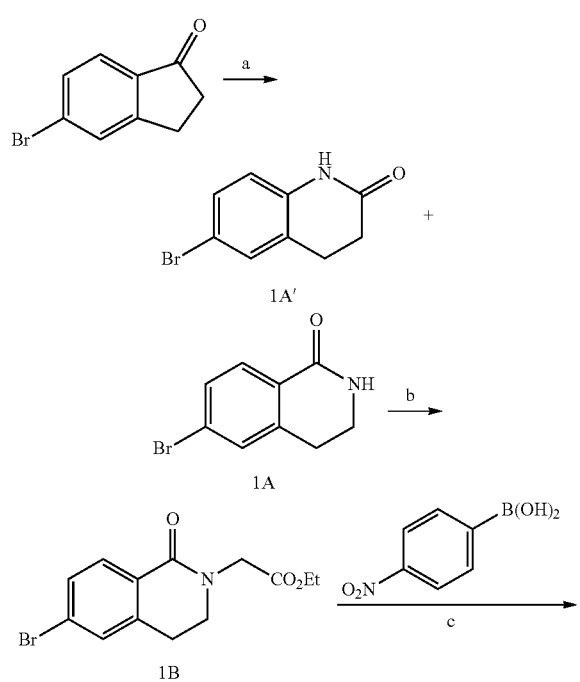

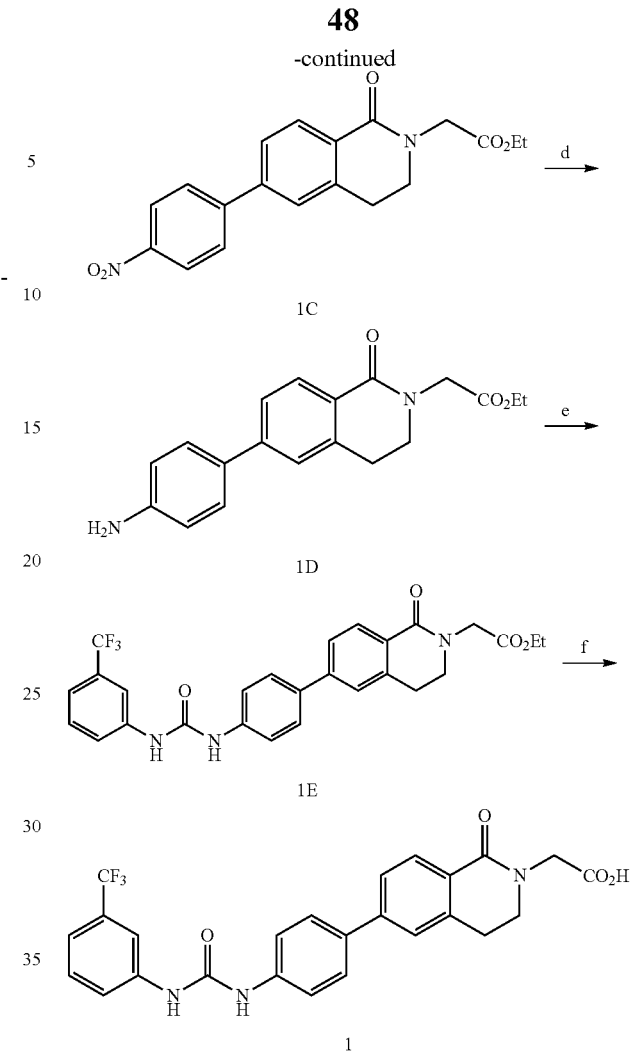

Regents and conditions: a) NaN₃, MeSO₃H, CH₂Cl₂, RT, 8 h; b) BrCH₂CO₂Et, NaH, THF, RT, 3 h; c) Pd(PPh₃)₄, Cs₂CO₃, Dioxane-H₂O, 80° C., 5 h; d) 10% Pd/C, EtOH, H₂, RT, 4 h; e) 3-CF₃PhNCO, Et₃N, THF, RT, 12 h; f) LiOH, THF—H₂O, RT, 14 h.

Procedures 2-(1-Oxo-6-(4-(3-(3-(trifluoromethyl)phenyl)ureido) phenyl)-3,4-dihydroisoquinolin-2(1H)-yl)acetic acid 6-Bromo-3,4-dihydroisoquinolin-1(2H)-one (1A)

NaN₃ (6.2 g, 94.78 mmol) was added to a solution of 5-bromo-1-indanone (10 g, 47.39 mmol) in 40 mL of mixture of methane sulphonic acid and dichloromethane (1:1) in portion wise at 0° C.-5° C. The resulting mixture was stirred for 8 h at room temperature. The reaction mixture was cooled to 0° C. in ice bath, neutralized with 5% aq. NaOH, and aqueous layer was extracted with ethyl acetate (2×100 mL). The combined organic layer was washed with water and brine solution, dried over $Na_2SO_4$ and filtered. The filtrate was concentrated under vacuum and purified by silica gel flash column chromatography using 30% ethyl acetate in hexane to afford title compound (6.4 g, 60%) as solid. $^1$H NMR (400 MHz, $CDCl_3$): δ 7.95 (d, J=8.4 Hz, 1H), 7.5 (d, J=8.4 Hz, 1H), 7.4 (s, 1H), 6.1 (bs, 1H), 3.6 (t, J=6.8 Hz, 2H), 3 (t, J=6.4 Hz, 2H).

Ethyl 2-(6-bromo-1-oxo-3,4-dihydroisoquinolin-2(1H)-yl)acetate (1B)

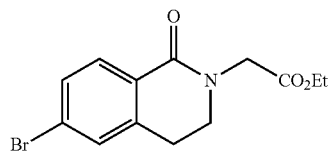

1B

NaH (0.42 g, 17.7 mmol) was added to an ice-cold solution of product of Example 1A (2 g, 8.8 mmol) in THF (40 ml) portion wise, and the mixture was stirred for 15 min. Ethyl bromo acetate (2.2 g, 13.2 mmol) was then added to the solution, and the mixture was stirred at room temperature for 3 h. Reaction mixture was quenched with ice-cold water and diluted with ethyl acetate. Organic layer was separated, washed with brine, dried over $Na_2SO_4$ and filtered. The filtrate was concentrated under vacuum to afford title compound (3.3 g, 80%) as solid. $^1$H NMR (300 MHz, $CDCl_3$): δ 7.93 (d, J=8.4 Hz, 1H), 7.47 (d, J=8.4 Hz, 1H), 7.36 (s, 2H), 4.24 (q, J=7.2 Hz, 2H), 3.65 (t, J=7.2 Hz, 2H), 3.04 (t, J=7.2 Hz, 2H), 1.28 (t, J=7.2 Hz, 3H).

Ethyl 2-(6-(4-nitrophenyl)-1-oxo-3,4-dihydroisoquinolin-2(1H)-yl)acetate (1C)

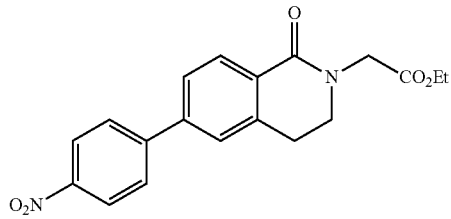

1C

Pd(PPh$_3$)$_4$ (0.133 g, 0.115 mmol) was added to a solution of product of Example 1B (3 g, 9.6 mmol) in 35 mL of 1,4 dioxane-H$_2$O (5:1) mixture under argon atmosphere, followed by cesium carbonate (9.38 g, 28.7 mmol) and 4-nitrophenyl boronic acid (1.6 g, 9.6 mmol). The reaction mixture was degassed for 10 min. The reaction mixture was then refluxed for 5 h, and solvent was removed under reduced pressure. The residue was partitioned between ethyl acetate and water. The separated organic layer was dried over sodium sulphate and filtered. The filtrate was concentrated under reduced pressure and purified by flash chromatography using 30% ethyl acetate in hexane to afford title compound (2 g, 64%) as solid. $^1$H NMR (300 MHz, $CDCl_3$): δ 8.33-8.3 (m, 2H), 8.2 (d, J=7.5 Hz, 1H), 7.79-7.75 (m, 2H), 7.61 (dd, J$_1$=2.1 Hz, J$_2$=8.4 Hz, 1H), 7.45 (s, 1H), 4.39 (s, 2H), 4.25 (q, J=7.2 Hz, 2H), 3.72 (t, J=6.9 Hz, 2H), 3.16 (t, J=6.9 Hz, 2H), 1.3 (t, J=6.9 Hz, 3H).

Ethyl 2-(6-(4-aminophenyl)-1-oxo-3,4-dihydroisoquinolin-2(1H)-yl)acetate (1D)

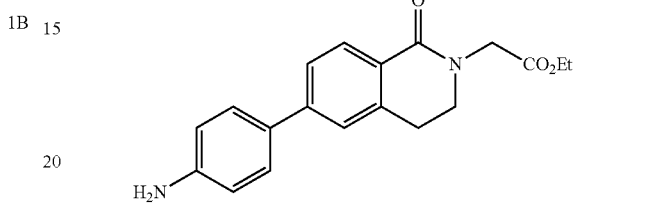

1D

Excess 10% Pd/C (0.5 g) was added to a solution of product of Example 1C (1.1 g, 3.09 mmol) in 20 mL of ethanol, and the mixture was stirred under H$_2$ atmosphere at room temperature for 4 h. The reaction mixture was filtered over celite bed, and filtrate was removed under reduced pressure and triturated with diethyl ether and pentane to afford title compound (0.97 g, 97%) as solid. $^1$H NMR (400 MHz, $CDCl_3$): δ 8.02 (d, J=8.0 Hz, 1H), 7.43 (dd, J$_1$=1.6 Hz, J$_2$=8.0 Hz, 1H), 7.39 (m, 2H), 7.27 (s, 1H), 6.7 (m, 2H), 4.28 (s, 2H), 4.15 (q, J=6.8 Hz, 2H), 3.69 (bs, 2H), 3.61 (t, J=6.4 Hz, 2H), 3.03 (t, J=6.8 Hz, 2H), 1.22 (t, J=7.2 Hz, 3H).

Ethyl 2-(1-oxo-6-(4-(3-(3-(trifluoromethyl)phenyl)ureido)phenyl)-3,4-dihydroisoquinolin-2(1H)-yl)acetate (1E)

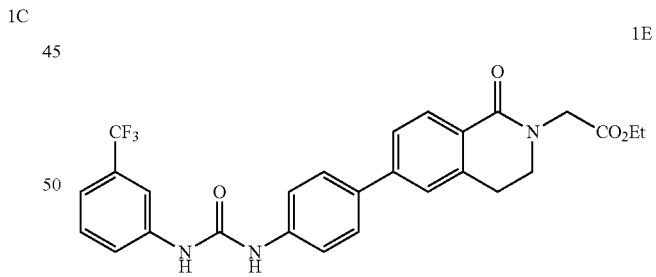

1E 3-(Trifluoromethyl)phenyl isocyanate (0.14 g, 0.769 mmol) was added to a solution of product of Example 1D (0.25 g, 0.76 mmol) and triethylamine (0.23 g, 2.3 mmol) in THF (10 mL), and the mixture was stirred at room temperature overnight. The solvent was removed under reduced pressure, and product was triturated with diethyl ether and pentane to afford title compound (0.26 g, 66%) as solid. $^1$H NMR (300 MHz, DMSO-d$_6$): δ 9.1 (bs, 1H), 8.97 (bs, 1H), 8.03 (s, 1H), 7.9 (d, J=7.5 Hz, 1H), 7.71-7.5 (m, 8H), 7.34 (d, J=7.5 Hz, 1H), 4.31 (s, 2H), 4.17 (q, J=7.5 Hz, 2H), 3.67 (t, J=6.3 Hz, 2H), 3.07 (t, J=6.3 Hz, 2H), 1.22 (t, J=6.9 Hz, 3H).

2-(1-Oxo-6-(4-(3-(3-(trifluoromethyl)phenyl)ureido)phenyl)-3,4-dihydroisoquinolin-2(1H)-yl)acetic acid (1)

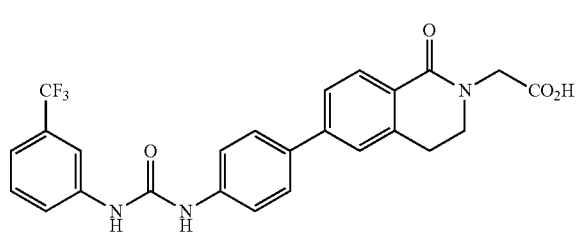

Lithium hydroxide (0.054 g, 1.17 mmol) was added to a solution of product of Example 1E (0.2 g, 0.39 mmol) in 10 mL of THF-water (4:1) mixture, and the mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.15 g, 79%) as solid. $^1$H NMR (300 MHz, DMSO-$d_6$): δ 9.2 (bs, 1H), 9.0 (bs, 1H), 8.05 (bs, 1H), 7.9 (d, J=8.4 Hz, 1H), 7.68 (m, 3H), 7.64-7.58 (m, 4H), 7.52 (m, 1H), 7.0 (m, 1H), 4.2 (s, 2H), 3.65 (m, 2H), 3.05 (m, 2H); ESI-MS m/z=482 (M−H)$^-$; HPLC purity: 96%.

Examples 2-9 were prepared using procedures analogous to those described in Example 1 with appropriate starting materials.

| Ex | Structure | $^1$H NMR data | Mass/Purity |
|---|---|---|---|
| 2 | 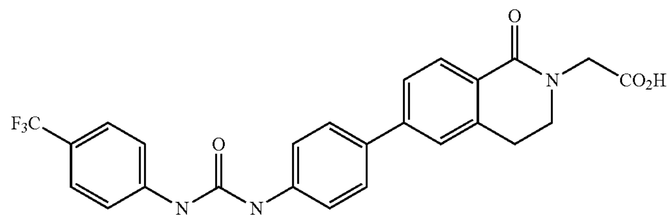 [SMILES: O=C(O)CN1CCc2cc(-c3ccc(NC(=O)Nc4ccc(C(F)(F)F)cc4)cc3)ccc2C1=O] | $^1$H NMR (300 MHz, DMSO-$d_6$): δ 10.6 (bs, 1H), 7.9-7.78 (m, 4H), 7.6-7.3 (m, 7H), 4.0 (s, 2H), 3.7 (m, 2H), 3.0 (m, 2H). | ESI-MS m/z = 482 (M − H)$^-$; HPLC purity: 98.5%. |
| 3 | 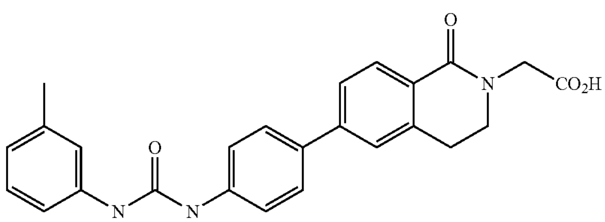 [SMILES: Cc1cccc(NC(=O)Nc2ccc(-c3ccc4c(c3)CCN(CC(=O)O)C4=O)cc2)c1] | $^1$H NMR (300 MHz, DMSO-$d_6$): δ 12.8 (bs, 1H), 9.2 (bs, 1H), 8.9 (bs, 1H), 7.9 (d, J = 8.4 Hz, 1H), 7.72-7.56 (m, 6H), 7.36-7.12 (m, 2H), 7.06 (t, 1H), 6.8 (d, J = 7.4 Hz, 1H), 4.2 (s, 2H), 3.65 (t, J = 6.8 Hz, 2H), 3.05 (t, J = 6.8 Hz, 2H), 2.26 (s, 3H). | ESI-MS m/z = 428 (M − H)$^-$; HPLC purity: 99%. |
| 4 | 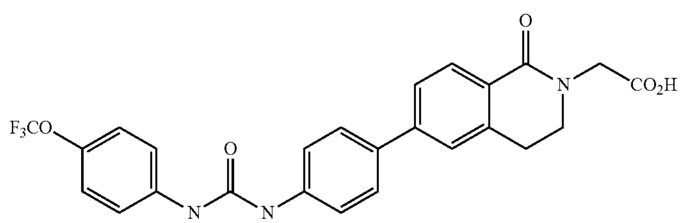 [SMILES: O=C(O)CN1CCc2cc(-c3ccc(NC(=O)Nc4ccc(OC(F)(F)F)cc4)cc3)ccc2C1=O] | $^1$H NMR (300 MHz, DMSO-$d_6$): δ 12.7 (bs, 1H), 9.1 (bs, 1H), 9.06 (bs, 1H), 7.9 (d, J = 8.4 Hz, 1H), 7.76-7.56 (m, 8H), 7.3 (m, 2H), 4.2 (s, 2H), 3.65 (t, J = 6.6 Hz, 2H), 3.05 (t, J = 6.6 Hz, 2H). | ESI-LCMS m/z: 500 (M + H)$^+$; (purity 97%). |
| 5 | 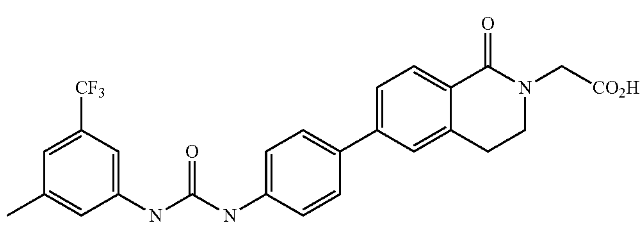 [SMILES: Cc1cc(NC(=O)Nc2ccc(-c3ccc4c(c3)CCN(CC(=O)O)C4=O)cc2)cc(C(F)(F)F)c1] | $^1$H NMR (300 MHz, DMSO-$d_6$): δ 12.8 (bs, 1H), 9.7 (bs, 1H), 9.6 (bs, 1H), 7.9 (d, J = 8.1, 1H), 7.85 (s, 1H), 7.7-7.6 (m, 6H), 7.5 (s, 1H), 7.1 (s, 1H), 4.1 (s, 2H), 3.7 (m, 2H), 3.1 (m, 2H), 2.3 (s, 3H). | ESI-LCMS m/z: 497 (purity 96%); HPLC purity 99%. |
| 6 | 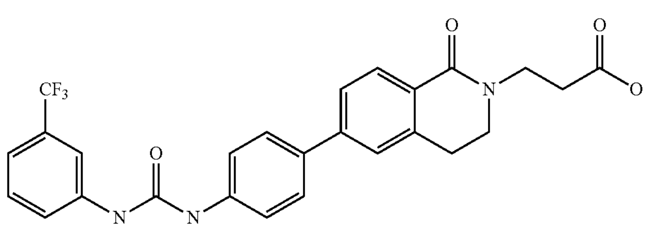 [SMILES: O=C(O)CCN1CCc2cc(-c3ccc(NC(=O)Nc4cccc(C(F)(F)F)c4)cc3)ccc2C1=O] | $^1$H NMR (400 MHz, DMSO-$d_6$): δ 12.2 (bs, 1H), 9.47 (bs, 1H), 9.32 (bs, 1H), 8.05 (s, 1H), 7.89 (d, J = 8.0 Hz, 1H), 7.67-7.56 (m, 7H), 7.51 (t, J = 8.0 Hz, 1H), 7.30 (d, J = 7.2 Hz, 1H), 3.69 (t, J = 7.2 Hz, 2H), 3.61 (t, J = 6.8 Hz, 2H), 3.0 (t, J = 6.0 Hz, 2H), 2.54 (t, J = 7.2 Hz, 2H). | ESI-LCMS m/z: 498 (purity 95%). HPLC purity 93%. |

-continued

| Ex | Structure | ¹H NMR data | Mass/Purity |
|---|---|---|---|
| 7 | 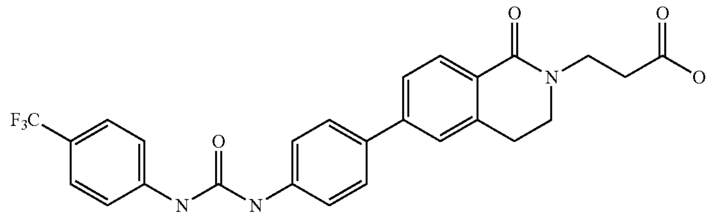 [SMILES: O=C(O)CCN1CCc2cc(-c3ccc(NC(=O)Nc4ccc(C(F)(F)F)cc4)cc3)ccc2C1=O] | ¹H NMR (400 MHz, DMSO-d₆): δ 12.4 (bs, 1H), 9.59 (bs, 1H), 9.39 (bs, 1H), 7.90 (d, J = 8.0 Hz, 1H), 7.71-7.57 (m, 10H), 3.69 (m, 2H), 3.62 (m, 2H), 3.0 (m, 2H), 2.54 (m, 2H). | ESI-LCMS m/z: 498 (purity 95%); HPLC purity 96.6%. |
| 8 | 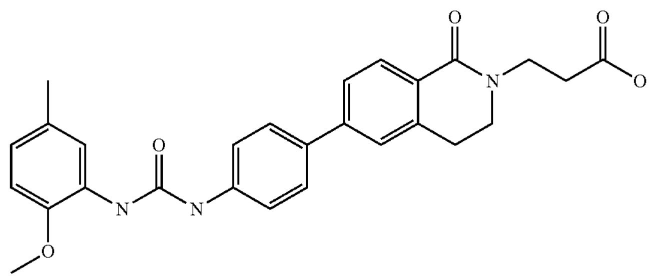 [SMILES: COc1ccc(C)cc1NC(=O)Nc1ccc(-c2ccc3c(c2)CCN(CCC(=O)O)C3=O)cc1] | ¹H NMR (400 MHz, DMSO-d₆): δ 12.4 (bs, 1H), 9.50 (s, 1H), 8.22 (s, 1H), 7.99 (s, 1H), 7.89 (d, J = 8 Hz, 1H), 7.68-7.55 (m, 6H), 6.90 (d, J = 8 Hz, 1H), 6.75 (d, J = 8.4 Hz, 1H), 3.84 (s, 3H), 3.68 (t, J = 7.2 Hz, 2H), 3.61 (t, J = 6.8 Hz, 2H), 3.0 (t, J = 6.0 Hz, 2H), 2.54 (m, 2H), 2.24 (s, 3H). | ESI-LCMS m/z: 474 (purity 98.5%); HPLC purity 98%. |
| 9 | 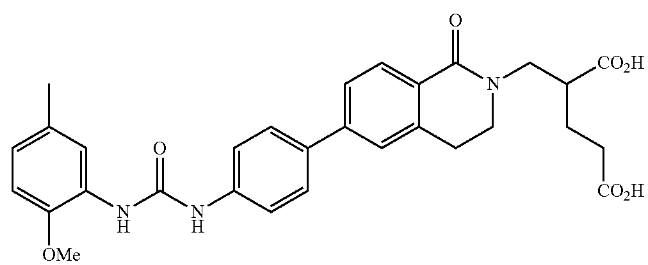 [SMILES: COc1ccc(C)cc1NC(=O)Nc1ccc(-c2ccc3c(c2)CCN(CC(CCC(=O)O)C(=O)O)C3=O)cc1] | ¹H NMR (400 MHz, DMSO-d₆): δ 12.4 (bs, 1H), 9.40 (s, 1H), 8.21 (s, 1H), 7.99 (s, 1H), 7.89 (d, J = 8.0 Hz, 1H), 7.67 (d, J = 8.4 Hz, 2H), 7.62 (d, J = 8.4 Hz, 1H), 7.57-7.55 (m, 3H), 6.90 (d, J = 8.0 Hz, 1H), 6.75 (d, J = 8.4 Hz, 1H), 3.84 (s, 3H), 3.75 (m, 1H), 3.57 (t, J = 6.0 Hz, 2H), 3.51 (m, 1H), 3.0 (t, J = 6.0 Hz, 2H), 2.74 (t, J = 7.2 Hz, 1H), 2.4-2.25 (m, 2H), 2.23 (s, 3H), 1.7 (q, J = 7.6 Hz, 2H). | ESI-LCMS m/z: 546 (M + H)⁺; HPLC purity: 96%. |

Example-10

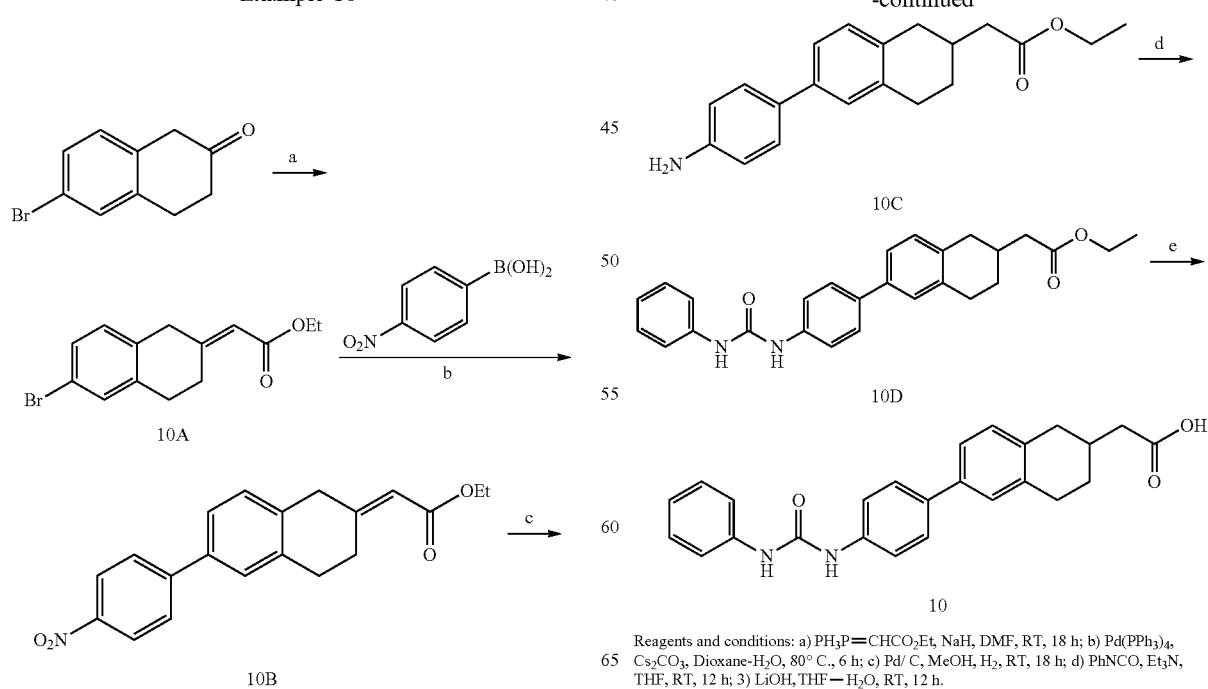

Reagents and conditions: a) PH₃P═CHCO₂Et, NaH, DMF, RT, 18 h; b) Pd(PPh₃)₄, Cs₂CO₃, Dioxane-H₂O, 80° C., 6 h; c) Pd/C, MeOH, H₂, RT, 18 h; d) PhNCO, Et₃N, THF, RT, 12 h; 3) LiOH, THF—H₂O, RT, 12 h.

Procedure

2-(6-(4-(3-(3,5-bis(Trifluoromethyl)phenyl)ureido) phenyl)-1,2,3,4-tetrahydronapthalen-2-yl)acetic acid

Ethyl 2-(6-bromo-3,4-dihydronapthalen-2(1H)-ylidene)acetate (10A)

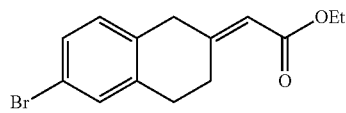

10A

Ph$_3$P=CHCO$_2$Et (5 g, 22.22 mmol) was added to an ice cold solution of 6-Bromo-2-tetralone (5.0 g, 22.22 mmol) and NaH (0.69 g, 28.88 mmol) in DMF (40 mL). The reaction mixture was stirred at room temperature for 18 h. The reaction mixture was diluted with water (20 mL) and extracted with diethyl ether (2×100 mL). The organic layer was dried over sodium sulphate, filtered and removed under reduced pressure to give crude product which was purified by flash chromatography using 2% ethyl acetate in hexanes to afford title compound (4.0 g, 61%) as solid. $^1$H NMR (300 MHz, CDCl$_3$): δ 7.28 (m, 2H), 6.96 (d, J=7.8 Hz, 1H), 6.33 (s, 1H), 4.07 (q, J=7.2 Hz, 2H), 3.22 (s, 2H), 2.74 (t, J=7.2 Hz, 2H), 2.21 (t, J=7.8 Hz, 2H), 1.17 (t, J=7.2 Hz, 3H); ESI-MS m/z=297 (M+H)$^+$.

Ethyl 2-(6-(4-nitrophenyl)-3,4-dihydronapthalen-2 (1H)-ylidene)acetate (10B)

10B

Pd(PPh$_3$)$_4$ (0.18 g, 0.16 mmol) was added to a solution of product of Example 10A (4.0 g, 13.55 mmol) in 80 mL of 1,4 dioxane-H$_2$O (3:1) mixture under Argon atmosphere, followed by cesium carbonate (8.8 g, 27.11 mmol) and 4-nitrophenyl boronic acid (2.25 g, 13.55 mmol). The reaction mixture was degassed for 5 min. The reaction mixture was refluxed for 6 h and solvent was removed under reduced pressure. The residue was partitioned between ethyl acetate and water. The separated organic layer was dried over sodium sulphate, filtered and removed under reduced pressure. The product was purified by flash chromatography using 12% ethyl acetate in hexanes to afford title compound (4.0 g, 87%) as solid. $^1$H NMR (300 MHz, CDCl$_3$): δ 8.28 (d, J=9.3 Hz, 2H), 7.73 (d, J=8.4 Hz, 2H), 7.40 (m, 2H), 7.12 (d, J=7.8 Hz, 1H), 6.41 (s, 1H), 4.19 (q, J=7.8 Hz, 2H), 3.25 (s, 2H), 2.93 (t, J=7.5 Hz, 2H), 2.41 (t, J=7.8 Hz, 2H), 1.28 (t, J=6.9 Hz, 3H).

Ethyl 2-(6-(4-aminoophenyl)-1,2,3,4-tetrahydronapthalen-2-yl)acetate (10C)

10C

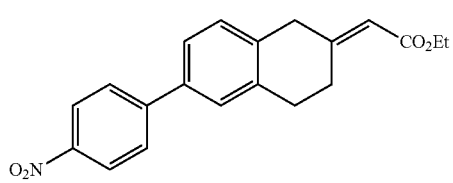

Excess 10% Pd/C (1.0 g) was added to a solution of product of Example 10B (4.0 g, 11.86 mmol) in 30 mL of ethanol. The mixture was stirred under H$_2$ atmosphere at room temperature for 18 h. The reaction mixture was filtered over celite bed, filtrate was removed under reduced pressure, and residue was partitioned between ethyl acetate and water. The separated organic layer was dried over sodium sulphate, filtered and removed in vacuum. The crude product was washed with diethyl ether and pentane to afford title compound (3.2 g, 87%) as solid. $^1$H NMR (400 MHz, DMSO-d$_6$): δ 7.40 (d, J=8.4 Hz, 2H), 7.26 (m, 2H), 7.05 (d, J=7.6 Hz, 2H), 6.80 (d, J=8.8 Hz, 1H), 4.10 (q, J=7.2 Hz, 2H), 2.86-2.78 (m, 3H), 2.50-2.35 (m, 3H), 2.12 (m, 1H), 1.90 (m, 1H), 1.42 (m, 1H), 1.20 (t, J=6.8 Hz, 3H). ESI-MS m/z=310 (M+H)$^+$.

Ethyl 2-(6-(4-(3-phenylureido)phenyl)-1,2,3,4-tetrahydronaphthalen-2-yl)acetate (10D)

10D

Phenyl isocyanate (0.084 g, 0.71 mmol) was added to a solution of product of Example 10C (0.2 g, 0.64 mmol) and triethylamine (0.098 g, 0.96 mmol) in THF (10 mL). The reaction mixture was stirred at room temperature overnight. The solvent was removed under reduced pressure and product purified by flash chromatography using 1% methanol in chloroform to afford title compound (0.14 g, 50%) as solid. $^1$H NMR (300 MHz, CDCl$_3$): δ 8.75 (bs, 1H), 8.65 (bs, 1H), 7.60-7.40 (m, 6H), 7.3-7.21 (m, 4H), 7.10 (d, J=8.4 Hz, 1H), 6.95 (m, 1H), 4.12 (q, J=6.9 Hz, 2H), 2.9 (m, 3H), 2.45 (m, 3H), 2.15 (m, 1H), 1.90 (m, 1H), 1.45 (m, 1H), 1.2 (t, J=7.2 Hz, 3H); ESI-MS m/z=429 (M+H)$^+$.

2-(6-(4-(3-Phenylureido)phenyl)-1,2,3,4-tetrahydronaphthalen-2-yl)acetic acid (10)

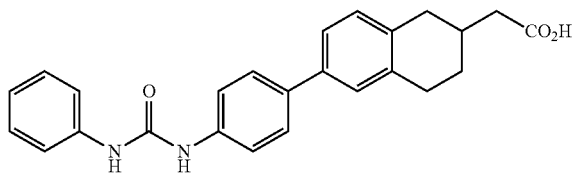

Lithium hydroxide (0.068 g, 1.62 mmol) was added to a solution of product of Example 10D (0.14 g, 0.327 mmol) in 10 mL of THF-water (3:1). Reaction mixture was stirred at room temperature overnight. After the solvent was removed in vacuum, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.1 g, 76%) as white solid. $^1$H NMR (300 MHz, DMSO-$d_6$): δ 12.13 (bs, 1H), 7.56-7.42 (m, 6H), 7.40-7.24 (m, 4H), 7.10 (d, J=8.4 Hz, 1H), 7.0-6.94 (m, 1H), 2.90-2.71 (m, 3H), 2.45 (m, 1H), 2.29 (d, J=6.9 Hz, 2H), 2.10 (m, 1H), 1.91 (m, 1H), 1.42 (m, 1H); ESI-MS m/z=401 (M+H)$^+$; HPLC purity: 90%.

Examples 11-39 were prepared by analogous procedures as described for Example 10 using appropriate starting materials. Chiral compounds were separated using procedures analogous to those described in Example 129.

| Ex | Structure | $^1$H NMR Data | Mass/purity |
|----|-----------|----------------|-------------|
| 11 | 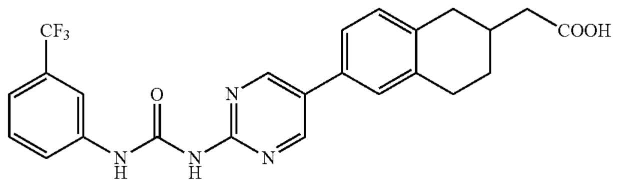 [SMILES: O=C(O)CC1CCc2cc(-c3cnc(NC(=O)Nc4cccc(C(F)(F)F)c4)nc3)ccc2C1] | $^1$H NMR (400 MHz, DMSO-$d_6$): δ 11.8 (s, 1H), 10.46 (s, 1H), 9.02 (s, 2H), 8.09 (s, 1H), 7.86 (d, J = 7.6 Hz, 1H), 7.58 (t, J = 8.4 Hz, 1H), 7.5-7.45 (m, 3H), 7.2 (d, J = 8.0 Hz, 1H), 2.95-2.8 (m, 4H), 2.28 (d, J = 7.2 Hz, 2H), 2.12 (m, 1H), 1.94 (m, 1H), 1.45 (m, 1H). | ESI-MS m/z = 471 (M + H)$^+$; HPLC purity: 92%. |
| 12 | 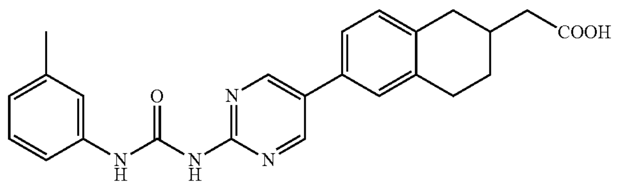 [SMILES: Cc1cccc(NC(=O)Nc2ncc(-c3ccc4c(c3)CCC(CC(=O)O)C4)cn2)c1] | $^1$H NMR (400 MHz, DMSO-$d_6$): δ 12.2 (bs, 1H), 11.5 (s, 1H), 10.23 (s, 1H), 9.0 (s, 2H), 7.5-7.4 (m, 4H), 7.3-7.1 (m, 2H), 6.88 (d, J = 7.2 Hz, 1H), 2.95-2.8 (m, 4H), 2.3 (m, 5H), 2.12 (m, 1H), 1.95 (m, 1H), 1.45 (m, 1H). | ESI-MS m/z = 417 (M + H)$^+$; HPLC purity: 92%. |
| 13 | 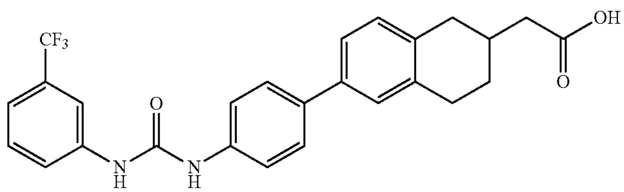 [SMILES: O=C(O)CC1CCc2cc(-c3ccc(NC(=O)Nc4cccc(C(F)(F)F)c4)cc3)ccc2C1] | $^1$H NMR (300 MHz, DMSO-$d_6$): δ 12.0 (bs, 1H), 9.46 (bs, 1H), 9.20 (bs, 1H), 8.04 (s, 1H), 7.63-7.47 (m, 6H), 7.36-7.27 (m, 3H), 7.10 (d, J = 8.4 Hz, 1H), 2.90-2.72 (m, 3H), 2.45 (m, 1H), 2.28 (d, J = 7.2 Hz, 2H), 2.13 (m, 1H), 1.92 (m, 1H), 1.43 (m, 1H). | ESI-MS m/z = 469 (M + H)$^+$. HPLC purity: 95.96%. |
| 14 | 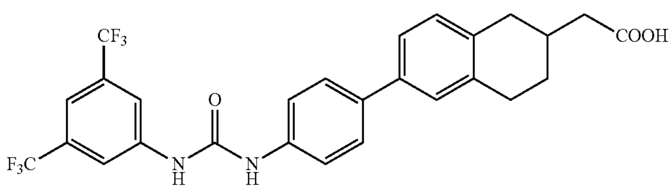 [SMILES: O=C(O)CC1CCc2cc(-c3ccc(NC(=O)Nc4cc(C(F)(F)F)cc(C(F)(F)F)c4)cc3)ccc2C1] | $^1$H NMR (400 MHz, DMSO-$d_6$): δ 12.11 (s, 1H), 9.61 (s, 1H), 9.19 (s, 1H), 8.14 (s, 2H), 7.64 (s, 1H), 7.65-7.52 (m, 4H), 7.35 (m, 2H), 7.11 (d, J = 8.4 Hz, 1H), 2.9-2.80 (m, 3H), 2.45 (m, 1H), 2.30 (d, J = 6.8 Hz, 2H), 2.11 (m, 1H), 1.92 (m, 1H), 1.45 (m, 1H). | ESI-MS m/z = 537 (M + H)$^+$; HPLC purity: 98.4%. |
| 15 | 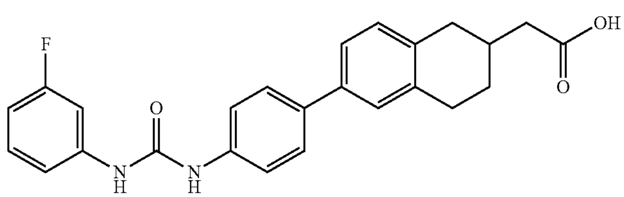 [SMILES: O=C(O)CC1CCc2cc(-c3ccc(NC(=O)Nc4cccc(F)c4)cc3)ccc2C1] | $^1$H NMR (400 MHz, DMSO-$d_6$): δ 12.1 (bs, 1H), 9.19 (s, 1H), 9.07 (s, 1H), 7.58-7.45 (m, 5H), 7.35-7.25 (m, 3H), 7.18-7.05 (m, 2H), 6.77 (t, J = 7.2 Hz, 1H), 2.9-2.8 (m, 3H), 2.42 (m, 1H), 2.28 (d, J = 6.8 Hz, 2H), 2.11 (m, 1H), 1.92 (m, 1H), 1.50-1.40 (m, 1H). | ESI-MS m/z = 419 (M + H)$^+$. HPLC purity: 94.4%. |
| 16 | 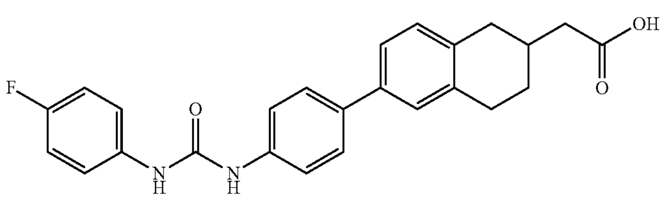 [SMILES: O=C(O)CC1CCc2cc(-c3ccc(NC(=O)Nc4ccc(F)cc4)cc3)ccc2C1] | $^1$H NMR (300 MHz, DMSO-$d_6$): δ 12.0 (bs, 1H), 8.9 (m, 2H), 7.58-7.45 (m, 6H), 7.35-7.31 (m, 2H), 7.1 (m, 3H), 2.91-2.70 (m, 3H), 2.42 (m, 1H), 2.29 (d, J = 7.2 Hz, 2H), 2.1 (m, 1H), 1.9 (m, 1H), 1.50 (m, 1H). | ESI-MS m/z = 419 (M + H)$^+$. HPLC purity: 96.14%. |

-continued

| Ex | Structure | ¹H NMR Data | Mass/purity |
|---|---|---|---|
| 17 | [structure: 3-cyanophenyl urea linked to phenyl-tetrahydronaphthalene acetic acid] | ¹H NMR (400 MHz, DMSO-d$_6$): δ 12.1 (bs, 1H), 9.28 (bs, 1H), 9.10 (bs, 1H), 7.99 (s, 1H), 7.68 (d, J = 8.4 Hz, 1H), 7.60-7.45 (m, 5H), 7.42 (d, J = 7.2 Hz, 1H), 7.34 (m, 2H), 7.10 (d, J = 8.0 Hz, 1H), 2.9-2.8 (m, 3H), 2.45 (m, 1H), 2.30 (d, J = 6.8 Hz, 2H), 2.11 (m, 1H), 1.91 (m, 1H), 1.41 (m, 1H). | ESI-MS m/z = 426 (M + H)⁺. HPLC purity: 93.67% |
| 18 | [structure: 3-nitrophenyl urea linked to phenyl-tetrahydronaphthalene acetic acid] | ¹H NMR (400 MHz, DMSO-d$_6$): δ 12.0 (bs, 1H), 9.67 (bs, 1H), 9.28 (bs, 1H), 8.55 (s, 1H), 7.80 (d, J = 8.4 Hz, 1H), 7.71 (d, J = 7.5 Hz, 1H), 7.54 (m, 5H), 7.33 (m, 2H), 7.09 (d, J = 8.1 Hz, 1H), 2.90-2.80 (m, 3H), 2.45 (m, 1H), 2.28 (d, J = 6.9 Hz, 2H), 2.10 (m, 1H), 1.88 (m, 1H), 1.42 (m, 1H). | ESI-MS m/z = 446 (M + H)⁺. HPLC purity: 93.25%. |
| 19 | [structure: 2-OCF$_3$-phenyl urea linked to phenyl-tetrahydronaphthalene acetic acid] | ¹H NMR (300 MHz, DMSO-d$_6$): δ 9.89 (bs, 1H), 9.00 (bs, 1H), 8.22 (d, J = 8.4 Hz, 1H), 7.55 (m, 4H), 7.38-7.30 (m, 4H), 7.12-7.05 (m, 2H), 2.91-2.72 (m, 3H), 2.45 (m, 1H), 2.19 (m, 2H), 2.11 (m, 1H), 1.91 (m, 1H), 1.42 (m, 1H). | ESI-MS m/z = 484 (M + H)⁺. HPLC purity: 94.0%. |
| 20 | [structure: 4-F-3-CF$_3$-phenyl urea linked to phenyl-tetrahydronaphthalene acetic acid] | ¹H NMR (400 MHz, DMSO-d$_6$): δ 12.2 (bs, 1H), 9.19 (s, 1H), 9.0 (s, 1H), 8.02 (s, 1H), 7.64 (m, 1H), 7.6-7.5 (m, 4H), 7.44 (m, 1H), 7.33 (m, 2H), 7.1 (d, J = 8.4 Hz, 1H), 2.95-2.75 (m, 3H), 2.5-2.35 (m, 1H), 2.35 (d, J = 6.8 Hz, 2H), 2.2 (m, 1H), 1.95 (m, 1H), 1.45 (m, 1H). | ESI-MS m/z = 487 (M + H)⁺; HPLC purity: 90%. |
| 21 | [structure: 3-OCF$_3$-phenyl urea linked to phenyl-tetrahydronaphthalene acetic acid] | ¹H NMR (300 MHz, DMSO-d$_6$): δ 12.1 bs, 1H), 9.05 (s, 1H 8.87 (s, 1H), 7.7 (s, 1H), 7.54 (m, 4H), 7.45-7.25 (m, 4H), 7.12 (d, J = 8.4 Hz, 1H), 6.94 (d, J = 7.8 Hz, 1H), 2.95-2.75 (m, 3H), 2.5-2.35 (m, 1H), 2.3 (d, J = 7.2 Hz, 2H), 2.15 (m, 1H), 1.95 (m, 1H), 1.45 (m, 1H). | ESI-MS m/z = 485 (M + H)⁺. LCMS purity: 96%. |
| 22 | [structure: 3-SF$_5$-phenyl urea linked to phenyl-tetrahydronaphthalene acetic acid] | ¹H NMR (300 MHz, DMSO-d$_6$): δ 12.2 (bs, 1H), 10.12 (bs, 1H 9.78 (bs, 1H), 8.3 (s, 1H), 7.65-7.45 (m, 9H), 7.1 (m, 1H), 2.95-2.75 (m, 3H), 2.45-2.25 (m, 3H), 2.0 (m, 2H), 1.43 (m, 1H). | ESI-MS m/z = 527 (M + H)⁺; HPLC purity: 96%. |
| 23 | [structure: 2-CF$_3$-phenyl urea linked to phenyl-tetrahydronaphthalene acetic acid] | ¹H NMR (400 MHz, DMSO-d$_6$): δ 12.10 (bs, 1H), 9.44 (bs, 1H), 8.08 (bs, 1H), 7.96 (d, J = 8.4 Hz, 1H), 7.69-7.62 (m, 2H), 7.54 (m, 4H), 7.35-7.26 (m, 3H), 7.09 (d, J = 8.0 Hz, 1H), 2.90-2.80 (m, 3H), 2.45 (m, 1H), 2.32 (d, J = 6.8 Hz, 2H), 2.10 (m, 1H), 1.92 (m, 1H), 1.42 (m, 1H). | ESI-MS m/z = 469 (M + H)⁺; HPLC purity: 92%. |

| Ex | Structure | ¹H NMR Data | Mass/purity |
|---|---|---|---|
| 24 | 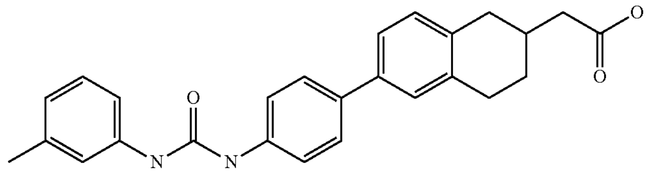 [SMILES: Cc1cccc(NC(=O)Nc2ccc(-c3ccc4c(c3)CCC(CC(=O)O)C4)cc2)c1] | ¹H NMR (400 MHz, DMSO-$d_6$): δ 12.1 (bs, 1H), 8.71 (bs, 4H), 8.58 (bs, 1H), 7.56-7.49 (q, J = 8.7 Hz, 4H), 7.32 (m, 3H), 7.24-7.08 (m, 3H), 6.78 (d, J = 7.5 Hz, 1H), 2.88 (m, 3H), 2.82 (m, 1H), 2.49 (m, 1H), 2.39 (m, 5H), 1.98 (m, 1H), 1.45 (m, 1H). | ESI-MS m/z = 415 (M + H)⁺; HPLC purity: 92%. |
| 25 | 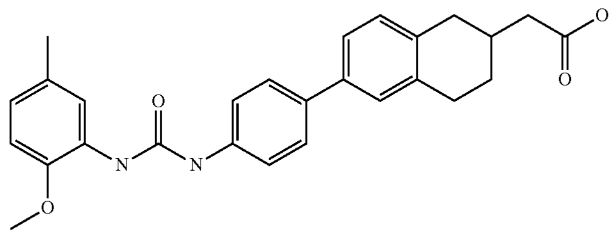 [SMILES: COc1ccc(C)cc1NC(=O)Nc1ccc(-c2ccc3c(c2)CCC(CC(=O)O)C3)cc1] | ¹H NMR (400 MHz, DMSO-$d_6$): δ 9.6 (bs, 1H), 8.3 (bs, 1H), 8.0 (s, 1H), 7.5 (m, 4H), 7.3 (m, 2H), 7.1 (d, J = 8.8 Hz, 1H), 6.9 (d, J = 8.4 Hz, 1H), 6.7 (dd, $J_1$ = 1.6 Hz, $J_2$ = 8.4 Hz, 1H), 3.85 (s, 3H), 2.8 (m, 2H), 2.4 (m, 1H), 2.35 (s, 3H), 2.2 (d, J = 8.8 Hz, 2H), 2.1 (s, 1H), 1.9 (m, 1H), 1.8 (s, 1H), 1.4 (m, 1H). | ESI-MS m/z = 445 (M + H)⁺; HPLC purity: 89%. |
| 26 | 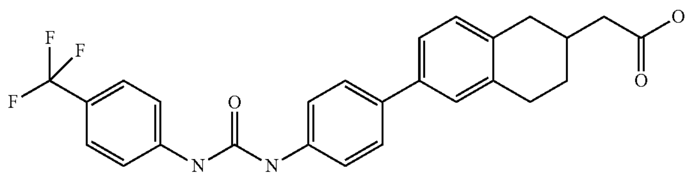 [SMILES: O=C(O)CC1CCc2cc(-c3ccc(NC(=O)Nc4ccc(C(F)(F)F)cc4)cc3)ccc2C1] | ¹H NMR (400 MHz, DMSO-$d_6$): δ 12.6 (bs, 1H), 12.2 (bs, 1H), 7.8 (d, J = 9.2 Hz, 2H), 7.65 (d, J = 8.4 Hz, 2H), 7.55 (d, J = 8.4 Hz, 2H), 7.45 (d, J = 8.4 Hz, 2H), 7.3 (m, 2H), 7.03 (d, J = 8.4 Hz, 1H), 2.80 (m, 3H), 2.15 (m, 2H), 2.0 (m, 3H), 1.45 (m, 1H). | ESI-MS m/z = 469 (M + H)⁺; HPLC purity: 90%. |
| 27 | 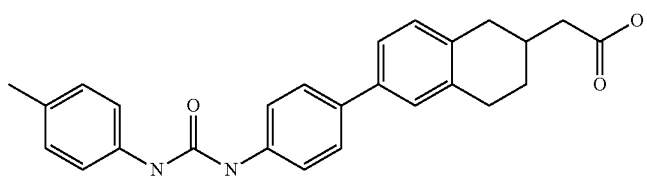 [SMILES: Cc1ccc(NC(=O)Nc2ccc(-c3ccc4c(c3)CCC(CC(=O)O)C4)cc2)cc1] | ¹H NMR (400 MHz, DMSO-$d_6$): δ 12.10 (bs, 1H), 8.68 (bs, 1H), 8.55 (bs, 1H), 7.55-7.49 (q, J = 8.8 Hz, 4H), 7.32 (m, 4H), 7.07 (m, 3H), 2.88-2.73 (m, 3H), 2.45 (m, 1H), 2.29 (d, J = 7.2 Hz, 2H), 2.24 (s, 3H), 2.11 (m, 1H) 1.92 (m, 1H), 1.42 (m, 1H). | ESI-MS m/z = 415 (M + H)⁺; HPLC purity: 92%. |
| 28 | 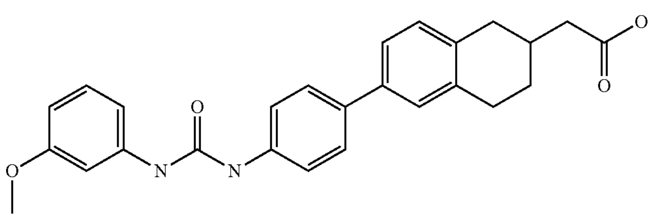 [SMILES: COc1cccc(NC(=O)Nc2ccc(-c3ccc4c(c3)CCC(CC(=O)O)C4)cc2)c1] | ¹H NMR (400 MHz, DMSO-$d_6$): δ 12.0 (bs, 1H), 9.0 (bs, 2H), 7.55 (m, 4H), 7.35 (m, 2H), 7.2 (m, 2H), 7.1 (d, J = 7.6 Hz, 1H), 6.95 (d, J = 8.0 Hz, 1H), 6.55 (dd, $J_1$ = 2.0 Hz, $J_2$ = 8.4 Hz, 1H), 3.75 (s, 3H), 3.15 (d, J = 8.8 Hz, 1H), 2.85 (m, 3H), 2.30 (d, J = 7.2 Hz, 2H), 2.15 (m, 1H), 1.95 (m, 1H), 1.45 (m, 1H). | ESI-MS m/z = 431 (M + H)⁺; HPLC purity: 92%. |
| 29 | 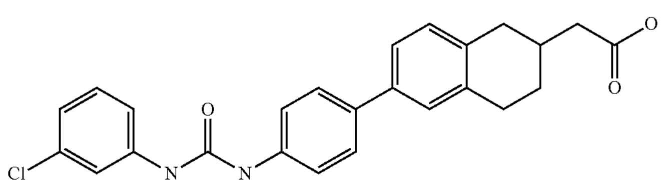 [SMILES: O=C(O)CC1CCc2cc(-c3ccc(NC(=O)Nc4cccc(Cl)c4)cc3)ccc2C1] | ¹H NMR (400 MHz, DMSO-$d_6$): δ 10.9 (bs, 1H), 10.8 (bs, 1H), 7.86 (s, 1H), 7.56 (d, J = 7.6 Hz, 2H), 7.47-7.41 (m, 3H), 7.29-7.24 (m, 3H), 7.03 (d, J = 7.6 Hz, 1H), 6.94 (d, J = 7.6 Hz, 1H), 2.90-2.83 (m, 3H), 2.45 (m, 1H), 2.20 (d, J = 6.0 Hz, 2H), 2.14 (m, 1H), 1.90 (m, 1H), 1.42 (m, 1H). | ESI-MS m/z = 435 (M + H)⁺; HPLC purity: 89%. |
| 30 | 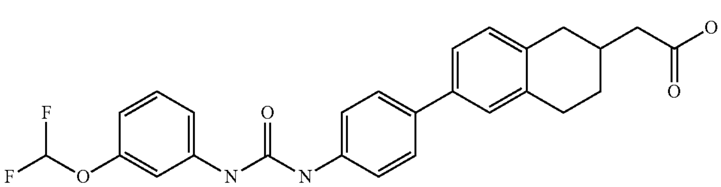 [SMILES: O=C(O)CC1CCc2cc(-c3ccc(NC(=O)Nc4cccc(OC(F)F)c4)cc3)ccc2C1] | ¹H NMR (400 MHz, DMSO-$d_6$): δ 12.10 (bs, 1H), 8.99 (bs, 1H), 8.88 (bs, 1H), 7.57-7.48 (m, 5H), 7.40-7.02 (m, 6H), 6.77 (d, J = 7.2 Hz, 1H), 2.89-2.80 (m, 3H), 2.45 (m, 1H), 2.29 (m, 2H), 2.11 (m, 1H), 1.92 (m, 1H), 1.42 (m, 1H). | ESI-MS m/z = 467 (M + H)⁺; HPLC purity: 91%. |

| Ex | Structure | ¹H NMR Data | Mass/purity |
|---|---|---|---|
| 31 | (3-CF₃-phenyl)-NH-C(O)-NH-(4-phenyl)-tetrahydronaphthalene-2-yl-CH₂-COOH; Chiral: enantiomer-1 | ¹H NMR (300 MHz, DMSO-d₆): δ 12.0 (bs, 1H), 9.07 (bs, 1H), 8.88 (bs, 1H), 8.04 (s, 1H), 7.60–7.47 (m, 6H), 7.36–7.27 (m, 3H), 7.10 (d, J = 8.0 Hz, 1H), 2.88–2.80 (m, 3H), 2.41 (m, 1H), 2.30 (d, J = 6.8 Hz, 2H), 2.16 (m, 1H), 1.92 (m, 1H), 1.43 (m, 1H). | ESI-MS m/z = 469 (M + H)⁺. HPLC purity: 97%. |
| 32 | (3-CF₃-phenyl)-NH-C(O)-NH-(4-phenyl)-tetrahydronaphthalene-2-yl-CH₂-COOH; Chiral: enantiomer-2 | ¹H NMR (300 MHz, DMSO-d₆): δ 12.0 (bs, 1H), 9.07 (bs, 1H), 8.88 (bs, 1H), 8.02 (s, 1H), 7.60–7.47 (m, 6H), 7.36–7.27 (m, 3H), 7.10 (d, J = 8.0 Hz, 1H), 2.88–2.80 (m, 3H), 2.41 (m, 1H), 2.30 (d, J = 6.8 Hz, 2H), 2.16 (m, 1H), 1.92 (m, 1H), 1.43 (m, 1H). | ESI-MS m/z = 469 (M + H)⁺. HPLC purity: 94%. |
| 33 | (3-CF₃-phenyl)-NH-C(O)-NH-(2-F-4-phenyl)-tetrahydronaphthalene-2-yl-CH₂-COOH | ¹H NMR (400 MHz, DMSO-d₆): δ 12.10 (bs, 1H), 9.41 (s, 1H), 8.69 (s, 1H), 8.18 (t, J = 8.8 Hz, 1H), 8.04 (s, 1H), 7.58–7.51 (m, 3H), 7.45 (d, J = 8.8 Hz, 1H), 7.39 (m, 2H), 7.34 (m, 1H), 7.12 (d, J = 8.0 Hz, 1H), 2.90–2.76 (m, 3H), 2.42 (m, 1H), 2.31 (d, J = 6.8 Hz, 2H), 2.11 (m, 1H), 1.92 (m, 1H), 1.45 (m, 1H). | ESI-MS m/z = 485 (M − H)⁻. HPLC purity: 91%. |
| 34 | (4-F-3-CF₃-phenyl)-NH-C(O)-NH-(2-F-4-phenyl)-tetrahydronaphthalene-2-yl-CH₂-COOH | ¹H NMR (400 MHz, DMSO-d₆): δ 12.0 (bs, 1H), 9.55 (bs, 1H), 8.80 (bs, 1H), 8.15 (m, 1H), 8.02 (dd, J₁ = 2.1 Hz, J₂ = 6.3 Hz, 1H), 7.75–7.30 (m, 6H), 7.15 (d, J = 8.4 Hz, 1H), 2.95–2.80 (m, 3H), 2.45 (m, 1H), 2.30 (d, J = 7.2 Hz, 2H), 2.10 (m, 1H), 1.95 (m, 1H), 1.45 (m, 1H). | ESI-MS m/z = 503 (M − H)⁻. HPLC purity: 97%. |
| 35 | (3-methyl-phenyl)-NH-C(O)-NH-(2-F-4-phenyl)-tetrahydronaphthalene-2-yl-CH₂-COOH | ¹H NMR (400 MHz, DMSO-d₆): δ 12.0 (bs, 1H), 9.03 (bs, 1H), 8.60 (s, 1H), 8.20 (t, J = 8.8 Hz, 1H), 7.52 (d, J = 12.0 Hz, 1H), 7.43 (m, 3H), 7.31 (s, 1H), 7.24–7.10 (m, 3H), 6.68 (d, J = 8.0 Hz, 1H), 2.89–2.80 (m, 3H), 2.45 (m, 1H), 2.30 (m, 5H), 2.11 (m, 1H), 1.92 (m, 1H), 1.43 (m, 1H). | ESI-MS m/z = 433 (M + H)⁺. HPLC purity: 97%. |
| 36 | (3,5-dimethyl-phenyl)-NH-C(O)-NH-(4-phenyl)-tetrahydronaphthalene-2-yl-CH₂-CO₂H | ¹H NMR (400 MHz, DMSO-d₆): δ 12.10 (bs, 1H), 9.05 (bs, 1H), 8.86 (bs, 1H), 7.52 (m, 4H), 7.31 (m, 2H), 7.08 (m, 3H), 6.60 (m, 1H), 2.87 (m, 3H), 2.45 (m, 1H), 2.26 (m, 2H), 2.23 (s, 6H), 2.11 (m, 1H), 1.90 (m, 1H), 1.42 (m, 1H). | ESI-MS m/z = 429 (M + 1); HPLC purity: 96%. |
| 37 | (3-CF₃-phenyl)-NH-C(O)-NH-(5-pyridyl)-tetrahydronaphthalene-2-yl-CH₂-CO₂H | ¹H NMR (300 MHz, DMSO-d₆): δ 12.0 (bs, 1H) 9.25 (bs, 1H), 9.1 (s, 1H), 8.7 (s, 1H), 8.0 (m, 2H), 7.85 (m, 1H), 7.75 (m, 2H), 7.65 (m, 1H), 7.5 (m, 1H), 7.35 (m, 1H), 7.15 (m, 1H), 2.8 (m, 3H), 2.5 (m, 1H), 2.3 (m, 2H), 2.1 (m, 1H), 2.0 (m, 1H), 1.5 (m, 1H). | ESI-LCMS m/z: 469 Purity: 97%. |

-continued

| Ex | Structure | ¹H NMR Data | Mass/purity |
|---|---|---|---|
| 38 | 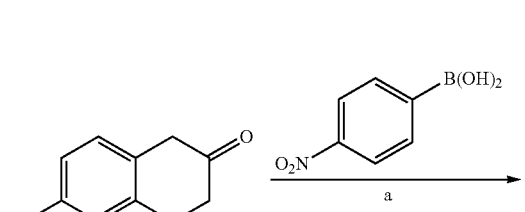 | ¹H NMR (300 MHz, DMSO-d₆): δ 10.67 (bs, 2H), 9.0 (s, 2H), 8.29 (d, J = 8.4 Hz, 1H), 8.24 (s, 1H), 8.06 (s, 1H), 7.97 (d, J = 8.4 Hz, 1H), 7.69 (d, J = 8.4 Hz, 1H), 7.51 (t, J = 7.5 Hz, 1H), 7.31 (d, J = 7.5 Hz, 1H), 3.11-3.07 (m, 3H), 2.92-2.86 (m, 1H), 2.68-2.54 (m, 2H), 2.20-2.07 (m, 2H), 1.4 (m, 1H). | ESI-LCMS m/z: 470 Purity: 94%; HPLC Purity: 94% |
| 39 | 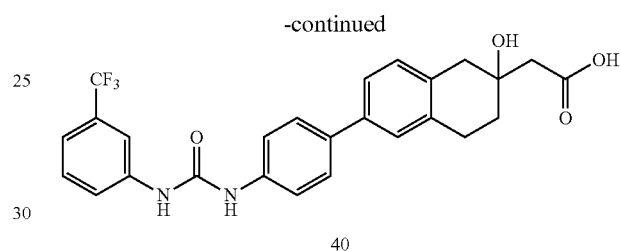 | ¹H NMR (400 MHz, DMSO-d₆): δ 12.1 (bs, 1H), 9.8 (s, 1H), 9.7 (s, 1H), 9.1 (s, 1H), 8.9 (d, J = 8.0 Hz, 1H), 7.8 (m, 3H), 7.4-7.3 (m, 2H), 7.2 (d, J = 8.0 Hz, 1H), 7.1 (m, 1H), 3-2.8 (m, 3H), 2.5-2.4 (m, 1H), 2.3 (d, J = 6.8 Hz, 2H), 2.1 (m, 1H), 2-1.9 (m, 1H), 1.5-1.4 (m, 1H). | ESI-LCMS m/z: 437 purity: 96% HPLC purity: 96% |

Example-40

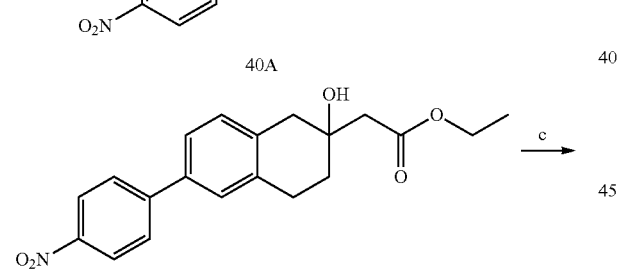

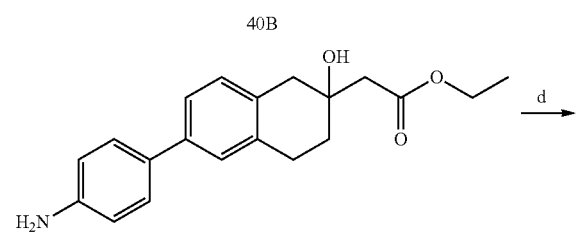

-continued

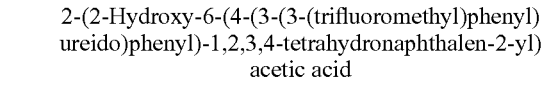

Reagents and conditions: a) Pd(PPh₃)₄, Cs₂CO₃, Dioxane-H₂O, 80° C., 4 h; b) EtOAc, LiHMDS, THF, -78° C. to RT, 4 h; c) Pd/C, MeOH, H₂, RT, 3 h; d) 3-CF₃PhNCO, Et₃N, THF, RT, 12 h; e) NaOH, MeOH—THF—H₂O, RT, 12 h.

Procedure 2-(2-Hydroxy-6-(4-(3-(3-(trifluoromethyl)phenyl) ureido)phenyl)-1,2,3,4-tetrahydronaphthalen-2-yl) acetic acid 6-(4-nitrophenyl)-3,4-dihydronaphthalen-2(1H)-one (40A)

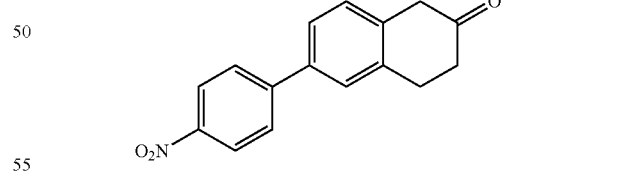

Pd(PPh₃)₄ (0.0736 g, 0.06 mmol) was added to a solution of 6-bromo-2-tetralone (1.5 g, 6.66 mmol) in 50 mL of 1,4 dioxane-H₂O (3:1) mixture under argon atmosphere, followed by cesium carbonate (6.49 g, 19.99 mmol) and 4-nitrophenyl boronic acid (1.32 g, 7.99 mmol). The reaction mixture was degassed for 5 min. The reaction mixture was refluxed for 4 h and solvent removed under reduced pressure. The residue partitioned between ethyl acetate and water. The separated organic layer was dried over sodium sulphate, filtered and removed under reduced pressure. The product was purified by flash chromatography using 18% ethyl acetate in hexane to afford title compound (0.9 g, 50%) as solid. $^1$H NMR (300 MHz, CDCl$_3$): δ 8.31 (d, J=9.0 Hz, 2H), 7.74 (d, J=8.4 Hz, 2H), 7.5 (m, 2H), 7.27 (s, 1H), 3.66 (s, 2H), 3.16 (t, J=6.9 Hz, 2H), 2.61 (t, J=6.9 Hz, 2H).

Ethyl 2-(2-hydroxy-6-(4-nitrophenyl)-1,2,3,4-tetrahydronaphthalen-2-yl)acetate (40B)

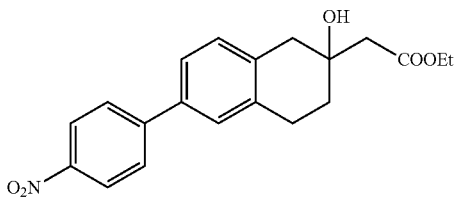

Ethyl acetate (0.44 g, 5.05 mmol) was added to a solution of Li-HMDS (0.83 g, 5.05 mmol) in 20 mL of THF at −78° C. The mixture was stirred for 15 min, followed by addition of product of Example 40A (0.4 g, 3.37 mmol). The reaction mixture was then brought to room temperature and stirred for 4 h. The reaction mixture was quenched with 1N HCl. The reaction mixture was partitioned between ethyl acetate and water. The separated organic layer was dried over sodium sulphate, filtered and removed under reduced pressure. The product was purified by flash chromatography using 30% ethyl acetate in hexane to afford title compound (0.35 g, 66%) as yellow solid. $^1$H NMR (400 MHz, CDCl$_3$): δ 8.27 (d, J=8.4 Hz, 2H), 7.70 (d, J=8.0 Hz, 2H), 7.38 (m, 2H), 7.18 (d, J=8.4 Hz, 1H), 4.24 (q, J=7.2 Hz, 2H), 3.8 (bs, 1H), 3.16 (m, 1H), 3.0 (d, J=16.8 Hz, 1H), 2.92-2.83 (m, 2H), 2.62 (s, 2H), 2.04 (m, 1H), 1.86 (m, 1H), 1.31 (t, J=8.0 Hz, 3H). ESI-MS m/z=356 (M+H)$^+$.

Ethyl 2-(6-(4-aminophenyl)-2-hydroxy-1,2,3,4-tetrahydronaphthalen-2-yl)acetate (40C)

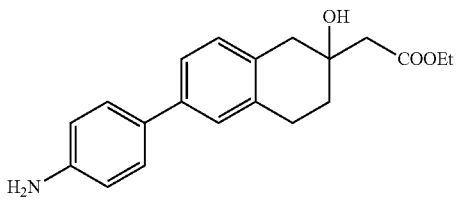

Excess 10% Pd/C (0.15 g) was added to a solution of product of Example 40B (0.35 g, 0.98 mmol) in 10 mL of ethanol. The reaction mixture was stirred under H$_2$ atmosphere at room temperature for 3 h. The reaction mixture was filtered over celite bed, filtrate was removed under reduced pressure and residue was partitioned between ethyl acetate and water. The separated organic layer was dried over sodium sulphate, filtered and removed in vacuum. The crude product was washed with diethyl ether and pentane to afford title compound (0.26 g, 81%) as solid. $^1$H NMR (400 MHz, CDCl$_3$): δ 7.38 (d, J=7.2 Hz, 2H), 7.28 (m, 2H), 7.08 (d, J=8.0 Hz, 1H), 6.74 (d, J=8.0 Hz, 2H), 4.24 (q, J=6.8 Hz, 2H), 3.80 (bs, 2H), 3.10 (m, 1H), 2.99-2.79 (m, 3H), 2.62 (s, 2H), 2.01 (m, 1H), 1.83 (m, 1H), 1.29 (t, J=6.4 Hz, 3H). ESI-MS m/z=326 (M+H)$^+$.

Ethyl 2-(2-hydroxy-6-(4-(3-(3-(trifluoromethyl)phenyl)ureido)phenyl)-1,2,3,4-tetrahydronaphthalen-2-yl)-acetate (40D)

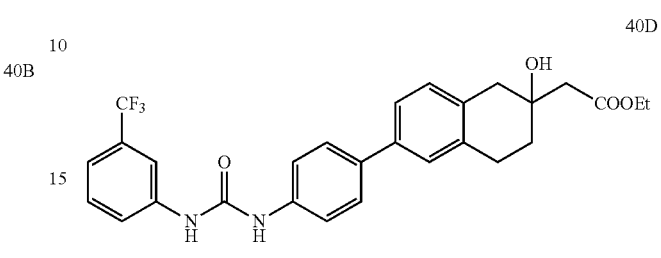

3-(Trifluoromethyl)phenyl isocyanate (0.082 g, 0.44 mmol) was added to a solution of product of Example 40C (0.13 g, 0.40 mmol) and triethylamine (0.12 g, 1.20 mmol) in THF (10 mL). The reaction mixture was stirred at room temperature overnight. The solvent was removed under reduced pressure, and product purified by flash chromatography using 20% ethyl acetate in hexanes to afford title compound (0.1 g, 50%) as pale yellow solid. $^1$H NMR (300 MHz, DMSO-d$_6$): δ 9.05 (s, 1H), 8.86 (s, 1H), 8.02 (s, 1H), 7.62-7.50 (m, 6H), 7.35-7.25 (m, 3H), 7.08 (m, 1H), 4.7 (s, 1H), 4.07 (q, J=6.9 Hz, 2H), 2.90 (m, 2H), 2.75 (m, 2H), 2.5 (s, 2H), 1.86 (m, 2H), 1.20 (t, J=7.8 Hz, 3H). ESI-MS m/z=513 (M+H)$^+$.

2-(2-Hydroxy-6-(4-(3-(3-(trifluoromethyl)phenyl)ureido)phenyl)-1,2,3,4-tetrahydronaphthalen-2-yl)acetic acid (40)

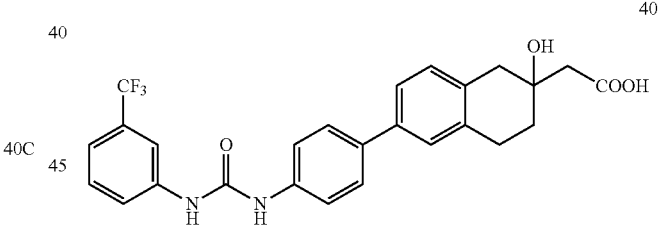

Sodium hydroxide (0.023 g, 0.58 mmol) was added to a solution of product of Example 40D (0.1 g, 0.19 mmol) in 15 mL THF-methanol-water (2:1:1) mixture. The reaction mixture was stirred at room temperature overnight. After the solvent was removed in vacuum, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.06 g, 63%) as brown solid. $^1$H NMR (300 MHz, DMSO-d$_6$): δ 12.2 (bs, 1H), 9.1 (s, 1H), 8.9 (s, 1H), 8.03 (s, 1H), 7.65-7.45 (m, 6H), 7.4-7.35 (m, 3H), 7.08 (d, J=8.4 Hz, 1H), 4.8 (bs, 1H), 3.05-2.95 (m, 2H), 2.8 (m, 2H), 2.5 (s, 2H), 1.85 (m, 2H); ESI-MS m/z=485 (M+H)$^+$.

Examples 41 was prepared by the procedures analogous to those described in Example 40 using appropriate starting materials.

| Ex | Structure | ¹H NMR Data | Mass/purity |
|---|---|---|---|
| 41 | 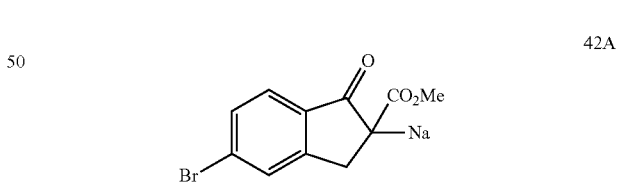 | ¹H NMR (400 MHz, DMSO-d$_6$): δ 12.2 (bs, 1H), 9.24 (s, 1H), 9.0 (s, 1H), 7.64 (m, 4H), 7.55 (m, 4H), 7.3 (m, 2H), 7.08 (d, J = 8.4 Hz, 1H), 4.7 (bs, 1H), 3.05-2.95 (m, 2H), 2.85-2.75 (m, 2H), 2.5 (s, 2H), 1.85 (m, 2H). | ESI-MS m/z = 485 (M + H)$^+$; LCMS purity: 96%. |

Example 42

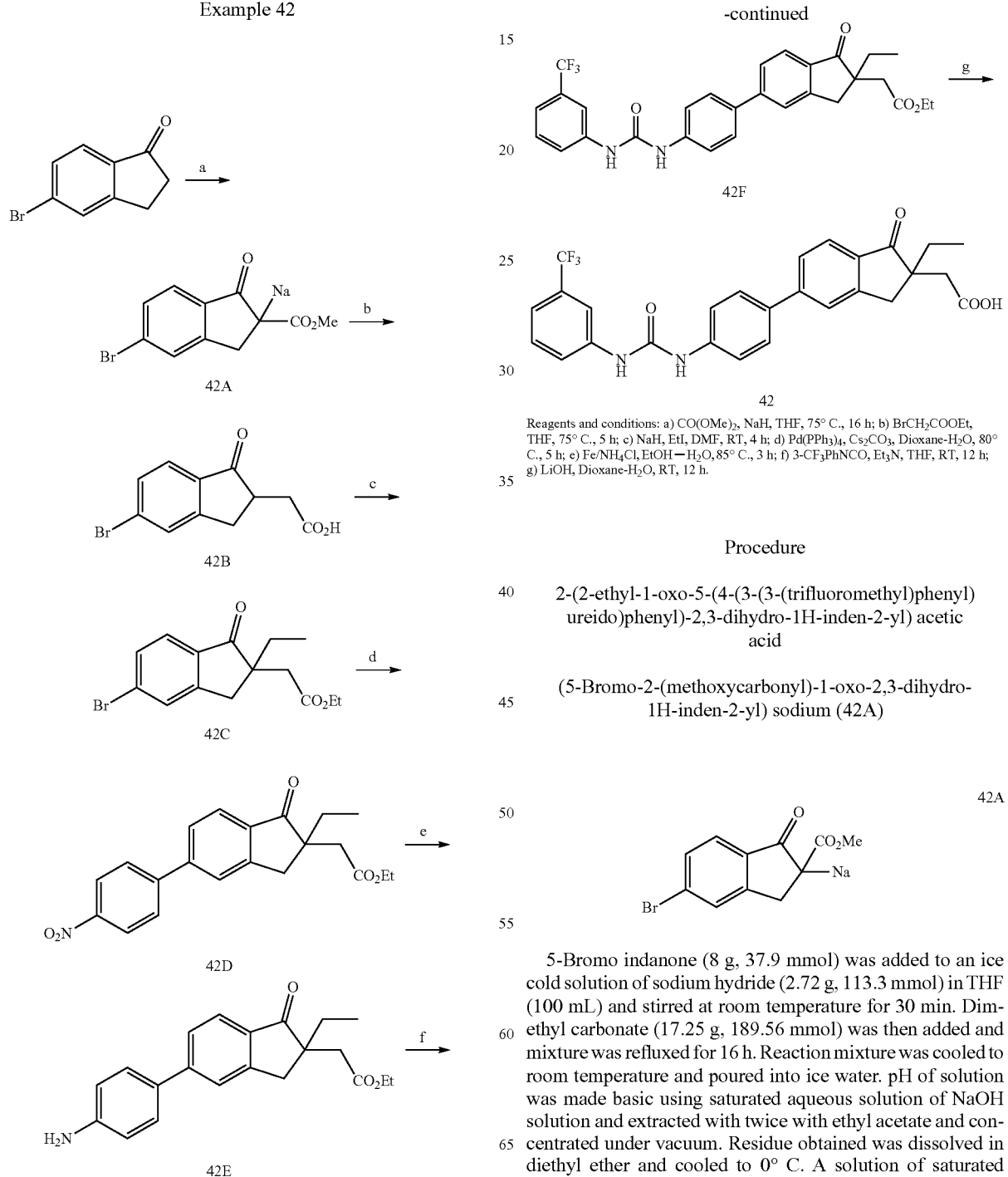

Reagents and conditions: a) CO(OMe)$_2$, NaH, THF, 75° C., 16 h; b) BrCH$_2$COOEt, THF, 75° C., 5 h; c) NaH, EtI, DMF, RT, 4 h; d) Pd(PPh$_3$)$_4$, Cs$_2$CO$_3$, Dioxane-H$_2$O, 80° C., 5 h; e) Fe/NH$_4$Cl, EtOH—H$_2$O, 85° C., 3 h; f) 3-CF$_3$PhNCO, Et$_3$N, THF, RT, 12 h; g) LiOH, Dioxane-H$_2$O, RT, 12 h.

Procedure 2-(2-ethyl-1-oxo-5-(4-(3-(3-(trifluoromethyl)phenyl) ureido)phenyl)-2,3-dihydro-1H-inden-2-yl) acetic acid (5-Bromo-2-(methoxycarbonyl)-1-oxo-2,3-dihydro-1H-inden-2-yl) sodium (42A)

5-Bromo indanone (8 g, 37.9 mmol) was added to an ice cold solution of sodium hydride (2.72 g, 113.3 mmol) in THF (100 mL) and stirred at room temperature for 30 min. Dimethyl carbonate (17.25 g, 189.56 mmol) was then added and mixture was refluxed for 16 h. Reaction mixture was cooled to room temperature and poured into ice water. pH of solution was made basic using saturated aqueous solution of NaOH solution and extracted with twice with ethyl acetate and concentrated under vacuum. Residue obtained was dissolved in diethyl ether and cooled to 0° C. A solution of saturated aqueous solution of NaOH was added (10 mL) while stirring.

Resulting sodium salt was collected by filtration and dried under vacuum to afford crude title compound (7 g) as solid. ¹H NMR (400 MHz, DMSO-$d_6$): δ 7.52 (s, 1H), 7.40 (m, 1H), 7.34 (m, 1H), 3.52 (s, 3H), 3.3 (s, 2H).

2-(5-Bromo-1-oxo-2,3-dihydro-1H-inden-2-yl)acetic acid (42B)

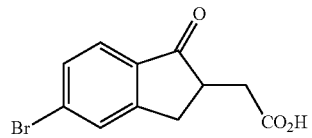

42B

Ethyl bromo acetate (10.08 g, 60 mmol) was added to a solution of product of Example 42A (7 g, 24 mmol) in THF (50 mL). The reaction mixture was refluxed for 5 h. Reaction mixture was cooled and partitioned between ethyl acetate and water. Separated organic layer was washed with brine, dried over sodium sulphate, filtered and concentrated under vacuum. 1:1 HCl-acetic acid mixture (40 mL) was added to residue and refluxed for 16 h. Reaction mixture was cooled to 0° C., and solids were collected by filtration, washed with water and dried under vacuum to afford title compound (6 g, 60%) as solid. ¹H NMR (400 MHz, DMSO-$d_6$): δ 7.84 (s, 1H), 7.62-7.56 (m, 2H), 3.4-3.3 (m, 1H), 3.0-2.84 (m, 2H), 2.8-2.6 (m, 2H).

Ethyl 2-(5-bromo-2-ethyl-1-oxo-2,3-dihydro-1H-inden-2-yl) acetate (42C)

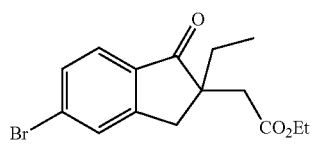

42C

A solution of product of Example 42B (4.5 g, 16.8 mmol) in DMF (30 mL) was added over a period of 30 min to an ice cold solution of NaH (2 g, 50 mmol) in DMF (50 mL). The reaction mixture was stirred for 10 min. Ethyl iodide (13.1 g, 84.2 mmol) was then added and the mixture was stirred for 4 h at room temperature. The reaction was then brought to 0° C., excess NaH was quenched with ice water and extracted aqueous layer with ethyl acetate (2×100 mL). The combined organic layers were dried over sodium sulphate, filtered and removed under vacuum to give crude title compound (1 g, 18%) as solid. ¹H NMR (400 MHz, CDCl₃): δ 7.64-7.6 (m, 2H), 7.5 (m, 1H), 4.0 (m, 2H), 3.18 (d, J=17.2 Hz, 1H), 3.01 (d, J=17.2 Hz, 1H), 2.86 (d, J=16.4 Hz, 1H), 2.66 (d, J=16.8 Hz, 1H), 1.6 (m, 2H), 1.1 (t, J=7.3 Hz, 3H), 0.75 (t, J=7.6 Hz, 3H).

Ethyl 2-(2-ethyl-5-(4-nitrophenyl)-1-oxo-2,3-dihydro-1H-inden-2-yl) acetate (42D)

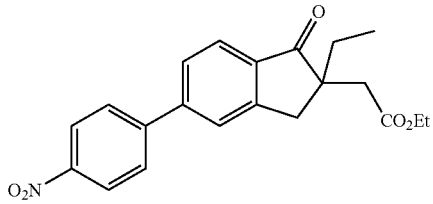

42D

Pd(PPh₃)₄ (0.037 g, 0.032 mmol) was added to a solution of product of Example 42C (0.87 g, 2.7 mmol) in 20 mL 1,4 dioxane-H₂O (3:1) mixture under Argon atmosphere, followed by cesium carbonate (2.6 g, 8.1 mmol) and 4-nitrophenyl boronic acid (0.497 g, 2.9 mmol). The reaction mixture was degassed for 10 min. The reaction mixture was refluxed for 5 h and solvent removed under reduced pressure. The residue partitioned between ethyl acetate and water. The separated organic layer was dried over sodium sulphate, filtered and removed under reduced pressure. The product was purified by flash chromatography eluting with 20% ethyl acetate in hexane to afford title compound (0.8 g, 90%) as solid. ¹H NMR (300 MHz, CDCl₃): δ 8.4-8.3 (m, 2H), 7.86 (m, 1H), 7.76 (m, 2H), 7.7-7.6 (m, 2H), 4.0 (q, J=6.3 Hz, 2H), 3.28 (d, J=17.7 Hz, 1H), 3.11 (d, J=17.4 Hz, 1H), 2.92 (d, J=16.2 Hz, 1H), 2.7 (d, J=16.8 Hz, 1H), 1.8-1.6 (m, 2H), 1.1 (t, J=7.2 Hz, 3H), 0.8 (t, J=6.9 Hz, 3H).

Ethyl 2-(5-(4-aminophenyl)-2-ethyl-1-oxo-2,3-dihydro-1H-inden-2-yl) acetate (42E)

42E

Iron powder (0.36 g, 6.5 mmol) was added to a solution of product of Example 42D (0.8 g, 2.17 mmol) in 15 mL ethanol-water mixture (2:1) followed by NH₄Cl (0.058 g, 1.08 mmol). The reaction mixture was refluxed for 3 h. The solvent was removed under reduced pressure and residue partitioned between ethyl acetate and water. The separated organic layer was dried over sodium sulphate, filtered and removed in vacuo to give title compound (0.65 g, 88%). ¹H NMR (300 MHz, CDCl₃): δ 7.76 (d, J=8.4 Hz, 1H), 7.58-7.52 (m, 2H), 7.5-7.44 (m, 2H), 6.8-6.76 (m, 2H), 4.0 (m, 2H), 3.2 (d, J=17.4 Hz, 1H), 3.05 (d, J=16.8 Hz, 1H), 2.84 (d, J=15.6 Hz, 1H), 2.66 (d, J=16.8 Hz, 1H), 1.8-1.6 (m, 2H), 1.05 (m, 3H), 0.8 (m, 3H).

73

Ethyl 2-(2-ethyl-1-oxo-5-(4-(3-(3-(trifluoromethyl)phenyl)ureido)phenyl)-2,3-dihydro-1H-inden-2-yl)acetate (42F)

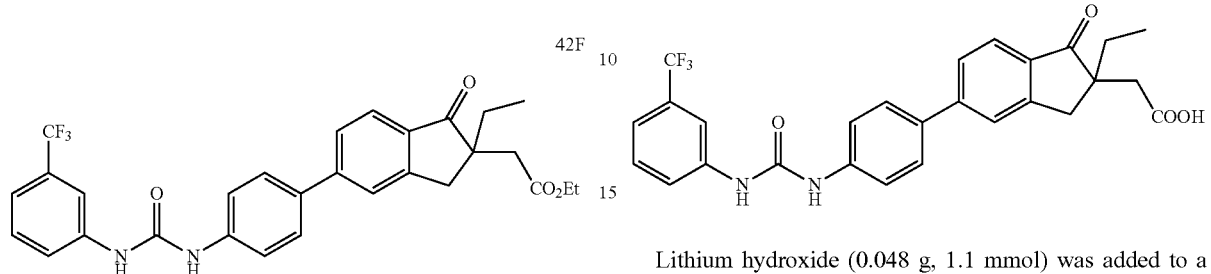

3-(Trifluoromethyl)phenyl isocyanate (0.12 g, 0.65 mmol) was added to a solution of product of Example 42E (0.22 g, 0.65 mmol) and triethylamine (0.2 g, 1.95 mmol) in THF (10 mL) and stirred at room temperature overnight. The solvent was removed under reduced pressure and product triturated with diethyl ether and pentane to afford title compound (0.21 g, 54%) as solid. $^1$H NMR (300 MHz, CDCl$_3$): δ 7.78-7.7 (m, 2H), 7.68-7.62 (m, 1H), 7.54 (m, 1H), 7.44-7.36 (m, 4H), 7.34 (m, 1H), 7.28 (m, 2H), 4.0 (q, J=6.9 Hz, 2H), 3.2 (d, J=17.4 Hz, 1H), 3.1 (d, J=17.4 Hz, 1H), 3.0 (d, J=16.5 Hz, 1H), 2.7 (d, J=16.8 Hz, 1H), 1.7 (m, 2H), 1.1 (t, J=6.9 Hz, 3H), 0.8 (t, J=7.8 Hz, 3H).

74

2-(2-Ethyl-1-oxo-5-(4-(3-(3-(trifluoromethyl)phenyl)ureido)phenyl)-2,3-dihydro-1H-inden-2-yl)acetic acid (42)

Lithium hydroxide (0.048 g, 1.1 mmol) was added to a solution of product of Example 42F (0.2 g, 0.38 mmol) in 4 mL of 1,4-dioxane-water (3:1) mixture. The reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.15 g, 79%) as solid. $^1$H NMR (400 MHz, DMSO-d6): δ 8.1 (s, 1H), 7.8-7.6 (m, 4H), 7.46-7.4 (m, 3H), 7.3-7.2 (m, 3H), 3.2 (d, J=17.2 Hz, 1H), 3.0 (d, J=17.2 Hz, 1H), 2.7 (d, J=16.4 Hz, 1H), 2.5 (d, J=16.4 Hz, 1H), 1.5 (m, 2H), 0.7 (t, J=7.2 Hz, 3H); ESI-MS m/z: 497 (M+H); HPLC purity: 95.6%.

Examples 43-46 were prepared by the procedures analogous to those described in Example 42 using appropriate starting materials except that for Examples 43-45, alkylation step with ethyl iodide in the presence of NaH as in Example 42 was not performed.

| Ex | Structure | $^1$H NMR Data | Mass/Purity |
|---|---|---|---|
| 43 | 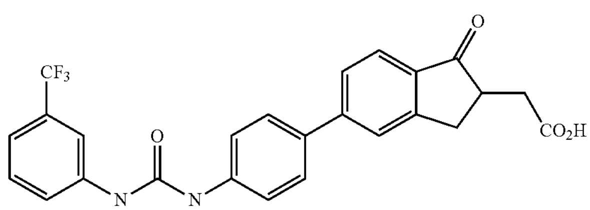 [SMILES: O=C(O)CC1Cc2cc(-c3ccc(NC(=O)Nc4cccc(C(F)(F)F)c4)cc3)ccc2C1=O] | $^1$H NMR (300 MHz, DMSO-d$_6$): δ 12.2 (bs, 1H), 9.15 (s, 1H), 9.05 (bs, 1H), 8.05 (bs, 1H), 7.85 (s, 1H), 7.75-7.66 (m, 4H), 7.65-7.5 (m, 5H), 3.4 (m, 1H), 3.0-2.9 (m, 2H), 2.8-2.6 (m, 2H). | ESI-MS m/z = 469 (M + H)$^+$; HPLC purity: 91.8%. |
| 44 | 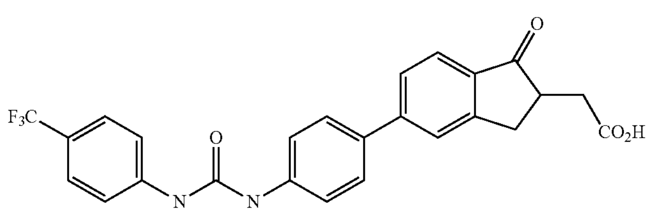 [SMILES: O=C(O)CC1Cc2cc(-c3ccc(NC(=O)Nc4ccc(C(F)(F)F)cc4)cc3)ccc2C1=O] | $^1$H NMR (300 MHz, DMSO-d$_6$): δ 12.3 (bs, 1H), 9.3 (bs, 1H), 9.1 (bs, 1H), 7.86 (s, 1H), 7.8-7.9 (m, 10H), 3.4 (m, 1H), 3.0-2.6 (m, 4H). | ESI-MS m/z = 469 (M + H)$^+$; HPLC purity: 93.7%. |
| 45 | 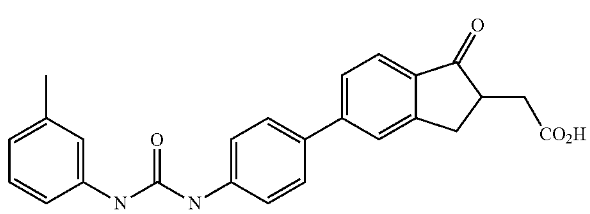 [SMILES: Cc1cccc(NC(=O)Nc2ccc(-c3ccc4c(c3)CC(CC(=O)O)C4=O)cc2)c1] | $^1$H NMR (300 MHz, DMSO-d$_6$): δ 12.3 (bs, 1H), 9.0 (bs, 1H), 8.8 (bs, 1H), 7.8 (s, 1H), 7.7 (m, 4H), 7.56 (m, 2H), 7.3 (s, 1H), 7.28-7.0 (m, 2H), 6.8 (m, 1H), 3.4 (m, 1H), 3.0-2.86 (m, 2H), 2.8-2.6 (m, 2H), 2.26 (s, 3H). | ESI-MS m/z = 415 (M + H)$^+$; LCMS purity: 91%. |

| Ex | Structure | ¹H NMR Data | Mass/Purity |
|---|---|---|---|
| 46 | 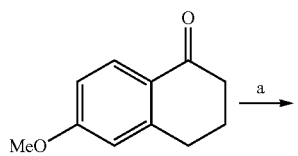 | ¹H NMR (400 MHz, DMSO-d₆): δ 9.25 (bs, 1H), 7.8-7.5 (m, 8H), 7.3 (bs, 2H), 7.0 (s, 1H), 3.2 (d, J = 17.2 Hz, 1H), 3.05 (d, J = 17.2 Hz, 1H), 2.7 (d, J = 16.4 Hz, 1H), 2.5 (d, J = 16.4 Hz, 1H), 1.5 (m, 2H), 0.8 (t, J = 6.8 Hz, 3H). | ESI-MS m/z: 463 (M + H); HPLC purity: 95%. |

Example 47

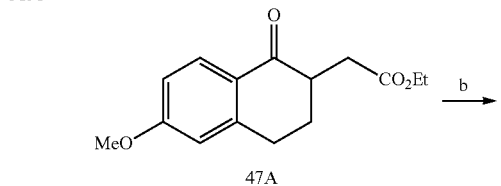

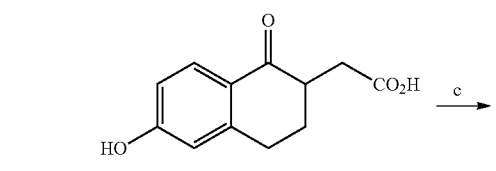

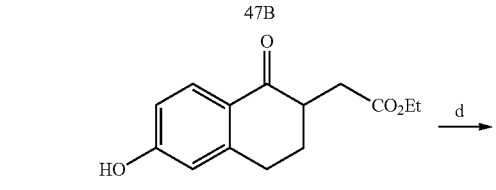

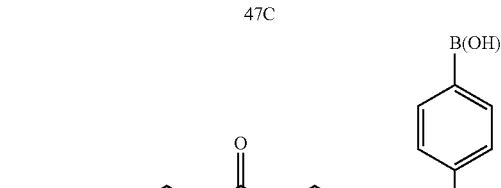

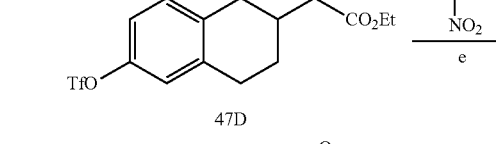

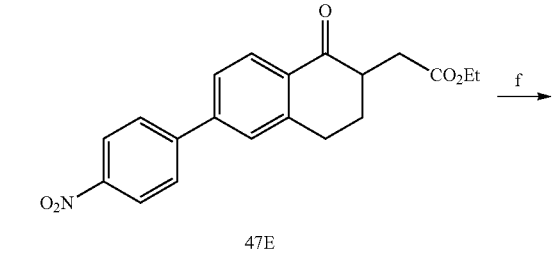

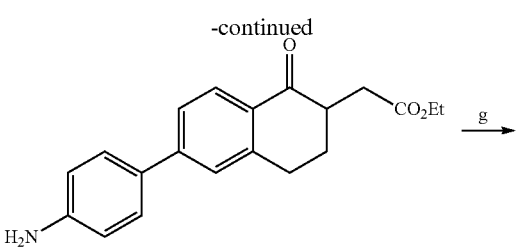

47F

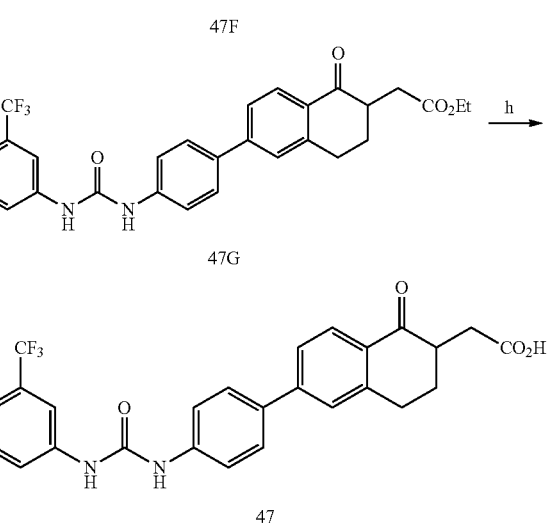

Reagents and conditions: a) n-BuLi, i-Pr₂NH₂, -60° C., 16 h; b) Aq. HBr, 100° C., 16 h; c) MeSO₃H, EtOH, RT, 5 h; d) Tf₂O, CH₂Cl₂, Et₃N, RT, 2 h; e) Pd(PPh₃)₄, Cs₂CO₃, Dioxane-H₂O, 80° C., 2 h; f) Pd/C, H₂, EtOH, RT, 3 h; g) 3-CF₃PhNCO, Et₃N, THF, RT, 12 h; h) LiOH, EtOH—H₂O, RT, 12 h.

Procedures 2-(1-Oxo-6-(4-(3-(3-(trifluoromethyl)phenyl)ureido)phenyl)-1,2,3,4-tetrahydronaphthalen-2-yl)acetic acid 2-(6-Methoxy-1-oxo-1,2,3,4-tetrahydronaphthalen-2-yl)acetic acid (47A)

n-Butyl lithium (3.27 g, 51.04 mmol) was added to a solution of di-isopropyl amine (6.88 g, 68.11 mmol) in THF (50 mL) at −60° C., and the mixture was stirred for 0.5 h. 6-methoxy-1-tetralone (6 g, 34.09 mmol) in THF (10 mL) was slowly added to the reaction mixture, the mixture was stirred for 45 min and ethyl bromoacetate (11.9 g, 71.25 mmol) was added. The reaction mixture was then stirred at room temperature for 16 h and quenched with saturated NH₄Cl solution. The reaction mixture was extracted with EtOAc (X2), combined organic layers were washed with brine, dried over anhydrous Na₂SO₄, filtered and concentration to give 5.3 g of the title compound.

Alternatively Example 47A can be obtained using similar procedures as described for Example 79C.

2-(6-Hydroxy-1-oxo-1,2,3,4-tetrahydronaphthalen-2-yl)acetic acid (47B)

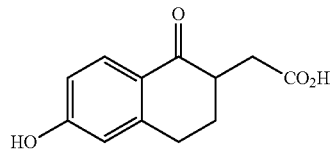

47B

Aqueous HBr (75 mL) was added to product of Example 47A (5 g, 19.08 mmol), and the reaction mixture was refluxed for 16 h. The reaction mixture was then brought to room temperature and extracted with ethyl acetate (2×100 mL). The organic layer was dried over sodium sulphate, filtered and removed under reduced pressure. The crude product was purified by flash chromatography using 25% ethyl acetate in pet ether to afford title compound (3 g, 71%) as solid. ¹H NMR (400 MHz, DMSO-d₆): δ 12.07 (bs, 1H), 10.3 (bs, 1H), 7.73 (d, J=8.4 Hz, 1H), 6.7 (m, 1H), 6.6 (m, 1H), 3.3-2.93 (m, 2H), 2.84-2.77 (m, 1H), 2.68 (m, 1H), 2.35 (m, 1H), 2.1 (m, 1H), 1.85 (m, 1H).

Ethyl 2-(6-hydroxy-1-oxo-1,2,3,4-tetrahydronaphthalen-2-yl)acetate (47C)

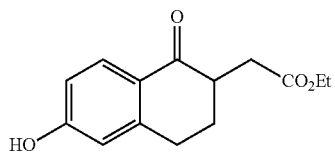

47C

Methanesulphonic acid (5 mL) was added to a solution of Example 47B (2 g, 9.09 mmol) in ethanol (30 mL), and the mixture was stirred at room temperature for 6 h. Ethanol was removed from reaction mixture under reduced pressure, and residue was diluted with ethyl acetate and washed with brine solution. The organic layer was dried over sodium sulphate, filtered and removed under vacuum to afford title compound (2.15 g, 97%) as solid. ¹H NMR (400 MHz, CDCl₃): δ 7.94 (d, J=8.4 Hz, 1H), 6.76 (d, J=8.4 Hz, 2H), 6.26 (bs, 1H), 4.2 (q, J=6.8 Hz, 2H), 3.1-2.85 (m, 4H), 2.4 (m, 1H), 2.2 (m, 1H), 1.95 (m, 1H), 0.8 (t, J=6.8 Hz, 3H).

Ethyl 2-(1-oxo-6-(trifluoromethylsulfonyloxy)-1,2,3,4-tetrahydronaphthalen-2-yl) acetate (47D)

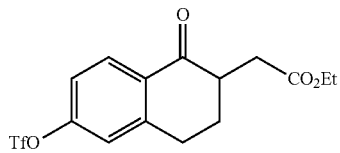

47D

Triflic anhydride (3.41 g, 12.09 mmol) was added to an ice cold solution of product of Example 47C (3 g, 12.09 mmol) and pyridine (1.05 g, 13.29 mmol) in dichloromethane (50 mL). The reaction mixture was stirred at room temperature for 2 h. The reaction mixture was diluted with dichloromethane (50 mL) and washed with saturated aqueous solution of NaCl (50 mL). The organic layer was dried over sodium sulphate, filtered and removed under reduced pressure. The product was purified by flash chromatography using 5% ethyl acetate in pet ether to give title compound (2.8 g, 62%) as solid. ¹H NMR (400 MHz, CDCl₃): δ 8.12 (d, J=8.8 Hz, 1H), 7.24-7.12 (m, 2H), 4.2 (q, J=6.8 Hz, 2H), 3.2 (m, 1H), 3.1-2.9 (m, 3H), 2.5 (m, 1H), 2.3 (m, 1H), 2.0 (m, 1H), 1.2 (t, J=6.8 Hz, 3H).

Ethyl 2-(6-(4-nitrophenyl)-1-oxo-1,2,3,4-tetrahydronaphthalen-2-yl) acetate (47E)

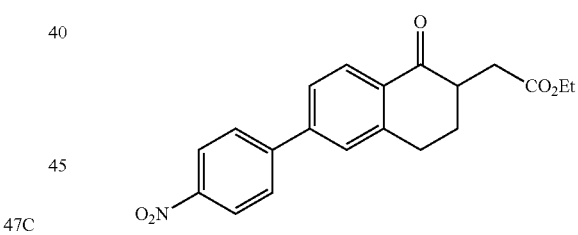

47E

Pd(PPh₃)₄ (0.174 g, 0.15 mmol) was added to a solution of product of Example 47D (4.8 g, 12.6 mmol) in 26 mL of 1,4 dioxane-H₂O (4:1) mixture under argon atmosphere, followed by cesium carbonate (11.73 g, 36 mmol) and 4-nitrophenyl boronic acid (2.3 g, 13.8 mmol). The reaction mixture was degassed for 5 min. The reaction mixture was refluxed for 2 h and solvent was removed under reduced pressure. The residue was partitioned between ethyl acetate and water. The separated organic layer was dried over sodium sulphate, filtered and concentrated under reduced pressure to give crude product which was purified by flash chromatography to afford title compound (2.2 g, 59%) as solid. ¹H NMR (400 MHz, CDCl₃): δ 8.4 (d, J=7.6 Hz, 2H), 8.15 (d, J=8.4 Hz, 1H), 7.78 (d, J=7.2 Hz, 2H), 7.58 (d, J=8.4 Hz, 1H), 7.5 (s, 1H), 4.2 (q, J=6.8 Hz, 2H), 3.3-3.0 (m, 4H), 2.5 (m, 1H), 2.3 (m, 1H), 2.05 (m, 1H), 1.3 (t, J=6.8 Hz, 3H).

Ethyl 2-(6-(4-aminophenyl)-1-oxo-1,2,3,4-tetrahydronaphthalen-2-yl) acetate (47F)

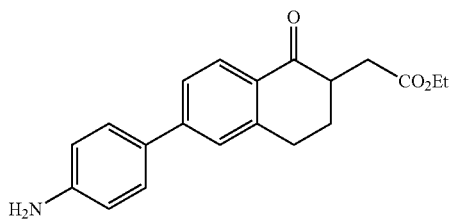

47F

Excess 10% Pd/C (0.2 g) was added to a solution of product of Example 47E (1.1 g, 3.11 mmol) in 30 mL of ethanol, and the mixture was stirred at room temperature for 3 h. The reaction mixture was filtered over celite bed, filtrate was concentrated under reduced pressure and the residue was partitioned between ethyl acetate and water. The separated organic layer was dried over sodium sulphate, filtered and concentrated in vacuo. The crude product was washed with diethylether and pentane to afford title compound (0.8 g, 80%) as solid. $^1$H NMR (400 MHz, CDCl$_3$): δ 8.04 (m, 1H), 7.46-7.39 (m, 4H), 6.75 (m, 2H), 4.19 (m, 2H), 3.8 (bs, 2H), 3.14-3.04 (m, 4H), 2.42 (m, 1H), 2.26 (m, 1H), 2.0 (m, 1H), 1.29 (m, 3H).

Ethyl 2-(1-oxo-6-(4-(3-(3-(trifluoromethyl)phenyl)ureido)phenyl)-1,2,3,4-tetrahydronaphthalen-2-yl) acetate (47G)

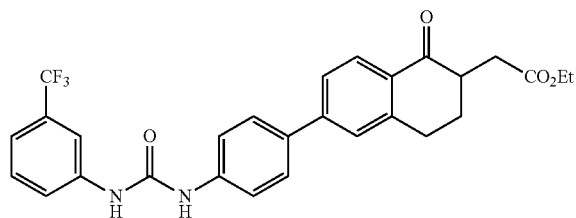

47G 3-(Trifluoromethyl)phenyl isocyanate (0.234 g, 0.18 mmol) was added to a solution of product of Example 47F (0.26 g, 0.18 mmol) and triethylamine (0.656 g, 0.55 mmol) in THF (5 mL). The reaction mixture was stirred at room temperature overnight. The solvent was removed under reduced pressure and product purified by flash chromatography using 20% ethyl acetate in hexanes to afford title compound (0.1 g, 31%) as solid. $^1$H NMR (300 MHz, DMSO-d$_6$): δ 9.3 (bs, 1H), 9.0 (bs, 1H), 8.04 (s, 1H), 7.9 (m, 1H), 7.79-7.46 (m, 8H), 7.34 (m, 1H), 4.1 (q, J=6.8 Hz, 2H), 3.2-2.9 (m, 3H), 2.75 (m, 2H), 2.2 (m, 1H), 1.2 (t, J=6.8 Hz, 3H).

2-(1-Oxo-6-(4-(3-(3-(trifluoromethyl)phenyl)ureido)phenyl)-1,2,3,4-tetrahydronaphthalen-2-yl)acetic acid (47)

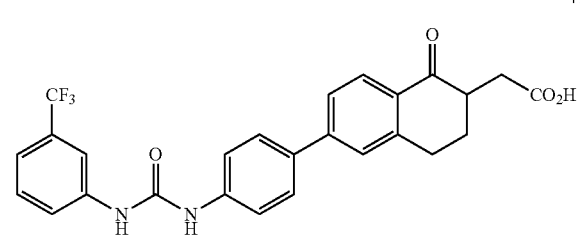

47

Lithium hydroxide (0.015 g, 0.35 mmol) was added to a solution of product of Example 47H (0.06 g, 0.11 mmol) in 4 mL of ethanol-water (3:1) mixture. The reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.042 g, 75%) as white solid. $^1$H NMR (300 MHz, DMSO-d$_6$): δ 12.0 (bs, 1H), 9.4-9.0 (bs, 2H), 8.0 (m, 1H), 7.9 (m, 1H), 7.7-7.54 (m, 7H), 7.46 (m, 1H), 7.3 (m, 1H), 3.2-3.0 (m, 2H), 2.8 (m, 1H), 2.5 (m, 2H), 2.2 (m, 1H), 2.0 (m, 1H); ESI-MS m/z=483 (M+H)$^+$; HPLC purity: 92.5%.

Examples 48-67 were prepared by the analogous procedures as described above for Example 47 using appropriate starting materials. The requisite boronic acids (and appropriately functional-group-protected versions thereof) utilized herein were purchased if available commercially, were synthesized as described in the literature or by routine modifications thereof known by those skilled in the art, or were synthesized by alternative procedures known by those skilled in the art.

| Ex | Structure | $^1$H NMR Data | Mass/Purity |
| --- | --- | --- | --- |
| 48 | ![structure] | $^1$H NMR (400 MHz, DMSO-d$_6$): δ 12.2 (bs, 1H), 9.25 (bs, 1H), 9.05 (bs, 1H), 7.9 (d, J = 8.4 Hz, 1H), 7.75-7.55 (m, 10H), 3.2-2.8 (m, 2H), 2.7 (m, 1H), 2.4 (m, 2H), 2.2 (m, 1H), 2.0 (m, 1H). | ESI-MS m/z = 483 (M + H)$^+$; HPLC purity: 90%. |

-continued

| Ex | Structure | ¹H NMR Data | Mass/Purity |
|---|---|---|---|
| 49 | 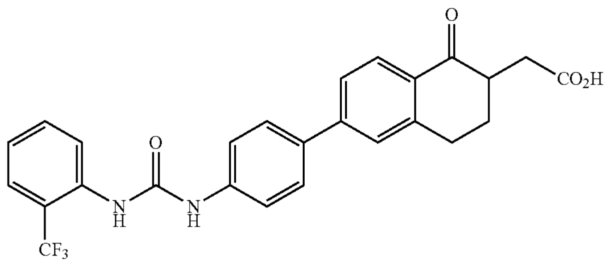 [SMILES: O=C(O)CC1CCc2cc(-c3ccc(NC(=O)Nc4ccccc4C(F)(F)F)cc3)ccc2C1=O] | ¹H NMR (400 MHz, DMSO-d₆): δ 12.2 (bs, 1H), 9.6 (bs, 1H), 8.2 (bs, 1H), 8.0-7.9 (m, 2H), 7.8-7.5 (m, 8H), 7.3 (t, J = 8.0 Hz, 1H), 3.2-2.9 (m, 2H), 2.7 (m, 1H), 2.4 (m, 2H), 2.2 (m, 1H), 2.0 (m, 1H). | ESI-MS m/z = 483 (M + H)⁺; HPLC purity: 95%. |
| 50 | 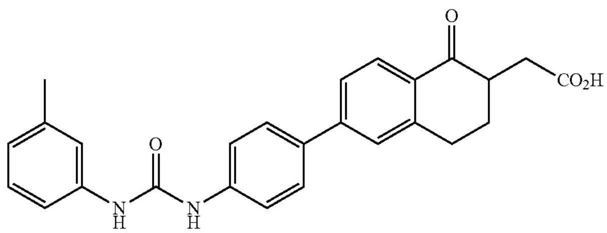 [SMILES: Cc1cccc(NC(=O)Nc2ccc(-c3ccc4c(c3)CCC(CC(=O)O)C4=O)cc2)c1] | ¹H NMR (400 MHz, DMSO-d₆): δ 12.2 (bs, 1H), 8.85 (bs, 1H), 8.65 (bs, 1H), 7.9 (d, J = 8.4 Hz, 1H), 7.74-7.54 (m, 6H), 7.3 (s, 1H), 7.24 (m, 1H), 7.16 (m, 1H), 6.8 (d, J = 6.8 Hz, 1H), 3.2-2.9 (m, 2H), 2.7 (m, 1H), 2.4 (m, 2H), 2.26 (s, 3H), 2.2 (m, 1H), 2.0 (m, 1H). | ESI-MS m/z = 429 (M + H)⁺; LCMS purity: 95%. |
| 51 | 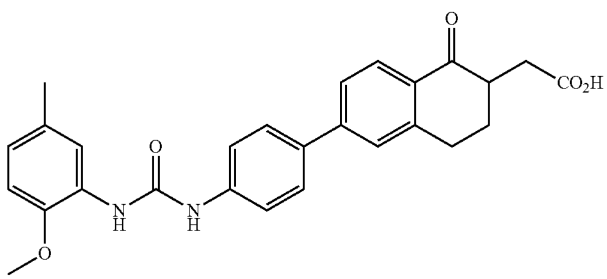 [SMILES: COc1ccc(C)cc1NC(=O)Nc1ccc(-c2ccc3c(c2)CCC(CC(=O)O)C3=O)cc1] | ¹H NMR (400 MHz, DMSO-d₆): δ 12.2 (bs, 1H), 9.5 (bs, 1H), 8.2 (bs, 1H), 8.0 (s, 1H), 7.9 (m, 1H), 7.7-7.5 (m, 6H), 6.9 (m, 1H), 6.8 (m, 1H), 3.8 (s, 3H), 3.2-2.9 (m, 2H), 2.7 (m, 1H), 2.4 (m, 2H), 2.26 (s, 3H), 2.2 (m, 1H), 2.0 (m, 1H). | ESI-MS m/z = 459 (M + H)⁺; LCMS purity: 96.7%. |
| 52 | 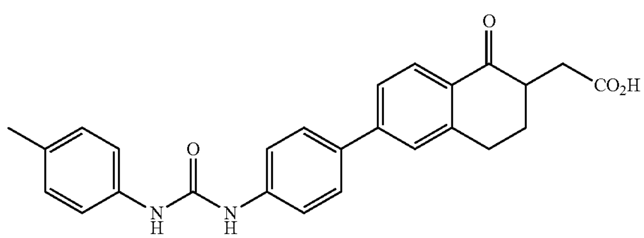 [SMILES: Cc1ccc(NC(=O)Nc2ccc(-c3ccc4c(c3)CCC(CC(=O)O)C4=O)cc2)cc1] | ¹H NMR (300 MHz, DMSO-d₆): δ 12.0 (bs, 1H), 9.6 (bs, 1H), 9.3 (bs, 1H), 7.9 (d, J = 8.4 Hz, 1H), 7.7-7.5 (m, 6H), 7.4 (m, 2H), 7.06 (m, 2H), 3.2-2.8 (m, 3H), 2.7-2.6 (m, 2H), 2.26 (s, 3H), 2.2 (m, 1H), 2.0 (m, 1H). | HPLC purity: 91%. |
| 53 | 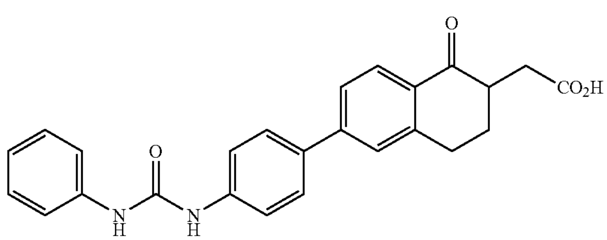 [SMILES: O=C(O)CC1CCc2cc(-c3ccc(NC(=O)Nc4ccccc4)cc3)ccc2C1=O] | ¹H NMR (400 MHz, DMSO-d₆): δ 12.0 (bs, 1H), 9.4 (bs, 1H), 9.2 (bs, 1H), 7.9 (d, J = 8.1 Hz, 1H), 7.7-7.45 (m, 8H), 7.25 (t, J = 7.5 Hz, 2H), 6.95 (t, J = 7.8 Hz, 1H), 3.2-2.85 (m, 2H), 2.7 (m, 1H), 2.4 (m, 2H), 2.2 (m, 1H), 2.0 (m, 1H). | HPLC purity: 92%. |
| 54 | 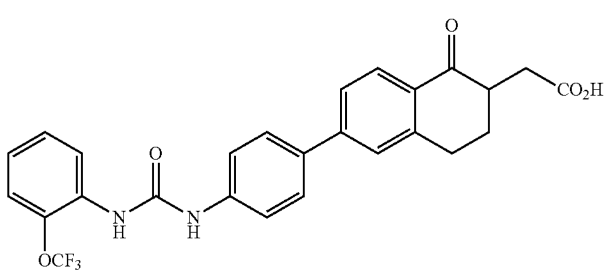 | ¹H NMR (300 MHz, DMSO-d₆): δ 12.0 (bs, 1H), 9.5 (bs, 1H), 8.6 (bs, 1H), 8.36 (m, 1H), 7.9 (m, 1H), 7.76-7.56 (m, 6H), 7.38 (m, 2H), 7.3 (m, 1H), 3.2-2.9 (m, 2H), 2.7 (m, 1H), 2.4 (m, 2H), 2.2 (m, 1H), 2.0 (m, 1H). | HPLC purity: 94.7%. |

-continued

| Ex | Structure | ¹H NMR Data | Mass/Purity |
|---|---|---|---|
| 55 | 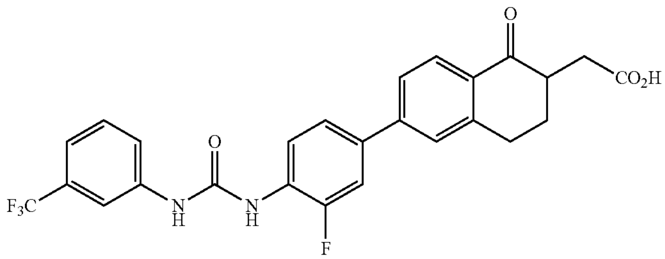 [SMILES: O=C(O)CC1CCc2cc(-c3ccc(NC(=O)Nc4cccc(C(F)(F)F)c4)c(F)c3)ccc2C1=O] | ¹H NMR (300 MHz, DMSO-d₆): δ 12.05 (bs, 1H), 9.7 (bs, 1H), 8.9 (bs, 1H), 8.27 (t, J = 8.4 Hz, 1H), 8.05 (s, 1H), 7.9 (d, J = 8.7 Hz, 1H), 7.7 (m, 3H), 7.65-7.5 (m, 3H), 7.35 (d, J = 6.6 Hz, 1H), 3.2-2.9 (m, 3H), 2.75 (m, 1H), 2.45 (m, 1H), 2.2 (m, 1H), 2.0 (m, 1H). | HPLC purity: 96.75%. |
| 56 | 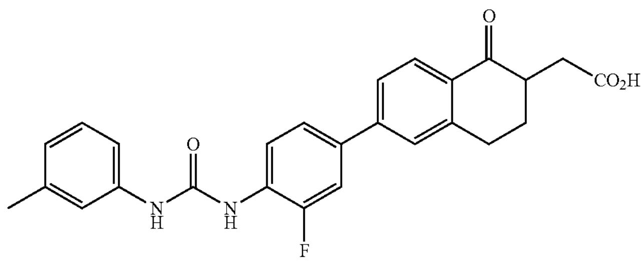 [SMILES: Cc1cccc(NC(=O)Nc2ccc(-c3ccc4c(c3)CCC(CC(=O)O)C4=O)cc2F)c1] | ¹H NMR (400 MHz, DMSO-d₆): δ 12.1 (bs, 1H), 9.15 (bs, 1H), 8.75 (bs, 1H), 8.3 (t, J = 8.8 Hz, 1H), 7.9 (d, J = 8.4 Hz, 1H), 7.7 (m, 3H), 7.6 (d, J = 8.8 Hz, 1H), 7.32 (s, 1H), 7.25 (d, J = 8.0 Hz, 1H), 7.18 (t, J = 7.6 Hz, 1H), 6.8 (d, J = 7.2 Hz, 1H), 3.2-2.9 (m, 3H), 2.75 (m, 1H), 2.45 (m, 1H), 2.3 (s, 3H), 2.2 (m, 1H), 2.0 (m, 1H). | ESI-MS m/z = 447 (M + H)⁺. HPLC purity: 94.65%. |
| 57 | 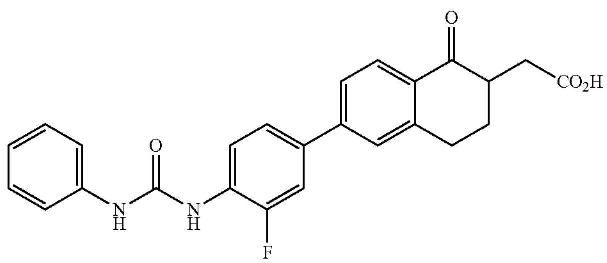 [SMILES: O=C(O)CC1CCc2cc(-c3ccc(NC(=O)Nc4ccccc4)c(F)c3)ccc2C1=O] | ¹H NMR (300 MHz, DMSO-d₆): δ 12.1 (bs, 1H), 9.2 (bs, 1H), 8.7 (s, 1H), 8.3 (t, J = 8.4 Hz, 1H), 7.9 (d, J = 9.0 Hz, 1H), 7.7 (m, 3H), 7.6 (d, J = 8.1 Hz, 1H), 7.5 (d, J = 8.4 Hz, 2H), 7.3 (t, J = 7.5 Hz, 2H), 7.0 (t, J = 7.8 Hz, 1H), 3.2-2.9 (m, 3H), 2.75 (m, 1H), 2.45 (m, 1H), 2.2 (m, 1H), 2.0 (m, 1H). | ESI-MS m/z = 433 (M + H)⁺. HPLC purity: 95.40%. |
| 58 | 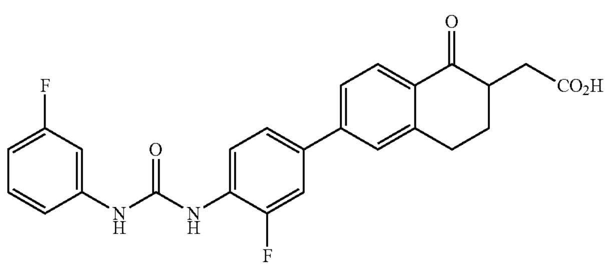 [SMILES: O=C(O)CC1CCc2cc(-c3ccc(NC(=O)Nc4cccc(F)c4)c(F)c3)ccc2C1=O] | ¹H NMR (400 MHz, DMSO-d₆): δ 12.2 (bs, 1H), 9.35 (s, 1H), 8.75 (s, 1H), 8.3 (t, J = 8.4 Hz, 1H), 7.9 (d, J = 8.0 Hz, 1H) 7.7 (m, 3H), 7.6 (d, J = 8.8 Hz, 1H), 7.5 (d, J = 11.6 Hz, 1H), 7.3 (m, 1H), 7.1 (d, J = 8.0 Hz, 1H), 6.82 (m, 1H), 3.2-2.9 (m, 3H), 2.75 (m, 1H), 2.45 (m, 1H), 2.2 (m, 1H), 2.0 (m, 1H). | ESI-MS m/z = 449 (M − H)⁻. LCMS purity: 90.46%. |
| 59 | 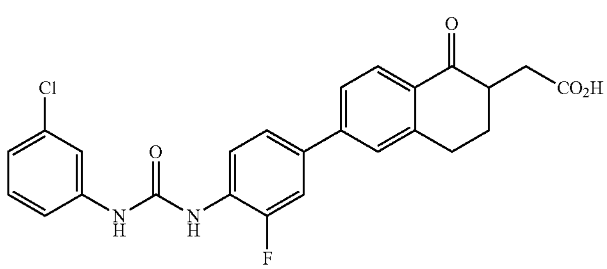 [SMILES: O=C(O)CC1CCc2cc(-c3ccc(NC(=O)Nc4cccc(Cl)c4)c(F)c3)ccc2C1=O] | ¹H NMR (400 MHz, DMSO-d₆): δ 12.1 (bs, 1H), 9.3 (s, 1H), 8.8 (s, 1H), 8.3 (t, J = 8.4 Hz, 1H), 7.9 (d, J = 8.4 Hz, 1H) 7.7 (m, 4H), 7.6 (d, J = 8.4 Hz, 1H), 7.35-7.2 (m, 2H), 7.05 (d, J = 7.6 Hz, 1H), 3.2-2.9 (m, 3H), 2.75 (m, 1H), 2.45 (m, 1H), 2.2 (m, 1H), 2.0 (m, 1H). | ESI-MS m/z = 467 (M + H)⁺. HPLC purity: 96.38%. |
| 60 | 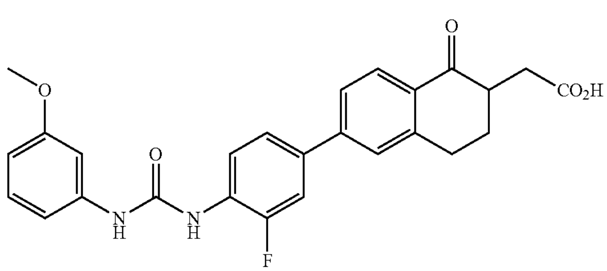 [SMILES: COc1cccc(NC(=O)Nc2ccc(-c3ccc4c(c3)CCC(CC(=O)O)C4=O)cc2F)c1] | ¹H NMR (400 MHz, DMSO-d₆): δ 12.1 (bs, 1H), 9.25 (s, 1H), 8.8 (s, 1H), 8.3 (t, J = 8.4 Hz, 1H), 7.9 (d, J = 9.0 Hz, 1H) 7.7 (m, 3H), 7.6 (d, J = 9.0 Hz, 1H), 7.2 (m, 2H), 6.95 (d, J = 8.4 Hz, 1H), 6.6 (d, J = 6.3 Hz, 1H), 3.75 (s, 3H), 3.2-2.9 (m, 3H), 2.75 (m, 1H), 2.45 (m, 1H), 2.2 (m, 1H), 2.0 (m, 1H). | ESI-MS m/z = 463 (M + H)⁺. HPLC purity: 97.89%. |

-continued

| Ex | Structure | ¹H NMR Data | Mass/Purity |
|---|---|---|---|
| 61 | 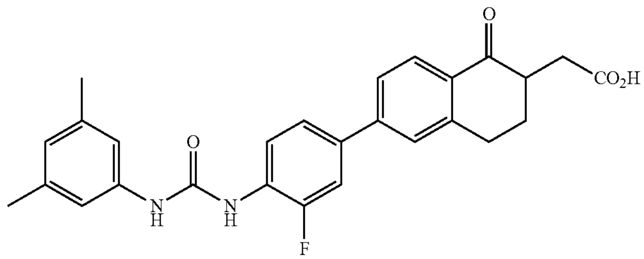 [SMILES: Cc1cc(C)cc(NC(=O)Nc2ccc(-c3ccc4c(c3)CCC(CC(=O)O)C4=O)cc2F)c1] | ¹H NMR (400 MHz, DMSO-d$_6$): δ 12.1 (bs, 1H), 9.0 (s, 1H), 8.7 (s, 1H), 8.3 (t, J = 8.4 Hz, 1H), 7.9 (d, J = 8.4 Hz, 1H) 7.7 (m, 3H), 7.6 (d, J = 8.4 Hz, 1H), 7.1 (s, 2H), 6.65 (s, 1H), 3.2-2.9 (m, 3H), 2.75 (m, 1H), 2.45 (m, 1H), 2.25 (s, 6H), 2.18 (m, 1H), 2.0 (m, 1H). | ESI-MS m/z = 461 (M + H)$^+$. HPLC purity: 93.13%. |
| 62 | 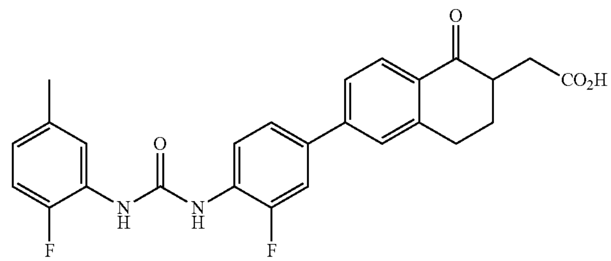 [SMILES: Cc1ccc(F)c(NC(=O)Nc2ccc(-c3ccc4c(c3)CCC(CC(=O)O)C4=O)cc2F)c1] | 1H NMR (300 MHz, DMSO-d$_6$): δ 12.1 (bs, 1H), 9.2 (s, 1H), 9.05 (s, 1H), 8.35 (t, J = 8.4 Hz, 1H), 8.0 (d, J = 6.9 Hz, 1H) 7.9 (d, J = 8.4 Hz, 1H), 7.75-7.65 (m, 3H), 7.6 (d, J = 8.1 Hz, 1H), 7.1 (m, 1H), 6.83 (m, 1H), 3.2-2.9 (m, 3H), 2.75 (m, 1H), 2.45 (m, 1H), 2.3 (s, 3H), 2.2 (m, 1H), 2.0 (m, 1H). | ESI-MS m/z = 465 (M + H)$^+$. HPLC purity: 90.7%. |
| 63 | 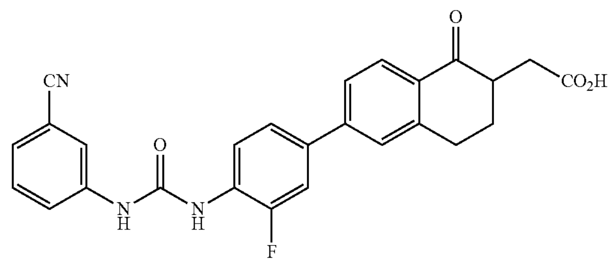 [SMILES: N#Cc1cccc(NC(=O)Nc2ccc(-c3ccc4c(c3)CCC(CC(=O)O)C4=O)cc2F)c1] | ¹H NMR (400 MHz, DMSO-d$_6$): δ 12.1 (bs, 1H), 9.45 (s, 1H), 8.85 (s, 1H), 8.25 (t, J = 8.8 Hz, 1H), 8.0 (s, 1H), 7.9 (d, J = 8.0 Hz, 1H) 7.75-7.65 (m, 4H), 7.6 (d, J = 8.8 Hz, 1H), 7.55-7.45 (m, 2H), 3.2-2.9 (m, 3H), 2.75 (m, 1H), 2.45 (m, 1H), 2.18 (m, 1H), 2.0 (m, 1H). | ESI-MS m/z = 458 (M + H)$^+$. HPLC purity: 94.94%. |
| 64 | 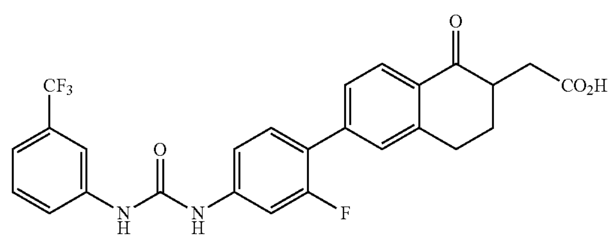 [SMILES: O=C(O)CC1CCc2cc(-c3ccc(NC(=O)Nc4cccc(C(F)(F)F)c4)cc3F)ccc2C1=O] | ¹H NMR (400 MHz, DMSO-d$_6$): δ 12.1 (bs, 1H), 9.4 (bs, 1H), 9.0 (bs, 1H), 8.0 (s, 1H), 7.9 (m, 1H), 7.7-7.45 (m, 6H), 7.3 (m, 2H), 3.2-2.9 (m, 4H), 2.7 (m, 1H), 2.2 (m, 1H), 2.0 (m, 1H). | ESI-MS m/z = 499 (M − H)$^-$; LCMS purity: 90%. |
| 65 | 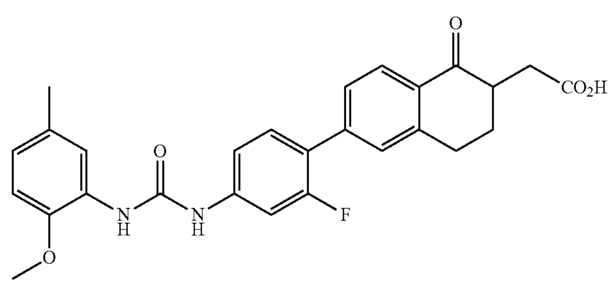 [SMILES: COc1ccc(C)cc1NC(=O)Nc1ccc(-c2ccc3c(c2)CCC(CC(=O)O)C3=O)c(F)c1] | ¹H NMR (400 MHz, DMSO-d$_6$): δ 9.7 (bs, 1H), 8.28 (bs, 1H), 7.98 (m, 1H), 7.95 (d, J = 8.4 Hz, 1H), 7.66 (m, 1H), 7.56-7.46 (m, 3H), 7.2 (m, 1H), 6.9 (m, 1H), 6.76 (m, 1H), 3.8 (s, 3H), 3.2-2.9 (m, 2H), 2.7 (m, 1H), 2.4 (m, 2H), 2.26 (s, 3H), 2.2 (m, 1H), 2.0 (m, 1H). | ESI-MS m/z = 477 (M + H)$^+$; LCMS purity: 93%. |
| 66 | 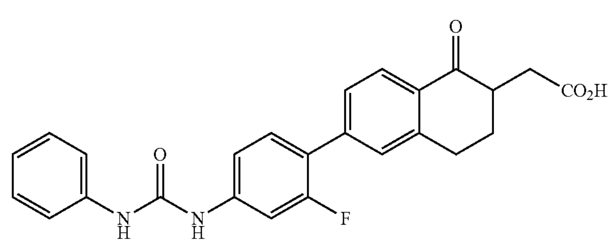 [SMILES: O=C(O)CC1CCc2cc(-c3ccc(NC(=O)Nc4ccccc4)cc3F)ccc2C1=O] | ¹H NMR (400 MHz, DMSO-d$_6$): δ 12.1 (bs, 1H), 9.05 (bs, 1H), 8.9 (bs, 1H), 7.9 (d, J = 8.4 Hz, 1H), 7.6 (m, 1H), 7.56-7.44 (m, 5H), 7.3 (m, 3H), 7.0 (m, 1H), 3.2-2.9 (m, 2H), 2.7 (m, 1H), 2.4 (m, 2H), 2.2 (m, 1H), 2.0 (m, 1H). | HPLC purity: 91%. |

| Ex | Structure | ¹H NMR Data | Mass/Purity |
|---|---|---|---|
| 67 | 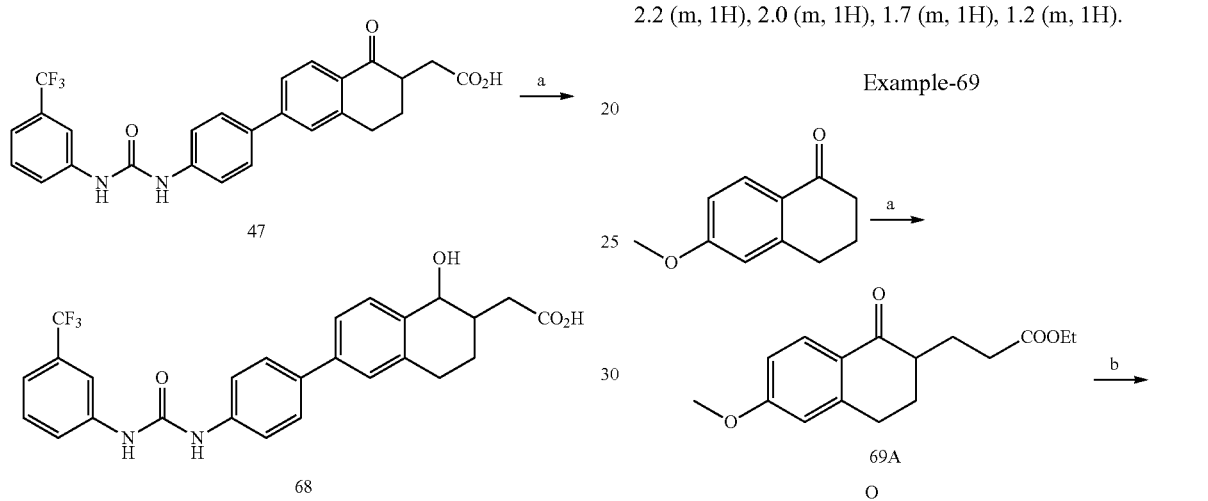 | ¹H NMR (300 MHz, DMSO-$d_6$): δ 10.7 (bs, 1H) 9.0 (2s, 2H) 8.35 (d, J = 8.4 Hz, 1H), 8.25 (s, 1H), 8.1 (m, 1H), 8.05 (d, J = 8.4 Hz, 1H), 7.7 (d, J = 8.4 Hz, 1H), 7.5 (t, J = 7.5 Hz, 1H), 7.3 (d, J = 7.5 Hz, 1H), 3.1 (m, 2H), 2.8 (m, 1H), 2.6 (m, 2H), 2.4 (m, 2H). | ESI-LCMS m/z: 486 (purity 89%); HPLC purity 96%. |

Example-68

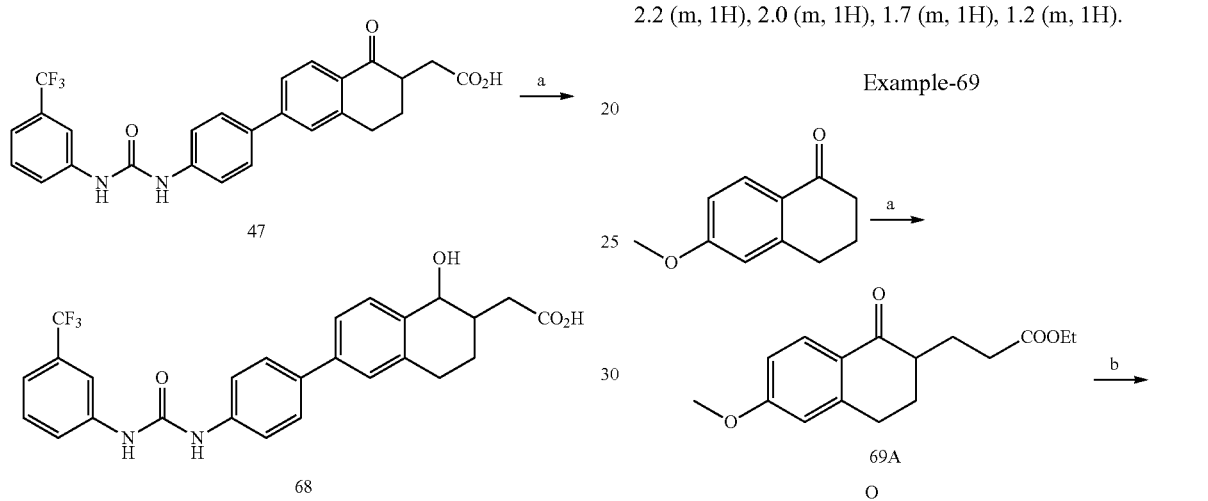

Reagents and conditions: a) NaBH$_4$, MeOH, RT, 16 h.

Procedures 2-(1-hydroxy-6-(4-(3-(3-(trifluoromethyl)phenyl) ureido)phenyl)-1,2,3,4-tetrahydronaphthalen-2-yl) acetic acid (68)

Sodium borohydride (0.025 g, 0.66 mmol) was added portion wise to an ice cold solution of product of Example 47 (0.08 g, 0.16 mmol) in methanol (5 mL), and the mixture was stirred at room temperature for 16 h. The reaction mixture was concentrated under reduced pressure and diluted with water. The resulting solids were filtered and triturated with diethyl ether and n-pentane to afford title compound (0.068 g, 85%) as solid. ¹H NMR (400 MHz, DMSO-$d_6$): δ 12.0 (bs, 1H), 9.4 (bs, 1H), 9.0 (bs, 1H), 8.1 (s, 1H), 7.7 (m, 1H), 7.6-7.44 (m, 6H), 7.4-7.2 (m, 4H), 4.6 (m, 1H), 4.3 (m, 1H), 2.8 (m, 2H), 2.2 (m, 1H), 2.0 (m, 1H), 1.7 (m, 1H), 1.2 (m, 1H).

Example-69

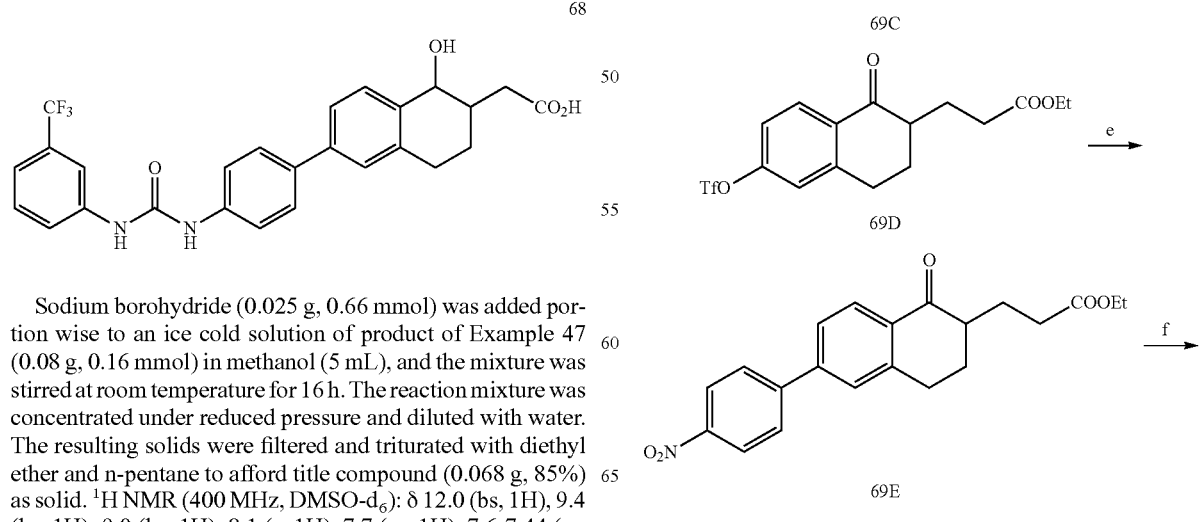

3-(6-Hydroxy-1-oxo-1,2,3,4-tetrahydronaphthalen-2-yl)propanoic acid (69B)

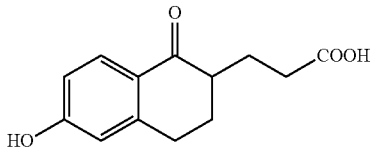

Aqueous HBr (50 mL) was added to product of Example 69A (4.5 g, 16.0 mmol), and the reaction mixture was refluxed for overnight. The reaction mixture was then brought to room temperature and extracted with ethyl acetate (2×100 mL). The organic layer was dried over $Na_2SO_4$ and removed under reduced pressure. The product was purified by flash chromatography using 40% ethyl acetate in hexanes to afford title compound (0.85 g, 24%) as solid. 1H NMR (300 MHz, DMSO-$d_6$): δ 12.01 (bs, 1H), 10.27 (s, 1H), 7.74 (d, J=9.0 Hz, 1H), 6.70 (dd, $J_1$=2.1 Hz, $J_2$=8.4 Hz, 1H), 6.62 (s, 1H), 2.86 (m, 2H), 2.43 (m, 1H), 2.31 (t, J=7.5 Hz, 2H), 2.12-1.98 (m, 2H), 1.78-1.69 (m, 1H), 1.65-1.53 (m, 1H).

Ethyl 3-(6-hydroxy-1-oxo-1,2,3,4-tetrahydronaphthalen-2-yl)propanoate (69C)

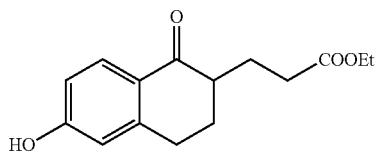

Methane sulphonic acid (0.3 mL) was added to a solution of product of Example 69B (0.85 g, 3.63 mmol) in ethanol (20 mL), and the mixture was stirred at room temperature for 18 h. Ethanol was removed from reaction mixture under reduced pressure, and residue was diluted with ethyl acetate and washed with brine solution. The organic layer was dried over $Na_2SO_4$ and filtered. The filtrate was concentrated under reduced pressure and purified by flash chromatography using 20% ethyl acetate in hexanes to afford the title compound (0.9 g, 24%) as solid. 1H NMR (300 MHz, DMSO-$d_6$): δ 10.27 (s, 1H), 7.73 (d, J=8.1 Hz, 1H), 6.70 (dd, $J_1$=2.1 Hz, $J_2$=9.0 Hz, 1H), 6.62 (s, 1H), 4.05 (q, J=6.9 Hz, 2H), 2.86 (m, 2H), 2.43 (m, 1H), 2.31 (t, J=7.5 Hz, 2H) 2.13-1.98 (m, 2H), 1.77-1.57 (m, 2H), 1.17 (t, J=6.9 Hz, 3H).

Ethyl 3-(1-oxo-6-(trifluoromethylsulfonyloxy)-1,2,3,4-tetrahydronaphthalen-2-yl)propanoate (69D)

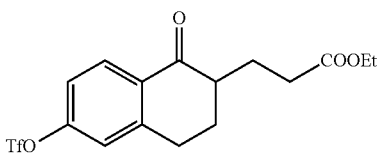

Triflic anhydride (1.16 g, 4.12 mmol) was added to an ice cold solution of product of Example 69C (0.9 g, 3.43 mmol) and pyridine (0.325 g, 4.12 mmol) in dichloromethane (30 mL), and the mixture was stirred at room temperature for 2 h.

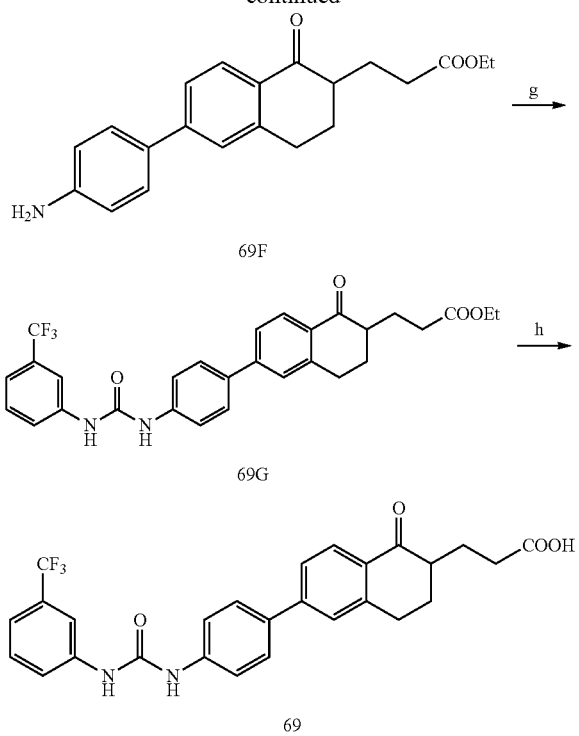

Reagents & conditions: a) LDA, Ethyl bromo propionate, THF, −78° C.-RT, 10 h; b) Aq. HBr, 100° C., 12 h; c) MeSO₃H, EtOH, RT, 18 h; d) Tf₂O, CH₂Cl₂, Py, RT, 2 h; e) Pd(PPh₃)₄, Cs₂CO₃, Dioxane-H₂O, 80° C., 3 h; f) Pd/C, H₂, EtOH, RT, 1 h; g) 3-CF₃PhNCO, Et₃N, THF, RT, 12 h; h) LiOH, THF−H₂O, RT, 12 h.

Procedures

3-(1-oxo-6-(4-(3-(3-(trifluoromethyl)phenyl)ureido)phenyl)-1,2,3,4-tetrahydronaphthalen-2-yl)propanoic acid

Ethyl-3-(6-methoxy-1-oxo-1,2,3,4-tetrahydronaphthalen-2-yl)propanoate (69A)

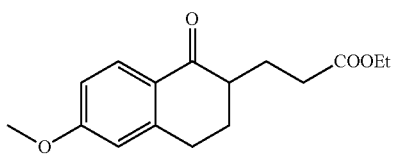

Freshly prepared 1.8M LDA (24.4 mL, 44.0 mmol) was added to pre-cooled solution of 6-methoxy-1-tetralone (4 g, 22.0 mmol) in THF (30 mL) over a period of 15 min at −78° C. The reaction mixture was stirred for 1 h at −78° C. Ethyl bromo propionate (4.4 mL, 39.37 mmol) was added over a period of 10 min at −78° C., and the mixture was stirred at room temperature for 10 h. The reaction mixture was then poured in saturated NH₄Cl (100 mL) solution and extracted with ethyl acetate (2×100 mL). The combined organic layers were washed with water followed by brine solution, dried over Na₂SO₄ and filtered. The filtrate was concentrated under reduced pressure to afford crude title product (4.5 g, 69%) as liquid.

The reaction mixture was diluted with dichloromethane (50 mL) and washed with saturated aqueous solution of NaCl (50 mL). The organic layer was dried over $Na_2SO_4$ and filtered. The filtrate was concentrated under reduced pressure and purified by flash chromatography using 5% ethyl acetate in hexanes to afford title compound (0.95 g, 70%) as solid. 1H NMR (400 MHz, DMSO-$d_6$): δ 8.02 (d, J=8.8 Hz, 1H), 7.54 (s, 1H), 7.45 (dd, $J_1$=2.0 Hz, $J_2$=8.8 Hz, 1H), 4.05 (q, J=6.9 Hz, 2H), 3.04 (m, 2H), 2.68-2.61 (m, 1H), 2.42 (t, J=7.6 Hz, 2H), 2.20-2.06 (m, 2H), 1.89-1.80 (m, 1H), 1.78-1.63 (m, 1H), 1.18 (t, J=6.8 Hz, 3H).

Ethyl 3-(6-(4-nitrophenyl)-1-oxo-1,2,3,4-tetrahydronaphthalen-2-yl)propanoate (69E)

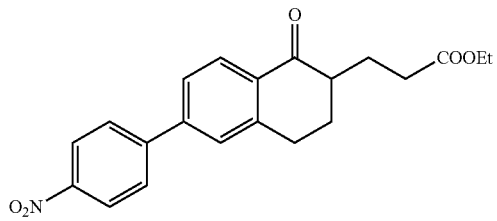

69E

Pd(PPh$_3$)$_4$ (0.034 g, 0.028 mmol) was added to a solution of product of Example 69D (0.95 g, 2.41 mmol) in 30 mL of 1,4 dioxane-$H_2O$ (4:1) mixture under argon atmosphere, followed by cesium carbonate (1.95 g, 6.02 mmol) and 4-nitro phenyl boronic acid (0.48 g, 2.89 mmol). The reaction mixture was degassed for 15 min. The reaction mixture was then refluxed for 3 h, and solvent was removed under reduced pressure. The residue was partitioned between ethyl acetate and water. The separated organic layer was dried over $Na_2SO_4$ and filtered. The filtrate was concentrated and purified by flash chromatography using 10% % ethyl acetate in hexanes to give title compound (0.7 g, 79%) as solid. 1H NMR (400 MHz, DMSO-$d_6$): δ 8.33 (d, J=8.4 Hz, 2H), 8.03 (d, J=8.4 Hz, 2H), 7.98 (d, J=8.4 Hz, 1H), 7.78-7.74 (m, 2H), 4.05 (q, J=7.2 Hz, 2H), 3.08 (m, 2H), 2.66-2.59 (m, 1H), 2.43 (t, J=8.0 Hz, 2H), 2.23-2.11 (m, 2H), 2.11-1.81 (m, 1H), 1.72-1.67 (m, 1H), 1.19 (t, J=7.2 Hz, 3H).

Ethyl 2-(6-(4-aminophenyl)-1-oxo-1,2,3,4-tetrahydronaphthalen-2-yl)propanoate (69F)

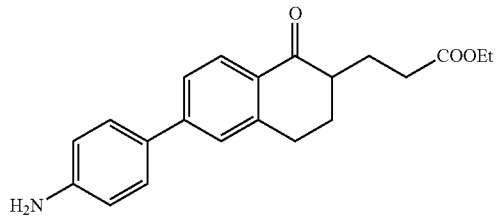

69F

Excess 10% Pd/C (0.2 g) was added to a solution of product of Example 69E (0.7 g, 1.90 mmol) in 20 mL of ethanol, and the mixture was stirred at room temperature for 1 h. The reaction mixture was filtered over celite bed, filtrate was removed under reduced pressure, and residue was partitioned between ethyl acetate and water. The separated organic layer was dried over $Na_2SO_4$, filtered and removed in vacuo. The crude product was washed with $Et_2O$ and pentane to afford title compound (0.61 g, 95%) as yellow solid. 1H NMR (300 MHz, DMSO-$d_6$): δ 7.83 (d, J=8.4 Hz, 1H), 7.53-7.44 (m, 4H), 6.64 (d, J=7.5 Hz, 2H), 5.41 (bs, 2H), 4.06 (q, J=6.9 Hz, 2H), 3.0 (m, 2H), 2.44 (m, 3H), 2.15-2.10 (m, 2H), 1.90-1.66 (m, 2H), 1.18 (t, J=6.9 Hz, 3H).

Ethyl 3-(1-oxo-6-(4-(3-(3-(trifluoromethyl)phenyl)ureido)phenyl)-1,2,3,4-tetrahydronaphthalen-2-yl)propanoate (69G)

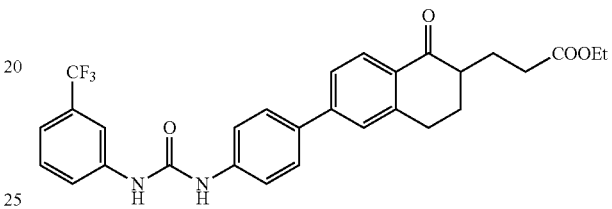

69G 3-(Trifluoromethyl)phenyl isocyanate (0.1 g, 0.534 mmol) was added to a solution of product of Example 69F (0.18 g, 0.534 mmol) and triethylamine (0.065 g, 0.64 mmol) in THF (5 mL). The reaction mixture was stirred at room temperature overnight. The solvent was removed under reduced pressure, and product was purified by flash chromatography using 20% ethyl acetate in hexanes to afford title compound (0.1 g, 35%) as solid. 1H NMR (300 MHz, DMSO-$d_6$): δ 9.10 (s, 1H), 8.98 (s, 1H), 8.03 (s, 1H), 7.91 (d, J=8.4 Hz, 1H), 7.72-7.69 (m, 2H), 7.62-7.49 (m, 6H), 7.31 (d, J=7.2 Hz, 1H), 4.06 (q, J=6.9 Hz, 2H), 3.05 (m, 2H), 2.43 (m, 3H), 2.19-2.11 (m, 2H), 1.82-1.65 (m, 2H), 1.18 (t, J=7.8 Hz, 3H).

3-(1-oxo-6-(4-(3-(3-(trifluoromethyl)phenyl)ureido)phenyl)-1,2,3,4-tetrahydronaphthalen-2-yl)propanoic acid (69)

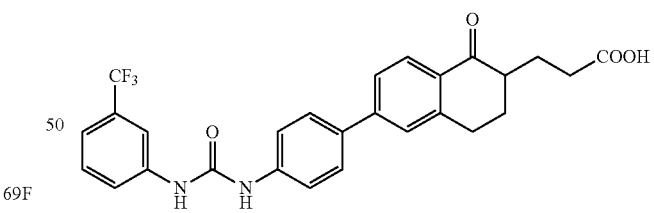

69

Lithium hydroxide (0.024 g, 0.572 mmol) was added to a solution of product of Example 69G (0.1 g, 0.19 mmol) in 20 mL of THF-water (2:1) mixture, and the mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.060 g, 63%) as white solid. $^1$H NMR (300 MHz, DMSO-$d_6$): δ 12.0 (bs, 1H), 9.20 (bs, 1H), 9.12 (bs, 1H), 8.02 (s, 1H), 7.91 (d, J=9.0 Hz, 1H) 7.72-7.68 (m, 2H), 7.65-7.49 (m, 6H), 7.32 (d, J=7.5 Hz, 1H), 3.06-3.02 (m, 2H), 2.56-2.50 (m, 1H), 2.35 (t, J=7.5 Hz, 2H) 2.27-2.08 (m, 2H), 1.82-1.63 (m, 2H). ESI-MS m/z=496 (M+H)+; HPLC purity: 99.22%.

Examples 70-75 were prepared by the procedures analogous to those described for Example 69 using appropriate starting materials. The requisite boronic acids (and appropriately functional-group-protected versions thereof) utilized herein were purchased if available commercially, were synthesized as described in the literature or by routine modifications thereof known by those skilled in the art, or were synthesized by alternative procedures known by those skilled in the art.

| Ex | Structure | $^1$H NMR Data | Mass/Purity |
|---|---|---|---|
| 70 | 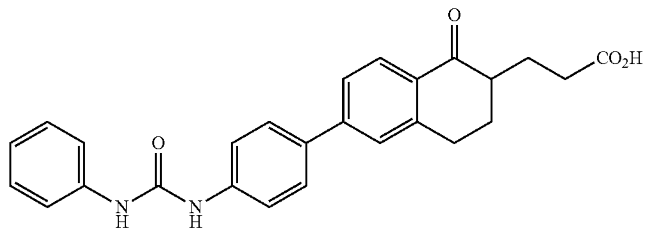 [SMILES: O=C(O)CCC1CCc2cc(-c3ccc(NC(=O)Nc4ccccc4)cc3)ccc2C1=O] | $^1$H NMR (400 MHz, DMSO-$d_6$): δ 12.0 (bs, 1H), 8.86 (s, 1H), 8.73 (s, 1H), 7.91 (d, J = 8.8 Hz, 1H), 7.69 (d, J = 9.2 Hz, 2H) 7.64-7.56 (m, 4H), 7.46 (d, J = 8.4 Hz, 2H), 7.29 (t, J = 7.6 Hz, 2H) 6.98 (t, J = 6.8 Hz, 1H), 3.05 (m, 2H), 2.68-2.53 (m, 1H), 2.35 (t, J = 7.6 Hz, 2H) 2.22-2.09 (m, 2H), 1.82 (m, 1H), 1.66 (m, 1H). | ESI-MS m/z = 429 (M + H)+. LCMS Purity: 95.03%. |
| 71 | 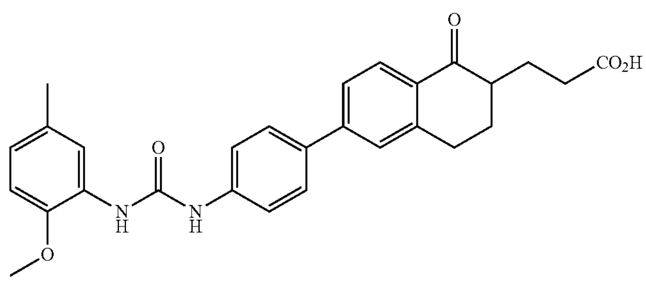 [SMILES: COc1ccc(C)cc1NC(=O)Nc1ccc(-c2ccc3c(c2)CCC(CCC(=O)O)C3=O)cc1] | $^1$H NMR (400 MHz, DMSO-$d_6$): δ 12.0 (bs, 1H), 9.51 (s, 1H), 8.22 (s, 1H), 7.99 (s, 1H), 7.91 (d, J = 8.4 Hz, 1H), 7.69 (d, J = 8.4 Hz, 2H) 7.64-7.56 (m, 4H), 6.90 (d, J = 8.4 Hz, 1H), 6.75 (d, J = 8.4 Hz, 1H), 3.85 (s, 3H), 3.05 (m, 2H), 2.59-2.54 (m, 1H) 2.35 (t, J = 8.0 Hz, 2H), 2.24 (s, 3H), 2.22-2.07 (m, 2H), 1.83 (m, 1H), 1.65 (m, 1H). | ESI-MS m/z = 473 (M + H)+. HPLC purity: 94.49%. |
| 72 | 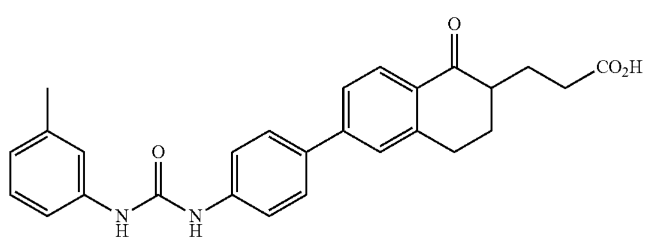 [SMILES: Cc1cccc(NC(=O)Nc2ccc(-c3ccc4c(c3)CCC(CCC(=O)O)C4=O)cc2)c1] | $^1$H NMR (300 MHz, DMSO-$d_6$): δ 12.0 (bs, 1H), 9.03 (bs, 1H), 8.83 (bs, 1H), 7.93-7.88 (m, 1H), 7.68-7.60 (m, 6H), 7.33-7.14 (m, 3H) 6.80 (m, 1H), 3.05 (m, 2H), 2.56 (m, 1H), 2.40-2.05 (m, 7H), 1.83-1.65 (m, 2H). | HPLC purity: 94.84%. |
| 73 | 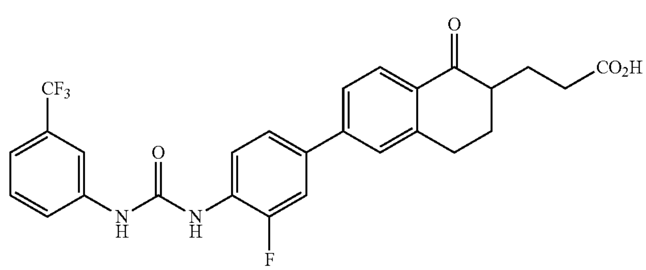 [SMILES: O=C(O)CCC1CCc2cc(-c3ccc(NC(=O)Nc4cccc(C(F)(F)F)c4)c(F)c3)ccc2C1=O] | $^1$H NMR (300 MHz, DMSO-$d_6$): δ 12.0 (bs, 1H), 9.51 (bs, 1H), 8.82 (bs, 1H), 8.27 (t, J = 8.4 Hz, 1H) 8.05 (s, 1H), 7.91 (d, J = 9.0 Hz, 1H) 7.79-7.65 (m, 3H), 7.62-7.50 (m, 3H), 7.35 (m, 1H), 3.06 (m, 2H), 2.59-2.55 (m, 1H), 2.35 (t, J = 7.8 Hz, 2H) 2.28-2.04 (m, 2H), 1.85 (m, 1H), 1.66 (m, 1H). | HPLC purity: 90.44%. |
| 74 | 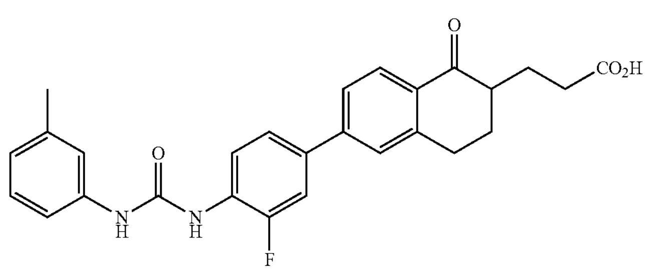 [SMILES: Cc1cccc(NC(=O)Nc2ccc(-c3ccc4c(c3)CCC(CCC(=O)O)C4=O)cc2F)c1] | $^1$H NMR (300 MHz, DMSO-$d_6$): δ 12.0 (s, 1H), 9.06 (s, 1H), 8.70 (s, 1H), 8.30 (t, J = 8.4 Hz, 1H), 7.91 (d, J = 8.4 Hz, 1H) 7.72-7.56 (m, 4H), 7.32-7.14 (m, 3H), 6.82 (d, J = 7.5 Hz, 1H), 3.05 (m, 2H), 2.55 (m, 1H), 2.39-2.21 (m, 5H), 2.19-2.06 (m, 2H), 1.82 (m, 1H), 1.64 (m, 1H). | ESI-MS m/z = 459 (M − H)−. HPLC purity: 96.45%. |

| Ex | Structure | ¹H NMR Data | Mass/Purity |
|---|---|---|---|
| 75 | 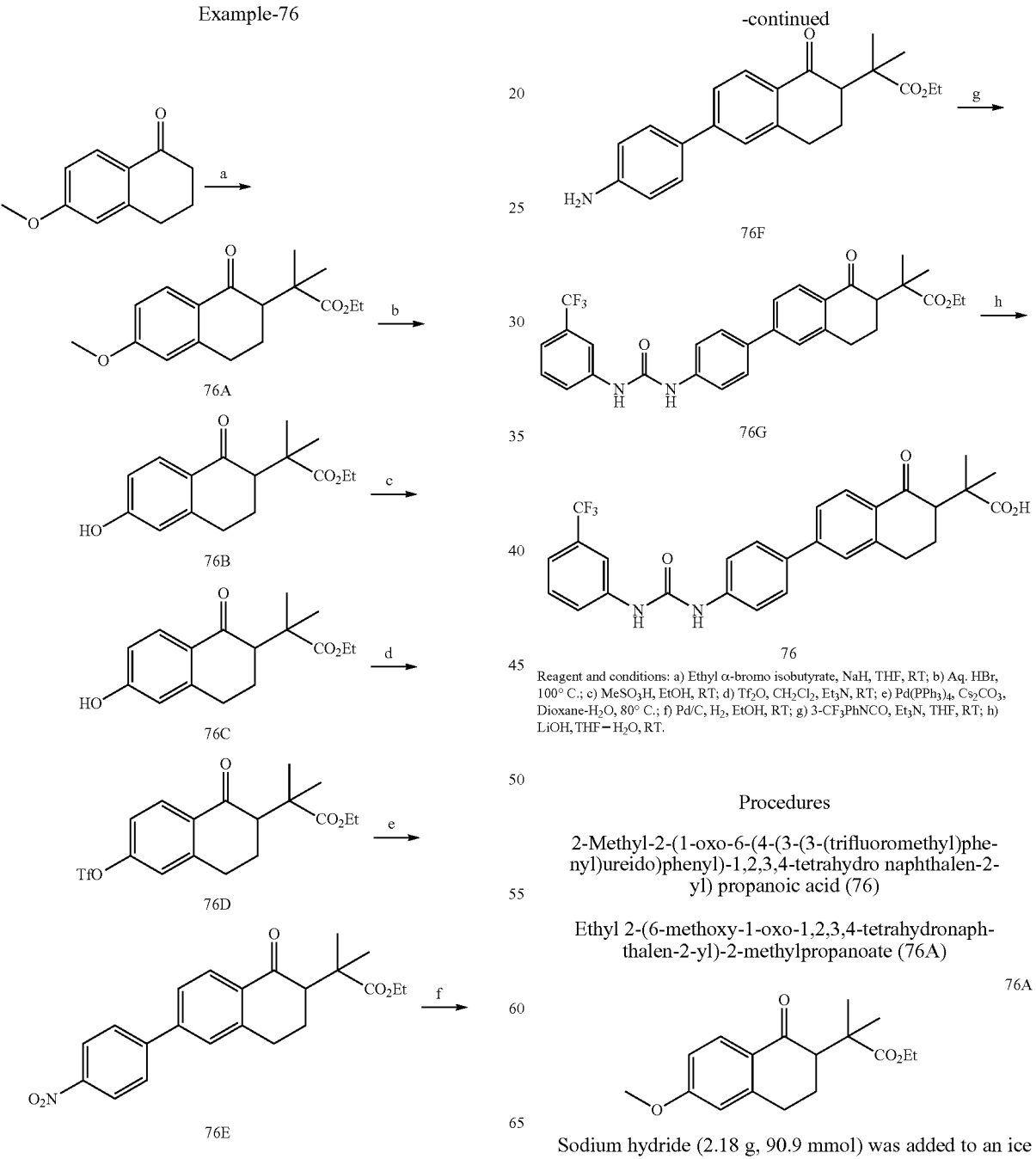 | ¹H NMR (400 MHz, DMSO-d₆): δ 12.0 (bs, 1H), 9.30 (s, 1H), 8.77 (s, 1H), 8.26 (t, J = 8.4 Hz, 1H), 7.91 (d, J = 7.6 Hz, 1H) 7.76-7.66 (m, 4H), 7.60 (d, J = 8.8 Hz, 1H), 7.33 (m, 1H), 7.25 (m, 1H), 7.05 (d, J = 8.0 Hz, 1H) 3.05 (m, 2H), 2.59-2.56 (m, 1H), 2.35 (t, J = 7.6 Hz, 2H), 2.23-2.07 (m, 2H), 1.82 (m, 1H), 1.66 (m, 1H). | ESI-MS m/z = 480 (M – H)⁻. LCMS purity: 98.96%. |

Example-76

Reagent and conditions: a) Ethyl α-bromo isobutyrate, NaH, THF, RT; b) Aq. HBr, 100° C.; c) MeSO₃H, EtOH, RT; d) Tf₂O, CH₂Cl₂, Et₃N, RT; e) Pd(PPh₃)₄, Cs₂CO₃, Dioxane-H₂O, 80° C.; f) Pd/C, H₂, EtOH, RT; g) 3-CF₃PhNCO, Et₃N, THF, RT; h) LiOH, THF—H₂O, RT.

Procedures

2-Methyl-2-(1-oxo-6-(4-(3-(3-(trifluoromethyl)phenyl)ureido)phenyl)-1,2,3,4-tetrahydro naphthalen-2-yl) propanoic acid (76)

Ethyl 2-(6-methoxy-1-oxo-1,2,3,4-tetrahydronaphthalen-2-yl)-2-methylpropanoate (76A)

Sodium hydride (2.18 g, 90.9 mmol) was added to an ice cold solution of 6-methoxy-1-tetralone (8 g, 136 mmol) in THF (90 mL), and the mixture was stirred for 10 min. Ethyl α-bromo isobutyrate (17.7 g, 90.9 mmol) was added, and the mixture was stirred for 3 h. Reaction mixture was quenched with ice cold water and extracted with ethyl acetate. The organic layer was washed with brine, dried over Na$_2$SO$_4$ and filtered. The filtrate was concentrated under vacuum to afford the title compound (13 g) as solid. $^1$H NMR (400 MHz, CDCl$_3$): δ 7.96 (d, J=9.2 Hz, 1H), 6.8 (m, 1H), 6.68 (m, 1H), 4.2 (m, 2H), 3.8 (s, 3H), 3.15-3.0 (m, 3H), 2.2 (m, 1H), 1.9 (m, 1H), 1.25 (m, 6H), 1.2 (s, 3H).

2-(6-Hydroxy-1-oxo-1,2,3,4-tetrahydronaphthalen-2-yl)-2-methylpropanoic acid (76B)

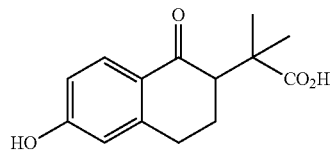

Aqueous HBr (190 mL) was added to product of Example 76A (13 g, 44.8 mmol), and the reaction mixture was refluxed for overnight. The reaction mixture was then brought to room temperature and extracted with ethyl acetate (2×100 mL). The organic layer was dried over Na$_2$SO$_4$ and filtered. The filtrate was concentrated under reduced pressure to afford title compound (11 g) as solid. $^1$H NMR (400 MHz, DMSO-d$_6$): δ 10.2 (bs, 1H), 7.7 (m, 1H), 6.7 (m, 1H), 6.6 (s, 1H), 3.1-2.8 (m, 3H), 2.15 (m, 1H), 1.7 (m, 1H), 1.15 (s, 3H), 1.0 (s, 3H).

Ethyl 2-(6-hydroxy-1-oxo-1,2,3,4-tetrahydronaphthalen-2-yl)-2-methyl propanoate (76C)

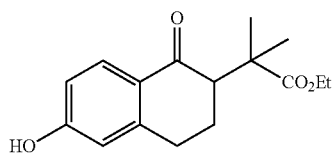

Methane sulphonic acid (20 mL) was added to a solution of product of Example 76B (11 g, 44.3 mmol) in ethanol (150 mL), and the mixture was stirred at room temperature for 5 h. Ethanol was removed from reaction mixture under reduced pressure, and residue was diluted with ethyl acetate and water. The organic layer was separated, dried over Na$_2$SO$_4$ and filtered. The filtrate was concentrated under vacuum to afford title compound (6.4 g, 51%) as solid. $^1$H NMR (300 MHz, CDCl$_3$): δ 7.84 (m, 1H), 6.74 (m, 1H), 6.66 (bs, 1H), 4.2 (m, 2H), 3.1-2.8 (m, 3H), 2.1 (m, 1H), 1.95 (m, 1H), 1.3 (m, 6H), 1.15 (s, 3H).

Ethyl 2-methyl-2-(1-oxo-6-(trifluoromethyl sulfonyloxy)-1,2,3,4-tetrahydro naphthalen-2-yl) propanoate (76D)

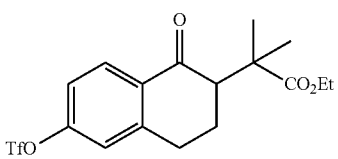

Triflic anhydride (6.53 g, 23.15 mmol) was added to an ice cold solution of product of Example 76C (6.4 g, 23.1 mmol) and pyridine (2.01 g, 25.44 mmol) in dichloromethane (75 mL), and the mixture was stirred at room temperature for 1 h.

The reaction mixture was diluted with dichloromethane (100 mL) and washed with saturated aqueous solution of NaCl (75 mL). The organic layer was dried over Na$_2$SO$_4$ and filtered. The filtrate was concentrated under reduced pressure and purified by flash chromatography using 5% ethyl acetate in hexanes to afford title compound (3.8 g, 40%) as solid. $^1$H NMR (300 MHz, CDCl$_3$): δ 8.08 (m, 1H), 7.18 (m, 2H), 4.2 (m, 2H), 3.2-3.0 (m, 3H), 2.3 (m, 1H), 2.0 (m, 1H), 1.25 (m, 6H), 1.2 (s, 3H).

Ethyl 2-methyl-2-(6-(4-nitrophenyl)-1-oxo-1,2,3,4-tetrahydronaphthalen-2-yl)propanoate (76E)

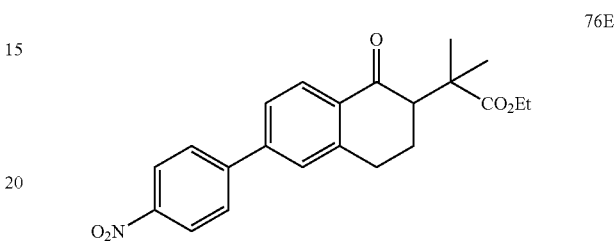

Pd(PPh$_3$)$_4$ (0.129 g, 0.11 mmol) was added to a solution of product of Example 76D (3.8 g, 9.3 mmol) in 35 mL of 1,4 dioxane-H$_2$O (3:1) mixture under Argon atmosphere, followed by cesium carbonate (9.1 g, 27.9 mmol) and 4-nitrophenyl boronic acid (1.71 g, 10.23 mmol). The reaction mixture was degassed for 5 min. The reaction mixture was then refluxed for 5 h, and solvent was removed under reduced pressure. The residue was partitioned between ethyl acetate and water. The separated organic layer was dried over Na$_2$SO$_4$ and filtered. The filtrate was concentrated under reduced pressure and purified by flash chromatography to afford title compound (2.5 g, 71%) as solid. $^1$H NMR (400 MHz, CDCl$_3$): δ 8.0 (m, 1H), 7.5-7.3 (m, 4H), 6.75 (m, 2H), 4.2 (m, 2H), 3.2-3.0 (m, 3H), 2.2 (m, 1H), 2.0 (m, 1H), 1.25 (m, 6H), 1.2 (s, 3H).

Ethyl 2-(6-(4-aminophenyl)-1-oxo-1,2,3,4-tetrahydronaphthalen-2-yl)-2-methylpropanoate (76F)

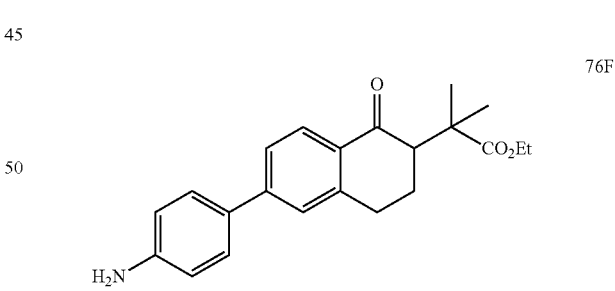

Iron powder (0.66 g, 11.81 mmol) was added to a solution of product of Example 76E (1.5 g, 3.93 mmol) in 15 mL of ethanol-water mixture (2:1) followed by NH$_4$Cl (0.106 g, 1.96 mmol). The mixture was refluxed for 3 h. The solvent was removed under reduced pressure, and residue was partitioned between ethyl acetate and water. The separated organic layer was dried over Na$_2$SO4, filtered and removed in vacuo to afford title compound (1.3 g, 95%). $^1$H NMR (400 MHz, CDCl$_3$): δ 8.6 (m, 2H), 8.2 (m, 1H), 7.55 (m, 2H), 7.51 (m, 1H), 7.5 (s, 1H), 4.2 (m, 2H), 3.2-3.0 (m, 3H), 2.3 (m, 1H), 2.0 (m, 1H), 1.25 (m, 6H), 1.2 (s, 3H).

Ethyl 2-methyl-2-(1-oxo-6-(4-(3-(3-(trifluoromethyl)phenyl)ureido)phenyl)-1,2,3,4-tetrahydro naphthalen-2-yl)propanoate (76G)

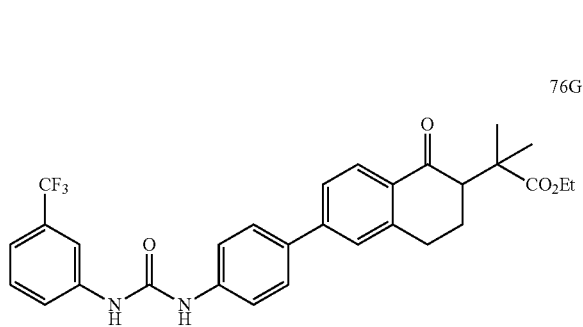 [SMILES: CCOC(=O)C(C)(C)C1CCc2cc(-c3ccc(NC(=O)Nc4cccc(C(F)(F)F)c4)cc3)ccc2C1=O]

76G 3-(Frifluoromethyl)phenyl isocyanate (0.18 g, 0.997 mmol) was added to a solution of product of Example 76F (0.25 g, 0.71 mmol) and triethylamine (0.28 g, 2.85 mmol) in THF (10 mL), and the mixture was stirred at room temperature overnight. The solvent was removed under reduced pressure, and product was triturated with diethyl ether and pentane to afford title compound (0.2 g, 59%) as solid. $^1$H NMR (400 MHz, CDCl$_3$): δ 7.86 (m, 1H), 7.74-7.6 (m, 4H), 7.44-7.28 (m, 8H), 4.2 (m, 2H), 3.15-3.0 (m, 3H), 2.26 (m, 1H), 1.9 (m, 1H), 1.3 (m, 6H), 1.2 (s, 3H).

2-Methyl-2-(1-oxo-6-(4-(3-(3-(trifluoromethyl)phenyl)ureido)phenyl)-1,2,3,4-tetrahydro naphthalen-2-yl) propanoic acid (76)

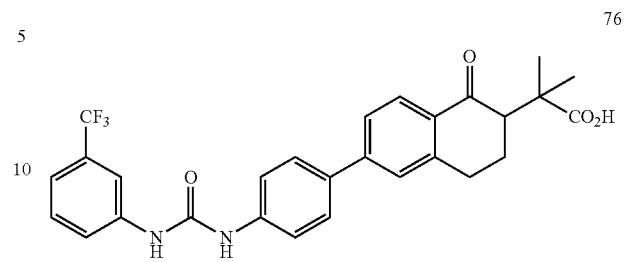

76

Lithium hydroxide (0.062 g, 1.48 mmol) was added to a solution of product of Example 76G (0.2 g, 0.37 mmol) in 4 mL of dioxane-water (3:1) mixture, and the reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration, and dried under vacuum to afford title compound (0.075 g, 40%) as solid. $^1$H NMR (400 MHz, DMSO-d$_6$): δ 9.1 (bs, 1H), 9.0 (bs, 1H), 8.04 (s, 1H), 7.86 (d, J=8.4 Hz, 1H), 7.7 (d, J=8.8 Hz, 2H), 7.68-7.58 (m, 5H), 7.52 (t, J=8 Hz, 1H), 7.3 (d, J=7.6 Hz, 1H), 3.2-3.0 (m, 3H), 2.25 (m, 1H), 1.8 (m, 1H), 1.2 (s, 3H), 1.05 (s, 3H). ESI-MS m/z=511 (M+H)$^+$; HPLC purity: 90%.

Examples 77-78 were prepared by the analogous procedures as described above for Example 76 using appropriate starting materials.

| Ex | Structure | $^1$H NMR Data | Mass/Purity |
|----|-----------|----------------|-------------|
| 77 | 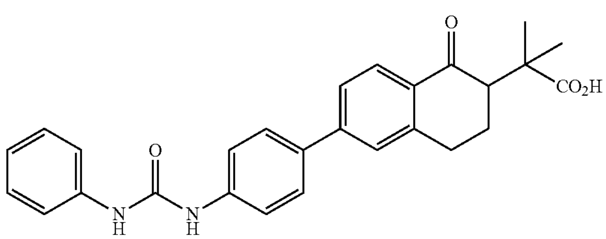 [SMILES: CC(C)(C(=O)O)C1CCc2cc(-c3ccc(NC(=O)Nc4ccccc4)cc3)ccc2C1=O] | $^1$H NMR (400 MHz, DMSO-d$_6$): δ 11.9 (bs, 1H), 8.85 (bs, 1H), 8.72 (bs, 1H), 7.87 (d, J = 8 Hz, 1H), 7.7 (d, J = 8.8, 1H), 7.64-7.56 (m, 5H), 7.46 (d, J = 8 Hz, 2H), 7.3 (t, J = 7.6 Hz, 2H), 6.98 (t, J = 7.2 Hz, 1H), 3.2-3.02 (m, 3H), 2.28-2.2 (m, 1H), 1.9-1.8 (m, 1H), 1.2 (s, 3H), 1.06 (s, 3H). | ESI-MS m/z = 443 (M + H)$^+$; HPLC purity: 97%. |
| 78 | 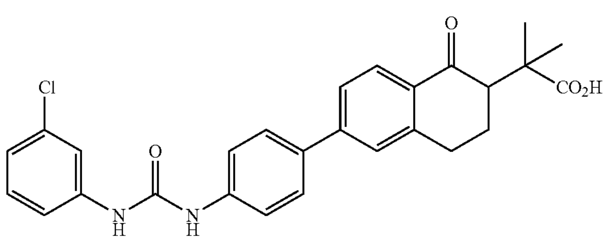 [SMILES: CC(C)(C(=O)O)C1CCc2cc(-c3ccc(NC(=O)Nc4cccc(Cl)c4)cc3)ccc2C1=O] | $^1$H NMR (400 MHz, DMSO-d$_6$): δ 9.0 (bs, 1H), 7.9 (d, J = 8.4 Hz, 1H), 7.75-7.65 (m, 3H), 7.64-7.55 (m, 4H), 7.3 (m, 2H), 7.0 (m, 1H), 3.1 (m, 3H), 2.3 (m, 1H), 1.8 (m, 1H), 1.2 (s, 3H), 1.06 (s, 3H). | ESI-MS m/z = 477 (M + H)$^+$; HPLC purity: 95%. |

Example-79

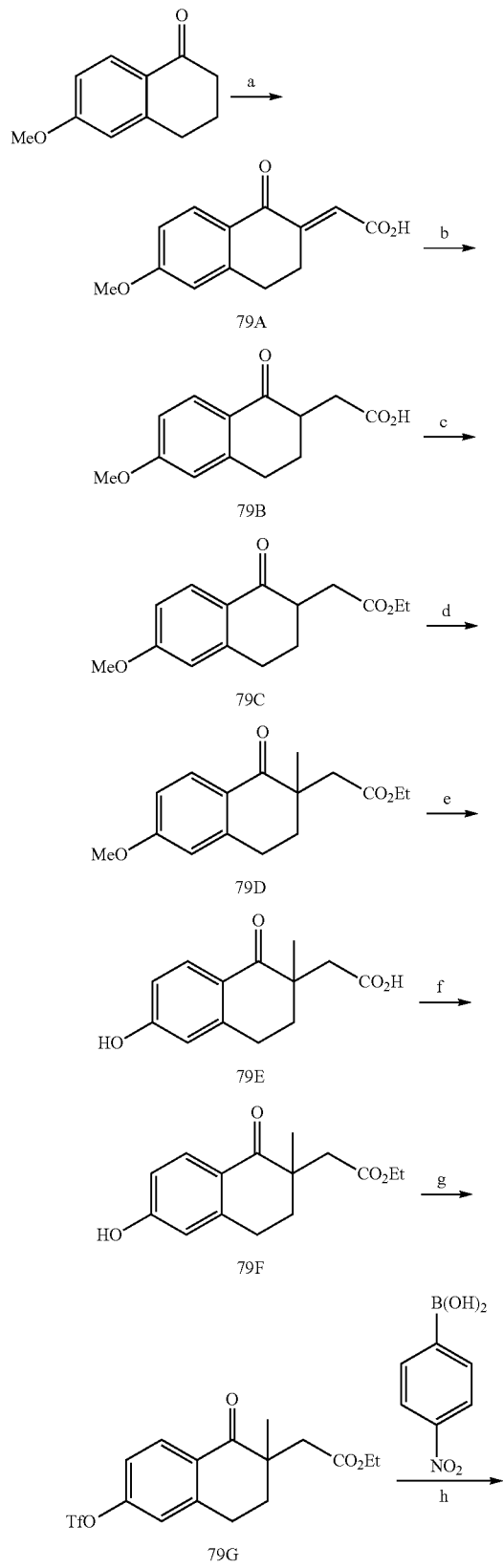

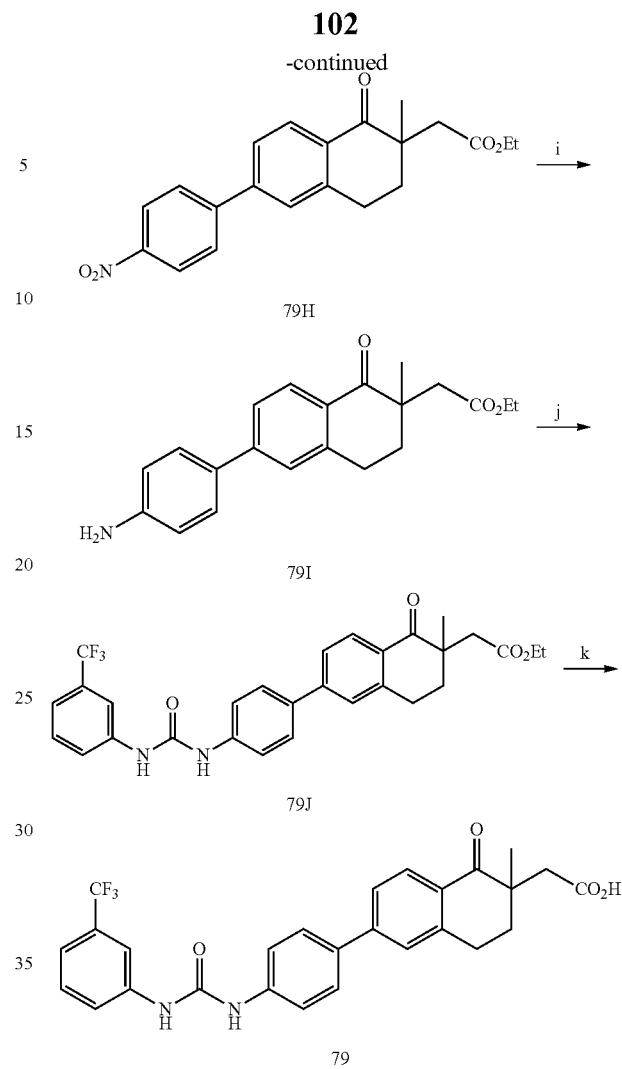

Reagents and conditions: a) Glyoxalic acid, H₂SO₄, diglyme, 85° C., 12 h; b) Zn, AcOH, 80° C., 2 h; c) MeSO₃H, EtOh, RT, 5 h; d) MeI, NaH, DMF, RT, 4 h; e) Aq. HBr, 100° C., 12 h; f) MeSO₃H, EtOH, RT, 5 h; g) Tf₂O, CH₂Cl₂, Et₃N, RT, 1 h; h) Pd(PPh₃)₄, Cs₂CO₃, Dioxane-H₂O, 80° C., 5 h; i) Fe—NH₄Cl, EtOH—H₂O, 85° C., 3 h; j) 3-CF₃PhNCO, Et₃N, THF, RT, 12 h: k) LiOH, EtOH—H₂O, RT, 12 h.

Procedure

2-(2-Methyl-1-oxo-6-(4-(3-(3-(trifluoromethyl)phenyl)ureido)phenyl)-1,2,3,4-tetrahydronaphthalen-2-yl)acetic acid

2-(6-Methoxy-1-oxo-3,4-dihydronaphthalen-2(1H)-ylidene)acetic acid (79A)

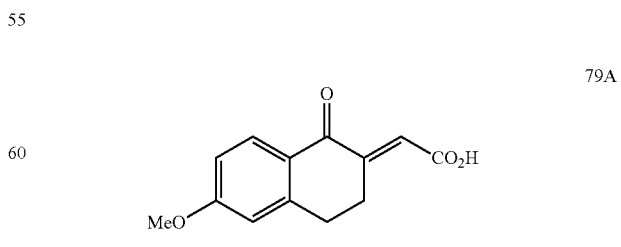

Glyoxalic acid (30 mL, 303 mmol) and water (14 mL) were added to a stirred solution of 6-methoxy tetralone (25 g, 141 mmol) in diglyme (50 mL) followed by sulphuric acid (6.5 mL, 35 mmol). The reaction mixture was heated to 85° C. overnight. The reaction mixture was cooled to 0° C., and resulting solids were filtered off and washed with water (3×25 mL), dried under reduced pressure to afford title compound (28 g, 85%) as solid. ¹H NMR (300 MHz, DMSO-$d_6$): δ 12.9 (bs, 1H), 7.9 (d, J=8.4 Hz, 1H), 7.0 (m, 2H), 6.6 (s, 1H), 3.8 (s, 3H), 3.3 (m, 2H), 3.0 (m, 2H). ESI-MS m/z: 233 (M+H)⁺.

2-(6-Methoxy-1-oxo-1,2,3,4-tetrahydronaphthalen-2-yl)acetic acid (79B)

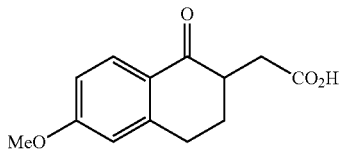

79B

Zinc (19.6 g, 300 mmol) was added to a solution of product of Example 79A (28 g, 120 mmol) in acetic acid-water mixture (224 mL+84 mL), and the mixture was stirred at 80° C. for 2 h. The reaction mixture was then filtered over celite bed, and the organic layer was removed under reduced pressure. Water (50 mL) was added to the residue. The resulting solids were collected by filtration and dried under vacuum to afford title compound (27 g, 95%) as solid. ¹H NMR (400 MHz, DMSO-$d_6$): δ 12.2 (bs, 1H), 7.8 (d, J=8.4 Hz, 1H), 6.9 (m, 2H), 3.8 (s, 3H), 3.1 (m, 1H), 3.0-2.8 (m, 2H), 2.7 (m, 1H), 2.4 (m, 1H), 2.2 (m, 1H), 1.9 (m, 1H).

Ethyl 2-(6-methoxy-1-oxo-1,2,3,4-tetrahydronaphthalen-2-yl) acetate (79C)

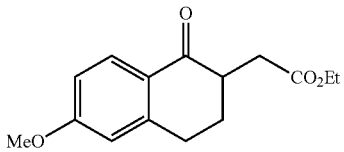

79C

Methane sulphonic acid (20 mL) was added to a solution of product of Example 79B (20 g, 47 mmol) in ethanol (150 mL), and the mixture was stirred at room temperature for 5 h. Ethanol was removed from reaction mixture under reduced pressure, and residue was diluted with ethyl acetate and extracted with brine solution. The organic layer was dried over sodium sulphate, filtered and removed under vacuum to afford title compound (10 g, 71%) as solid. ¹H NMR (400 MHz, CDCl₃): δ 7.99 (d, J=8.8 Hz, 1H), 6.82 (dd, $J_1$=2.4 Hz, $J_2$=8.8 Hz, 1H), 6.67 (s, 1H), 4.2 (m, 2H), 3.8 (s, 3H), 3.12-2.89 (m, 4H), 2.4 (m, 1H), 2.26 (m, 1H), 1.98 (m, 1H), 1.28 (t, J=7.6 Hz, 3H).
Alternative Route:
To a solution of LDA (4.5 g, 42.6 mmol) in THF (45 mL) at −60° C., 6-methoxy-1-tetralone (5 g, 28.4 mmol) was slowly added. The reaction mixture was stirred for 40 min. Ethyl bromoacetate (5.69 g, 34.09 mmol) was then added, and the reaction mixture was stirred at rt for 5 h. Reaction mixture was then quenched with saturated NH₄Cl solution and extracted with EtOAc several times. The combined organic layers were washed with brine, dried over anhydrous Na₂SO₄, filtered and concentration to give 7 g of the title compound.

Ethyl 2-(6-methoxy-2-methyl-1-oxo-1,2,3,4-tetrahydronaphthalen-2-yl) acetate (79D)

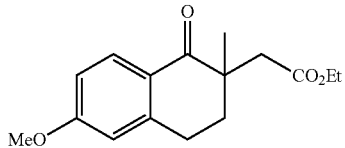

79D

A solution of product of Example 79C (10 g, 38 mmol) in DMF (50 mL) was added over a period of 30 min to an ice cold solution of NaH (4.58 g, 114 mmol) in DMF (100 mL). The reaction mixture was stirred for 10 min. Methyl iodide (27.08 g, 191 mmol) was then added and mixture was stirred for 4 h at room temperature. The reaction was then brought to 0° C., excess NaH was quenched with ice water and aqueous layer was extracted with ethyl acetate (2×100 mL). The combined organic layers were dried over sodium sulphate, filtered and removed under vacuum to give crude title compound (12 g) as solid. ¹H NMR (400 MHz, DMSO-$d_6$): δ 7.75 (d, J=8.4 Hz, 2H), 6.7 (dd, $J_1$=1.6 Hz, $J_2$=8.4 Hz, 1H), 6.62 (m, 1H), 4.0 (m, 2H), 3.0-2.7 (m, 3H), 2.4 (d, J=16.0 Hz, 1H), 2.25 (m, 1H), 1.8 (m, 1H), 1.15 (m, 3H), 1.1 (s, 3H).

2-(6-Hydroxy-2-methyl-1-oxo-1,2,3,4-tetrahydronaphthalen-2-yl)acetic acid (79E)

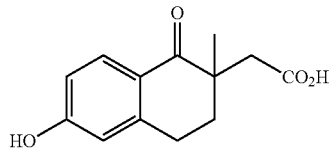

79E

Aqueous HBr (180 mL) was added to the product of Example 79D (12 g, 43.47 mmol) and the reaction mixture was refluxed for overnight. The reaction mixture was then brought to room temperature and extracted with ethyl acetate (2×100 mL). The organic layer was dried over sodium sulphate, filtered and removed under reduced pressure to give crude product which was purified using flash chromatography with 40% ethyl acetate in hexanes to afford title compound (8.2 g, 80.6%) as solid. ¹H NMR (400 MHz, DMSO-$d_6$): δ 12.08 (bs, 1H), 10.29 (s, 1H), 7.74 (d, J=8.4 Hz, 1H), 6.7 (m, 1H), 6.62 (m, 1H), 3.0-2.71 (m, 3H), 2.49-2.33 (m, 2H), 1.8 (m, 1H), 1.1 (s, 3H).

Ethyl 2-(6-hydroxy-2-methyl-1-oxo-1,2,3,4-tetrahydronaphthalen-2-yl) acetate (79F)

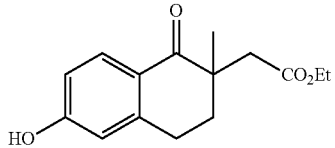

79F

Methane sulphonic acid (15 mL) was added to a solution of product of Example 79E (8.2 g, 35 mmol) in ethanol (100 mL), and the mixture was stirred at room temperature for 5 h. Ethanol was removed from reaction mixture under reduced pressure, and residue was diluted with ethyl acetate and extracted with brine solution. The organic layer was dried over sodium sulphate, filtered and removed under vacuum to afford title compound (7.1 g, 77%) as solid. $^1$H NMR (400 MHz, DMSO-d$_6$): δ 7.92 (d, J=9.0 Hz, 1H), 6.72 (dd, J$_1$=2.1 Hz, J$_2$=8.4 Hz, 1H), 6.63 (s, 1H), 4.1 (q, J=6.9 Hz, 2H), 3.06-2.8 (m, 3H), 2.5-2.33 (m, 2H), 1.9 (m, 1H), 1.3-1.18 (m, 6H).

Ethyl 2-(2-methyl-1-oxo-6-(trifluoromethylsulfonyloxy)-1,2,3,4-tetrahydronaphthalen-2-yl) acetate (79G)

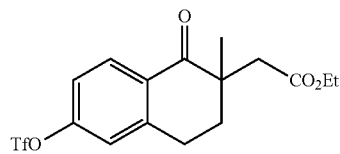

79G

Triflic anhydride (5.38 g, 19.08 mmol) was added to an ice cold solution of product of Example 79F (5 g, 19.08 mmol) and pyridine (1.65 g, 20.88 mmol) in dichloromethane (40 mL). The reaction mixture was stirred at room temperature for 1 h. The reaction mixture was diluted with dichloromethane (100 mL) and washed with saturated aqueous solution of NaCl (75 mL). The organic layer was dried over sodium sulphate, filtered and removed under reduced pressure. The product was purified by flash chromatography using 5% ethyl acetate in hexanes to give title compound (4 g, 53%) as syrup. $^1$H NMR (300 MHz, CDCl$_3$): δ 8.16 (d, J=8.4 Hz, 1H), 7.2 (dd, J$_1$=2.7 Hz, J$_2$=9.0 Hz, 1H), 7.16 (s, 1H), 4.1 (q, J=7.8 Hz, 2H), 3.2-2.9 (m, 3H), 2.52-2.4 (m, 2H), 1.95 (m, 1H), 1.3 (s, 3H), 1.2 (t, J=7.2 Hz, 3H).

Ethyl 2-(2-methyl-6-(4-nitrophenyl)-1-oxo-1,2,3,4-tetrahydronaphthalen-2-yl) acetate (79H)

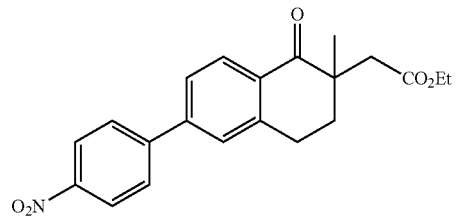

79H

Pd(PPh$_3$)$_4$ (0.09 g, 0.077 mmol) was added to a solution of product of Example 79G (2.6 g, 6.59 mmol) in 20 mL of 1,4-dioxane-H$_2$O (3:1) mixture under Argon atmosphere, followed by cesium carbonate (6.45 g, 19.78 mmol) and 4-nitro phenyl boronic acid (1.21 g, 7.24 mmol). The reaction mixture was degassed for 5 min. The reaction mixture was refluxed for 5 h, and solvent was removed under reduced pressure. The residue was partitioned between ethyl acetate and water. The separated organic layer was dried over sodium sulphate, filtered and removed under reduced pressure. The product was purified by flash chromatography to afford title compound (1.6 g, 69%) as solid. $^1$H NMR (300 MHz, CDCl$_3$): δ 8.32 (d, J=8.4 Hz, 2H), 8.18 (d, J=7.8 Hz, 1H), 7.76 (m, 2H), 7.58 (m, 1H), 7.46 (s, 1H), 4.1 (m, 2H), 3.2-2.95 (m, 3H), 2.5 (m, 2H), 2.0 (m, 1H), 1.3 (s, 3H), 1.25 (m, 3H).

Ethyl 2-(6-(4-aminophenyl)-2-methyl-1-oxo-1,2,3,4-tetrahydronaphthalen-2-yl) acetate (79I)

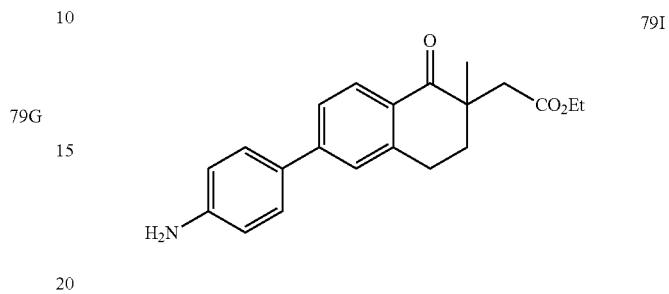

79I

Iron powder (0.73 g, 13 mmol) was added to a solution of product of Example 79H (1.6 g, 4.35 mmol) in 45 mL of ethanol-water mixture (2:1) followed by NH$_4$Cl (0.117 g, 2.16 mmol). The mixture was refluxed for 3 h. The solvent was removed under reduced pressure, and residue was partitioned between ethyl acetate and water. The separated organic layer was dried over sodium sulphate, filtered and removed in vacuo to give title compound (1.3 g, 88%). $^1$H NMR (400 MHz, CDCl$_3$): δ 8.07 (d, J=8.4 Hz, 1H), 7.49-7.46 (m, 3H), 7.37 (s, 1H), 6.75 (d, J=8.4 Hz, 2H), 4.11 (m, 2H), 3.8 (bs, 2H), 3.11-2.9 (m, 3H), 2.5-2.39 (m, 2H), 1.96 (m, 1H), 1.29 (s, 3H), 1.2 (m, 3H).

Ethyl 2-(2-methyl-1-oxo-6-(4-(3-(3-(trifluoromethyl)phenyl)ureido)phenyl)-1,2,3,4-tetrahydronaphthalen-2-yl) acetate (79J)

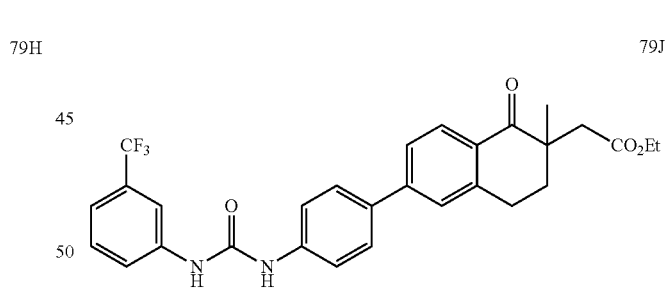

79J 3-(Trifluoromethyl)phenyl isocyanate (0.45 g, 2.44 mmol) was added to a solution of product of Example 79I (0.55 g, 1.63 mmol) and triethylamine (0.49 g, 4.89 mmol) in THF (20 mL). The reaction mixture was stirred at room temperature overnight. The solvent was removed under reduced pressure, and product was purified by flash chromatography using 20% ethyl acetate in hexanes to afford title compound (0.45 g, 53%) as solid. $^1$H NMR (300 MHz, CDCl$_3$): δ 8.06 (d, J=7.8 Hz, 1H), 7.7 (s, 1H), 7.62 (m, 1H), 7.5-7.42 (m, 2H), 7.4-7.3 (m, 6H), 7.1 (m, 1H), 4.1 (q, J=7.2 Hz, 2H), 3.2-2.9 (m, 3H), 2.56-2.44 (m, 2H), 1.95 (m, 1H), 1.3 (s, 3H), 1.2 (t, J=7.2 Hz, 3H).

2-(2-Methyl-1-oxo-6-(4-(3-(3-(trifluoromethyl)phenyl)ureido)phenyl)-1,2,3,4-tetrahydronaphthalen-2-yl)acetic acid (79)

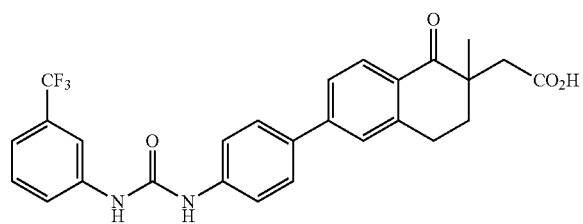

Lithium hydroxide (0.026 g, 0.66 mmol) was added to a solution of product of Example 79J (0.12 g, 0.22 mmol) in 10 mL of ethanol-water (4:1) mixture. The mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.06 g, 54%) as white solid. $^1$H NMR (400 MHz, DMSO-$d_6$): δ 12.0 (bs, 1H), 9.16 (bs, 1H), 9.04 (bs, 1H), 8.04 (m, 1H), 7.92 (d, J=8.4 Hz, 1H), 7.7 (d, J=8 Hz, 2H), 7.66-7.56 (m, 5H), 7.52 (t, J=8.0 Hz, 1H), 7.32 (d, J=7.6 Hz, 1H), 3.2-2.9 (m, 2H), 2.6 (d, J=15.6 Hz, 1H), 2.4 (m, 2H), 1.9 (m, 1H), 1.2 (s, 3H); ESI-MS m/z=497 (M+H)$^+$; LCMS Purity: 98%.

Examples 80-114 were prepared by the procedures analogous to those described in Example 79 using appropriate starting materials. The requisite boronic acids (and appropriately functional-group-protected versions thereof) utilized herein were purchased if available commercially, were synthesized as described in the literature or by routine modifications thereof known by those skilled in the art, or were synthesized by alternative procedures known by those skilled in the art. Chiral compounds were obtained using similar procedures as described in Example 129.

| Ex | Structure | $^1$H NMR Data | Mass/purity |
|---|---|---|---|
| 80 | 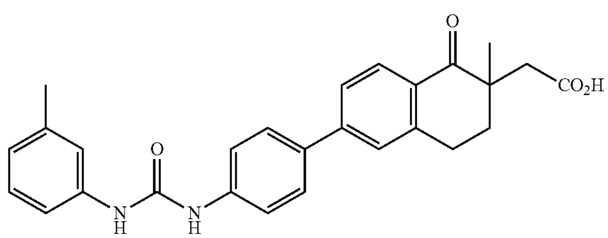 [SMILES: Cc1cccc(NC(=O)Nc2ccc(-c3ccc4c(c3)CCC(C)(CC(=O)O)C4=O)cc2)c1] | $^1$H NMR (400 MHz, DMSO-$d_6$): δ 12.1 (bs, 1H), 9.2 (bs, 1H), 8.9 (bs, 1H), 7.9 (d, J = 7.5 Hz, 1H), 7.7-7.5 (m, 6H), 7.32 (s, 1H), 7.25 (m, 1H), 7.23 (t, J = 7.8 Hz, 1H), 6.8 (d, J = 7.8 Hz, 1H), 3.3-2.9 (m, 2H), 2.85 (d, J = 15.9 Hz, 1H), 2.4 (m, 2H), 2.3 (s, 3H), 1.9 (m, 1H), 1.2 (s, 3H). | ESI-MS m/z = 441 (M − H)$^-$; LCMS Purity: 92%. |
| 81 | 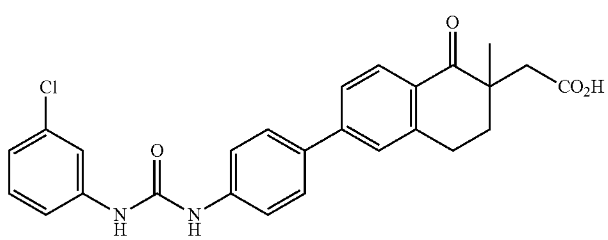 [SMILES: CC1(CC(=O)O)CCc2cc(-c3ccc(NC(=O)Nc4cccc(Cl)c4)cc3)ccc2C1=O] | $^1$H NMR (400 MHz, DMSO-$d_6$): δ 7.96 (d, J = 8 Hz, 1H), 7.76 (s, 1H), 7.65 (d, J = 8.4 Hz, 1H), 7.5 (s, 1H), 7.48-7.36 (m, 5H), 7.25 (t, J = 12 Hz, 1H), 6.95 (d, J = 8 Hz, 1H), 3.2-2.8 (m, 2H), 2.7-2.5 (m, 2H), 2.2 (d, J = 15 Hz, 1H), 1.75 (d, J = 12 Hz, 1H), 1.2 (s, 3H). | ESI-MS m/z = 463 (M + H)$^+$; HPLC Purity: 96% |
| 82 | 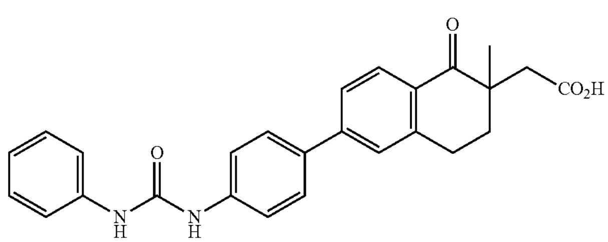 [SMILES: CC1(CC(=O)O)CCc2cc(-c3ccc(NC(=O)Nc4ccccc4)cc3)ccc2C1=O] | $^1$H NMR (300 MHz, DMSO-$d_6$): δ 12.2 (bs, 1H), 8.85 (bs, 1H), 8.75 (bs, 1H), 7.84 (d, J = 8.4 Hz, 1H), 7.74-7.54 (m, 6H), 7.46 (d, J = 7.8 Hz, 2H), 7.3 (t, J = 7.5 Hz, 2H), 6.98 (t, J = 7.8 Hz, 1H), 3.2-2.9 (m, 2H), 2.8 (d, J = 16 Hz, 1H), 2.4 (d, J = 16.2 Hz, 2H), 1.9 (m, 1H), 1.2 (s, 3H). | ESI-MS m/z = 429 (M + H)$^+$; HPLC Purity: 97%. |
| 83 | 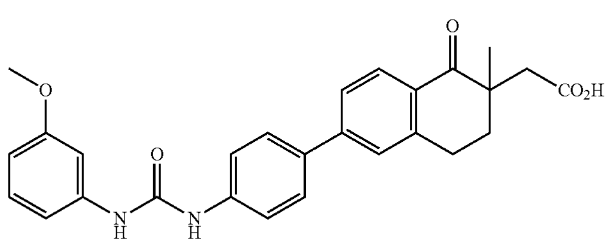 [SMILES: COc1cccc(NC(=O)Nc2ccc(-c3ccc4c(c3)CCC(C)(CC(=O)O)C4=O)cc2)c1] | $^1$H NMR (400 MHz, DMSO-$d_6$): δ 12.1 (bs, 1H), 9.15 (bs, 1H), 9.05 (bs, 1H), 7.8 (d, J = 8 Hz, 2H), 7.75-7.55 (m, 5H), 7.2 (m, 2H), 6.95 (d, J = 6 Hz, 1H), 6.55 (m, 1H), 3.75 (s, 3H), 3.3-2.9 (m, 2H), 2.8 (m, 1H), 2.4 (m, 2H), 1.9 (m, 1H), 1.2 (s, 3H). | ESI-MS m/z = 459 (M + H)$^+$; HPLC Purity: 97%. |

-continued

| Ex | Structure | ¹H NMR Data | Mass/purity |
|---|---|---|---|
| 84 | 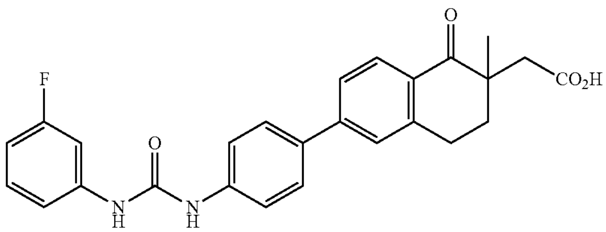 [SMILES: CC1(CC(=O)O)CCc2cc(-c3ccc(NC(=O)Nc4cccc(F)c4)cc3)ccc2C1=O] | ¹H NMR (400 MHz, DMSO-d₆): δ 12.0 (bs, 1H), 9.3 (bs, 1H), 9.1 (bs, 1H), 7.8 (d, J = 8 Hz, 2H), 7.7 (d, J = 8.8 Hz, 2H), 7.65-7.55 (m, 3H), 7.5 (d, J = 12.4 Hz, 1H), 7.3 (q, J = 8 Hz, 1H), 7.15 (d, J = 8 Hz, 1H), 6.8 (m, 1H), 3.2-2.85 (m, 2H), 2.8 (m, 1H), 2.4 (m, 2H), 1.9 (m, 1H), 1.2 (s, 3H). | ESI-MS m/z = 447 (M + H)⁺; HPLC Purity: 98%. |
| 85 | 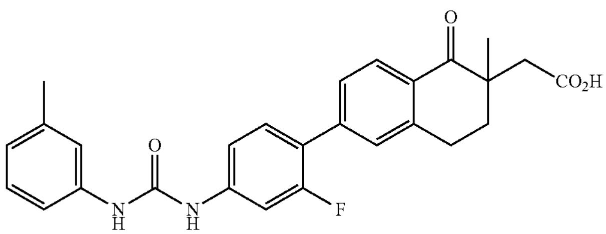 [SMILES: Cc1cccc(NC(=O)Nc2ccc(-c3ccc4c(c3)CCC(C)(CC(=O)O)C4=O)c(F)c2)c1] | ¹H NMR (300 MHz, DMSO-d₆): δ 12.2 (s, 1H), 7.9 (d, J = 8.4 Hz, 1H), 7.8-7.7 (d, J = 14.4 Hz, 1H), 7.58-7.3 (m, 6H), 7.18-7.08 (t, J = 7.8 Hz, 1H), 6.76 (d, J = 6.9 Hz, 1H), 3.2-2.8 (m, 3H), 2.6 (m, 2H), 2.3 (s, 3H), 1.8 (m, 1H), 1.2 (s, 3H). | HPLC Purity: 98% |
| 86 | 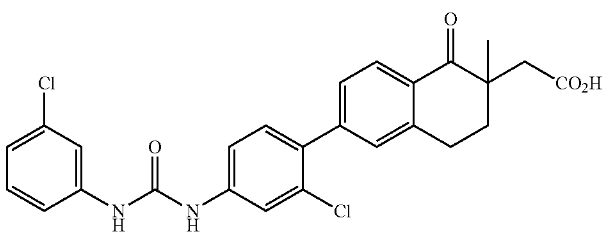 | ¹H NMR (400 MHz, DMSO-d₆): δ 12.1 (bs, 1H), 9.2 (2s, 2H), 7.9 (d, J = 8.4 Hz, 1H), 7.8 (m, 1H), 7.7 (bs, 1H), 7.48-7.26 (m, 6H), 7.05 (m, 1H), 3.2-2.8 (m, 3H), 2.35 (m, 2H), 1.9 (m, 1H), 1.25 (s, 3H). | HPLC Purity: 95% |
| 87 | Chiral: enantiomer-1 | ¹H NMR (300 MHz, DMSO-d₆): δ 12.2 (s, 1H), 9.12 (bs, 1H), 9.0 (bs, 1H), 8.02 (s, 1H), 7.93 (d, J = 8.4 Hz, 1H), 7.75-7.5 (m, 8H), 7.3 (d, J = 7.8 Hz, 1H), 3.2-2.9 (m, 2H), 2.8 (d, J = 16.2 Hz, 1H), 2.4 (d, J = 15.9 Hz, 2H), 1.9 (m, 1H), 1.2 (s, 3H). | HPLC Purity: 98%; Chiral HPLC purity: 99% |
| 88 | Chiral: enantiomer-2 | ¹H NMR (300 MHz, DMSO-d₆): δ 12.2 (s, 1H), 9.12 (bs, 1H), 9.0 (bs, 1H), 8.02 (s, 1H), 7.93 (d, J = 8.4 Hz, 1H), 7.75-7.5 (m, 8H), 7.3 (d, J = 7.8 Hz, 1H), 3.2-2.9 (m, 2H), 2.8 (d, J = 16.2 Hz, 1H), 2.4 (d, J = 15.9 Hz, 2H), 1.9 (m, 1H), 1.2 (s, 3H). | HPLC Purity: 98.7%; Chiral HPLC purity: 97.5% |
| 89 | 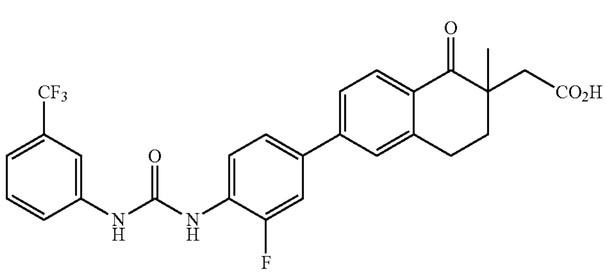 [SMILES: CC1(CC(=O)O)CCc2cc(-c3ccc(NC(=O)Nc4cccc(C(F)(F)F)c4)c(Cl)c3)ccc2C1=O] | ¹H NMR (300 MHz, DMSO-d₆): δ 12.1 (bs, 1H), 9.54 (s, 1H), 8.85 (s, 1H), 8.25 (t, J = 8.4 Hz, 1H), 8.05 (s, 1H), 7.92 (d, J = 9.0 Hz, 1H) 7.75-7.65 (m, 3H), 7.62-7.5 (m, 3H), 7.35 (m, 1H), 3.2-2.9 (m, 2H), 2.84 (m, 1H), 2.4 (m, 2H), 1.9 (m, 1H), 1.2 (s, 3H). | ESI-MS m/z = 513 (M − H)⁻. HPLC purity: 97.11%. |

-continued

| Ex | Structure | ¹H NMR Data | Mass/purity |
|---|---|---|---|
| 90 | (3-chlorophenyl urea linked to fluorophenyl tetralone acetic acid) | ¹H NMR (300 MHz, DMSO-d₆): δ 12.1 (bs, 1H), 9.33 (s, 1H), 9.0 (s, 1H), 8.25 (t, J = 8.4 Hz, 1H), 7.9 (d, J = 9.0 Hz, 1H) 7.75-7.65 (m, 4H), 7.6 (d, J = 8.4 Hz, 1H), 7.35-7.25 (m, 2H), 7.05 (t, J = 7.5 Hz, 1H), 3.2-2.9 (m, 2H), 2.83 (m, 1H), 2.4 (m, 2H), 1.9 (m, 1H), 1.2 (s, 3H). | ESI-MS m/z = 481 (M + H)⁺. HPLC purity: 97.55%. |
| 91 | (phenyl urea linked to fluorophenyl tetralone acetic acid) | ¹H NMR (400 MHz, DMSO-d₆): δ 12.1 (bs, 1H), 9.24 (s, 1H), 8.8 (s, 1H), 8.27 (t, J = 8.4 Hz, 1H), 7.9 (d, J = 8.8 Hz, 1H) 7.75-7.65 (m, 3H), 7.6 (d, J = 8.8 Hz, 1H), 7.45 (d, J = 7.6 Hz, 2H), 7.3 (t, J = 7.6 Hz, 2H), 7.0 (t, J = 7.2 Hz, 1H), 3.2-2.9 (m, 2H), 2.82 (m, 1H), 2.35 (m, 2H), 1.9 (m, 1H), 1.2 (s, 3H). | ESI-MS m/z = 445 (M − H)⁻. HPLC purity: 95.51%. |
| 92 | (3-fluorophenyl urea linked to fluorophenyl tetralone acetic acid) | ¹H NMR (400 MHz, DMSO-d₆): δ 12.1 (bs, 1H), 9.35 (s, 1H), 8.76 (s, 1H), 8.3 (t, J = 8.4 Hz, 1H), 7.92 (d, J = 8.0 Hz, 1H) 7.7 (m, 3H), 7.6-7.5 (m, 1H), 7.35 (m, 1H), 7.1 (d, J = 7.6 Hz, 1H), 6.83 (m, 2H), 3.2-2.9 (m, 2H), 2.8 (m, 1H), 2.4 (m, 2H), 1.9 (m, 1H), 1.2 (s, 3H). | ESI-MS m/z = 465 (M + H)⁺. HPLC purity: 92.08%. |
| 93 | (3-methoxyphenyl urea linked to fluorophenyl tetralone acetic acid) | ¹H NMR (400 MHz, DMSO-d₆): δ 12.1 (bs, 1H), 9.25 (s, 1H), 8.8 (s, 1H), 8.3 (t, J = 8.4 Hz, 1H), 7.9 (d, J = 8.8 Hz, 1H) 7.7 (m, 3H), 7.57 (d, J = 8.8 Hz, 1H), 7.2 (m, 2H), 6.95 (d, J = 9.2 Hz, 1H), 6.6 (dd, J = 2.0 Hz, 8.0 Hz, 1H), 3.75 (s, 3H), 3.2-2.9 (m, 2H), 2.81 (d, J = 16.4 Hz, 1H), 2.36 (m, 2H), 1.9 (m, 1H), 1.2 (s, 3H). | ESI-MS m/z = 477 (M + H)⁺. LCMS purity: 99.34%. |
| 94 | (3-trifluoromethylphenyl urea linked to chlorophenyl tetralone acetic acid) | ¹H NMR (400 MHz, DMSO-d₆): δ 12.1 (bs, 1H), 9.95 (bs, 1), 8.65 (s, 1H), 8.3 (m, 1H), 8.1 (s, 1H), 7.95-7.85 (m, 2H), 7.75-7.65 (m, 3H), 7.6-7.5 (m, 2H), 7.35 (d, J = 7.2 Hz, 1H), 3.2-2.8 (m, 2H), 2.6 (m, 1H), 2.3 (m, 2H), 1.9 (m, 1H), 1.3 (s, 3H). | HPLC purity: 95%. |
| 95 | (3-chlorophenyl urea linked to difluorophenyl tetralone acetic acid) | ¹H NMR (400 MHz, DMSO-d₆): δ 12.2 (bs, 1H), 9.5 (s, 1H), 9.0 (s, 1H), 8.2 (m, 1H), 7.9 (d, J = 8.8 Hz, 1H), 7.75 (s, 1H), 7.6-7.5 (m, 3H), 7.4-7.2 (m, 2H), 7.1 (d, J = 8 Hz, 1H), 3.2-2.9 (m, 2H), 2.8 (d, J = 16 Hz, 1H), 2.4 (m, 2H), 1.9 (m, 1H), 1.2 (s, 3H). | ESI-MS m/z = 499 (M + H)⁺; HPLC Purity: 95.4% |

-continued

| Ex | Structure | ¹H NMR Data | Mass/purity |
|---|---|---|---|
| 96 | 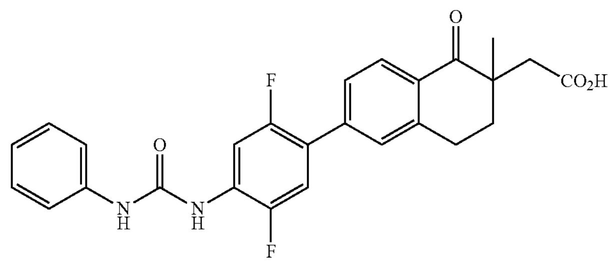 [SMILES: CC1(CC(=O)O)CCc2cc(-c3cc(F)c(NC(=O)Nc4ccccc4)cc3F)ccc2C1=O] | ¹H NMR (400 MHz, DMSO-d₆): δ 12.2 (bs, 1H), 9.42 (bs, 1H), 9.1 (bs, 1H), 8.16 (m, 1H), 7.95 (d, J = 8.4 Hz,, 1H), 7.6-7.4 (m, 5H), 7.3 (t, J = 7.6 Hz, 2H), 7.0 (t, J = 7.2 Hz, 1H), 3.3-2.9 (m, 2H), 2.8 (d, J = 16 Hz, 1H), 2.4 (m, 2H), 1.8 (m, 1H), 1.2 (s, 3H). | HPLC Purity: 93.4% |
| 97 | 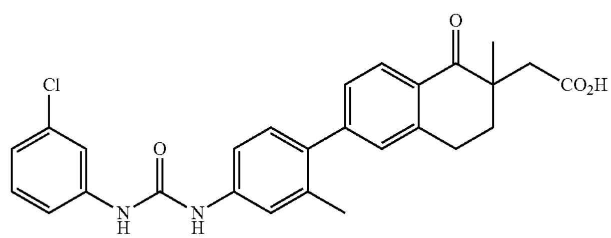 [SMILES: Cc1cc(NC(=O)Nc2cccc(Cl)c2)ccc1-c1ccc2c(c1)CCC(C)(CC(=O)O)C2=O] | ¹H NMR (300 MHz, DMSO-d₆): δ 12.0 (s, 1H), 8.95 (bs, 1H), 8.85 (bs, 1H), 7.9 (d, J = 8.4 Hz, 1H), 7.85 (s, 1H), 7.45-7.3 (m, 6H), 7.15 (d, J = 8.4 Hz, 1H), 7.0 (m, 1H), 3.2-2.9 (m, 2H), 2.8 (m, 1H), 2.4 (m, 2H), 2.3 (s, 3H), 1.9 (m, 1H), 1.2 (s, 3H). | ESI-MS m/z = 477 (M + H)⁺; HPLC purity: 98.7%. |
| 98 | 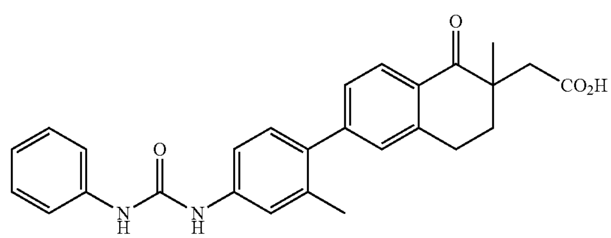 [SMILES: Cc1cc(NC(=O)Nc2ccccc2)ccc1-c1ccc2c(c1)CCC(C)(CC(=O)O)C2=O] | ¹H NMR (400 MHz, DMSO-d₆): δ 12.0 (s, 1H), 8.9 (2s, 2H), 7.9 (d, J = 7.6 Hz, 1H), 7.5-7.28 (m, 8H), 7.18 (d, J = 8.0 Hz, 1H), 7.0 (t, J = 7.2 Hz, 1H), 3.2-2.8 (m, 2H), 2.78 (d, J = 15.9 Hz, 1H), 2.4 (m, 2H), 2.3 (s, 3H), 1.9 (m, 1H), 1.2 (s, 3H). | ESI-MS m/z = 445 (M + H)⁺; HPLC purity: 95%. |
| 99 | 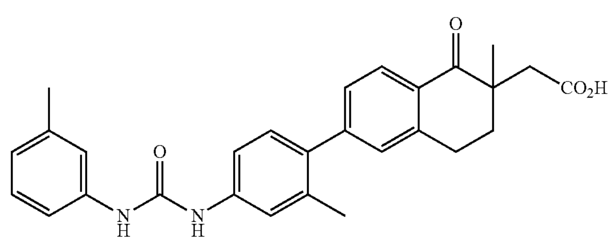 [SMILES: Cc1cccc(NC(=O)Nc2ccc(-c3ccc4c(c3)CCC(C)(CC(=O)O)C4=O)c(C)c2)c1] | ¹H NMR (300 MHz, DMSO-d₆): δ 12.2 (bs, 1H), 9.6-9.0 (bs, 2H), 7.9 (d, J = 7.5 Hz, 1H), 7.56 (s, 1H), 7.4-7.25 (m, 4H), 7.12 (m, 2H), 7.0 (bs, 1H), 6.78 (d, J = 7.8 Hz, 1H), 3.2-2.95 (m, 2H), 2.85 (d, J = 16.2 Hz, 1H), 2.56 (m, 2H), 2.3 (s, 3H), 2.26 (s, 3H), 1.8 (m, 1H), 1.2 (s, 3H); | ESI-MS m/z = 456 (M + H); HPLC Purity: 95%. |
| 110 | 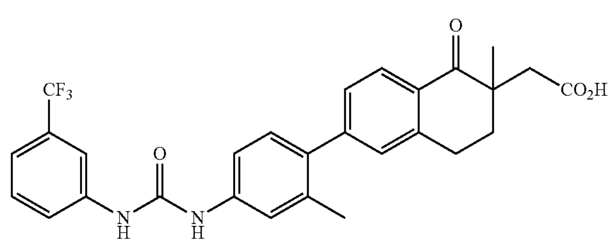 | ¹H NMR (300 MHz, DMSO-d₆): δ 12.2 (bs, 1H), 9.6-9.0 (bs, 2H), 8.08 (s, 1H), 7.9 (d, J = 8.4 Hz, 1H), 7.6 (m, 1H), 7.5 (m, 2H), 7.36-7.24 (m, 4H), 7.18 (m, 1H), 3.2-2.9 (m, 2H), 2.8 (d, J = 15.9 Hz, 1H), 2.4 (d, J = 16.2 Hz, 2H), 2.3 (s, 3H), 1.85 (m, 1H), 1.2 (s, 3H); | ESI-MS m/z = 510 (M + H)⁺; HPLC purity: 96%. |
| 101 | 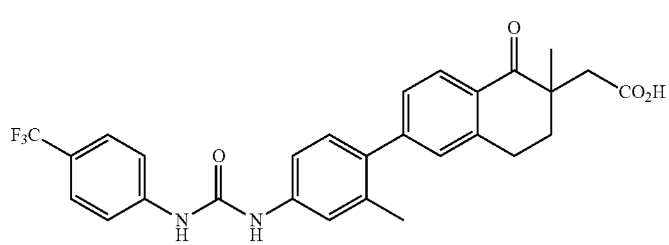 [SMILES: Cc1cc(NC(=O)Nc2ccc(C(F)(F)F)cc2)ccc1-c1ccc2c(c1)CCC(C)(CC(=O)O)C2=O] | ¹H NMR (300 MHz, DMSO-d₆): δ 12.0 (bs, 1H), 7.9 (d, J = 8.4 Hz, 1H), 7.76 (d, J = 8.1 Hz, 2H), 7.6 (d, J = 8.1 Hz, 3H), 7.3 (m, 2H), 6.9 (m, 2H), 3.2-2.8 (m, 3H), 2.6 (m, 2H), 2.2 (s, 3H), 1.8 (m, 1H), 1.2 (s, 3H); | ESI-MS m/z = 510 (M + H)⁺; HPLC purity: 96.5%. |

-continued

| Ex | Structure | ¹H NMR Data | Mass/purity |
|---|---|---|---|
| 102 | 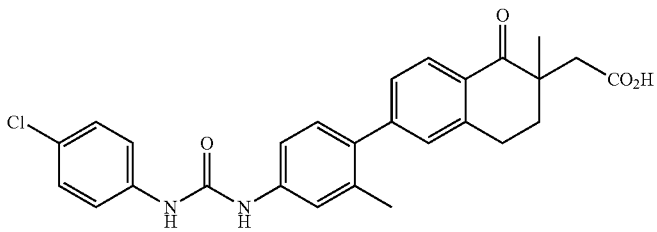 [SMILES: Cc1cc(NC(=O)Nc2ccc(Cl)cc2)ccc1-c1ccc2c(c1)CCC(C)(CC(=O)O)C2=O] | ¹H NMR (400 MHz, DMSO-d₆): δ 7.9 (d, J = 8.4 Hz, 1H), 7.6 (m, 3H), 7.32-7.2 (m, 5H), 7.0 (bs, 1H), 3.2-2.9 (m, 3H), 2.4 (m, 2H), 2.2 (m, 3H), 1.8 (m, 1H), 1.2 (s, 3H). | ESI-MS m/z = 477 (M + H)⁺; HPLC purity: 92%. |
| 103 | 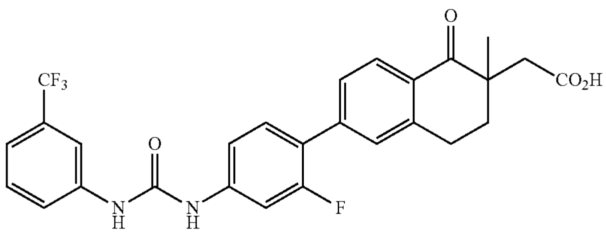 [SMILES: CC1(CC(=O)O)CCc2cc(-c3ccc(NC(=O)Nc4cccc(C(F)(F)F)c4)cc3F)ccc2C1=O] | ¹H NMR (300 MHz, DMSO-d₆): δ 12.2 (s, 1H), 9.2 (bs, 2H), 8.03 (s, 1H), 7.9 (d, J = 8.4 Hz, 1H), 7.64-7.48 (m, 6H), 7.38-7.24 (m, 2H), 3.2-2.9 (m, 2H), 2.8 (d, J = 15.9 Hz, 1H), 2.4 (m, 2H), 1.9 (m, 1H), 1.2 (s, 3H). | ESI-MS m/z = 515 (M + H)⁺; HPLC Purity: 97% |
| 104 | 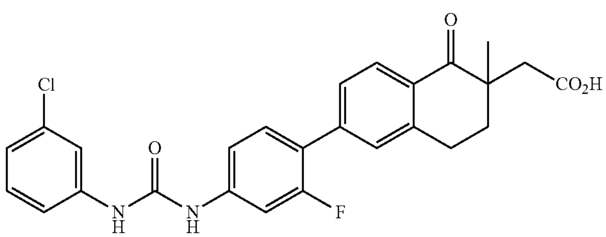 [SMILES: CC1(CC(=O)O)CCc2cc(-c3ccc(NC(=O)Nc4cccc(Cl)c4)cc3F)ccc2C1=O] | ¹H NMR (300 MHz, DMSO-d₆): δ 12.2 (bs, 1H), 9.2 (bs, 2H), 7.95 (d, J = 7.8 Hz, 1H), 7.7 (s, 1H), 7.6 (d, J = 14 Hz, 1H), 7.54-7.44 (m, 3H), 7.35-7.25 (m, 3H), 7.0 (m, 1H), 3.2-2.9 (m, 2H), 2.85 (d, J = 15.3 Hz, 1H), 2.4 (d, J = 16.2 Hz, 2H), 1.8 (m, 1H), 1.2 (s, 3H). | ESI-MS m/z = 481 (M + H)⁺; HPLC Purity: 99% |
| 105 | 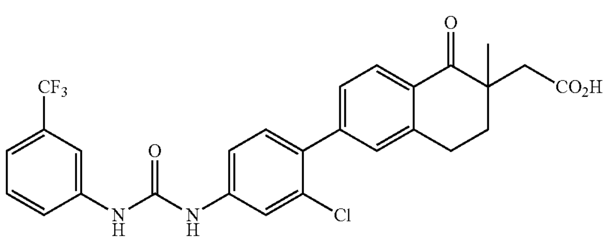 | ¹H NMR (300 MHz, DMSO-d₆): δ 12.0 (s, 1H), 9.4 (s, 1H), 8.04 (s, 1H), 7.94 (d, J = 8 Hz, 1H), 7.88 (bs, 1H), 7.62 (m, 1H), 7.5 (t, J = 7.6 Hz, 1H), 7.4-7.3 (m, 6H), 3.2-2.8 (m, 3H), 2.4 (m, 2H), 1.8 (m, 1H), 1.2 (s, 3H). | HPLC purity: 94%. |
| 106 | 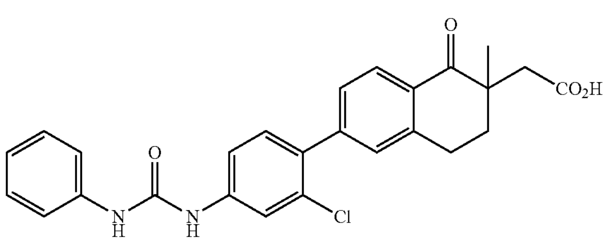 [SMILES: CC1(CC(=O)O)CCc2cc(-c3ccc(NC(=O)Nc4ccccc4)cc3Cl)ccc2C1=O] | ¹H NMR (300 MHz, DMSO-d₆): δ 7.95 (d, J = 8.4 Hz, 2H), 7.7 (s, 1H), 7.4-7.3 (m, 6H), 7.2 (m, 1H), 7.0 (m, 1H), 3.2-2.8 (m, 3H), 2.3 (m, 2H), 1.8 (m, 1H), 1.2 (s, 3H). | HPLC purity: 95%. |
| 107 | 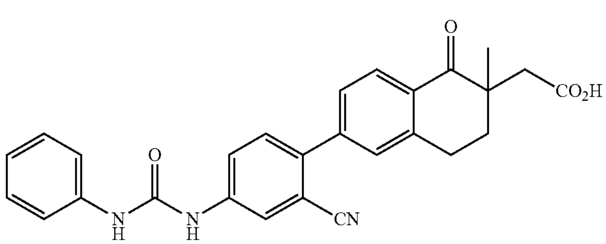 [SMILES: CC1(CC(=O)O)CCc2cc(-c3ccc(NC(=O)Nc4ccccc4)cc3C#N)ccc2C1=O] | ¹H NMR (300 MHz, DMSO-d₆): δ 12.2 (s, 1H), 9.15 (bs, 1H), 8.9 (bs, 1H), 8.1 (s, 1H), 8.0 (d, J = 7.5 Hz, 1H), 7.8 (m, 1H), 7.65-7.45 (m, 6H), 7.3 (t, J = 6.9 Hz, 2H), 3.2-2.8 (m, 3H), 2.4 (m, 2H), 2.0 (m, 1H), 1.2 (s, 3H). | ESI-MS m/z = 453 (M + H)⁺; HPLC purity: 92%. |

| Ex | Structure | ¹H NMR Data | Mass/purity |
|---|---|---|---|
| 108 | 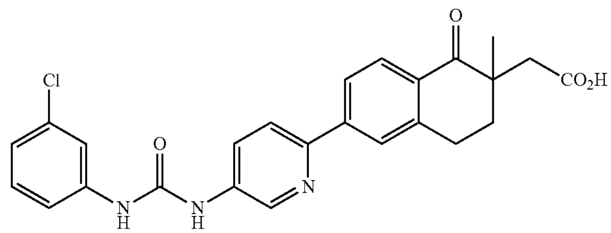 | ¹H NMR (400 MHz, DMSO-d₆): δ 9.56 (s, 1H), 9.48 (s, 1H), 8.75 (s, 1H), 8.15-7.95 (m, 5H), 7.72 (s, 1H), 7.32 (m, 2H), 7.05 (s, 1H), 3.2-2.95 (m, 2H), 2.84 (m, 1H), 2.5-2.3 (m, 2H), 1.9 (m, 1H), 1.17 (s, 3H). | ESI-MS m/z = 464 (M + H)⁺; HPLC purity: 96.3%. |
| 109 | 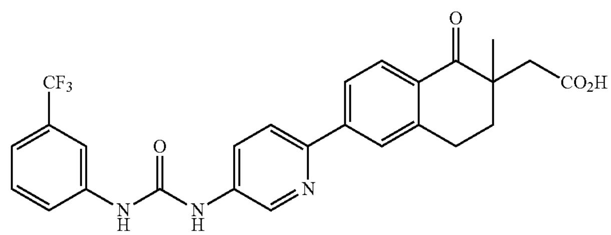 [SMILES: CC1(CC(=O)O)CCc2cc(-c3ccc(NC(=O)Nc4cccc(Cl)c4)cn3)ccc2C1=O] | ¹H NMR (400 MHz, DMSO-d₆): δ 9.48-9.45 (2bs, 2H), 8.76 (s, 1H), 8.2-7.95 (m, 6H), 7.63 (d, J = 8.4 Hz, 1H), 7.54 (t, J = 7.6 Hz, 1H), 7.34 (d, J = 7.2 Hz, 1H), 3.2-2.95 (m, 2H), 2.84 (d, J = 16 Hz, 1H), 2.5-2.3 (m, 2H), 1.92 (m, 1H), 1.18 (s, 3H). | ESI-MS m/z = 498 (M + H)⁺; HPLC purity: 93.9%. |
| 110 | 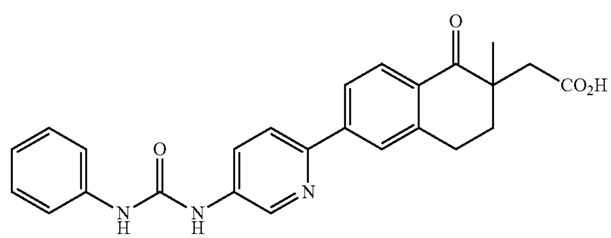 [SMILES: CC1(CC(=O)O)CCc2cc(-c3ccc(NC(=O)Nc4ccccc4)cn3)ccc2C1=O] | ¹H NMR (400 MHz, DMSO-d₆): δ 9.6 (s, 1H), 9.22 (s, 1H), 8.79 (s, 1H), 8.2-7.95 (m, 5H), 7.48 (d, J = 8.0 Hz, 2H), 7.3 (t, J = 8.4 Hz, 2H), 7.0 (t, J = 7.2 Hz, 1H), 3.18-2.95 (m, 2H), 2.83 (d, J = 16.4 Hz, 1H), 2.5-2.3 (m, 2H), 1.9 (m, 1H), 1.18 (s, 3H). | ESI-MS m/z = 430 (M + H)⁺; HPLC purity: 97.4%. |
| 111 | 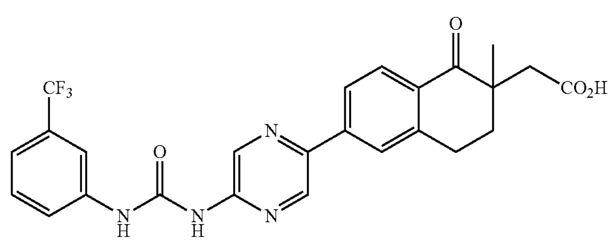 [SMILES: CC1(CC(=O)O)CCc2cc(-c3cnc(NC(=O)Nc4cccc(C(F)(F)F)c4)cn3)ccc2C1=O] | ¹H NMR (400 MHz, DMSO-d₆): δ 12.2 (bs, 1H), 10.06 (s, 1H), 9.91 (s, 1H), 9.19 (s, 1H), 9.02 (s, 1H), 8.1-7.95 (m, 4H), 7.68 (d, J = 8.4 Hz, 1H), 7.57 (t, J = 8.4 Hz, 1H), 7.4 (d, J = 7.2 Hz, 1H), 3.2-2.95 (m, 2H), 2.85 (d, J = 16.0 Hz, 1H), 2.5-2.35 (m, 2H), 1.9 (m, 1H), 1.18 (s, 3H). | ESI-MS m/z = 497 (M − H)⁻; HPLC purity: 95.7%. |
| 112 | 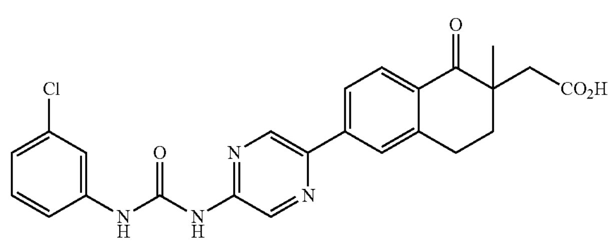 [SMILES: CC1(CC(=O)O)CCc2cc(-c3cnc(NC(=O)Nc4cccc(Cl)c4)cn3)ccc2C1=O] | ¹H NMR (300 MHz, DMSO-d₆): δ 12.2 (bs, 1H), 10.24 (bs, 1H), 9.98 (bs, 1H), 9.22 (s, 1H), 9.01 (s, 1H), 8.1-7.95 (m, 3H), 7.76 (s, 1H), 7.35 (m, 2H), 7.09 (m, 1H), 3.15-2.95 (m, 2H), 2.84 (d, J = 15.9 Hz, 1H), 2.5-2.35 (m, 2H), 1.9 (m, 1H), 1.18 (s, 3H). | ESI-MS m/z = 465 (M + H)⁺; HPLC purity: 97.5%. |
| 113 | 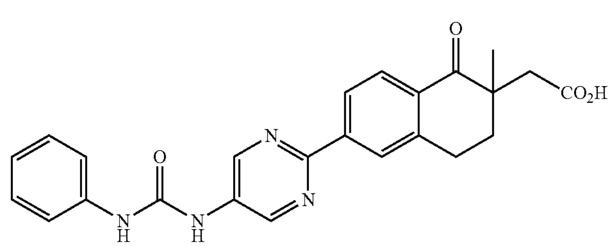 [SMILES: CC1(CC(=O)O)CCc2cc(-c3ncc(NC(=O)Nc4ccccc4)cn3)ccc2C1=O] | ¹H NMR (300 MHz, DMSO-d₆): δ 12.1 (bs, 1H), 9.4 (bs, 1H), 9.2 (bs, 1H), 9.0 (s, 2H), 8.3 (m, 2H), 8.0 (d, J = 8.4 Hz, 1H), 7.5 (d, J = 7.8 Hz, 2H), 7.3 (t, J = 7.8 Hz, 2H), 7.0 (t, J = 7.2 Hz, 1H), 3.3 (m, 2H), 2.8 (d, J = 16.8 Hz, 1H), 2.4 (m, 2H), 1.8 (m, 1H), 1.2 (s, 3H). | ESI-LCMS m/z: 431 (purity 91.3%); HPLC purity 98%. |

| Ex | Structure | ¹H NMR Data | Mass/purity |
|---|---|---|---|
| 114 | 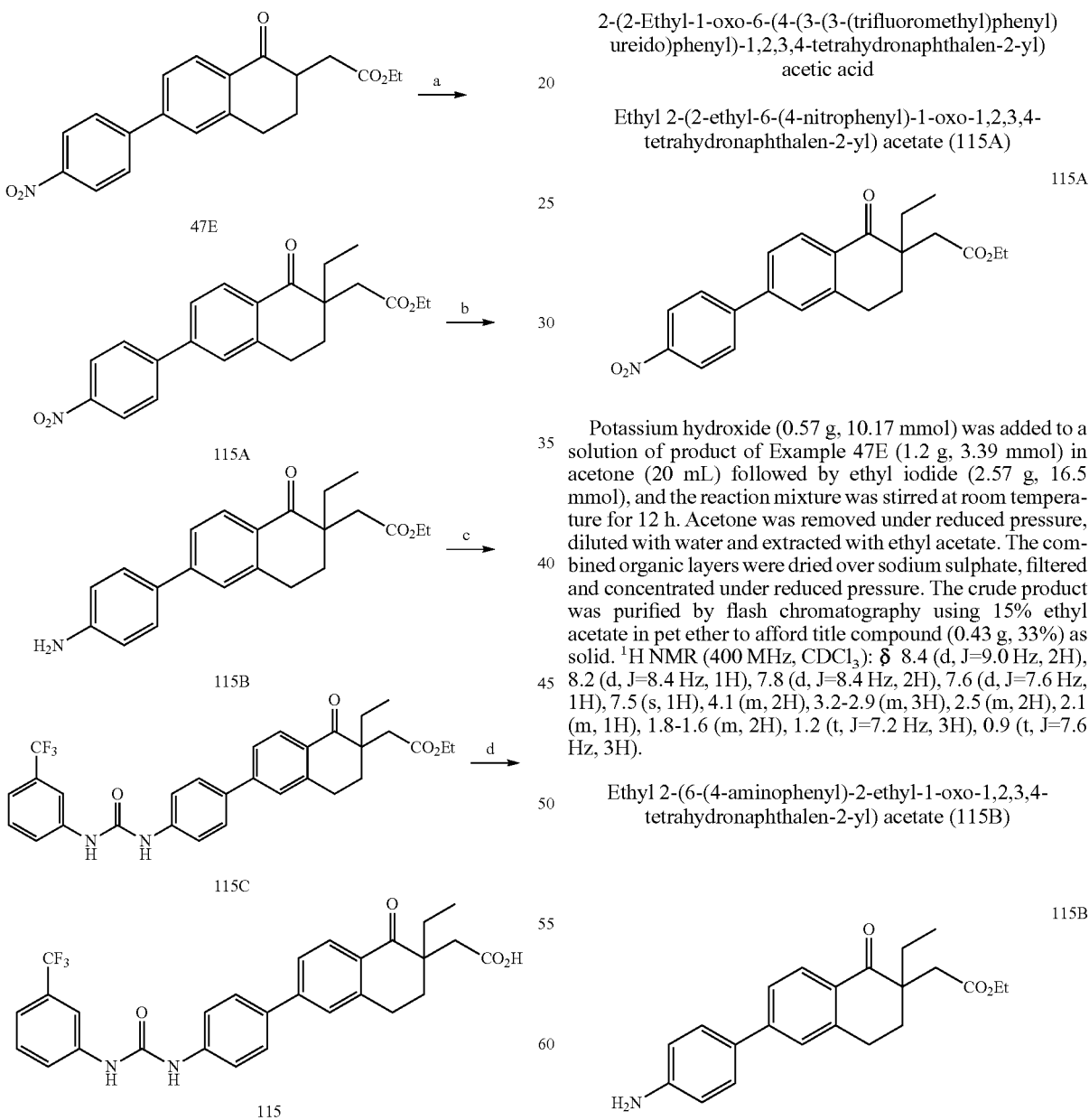 | ¹H NMR (300 MHz, DMSO-d₆): δ 12.1 (bs, 1H), 10.0 (bs, 2H), 9.0 (s, 2H), 8.4 (m, 2H), 8.0 (m, 2H), 7.7 (d, J = 7.5 Hz, 1H), 7.5 (t, J = 7.8 Hz, 1H), 7.3 (d, J = 6.9 Hz, 1H), 3.1 (m, 3H), 2.8 (m, 1H), 2.4 (m, 1H), 1.9 (d, J = 12.6 Hz, 1H), 1.2 (s, 3H). | ESI-LCMS m/z: 498 (purity 98%). HPLC purity 98%. |

Example-115

Reagents and conditions: a) EtI, KOH, Acetone, RT, 12 h; b) Fe—NH₄Cl, EtOH—H₂O, 85° C., 2 h; c) 3-CF₃PhNCO, Et₃N, THF, RT, 12 h; d) LiOH, THF—H₂O, RT, 12 h.

Procedure 2-(2-Ethyl-1-oxo-6-(4-(3-(3-(trifluoromethyl)phenyl)ureido)phenyl)-1,2,3,4-tetrahydronaphthalen-2-yl) acetic acid Ethyl 2-(2-ethyl-6-(4-nitrophenyl)-1-oxo-1,2,3,4-tetrahydronaphthalen-2-yl) acetate (115A)

Potassium hydroxide (0.57 g, 10.17 mmol) was added to a solution of product of Example 47E (1.2 g, 3.39 mmol) in acetone (20 mL) followed by ethyl iodide (2.57 g, 16.5 mmol), and the reaction mixture was stirred at room temperature for 12 h. Acetone was removed under reduced pressure, diluted with water and extracted with ethyl acetate. The combined organic layers were dried over sodium sulphate, filtered and concentrated under reduced pressure. The crude product was purified by flash chromatography using 15% ethyl acetate in pet ether to afford title compound (0.43 g, 33%) as solid. ¹H NMR (400 MHz, CDCl₃): δ 8.4 (d, J=9.0 Hz, 2H), 8.2 (d, J=8.4 Hz, 1H), 7.8 (d, J=8.4 Hz, 2H), 7.6 (d, J=7.6 Hz, 1H), 7.5 (s, 1H), 4.1 (m, 2H), 3.2-2.9 (m, 3H), 2.5 (m, 2H), 2.1 (m, 1H), 1.8-1.6 (m, 2H), 1.2 (t, J=7.2 Hz, 3H), 0.9 (t, J=7.6 Hz, 3H).

Ethyl 2-(6-(4-aminophenyl)-2-ethyl-1-oxo-1,2,3,4-tetrahydronaphthalen-2-yl) acetate (115B)

Iron powder (0.189 g, 3.37 mmol) was added to a solution of product of Example 115A (0.43 g, 1.12 mmol) in 22 mL of ethanol-water mixture (2:1) followed by NH₄Cl (0.030 g, 0.55 mmol), and the mixture was refluxed for 2 h. The solvent was removed under reduced pressure, and residue was partitioned between ethyl acetate and water. The separated organic layer was dried over sodium sulphate, filtered, concentrated in vacuo and triturated with n-pentane to give title compound (0.35 g, 89%). $^1$H NMR (400 MHz, CDCl$_3$): δ 8.1 (d, J=8.4 Hz, 1H), 7.8 (d, J=8.4 Hz, 2H), 7.6-7.3 (m, 4H), 4.1 (m, 2H), 3.8 (bs, 2H), 3.1 (m, 1H), 3.0-2.8 (m, 2H), 2.6-2.4 (m, 2H), 2.1 (m, 1H), 1.8-1.6 (m, 2H), 1.3 (t, J=7.6 Hz, 3H), 0.9 (t, J=7.2 Hz, 3H).

Ethyl 2-(2-ethyl-1-oxo-6-(4-(3-(3-(trifluoromethyl)phenyl)ureido)phenyl)-1,2,3,4-tetrahydronaphthalen-2-yl)acetate (115C)

115C

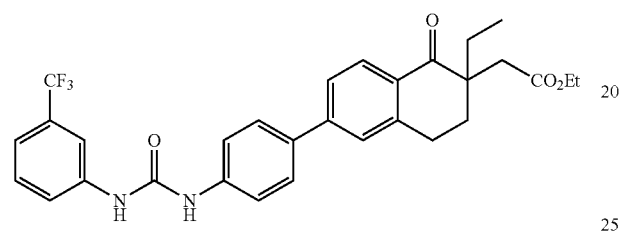

3-(Trifluoromethyl)phenyl isocyanate (0.084 mL, 0.56 mmol) was added to a solution of product of Example 115B (0.2 g, 0.56 mmol) and triethylamine (0.234 mL, 1.70 mmol) in THF (4 mL). The mixture was stirred at room temperature for 12 h. The solvent was removed under reduced pressure, and product was purified by flash chromatography using 25-30% ethyl acetate in pet ether to afford title compound (0.25 g, 81%) as solid. $^1$H NMR (400 MHz, CDCl$_3$): δ 8.1 (d, 8.4 Hz, 1H), 7.7 (m, 1H), 7.6 (m, 1H), 7.5-7.3 (m, 9H), 7.1 (s, 1H), 4.1 (q, J=6.9 Hz, 2H), 3.2-2.8 (m, 3H), 2.5 (m, 2H), 2.1 (m, 1H), 1.8-1.6 (m, 2H), 1.4-1.2 (m, 5H), 0.9 (t, J=7.2 Hz, 3H).

2-(2-Ethyl-1-oxo-6-(4-(3-(3-(trifluoromethyl)phenyl)ureido)phenyl)-1,2,3,4-tetrahydronaphthalen-2-yl)acetic acid (115)

115

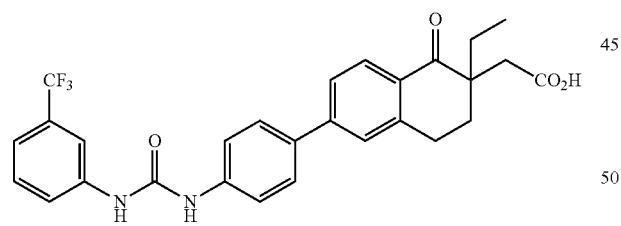

Lithium hydroxide (0.054 g, 1.38 mmol) was added to a solution of product of Example 115C (0.25 g, 0.46 mmol) in 3 mL of ethanol-water (2:1) mixture. The mixture was stirred at room temperature for 12 h. After the solvent was removed in vacuo, the residue was dissolved in water and washed with ethyl acetate. The aqueous layer was acidified with addition of 2N aqueous solution of HCl until pH 2 was attained. The resulting solids were collected by filtration, triturated with n-pentane and diethyl ether and dried under vacuum to afford title compound (0.15 g, 63%) as white solid. $^1$H NMR (400 MHz, DMSO-d$_6$): δ 12.1 (bs, 1H), 9.3 (bs, 1H), 9.1 (bs, 1H), 8.1 (s, 1H), 7.9 (d, J=8.4 Hz, 1H), 7.7-7.5 (m, 8H), 7.3 (d, J=6.9 Hz, 1H), 3.2-2.8 (m, 3H), 2.4 (m, 2H), 2.0 (m, 1H), 1.8-1.6 (m, 2H), 0.9 (t, J=7.8 Hz, 3H); ESI-MS m/z: 511 (M+H)$^+$; HPLC purity: 95%.

Example-116

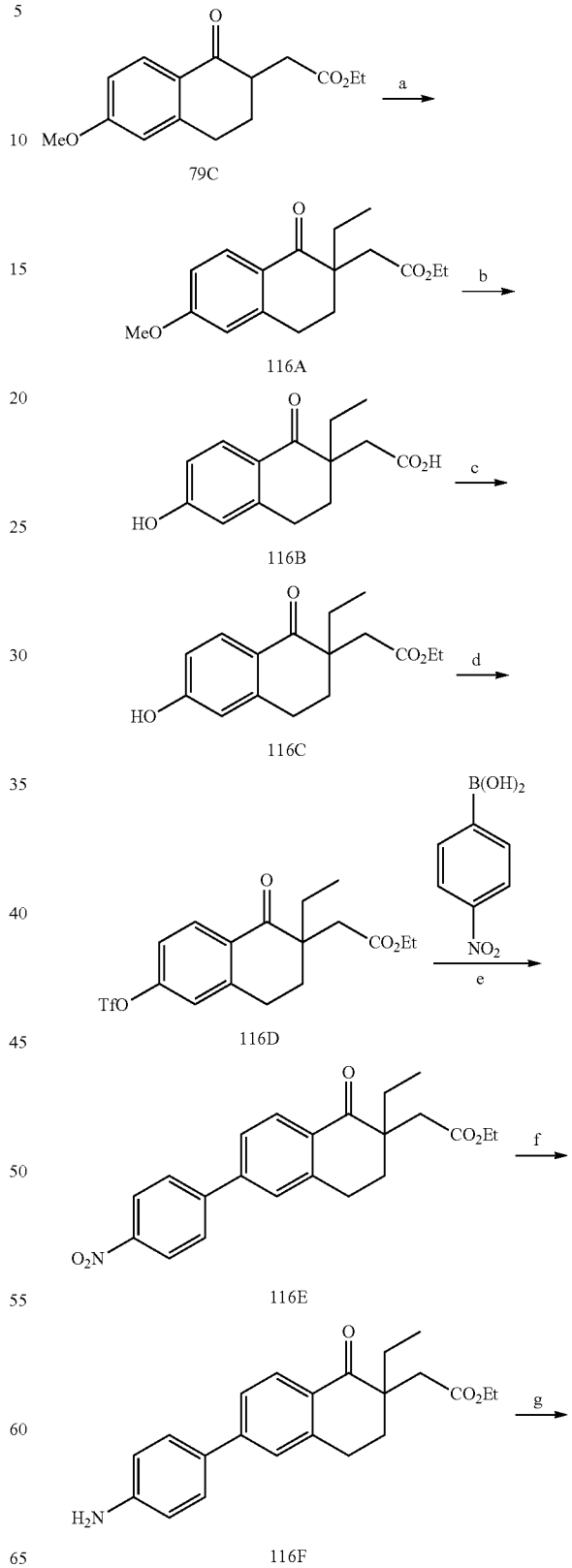

-continued

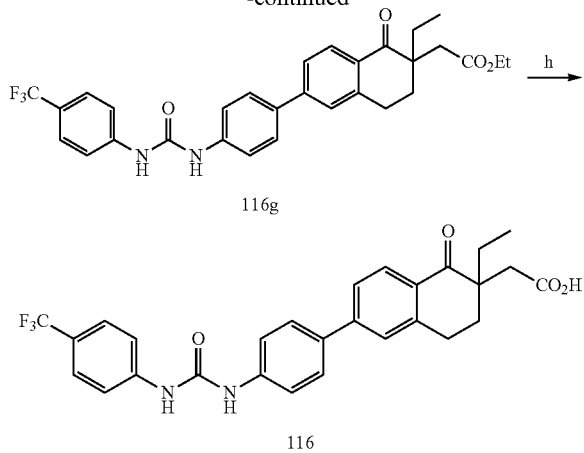

Reagents and conditions: a) EtI, NaH, DMF, RT, 5 h; b) Aq. HBr, 100° C., 3 h; c) MeSO₃H, EtOH, RT, 16 h; d) Tf₂O, CH₂Cl₂, Et₃N, RT, 2 h; e) Ph(PPh₃)₄, Cs₂CO₃, Dioxane-H₂O, 80° C., 4 h; f) Fe—NH₄Cl, EtOH—H₂O, 85° C., 4 h; g) 4-CF₃PhNCO, Et₃N, THF, RT, 12 h; h) LiOH, THF—H₂O, RT, 12 h.

Procedure 2-(2-Ethyl-1-oxo-6-(4-(3-(4-(trifluoromethyl)phenyl) ureido)phenyl)-1,2,3,4-tetrahydronaphthalen-2-yl) acetic acid Ethyl 2-(2-ethyl-6-methoxy-1-oxo-1,2,3,4-tetrahydronaphthalen-2-yl) acetate (116A)

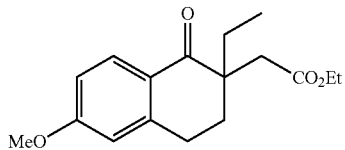

To an ice-cold solution of product of Example 79C (7 g, 26.8 mmol) in DMF (80 mL) was added NaH (1.93 g, 80.4 mmol) in portion wise, and the reaction mixture was stirred for 10 min. Ethyl iodide (20.91 g, 134.03 mmol) was then added, and the mixture was stirred for 5 h at room temperature. The reaction mixture was poured in to ice water and aqueous layer was extracted with ethyl acetate. The combined organic layers were dried over sodium sulphate, filtered and removed under vacuum to give title compound (7.8 g) as solid.

2-(2-Ethyl-6-hydroxy-1-oxo-1,2,3,4-tetrahydronaphthalen-2-yl)acetic acid (116B)

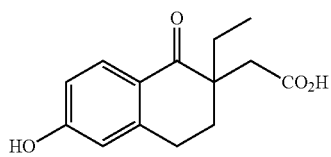

Aqueous HBr (120 mL) was added to product of Example 116A (7.8 g, 26.9 mmol), and the reaction mixture was refluxed for 3 h. The reaction mixture was then brought to room temperature and extracted with ethyl acetate. The organic layers were dried over sodium sulphate, filtered and removed under reduced pressure to give crude product which was purified by flash chromatography using 30% ethyl acetate in pet ether to afford title compound (3.5 g, 53%) as solid. $^1$H NMR (400 MHz, DMSO-d$_6$): δ 12.0 (s, 1H), 10.3 (s, 1H), 7.8 (d, J=8.4 Hz, 1H), 6.7 (d, J=7.4 Hz, 1H), 6.6 (s, 1H), 3.0 (m, 1H), 2.7 (m, 2H), 2.4 (m, 2H), 1.9 (m, 1H), 1.7-1.5 (m, 2H), 0.9 (t, J=7.6 Hz, 3H).

Ethyl 2-(2-ethyl-6-hydroxy-1-oxo-1,2,3,4-tetrahydronaphthalen-2-yl)acetate (116C)

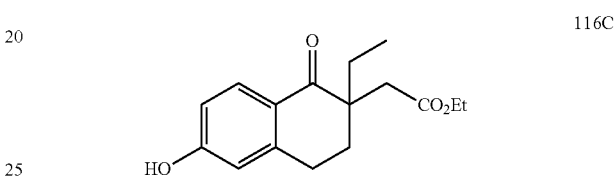

Methane sulphonic acid (6 mL) was added to a solution of product of Example 116B (3.5 g, 14.17 mmol) in ethanol (50 mL), and the reaction mixture was stirred at room temperature for 16 h. Ethanol was removed from reaction mixture under reduced pressure, and residue was diluted with ethyl acetate and washed with brine solution. The organic layer was dried over sodium sulphate, filtered and removed under reduced pressure to give crude product which was purified by flash chromatography using 20% ethyl acetate in pet ether to afford title compound (3.2 g, 82%) as solid. $^1$H NMR (300 MHz, CDCl$_3$): δ 10.2 (s, 1H), 8.0 (d, J=8.4 Hz, 1H), 6.7 (d, J=7.4 Hz, 1H), 6.6 (s, 1H), 4.0 (m, 2H), 3.2-2.7 (m, 3H), 2.5-2.3 (m, 2H), 2.2-1.9 (m, 1H), 1.8-1.6 (m, 2H), 1.2 (t, J=7.2 Hz, 3H), 0.8 (t, J=7.6 Hz, 3H).

Ethyl 2-(2-ethyl-1-oxo-6-(trifluoromethylsulfonyloxy)-1,2,3,4-tetrahydronaphthalen-2-yl) acetate (116D)

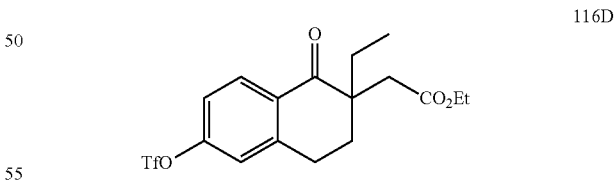

Triflic anhydride (3.28 g, 11.6 mmol) was added to an ice cold solution of product of Example 116C (3.2 g, 11.6 mmol) and pyridine (1.01 g, 12.7 mmol) in dichloromethane (40 mL). The reaction mixture was stirred at room temperature for 2 h. The reaction mixture was diluted with dichloromethane and extracted with saturated aqueous solution of NaCl. The organic layer was dried over sodium sulphate, filtered and removed under reduced pressure. The product was purified by flash chromatography using 5% ethyl acetate in pet ether to give title compound (3 g, 63%) as syrup. $^1$H NMR (300 MHz, CDCl$_3$): δ 8.2 (d, J=8.4 Hz, 1H), 7.3-7.2

(m, 2H), 4.2 (m, 2H), 3.2-2.8 (m, 3H), 2.5 (m, 2H), 2.1 (m, 1H), 1.8-1.6 (m, 2H), 1.2 (t, J=7.2 Hz, 3H), 1.0 (t, J=7.6 Hz, 3H).

Ethyl 2-(2-ethyl-6-(4-nitrophenyl)-1-oxo-1,2,3,4-tetrahydronaphthalen-2-yl) acetate (116E)

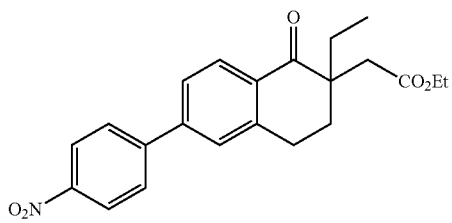

Pd(PPh₃)₄ (0.02 g, 0.017 mmol) was added to a solution of product of Example 116D (0.6 g, 1.47 mmol) in 14 mL of 1,4 dioxane-H₂O (2:1) mixture under argon atmosphere, followed by cesium carbonate (1.44 g, 4.41 mmol) and 4-nitrophenyl boronic acid (0.246 g, 1.47 mmol). The reaction mixture was degassed for 5 min and refluxed for 4 h. Solvent was then removed under reduced pressure and the residue was partitioned between ethyl acetate and water. The separated organic layer was dried over sodium sulphate, filtered and removed under reduced pressure. The product was purified by flash chromatography using 15% ethyl acetate in pet ether to afford title compound (0.5 g, 89%) as solid. ¹H NMR (400 MHz, CDCl₃): δ 8.4 (d, J=9.0 Hz, 2H), 8.2 (d, J=8.4 Hz, 1H), 7.8 (d, J=8.4 Hz, 2H), 7.6 (d, J=7.6 Hz, 1H), 7.5 (s, 1H), 4.1 (m, 2H), 3.2-2.9 (m, 3H), 2.5 (m, 2H), 2.1 (m, 1H), 1.8-1.6 (m, 2H), 1.2 (t, J=7.2 Hz, 3H), 0.9 (t, J=7.6 Hz, 3H).

Ethyl 2-(6-(4-aminophenyl)-2-ethyl-1-oxo-1,2,3,4-tetrahydronaphthalen-2-yl) acetate (116F)

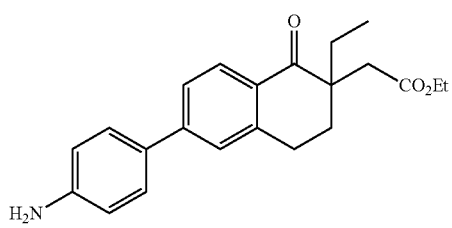

Iron powder (0.24 g, 4.3 mmol) was added to a solution of product of Example 116E (0.55 g, 1.44 mmol) in 30 mL of ethanol-water mixture (2:1) followed by NH₄Cl (0.039 g, 0.72 mmol). The reaction mixture was stirred and refluxed for 4 h. The solvent was removed under reduced pressure, and residue was partitioned between ethyl acetate and water. The separated organic layer was dried over sodium sulphate, filtered and the filtrate was concentrated under reduced pressure, triturated with n-pentane to afford title compound (0.3 g, 60%). ¹H NMR (400 MHz, CDCl₃): δ 8.1 (d, J=8.4 Hz, 1H), 7.8 (d, J=8.4 Hz, 2H), 7.6-7.3 (m, 4H), 4.1 (m, 2H), 3.8 (bs, 2H), 3.1 (m, 1H), 3.0-2.8 (m, 2H), 2.6-2.4 (m, 2H), 2.1 (m, 1H), 1.8-1.6 (m, 2H), 1.3 (t, J=7.6 Hz, 3H), 0.9 (t, J=7.2 Hz, 3H).

Ethyl 2-(2-ethyl-1-oxo-6-(4-(3-(4-(trifluoromethyl) phenyl)ureido)phenyl)-1,2,3,4-tetrahydronaphthalen-2-yl)acetate (116G)

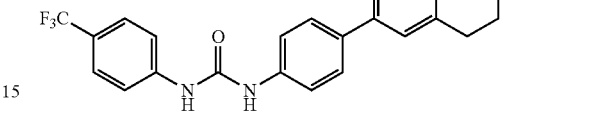

4-(Trifluoromethyl)phenyl isocyanate (0.106 g, 0.57 mmol) was added to a solution of product of Example 116F (0.2 g, 0.56 mmol) and triethylamine (0.17 g, 1.68 mmol) in THF (5 mL). The mixture was stirred at room temperature for 12 h. The solvent was removed under reduced pressure, and product was purified by flash chromatography using 25% ethyl acetate in pet ether to afford title compound (0.18 g, 58%) as solid. ¹H NMR (300 MHz, CDCl₃): δ 8.0 (d, 8.4 Hz, 1H), 7.7 (bs, 1H), 7.52-7.42 (m, 5H), 7.38-7.32 (m, 2H), 7.28-7.20 (m, 4H), 4.1 (q, J=7.2 Hz, 2H), 3.14-2.8 (m, 3H), 2.55-2.4 (m, 2H), 2.05 (m, 1H), 1.8-1.64 (m, 2H), 1.2 (t, J=7.2 Hz, 3H), 0.94 (t, J=7.5 Hz, 3H).

2-(2-Ethyl-1-oxo-6-(4-(3-phenylureido)phenyl)-1,2,3,4-tetrahydronaphthalen-2-yl)acetic acid (116)

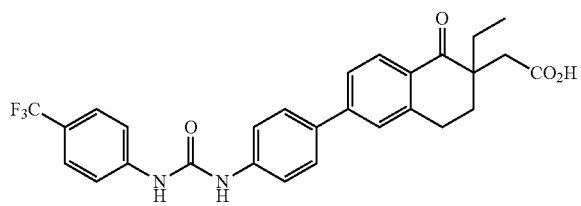

Lithium hydroxide (0.128 g, 2.28 mmol) was added to a solution of product of Example 116G (0.18 g, 0.76 mmol) in 6 mL of ethanol-water (2:1) mixture. The mixture was stirred at room temperature for 12 h. After the solvent was removed in vacuo, the residue was dissolved in water and washed with ethyl acetate. The aqueous layer was acidified with addition of 2N aqueous solution of HCl until pH 2 was attained. The resulting solids were collected by filtration, triturated with n-pentane and dried under vacuum to afford title compound (0.1 g, 59%) as white solid. ¹H NMR (300 MHz, DMSO-d₆): δ 12.0 (bs, 1H), 9.4 (bs, 1H), 9.2 (bs, 1H), 7.9 (d, J=8.4 Hz, 1H), 7.8-7.5 (m, 10H), 3.2-2.9 (m, 2H), 2.85-2.7 (d, J=15.9 Hz, 1H), 2.4 (m, 2H), 2.0 (m, 1H), 1,8-1.45 (m, 2H), 0.95 (m, 3H); ESI-MS m/z: 511 (M+H)⁺; HPLC purity: 94%.

Examples 117-128 were prepared by the procedures analogous to those described in Example 116 using appropriate starting materials.

| Ex | Structure | Analytical Data | (M + H)+ |
|---|---|---|---|
| 117 | 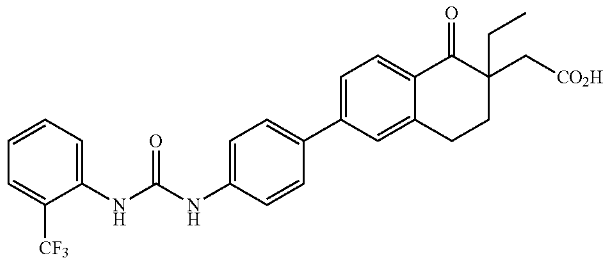 [SMILES: CCC1(CC(=O)O)CCc2cc(-c3ccc(NC(=O)Nc4ccccc4C(F)(F)F)cc3)ccc2C1=O] | ¹H NMR (300 MHz, DMSO-d₆): δ 12.0 (bs, 1H), 9.7 (bs, 1H), 8.35 (bs, 1H), 7.9 (d, J = 8.4 Hz, 2H), 7.7-7.5 (m, 8H), 7.3 (t, J = 6.3 Hz, 1H), 3.3-2.9 (m, 2H), 2.8 (d, J = 16.8 Hz, 1H), 2.3 (m, 2H), 2.0 (m, 1H), 1.8-1.5 (m, 2H), 0.9 (m, 3H). | HPLC Purity: 92% |
| 118 | 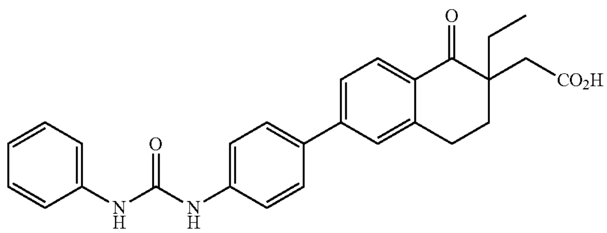 [SMILES: CCC1(CC(=O)O)CCc2cc(-c3ccc(NC(=O)Nc4ccccc4)cc3)ccc2C1=O] | ¹H NMR (300 MHz, DMSO-d₆): δ 12.2 (bs, 1H), 9.2-8.8 (m, 2H), 7.8 (d, J = 8.4 Hz, 1H), 7.7-7.55 (m, 6H), 7.45 (d, J = 8.4 Hz, 2H), 7.3 (t, J = 7.5 Hz, 2H), 6.95 (t, J = 7.5 Hz, 1H), 3.2-2.6 (m, 3H), 2.4 (m, 2H), 2.0 (m, 1H), 1.8-1.5 (m, 2H), 0.85 (t, J = 7.8 Hz, 3H). | HPLC purity: 91% |
| 119 | 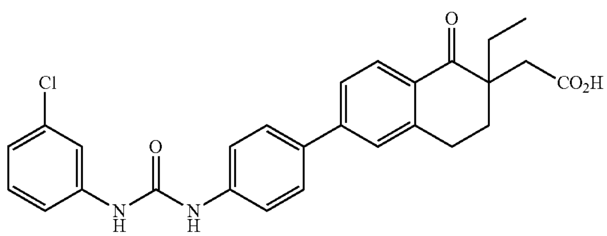 [SMILES: CCC1(CC(=O)O)CCc2cc(-c3ccc(NC(=O)Nc4cccc(Cl)c4)cc3)ccc2C1=O] | ¹H NMR (300 MHz, DMSO-d₆): δ 12.1 (s, 1H), 9.0 (bs, 1H), 7.95 (d, J = 8.4 Hz, 1H), 7.73-7.56 (m, 6H), 7.3 (m, 3H), 7.02 (m, 1H), 3.2-2.7 (m, 3H), 2.4 (m, 2H), 2.0 (m, 1H), 1.75-1.45 (m, 2H), 0.9 (t, J = 7.5 Hz, 3H). | HPLC purity: 92% |
| 120 | 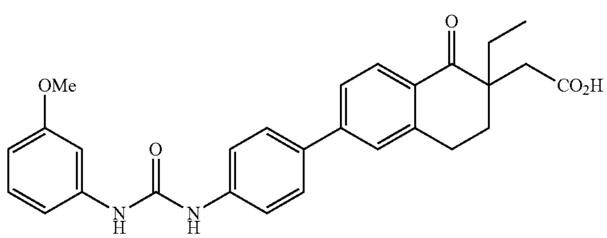 [SMILES: CCC1(CC(=O)O)CCc2cc(-c3ccc(NC(=O)Nc4cccc(OC)c4)cc3)ccc2C1=O] | ¹H NMR (300 MHz, DMSO-d₆): δ 12.0 (bs, 1H), 9.6-9.0 (bs, 2H), 7.96 (d, J = 8.4 Hz, 1H), 7.66-7.48 (m, 6H), 7.26 (s, 1H), 7.16 (t, J = 8.4 Hz, 1H), 7.0 (d, J = 8.4 Hz, 1H), 6.56 (m, 1H), 3.8 (s, 3H), 3.2-2.9 (m, 2H), 2.8 (d, J = 16.4 Hz, 1H), 2.4 (m, 1H), 2.3 (d, J = 16.2 Hz, 1H), 2.0 (m, 1H), 1.78-1.5 (m, 2H), 0.85 (t, J = 6.9 Hz, 3H). | ESI-MS m/z = 473 (M + H)+; HPLC purity: 90%. |
| 121 | 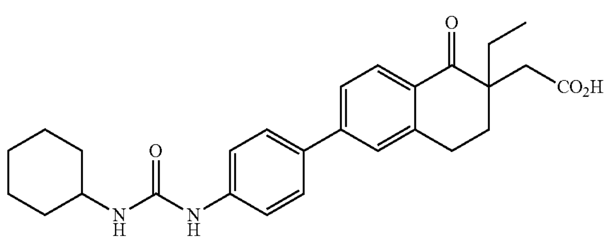 [SMILES: CCC1(CC(=O)O)CCc2cc(-c3ccc(NC(=O)NC4CCCCC4)cc3)ccc2C1=O] | ¹H NMR (300 MHz, DMSO-d₆): δ 12.0 (s, 1H), 8.8 (bs, 1H), 7.9 (d, J = 8.4 Hz, 1H), 7.65-7.52 (m, 4H), 7.45 (d, J = 8.4 Hz, 2H), 6.4 (bs, 1H), 3.5 (s, 1H), 3.2-2.8 (m, 2H), 2.6 (d, J = 16 Hz, 1H), 2.35 (d, J = 16 Hz, 1H), 2.0 (m, 1H), 1.9-1.5 (m, 8H), 1.4-1.0 (m, 5H), 0.85 (t, J = 7.6 Hz, 3H). | HPLC Purity: 90%. |
| 122 | 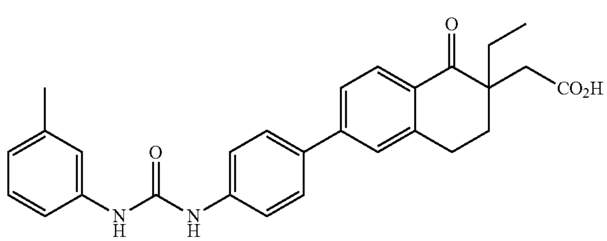 [SMILES: CCC1(CC(=O)O)CCc2cc(-c3ccc(NC(=O)Nc4cccc(C)c4)cc3)ccc2C1=O] | ¹H NMR (300 MHz, DMSO-d₆): δ 12.0 (s, 1H), 9.0 (bs, 1H), 8.8 (bs, 1H), 7.9 (d, J = 8.4 Hz, 1H), 7.7-7.5 (m, 6H), 7.31 (s, 1H), 7.28-7.1 (m, 2H), 6.8 (d, J = 7.5 Hz, 1H), 3.2-2.9 (m, 2H), 2.8 (d, J = 15.9 Hz, 1H), 2.4 (m, 2H), 2.3 (s, 3H), 2.0 (m, 1H), 1.8-1.4 (m, 2H), 0.9 (t, J = 6.9 Hz, 3H). | ESI-MS m/z = 457 (M + H)+; HPLC Purity: 98%. |

-continued

| Ex | Structure | Analytical Data | (M + H)+ |
|---|---|---|---|
| 123 | (structure) | ¹H NMR (400 MHz, DMSO-d₆): δ 12.0 (s, 1H), 8.8 (bs, 1H), 8.58 (bs, 1H), 7.9 (d, J = 7.8 Hz, 1H), 7.7-7.66 (d, J = 8.4 Hz, 2H), 7.64-7.52 (m, 4H), 7.38 (d, J = 8.8 Hz, 2H), 6.86 (d, J = 8.8 Hz, 2H), 3.8 (s, 3H), 3.2-2.8 (m, 2H), 2.6 (d, J = 15.9 Hz, 1H), 2.4 (m, 2H), 2.0 (m, 1H), 1.8-1.6 (m, 2H), 0.9 (m, 3H). | ESI-MS m/z = 473 (M + H)+; HPLC purity: 99%. |
| 124 | (structure) | ¹H NMR (300 MHz, DMSO-d₆): δ 12.1 (s, 1H), 8.95 (2s, 2H), 7.9 (d, J = 7.8 Hz, 1H), 7.7 (d, J = 8.4 Hz, 2H), 7.6 (m, 4H), 7.5 (d, J = 8.4 Hz, 2H), 7.3 (d, J = 8.4 Hz, 2H), 3.2-2.9 (m, 2H), 2.8 (d, J = 16.5 Hz, 1H), 2.4 (m, 2H), 2.0 (m, 1H), 1.8-1.5 (m, 2H), 0.85 (t, J = 7.5 Hz, 3H). | ESI-MS m/z = 477 (M + H)+; HPLC purity: 98%. |
| 125 | (structure) | ¹H NMR (400 MHz, DMSO-d₆): δ 12.0 (bs, 1H), 9.0-8.6 (bs, 2H), 7.92 (d, J = 8.0 Hz, 1H), 7.68 (d, J = 8.4 Hz, 1H), 7.62-7.54 (m, 5H), 7.36 (d, J = 8.4 Hz, 2H), 7.1 (d, J = 8.4 Hz, 2H), 3.2-2.9 (m, 2H), 2.8 (d, J = 16.4 Hz, 1H), 2.4 (m, 2H), 2.25 (s, 3H), 2.0 (m, 1H), 1.8-1.5 (m, 2H), 0.85 (t, J = 7.2 Hz, 3H). | HPLC purity: 98% |
| 126 | (structure) | ¹H NMR (400 MHz, DMSO-d₆): δ 12.0 (bs, 1H), 7.9 (d, J = 8.4 Hz, 1H), 7.7-7.4 (m, 7H), 7.3 (m, 1H), 7.15 (d, J = 8.4 Hz, 1H), 6.8 (t, J = 6.8 Hz, 1H), 3.2-2.8 (m, 3H), 2.4 (m, 2H), 1.9 (m, 1H), 1.8-1.4 (m, 2H), 0.9 (t, J = 7.6 Hz, 3H). | HPLC purity: 91%. |
| 127 | (structure) | ¹H NMR (400 MHz, DMSO-d₆): δ 12.0 (bs, 1H), 8.92 (bs, 1H), 8.62 (bs, 1H), 7.9 (d, J = 8.0 Hz, 1H), 7.7-7.5 (m, 6H), 7.1 (m, 2H), 6.6 (m, 1H), 3.2-2.8 (m, 2H), 2.6 (d, J = 16.4 Hz, 1H), 2.4 (m, 2H), 2.2 (s, 6H), 2.0 (m, 1H), 1.8-1.6 (m, 2H), 0.9 (t, J = 7.6 Hz, 3H). | ESI-MS m/z = 470 (M + H)+; HPLC purity: 90%. |
| 128 | (structure) | ¹H NMR (400 MHz, DMSO-d₆): δ 10.6 (bs, 1H), 8.8 (bs, 1H), 7.9 (d, J = 8.4 Hz, 1H), 7.8 (m, 2H), 7.6-7.4 (m, 5H), 6.9 (d, J = 7.8 Hz, 1H), 6.8 (d, J = 7.5 Hz, 1H), 3.8 (s, 3H), 3.0-2.6 (m, 3H), 2.4 (m, 1H), 2.3 (s, 3H), 2.1 (m, 1H), 1.9 (m, 1H), 1.8-1.6 (m, 2H), 0.9 (m, 3H). | HPLC purity: 90%. |

Example-129

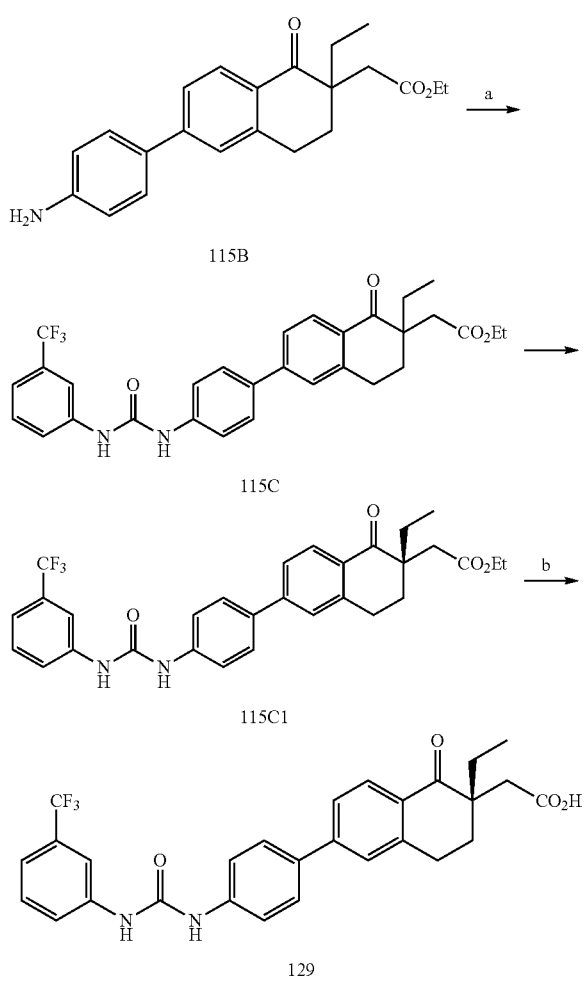

Reagents and conditions: a) 3-CF₃PhNCO, Et₃N, THF, RT, 6 h; b) LiOH, Dioxane-H₂O, RT, 12 h.

Procedures (S)-2-(2-Ethyl-1-oxo-6-(4-(3-(3-(trifluoromethyl)phenyl)ureido)phenyl)-1,2,3,4-tetrahydronaphthalen-2-yl)acetic acid (S)-ethyl 2-(2-ethyl-1-oxo-6-(4-(3-(3-(trifluoromethyl)phenyl)ureido)phenyl)-1,2,3,4-tetrahydronaphthalen-2-yl)acetate (115C1)

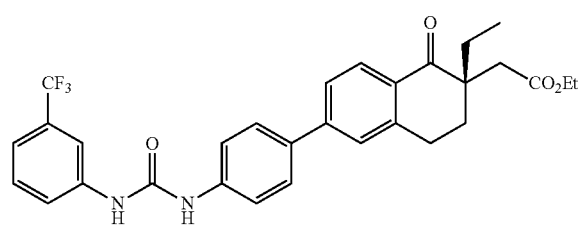

3-(Trifluoromethyl)phenyl isocyanate (0.185 g, 0.98 mmol) was added to a solution of product of Example 115B (0.29 g, 0.82 mmol) and triethylamine (0.25 g, 2.47 mmol) in THF (10 mL). The mixture was stirred at room temperature for 6 h. The solvent was removed under reduced pressure, and product was purified by flash chromatography using 20% ethyl acetate in pet ether to afford Example 115C (0.34 g, 77%) as solid. ¹H NMR (400 MHz, CDCl₃): δ 8.1 (d, 8.4 Hz, 1H), 7.7 (m, 1H), 7.6 (m, 1H), 7.5-7.3 (m, 9H), 7.1 (s, 1H), 4.1 (q, J=6.9 Hz, 2H), 3.2-2.8 (m, 3H), 2.5 (m, 2H), 2.1 (m, 1H), 1.8-1.6 (m, 2H), 1.4-1.2 (m, 5H), 0.9 (t, J=7.2 Hz, 3H).

Example 115C (0.5 g, which derived from 0.32 g obtained above and another batch of 180 mg using similar procedures as described for Example 115C) was racemic mixture with 1:1 enantiomeric ratio and was separated on chiral column to obtain single enantiomers of 115C1 (Rt 15.67 min) and 115C2 (Rt 20.16 min) using following conditions.

Column: CHIRAL PAK ODH (4.6×250 mm) 5µ
Mobile phase: A: Hexane, B: Ethanol
A: B(Iso) 85:15; Flow rate: 0.8 mL/min
115C1: 0.17 g, 15.67 min RT, Optical rotation +22 (cl CHCl₃)
115C2: 0.168 g, 20.16 min RT, Optical rotation −22 (cl CHCl₃)
Absolute configurations confirmed by VCD studies:
Absolute configuration of 115G1 is S and 115G2 is R.

(S)-2-(2-Ethyl-1-oxo-6-(4-(3-(3-(trifluoromethyl)phenyl)ureido)phenyl)-1,2,3,4-tetrahydronaphthalen-2-yl)acetic acid (129)

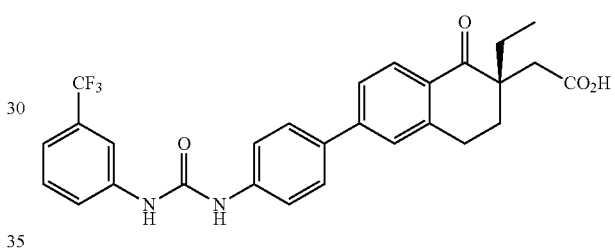

Lithium hydroxide (0.028 g, 0.67 mmol) was added to a solution of product of Example 115C1 (0.12 g, 0.22 mmol) in 4 mL of ethanol-water (3:1) mixture, and the reaction mixture was stirred at room temperature for 16 h. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration, triturated with n-pentane and dried under vacuum to afford title compound (0.08 g, 72%) as solid. ¹H NMR (300 MHz, DMSO-d₆): δ 12.0 (s, 1H), 9.22 (bs, 1H), 9.09 (bs, 1H), 8.05 (s, 1H), 7.9 (d, J=8.4 Hz, 1H), 7.6-7.4 (m, 8H), 7.3 (d, J=6.9 Hz, 1H), 3.2-2.9 (m, 2H), 2.8 (d, J=16.8 Hz, 1H), 2.4 (m, 2H), 2.0 (m, 1H), 1.8-1.5 (m, 2H), 0.9 (t, J=5.7 Hz, 3H); ESI-MS m/z: 511 (M+H)⁺.

Alternative Synthesis of Example 129

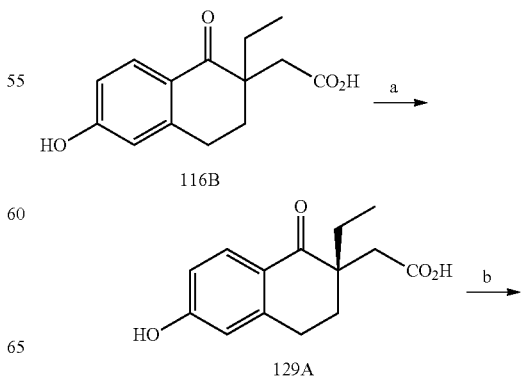

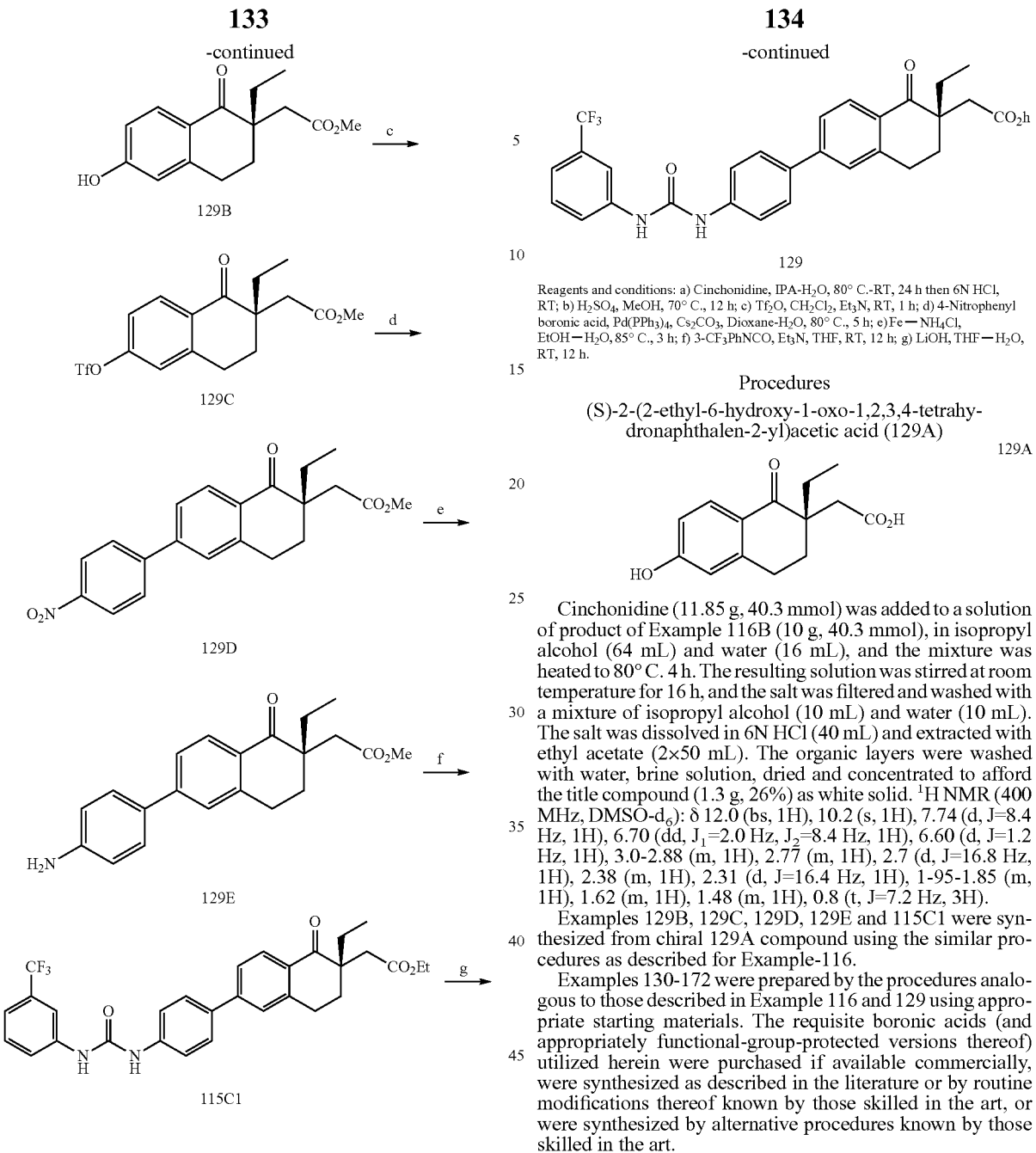

Reagents and conditions: a) Cinchonidine, IPA-H₂O, 80° C.-RT, 24 h then 6N HCl, RT; b) H₂SO₄, MeOH, 70° C., 12 h; c) Tf₂O, CH₂Cl₂, Et₃N, RT, 1 h; d) 4-Nitrophenyl boronic acid, Pd(PPh₃)₄, Cs₂CO₃, Dioxane-H₂O, 80° C., 5 h; e) Fe—NH₄Cl, EtOH—H₂O, 85° C., 3 h; f) 3-CF₃PhNCO, Et₃N, THF, RT, 12 h; g) LiOH, THF—H₂O, RT, 12 h.

Procedures (S)-2-(2-ethyl-6-hydroxy-1-oxo-1,2,3,4-tetrahydronaphthalen-2-yl)acetic acid (129A)

Cinchonidine (11.85 g, 40.3 mmol) was added to a solution of product of Example 116B (10 g, 40.3 mmol), in isopropyl alcohol (64 mL) and water (16 mL), and the mixture was heated to 80° C. 4 h. The resulting solution was stirred at room temperature for 16 h, and the salt was filtered and washed with a mixture of isopropyl alcohol (10 mL) and water (10 mL). The salt was dissolved in 6N HCl (40 mL) and extracted with ethyl acetate (2×50 mL). The organic layers were washed with water, brine solution, dried and concentrated to afford the title compound (1.3 g, 26%) as white solid. ¹H NMR (400 MHz, DMSO-d₆): δ 12.0 (bs, 1H), 10.2 (s, 1H), 7.74 (d, J=8.4 Hz, 1H), 6.70 (dd, J₁=2.0 Hz, J₂=8.4 Hz, 1H), 6.60 (d, J=1.2 Hz, 1H), 3.0-2.88 (m, 1H), 2.77 (m, 1H), 2.7 (d, J=16.8 Hz, 1H), 2.38 (m, 1H), 2.31 (d, J=16.4 Hz, 1H), 1-95-1.85 (m, 1H), 1.62 (m, 1H), 1.48 (m, 1H), 0.8 (t, J=7.2 Hz, 3H).

Examples 129B, 129C, 129D, 129E and 115C1 were synthesized from chiral 129A compound using the similar procedures as described for Example-116.

Examples 130-172 were prepared by the procedures analogous to those described in Example 116 and 129 using appropriate starting materials. The requisite boronic acids (and appropriately functional-group-protected versions thereof) utilized herein were purchased if available commercially, were synthesized as described in the literature or by routine modifications thereof known by those skilled in the art, or were synthesized by alternative procedures known by those skilled in the art.

| Ex | Structure | Analytical Data | (M + H)⁺ |
| --- | --- | --- | --- |
| 130 | (Chiral structure shown) | ¹H NMR (300 MHz, DMSO-d₆): δ 12.0 (s, 1H), 9.22 (bs, 1H), 9.09 (bs, 1H), 8.05 (s 1H), 7.9 (d, J = 8.4 Hz, 1H), 7.6-7.4 (m, 8H), 7.3 (d, J = 6.9 Hz, 1H), 3.2-2.9 (m, 2H), 2.8 (d, J = 16.8 Hz, 1H), 2.4 (m, 2H), 2.0 (m, 1H), 1.8-1.5 (m, 2H), 0.9 (t, J = 5.7 Hz, 3H). | HPLC purity: 97% |

| Ex | Structure | Analytical Data | (M + H)+ |
|---|---|---|---|
| 131 | Chiral: enantiomer-1 | 1H NMR (400 MHz, DMSO-d6): δ 12.0 (s, 1H), 9.1 (bs, 2H), 7.84 (d, J = 8.0 Hz, 1H), 7.7-7.54 (m, 6H), 7.5 (d, J = 8.8 Hz, 2H), 7.34 (d, J = 8.8 Hz, 2H), 3.2-2.9 (m, 2H), 2.79 (d, J = 16.8 Hz, 1H), 2.45 (m, 1H), 2.41 (d, J = 16.4 Hz, 1H), 2.0 (m, 1H), 1.7-1.5 (m, 2H), 0.8 (t, J = 7.2 Hz, 3H). | HPLC Purity: 99% |
| 132 | Chiral: enantiomer-2 | 1H NMR (400 MHz, DMSO-d6): δ 12.0 (s, 1H), 9.1 (bs, 2H), 7.84 (d, J = 8.0 Hz, 1H), 7.7-7.54 (m, 6H), 7.5 (d, J = 8.8 Hz, 2H), 7.34 (d, J = 8.8 Hz, 2H), 3.2-2.9 (m, 2H), 2.79 (d, J = 16.8 Hz, 1H), 2.45 (m, 1H), 2.41 (d, J = 16.4 Hz, 1H), 2.0 (m, 1H), 1.7-1.5 (m, 2H), 0.8 (t, J = 7.2 Hz, 3H). | HPLC purity: 97% |
| 133 | 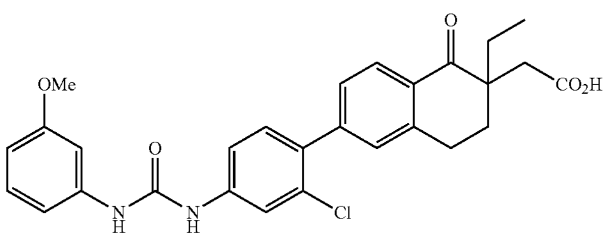 [SMILES: CCC1(CC(=O)O)CCc2cc(-c3ccc(NC(=O)Nc4cccc(OC)c4)cc3Cl)ccc2C1=O] | 1H NMR (300 MHz, DMSO-d6): δ δ 12.1 (bs, 1H), 9.1 (bs, 1H), 8.9 (bs, 1H), 7.95 (d, J = 8.4 Hz, 1H), 7.85 (s, 1H), 7.45-7.3 (m, 4H), 7.2 (m, 2H), 6.95 (d, J = 9.0 Hz, 1H), 6.6 (m, 1H), 3.78 (s, 3H), 3.3-2.9 (m, 2H), 2.8 (d, J = 15.9 Hz, 1H), 2.4 (m, 2H), 2.0 (m, 1H), 1.7-1.5 (m, 2H), 0.8 (t, J = 6.9 Hz, 3H). | ESI-MS m/z = 507 (M + H)+; HPLC purity: 96% |
| 134 | 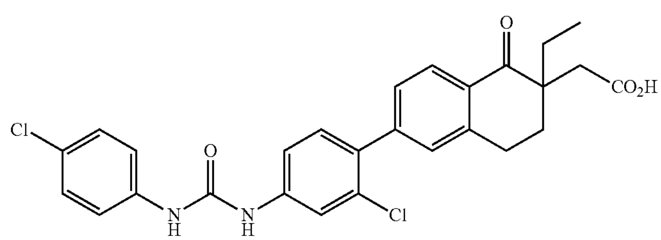 [SMILES: CCC1(CC(=O)O)CCc2cc(-c3ccc(NC(=O)Nc4ccc(Cl)cc4)cc3Cl)ccc2C1=O] | 1H NMR (300 MHz, DMSO-d6): δ 12.1 (bs, 1H), 8.24 (s, 1H), 7.94 (d, J = 7.5 Hz, 1H), 7.64 (d, J = 9.3 Hz, 2H), 7.36-7.25 (m, 4H), 6.66 (m, 1H), 6.49 (m, 1H), 3.29-2.73 (m, 4H), 2.22 (m, 1H), 1.84 (m, 1H), 1.7-1.45 (m, 2H), 0.9 (t, J = 6.9 Hz, 3H). | HPLC purity: 98.89%. |
| 135 | 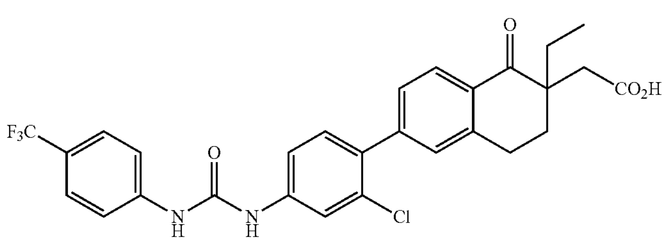 [SMILES: CCC1(CC(=O)O)CCc2cc(-c3ccc(NC(=O)Nc4ccc(C(F)(F)F)cc4)cc3Cl)ccc2C1=O] | 1H NMR (300 MHz, DMSO-d6): δ 12.1 (bs, 1H), 8.02 (s, 1H), 7.98 (d, J = 8.4 Hz, 1H), 7.7 (m, 3H), 7.6 (m 3H), 7.4 (m, 2H), 7.1 (m, 1H), 3.2-2.96 (m, 2H), 2.85 (d, J = 15.9 Hz, 1H), 2.6 (m, 1H), 2.3 (d, J = 16.8 Hz, 1H), 1.9 (m, 1H), 1.7-1.45 (m, 2H), 0.9 (t, J = 7.5 Hz, 3H). | ESI-MS m/z = 545 (M + H)+; HPLC purity: 97.6%. |
| 136 | 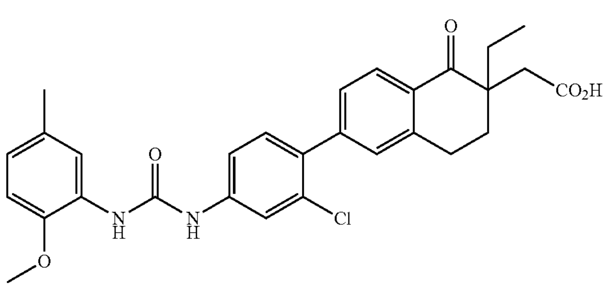 [SMILES: CCC1(CC(=O)O)CCc2cc(-c3ccc(NC(=O)Nc4cc(C)ccc4OC)cc3Cl)ccc2C1=O] | 1H NMR (300 MHz, DMSO-d6): δ 12.1 (bs, 1H), 9.7 (bs, 1H), 8.8 (bs, 1H), 8.0-7.85 (m, 3H), 7.42-7.3 (m, 4H), 6.9 (m, 1H), 6.78 (m, 1H), 3.8 (s, 3H), 3.2-2.8 (m, 3H), 2.4 (m, 2H), 2.26 (s, 3H), 2.0 (m, 1H), 1.8-1.5 (m, 2H), 0.9 (m, 3H). | ESI-MS m/z = 521 (M + H)+; HPLC purity: 95.8%. |

-continued

| Ex | Structure | Analytical Data | (M + H)+ |
|---|---|---|---|
| 137 | 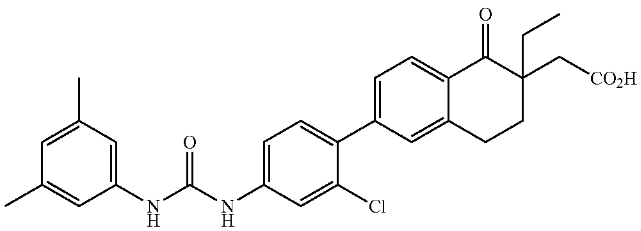 [SMILES: CCC1(CC(=O)O)CCc2cc(-c3ccc(NC(=O)Nc4cc(C)cc(C)c4)cc3Cl)ccc2C1=O] | $^1$H NMR (300 MHz, DMSO-$d_6$): δ 12.1 (bs, 1H), 9.0 (bs, 1), 8.7 (bs, 1H), 7.95 (d, J = 8.4 Hz, 1H), 7.86 (s, 1H), 7.45-7.3 (m, 3H), 7.0 (m, 3H), 6.65 (s, 1H), 3.2-2.9 (m, 2H), 2.8 (d, J = 16.8 Hz, 1H), 2.4 (m, 2H), 2.26 (s, 6H), 2.0 (m, 1H), 1.7-1.5 (m, 2H), 0.85 (t, J = 6.9 Hz, 3H). | ESI-MS m/z = 505 (M + H)+; HPLC purity: 97%. |
| 138 | 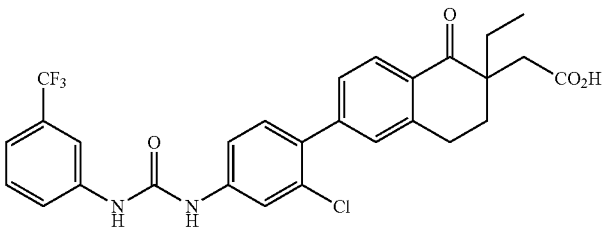 | $^1$H NMR (300 MHz, DMSO-$d_6$): δ 12.2 (bs, 1H), 9.3 (bs, 2H), 8.1 (s, 1H), 7.9 (m, 2H), 7.6-7.0 (m, 7H), 3.2-2.8 (m, 3H), 2.4 (m, 2H), 2.0 (m, 1H), 1.8-1.4 (m, 2H), 0.85 (m, 3H). | HPLC Purity: 90%. |
| 139 | 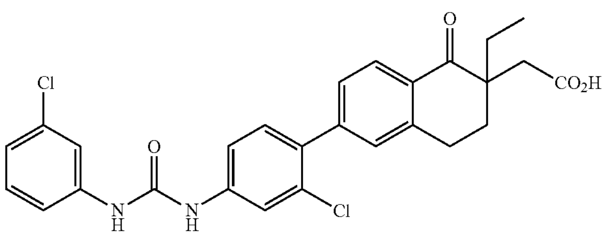 [SMILES: CCC1(CC(=O)O)CCc2cc(-c3ccc(NC(=O)Nc4cccc(Cl)c4)cc3Cl)ccc2C1=O] | $^1$H NMR (300 MHz, DMSO-$d_6$): δ 12.2 (bs, 1), 9.15 (bs, 1H), 9.1 (bs, 1H), 7.95 (m, 1H), 7.85 (bs, 1H), 7.7 (s, 1H), 7.5-7.2 (m, 6H), 7.0 (s, 1H), 3.2-2.8 (m, 3H), 2.4 (m, 2H), 2.0 (m, 1H), 1.8-1.4 (m, 2H), 0.9 (t, J = 6.9 Hz, 3H). | ESI-MS m/z = 510 (M + H)+; HPLC purity: 90%. |
| 140 | 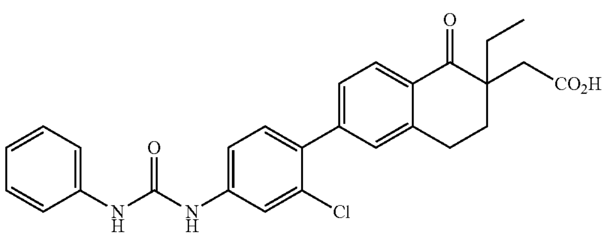 [SMILES: CCC1(CC(=O)O)CCc2cc(-c3ccc(NC(=O)Nc4ccccc4)cc3Cl)ccc2C1=O] | $^1$H NMR (300 MHz, DMSO-$d_6$): δ 12.2 (bs, 1H), 9.05 (bs, 1H), 8.95 (bs, 1H), 7.92 (d, J = 8.4 Hz, 1H), 7.85 (s, 1H), 7.6-7.2 (m, 8H), 7.0 (d, J = 7.8 Hz, 1H), 3.2-2.8 (m, 2H), 2.6 (d, J = 15.9 Hz, 1H), 2.4 (m, 2H), 2.0 (m, 1H), 1.9-1.6 (m, 2H), 0.9 (t, J = 6.9 Hz, 3H). | HPLC purity: 97%. |
| 141 | 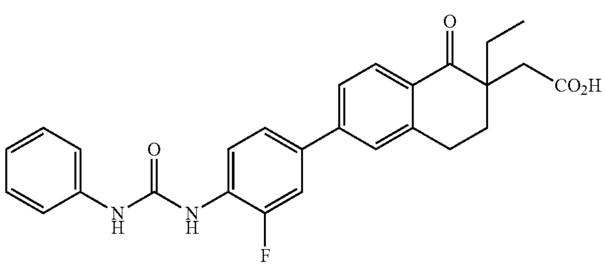 [SMILES: CCC1(CC(=O)O)CCc2cc(-c3ccc(NC(=O)Nc4ccccc4)c(F)c3)ccc2C1=O] | $^1$H NMR (300 MHz, DMSO-$d_6$): δ 12.1 (bs, 1H), 9.6 (bs, 1H), 9.0 (bs, 1H), 8.2 (m, 1H), 7.9 (d, J = 8.1 Hz, 1H), 7.7-7.4 (m, 6H), 7.3 (t, J = 7.5 Hz, 2H), 7.0 (t, J = 6.9 Hz, 1H), 3.2-2.9 (m, 2H), 2.8 (m, 1H), 2.3 (m, 2H), 2.0 (m, 1H), 1.8-1.5 (m, 2H), 0.9 (m, 3H). | ESI-MS m/z = 461 (M + H)+; HPLC purity: 90%. |
| 142 | 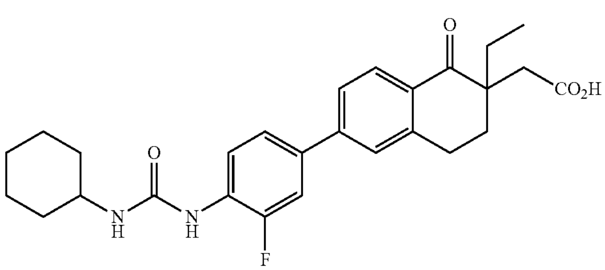 [SMILES: CCC1(CC(=O)O)CCc2cc(-c3ccc(NC(=O)NC4CCCCC4)c(F)c3)ccc2C1=O] | $^1$H NMR (300 MHz, DMSO-$d_6$): δ 8.36 (s, 1H), 8.28 (t, J = 9 Hz, 1H), 7.9 (d, J = 8.1 Hz, 1H), 7.7-7.6 (m, 3H), 7.5 (d, J = 9.9 Hz, 1H), 6.7 (d, J = 6.9 Hz, 1H), 3.6-3.4 (m, 1H), 3.2-2.8 (m, 3H), 2.57 (d, J = 16.2 Hz, 1H), 2.4 (m, 2H), 2.0 (m, 1H), 1.8-1.5 (m, 4H), 1.4-1.2 (m, 7H), 0.85 (t, J = 6.9 Hz, 3H). | HPLC purity: 97%. |

| Ex | Structure | Analytical Data | (M + H)+ |
|---|---|---|---|
| 143 | 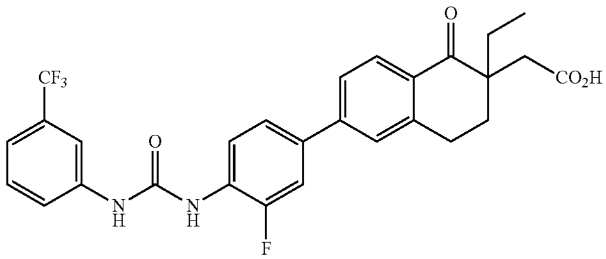 [SMILES: CCC1(CC(=O)O)CCc2cc(-c3ccc(NC(=O)Nc4cccc(C(F)(F)F)c4)c(F)c3)ccc2C1=O] | ¹H NMR (300 MHz, DMSO-d₆): δ 12.0 (bs, 1H), 9.6 (bs, 1H), 8.9 (bs, 1H), 8.25 (m, 1H), 8.05 (s, 1H), 7.9 (m, 1H), 7.72-7.5 (m, 6H), 7.36 (m, 1H), 3.2-2.9 (m, 2H), 2.8 (d, J = 15.9 Hz, 1H), 2.3 (m, 2H), 2.0 (m, 1H), 1.8-1.5 (m, 2H), 0.85 (t, J = 7.2 Hz, 3H). | ESI-MS m/z = 528 (M + H)+; HPLC purity: 95%. |
| 144 | 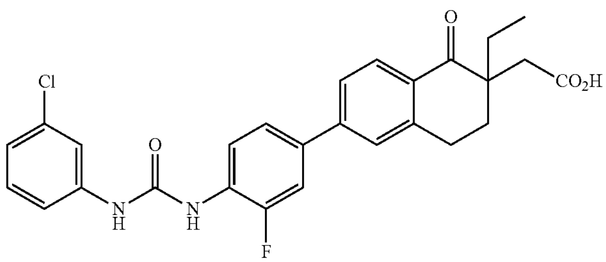 | ¹H NMR (400 MHz, DMSO-d₆): δ 12.0 (bs, 1H), 9.4 (s, 1H), 8.85 (s, 1H), 8.25 (m, 1H), 7.92 (d, J = 8.8 Hz, 1H), 7.8-7.55 (m, 5H), 7.35-7.2 (m, 2H), 7.1 (t, J = 8 Hz, 1H), 3.2-2.9 (m, 2H), 2.8 (d, J = 16.2 Hz, 1H), 2.4 (m, 2H), 2.0 (m, 1H), 1.8-1.5 (m, 2H), 0.85 (t, J = 7.6 Hz, 3H). | ESI-MS m/z = 494 (M + H)+; HPLC purity: 90% |
| 145 | 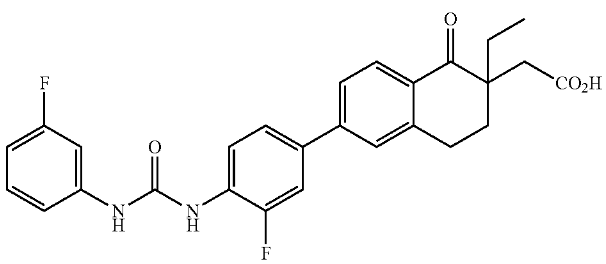 [SMILES: CCC1(CC(=O)O)CCc2cc(-c3ccc(NC(=O)Nc4cccc(F)c4)c(F)c3)ccc2C1=O] | ¹H NMR (300 MHz, DMSO-d₆): δ 10.8 (bs, 1H), 10.4 (bs, 1H), 7.87 (d, J = 8.0 Hz, 2H), 7.56-7.40 (m, 5H), 7.29-7.13 (m, 2H), 6.74 (m, 1H), 3.2-2.7 (m, 3H), 2.6 (d, J = 16.2 Hz, 1H), 2.2 (m, 2H), 1.7-1.5 (m, 2H), 0.9 (t, J = 6.9 Hz, 3H). | HPLC purity: 92%. |
| 146 | 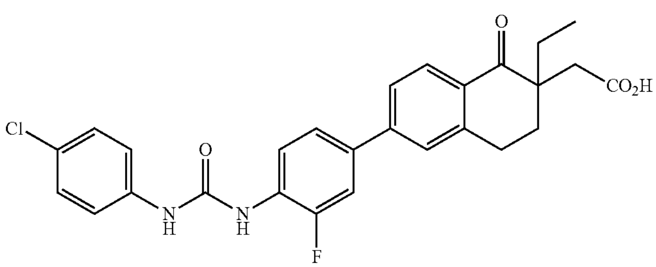 [SMILES: CCC1(CC(=O)O)CCc2cc(-c3ccc(NC(=O)Nc4ccc(Cl)cc4)c(F)c3)ccc2C1=O] | ¹H NMR (300 MHz, DMSO-d₆): δ 9.26 (m, 1H), 8.76 (m, 1H), 8.27 (t, J = 9.0 Hz, 1H), 7.92 (d, J = 9.3 Hz, 1H), 7.74-7.56 (m, 4H), 7.54 (d, J = 6.4 Hz, 2H), 7.3 (d, J = 6.3 Hz, 2H), 3.2-2.9 (m, 2H), 2.8 (d, J = 16.1 Hz, 1H), 2.4 (m, 2H), 2.0 (m, 1H), 1.75-1.5 (m, 2H), 0.8 (t, J = 7.8 Hz, 3H). | HPLC purity: 96%. |
| 147 | 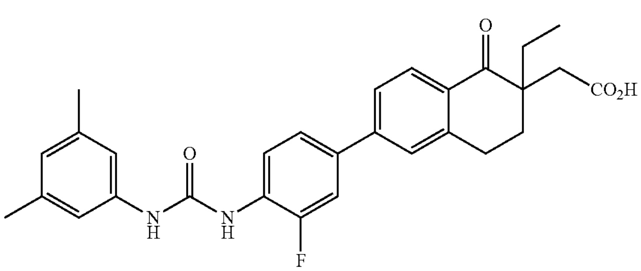 [SMILES: CCC1(CC(=O)O)CCc2cc(-c3ccc(NC(=O)Nc4cc(C)cc(C)c4)c(F)c3)ccc2C1=O] | ¹H NMR (300 MHz, DMSO-d₆): δ 9.05 (bs, 1H), 8.75 (s, 1H), 8.3 (m, 1H), 7.9 (d, J = 8.4 Hz, 1H), 7.72-7.62 (m, 3H), 7.58 (d, J = 8.4 Hz, 1H), 7.2 (s, 2H), 6.6 (s, 1H), 3.2-2.9 (m, 2H), 2.8 (d, J = 16 Hz, 1H), 2.4 (m, 2H), 2.3 (s, 6H), 2.0 (m, 1H), 1.8-1.5 (m, 2H), 0.8 (t, J = 7.8 Hz, 3H). | HPLC purity: 91%. |
| 148 | 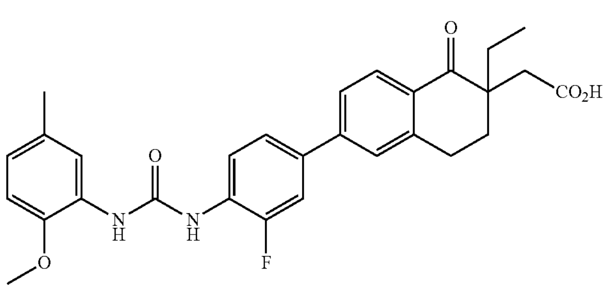 [SMILES: CCC1(CC(=O)O)CCc2cc(-c3ccc(NC(=O)Nc4cc(C)ccc4OC)c(F)c3)ccc2C1=O] | ¹H NMR (300 MHz, DMSO-d₆): δ 12.0 (bs, 1H), 9.4 (bs, 1H), 8.8 (bs, 1H), 8.3 (t, J = 8.4 Hz, 1H), 8.0 (s, 1H), 7.9 (d, J = 9 Hz, 1H), 7.7-7.65 (m, 3H), 7.54 (m, 1H), 6.9 (d, J = 8.4 Hz, 1H), 6.8 (d, J = 8.4 Hz, 1H), 3.8 (s, 3H), 3.2-2.9 (m, 2H), 2.8 (d, J = 16 Hz, 1H), 2.35 (m, 2H), 2.25 (s, 3H), 2.0 (m, 1H), 1.7-1.5 (m, 2H), 0.8 (t, J = 7.8 Hz, 3H). | HPLC purity: 92%. |

-continued

| Ex | Structure | Analytical Data | (M + H)+ |
|---|---|---|---|
| 149 | 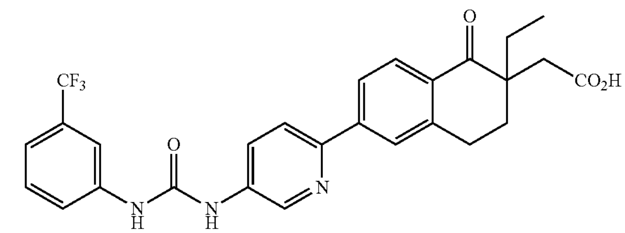 [SMILES: CCC1(CC(=O)O)CCc2cc(-c3ccc(NC(=O)Nc4cccc(Cl)c4)cn3)ccc2C1=O] | 1H NMR (300 MHz, DMSO-d6): δ 9.50 (bs, 1H), 8.76 (s, 1H), 8.20-7.90 (m, 6H), 7.70-7.50 (m, 2H), 7.36-7.33 (m, 1H), 3.16-2.76 (m, 3H), 2.50-2.20 (m, 2H), 2.0-1.98 (m, 1H), 1.68-1.54 (m, 2H), 0.84 (m, 3H). | ESI-MS m/z = 512 (M + H)+. HPLC purity: 95.3%. |
| 150 | 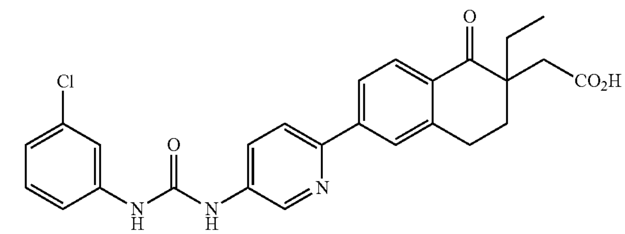 | 1H NMR (300 MHz, DMSO-d6): δ 9.78 (bs, 1H), 9.64 (bs, 1H), 8.80 (s, 1H), 8.15-8.06 (m, 2H), 8.0-7.95 (m, 3H), 7.72 (s, 1H), 7.3 (t, J = 8.4 Hz, 2H), 7.06-7.03 (m, 1H), 3.2-2.95 (m, 2H), 2.8 (d, J = 15.9 Hz, 1H), 2.5-2.3 (m, 2H), 2.02-1.98 (m, 1H), 1.70-1.52 (m, 2H), 0.84 (t, J = 7.8 Hz, 3H). | ESI-MS m/z = 478 (M + H)+. HPLC purity: 95.66%. |
| 151 | 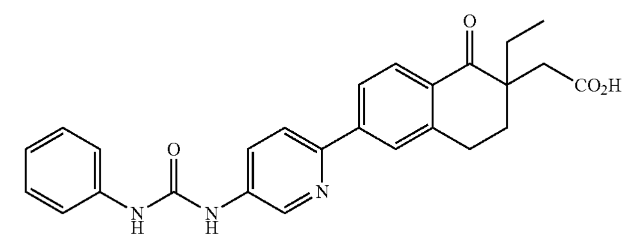 [SMILES: CCC1(CC(=O)O)CCc2cc(-c3ccc(NC(=O)Nc4ccccc4)cn3)ccc2C1=O] | 1H NMR (300 MHz, DMSO-d6): δ 9.2 (bs, 1H), 8.9 (bs, 1H), 8.73 (s, 1H), 8.12-7.96 (m, 5H), 7.4 (d, J = 7.8 Hz, 2H), 7.3 (t, J = 8.4 Hz, 2H), 7.0 (m, 1H), 3.2-2.95 (m, 2H), 2.8 (d, J = 16.8 Hz, 1H), 2.5-2.3 (m, 2H), 2.02-1.98 (m, 1H), 1.70-1.52 (m, 2H), 0.84 (t, J = 7.2 Hz, 3H). | ESI-MS m/z = 444 (M + H)+. HPLC purity: 91.6%. |
| 152 | 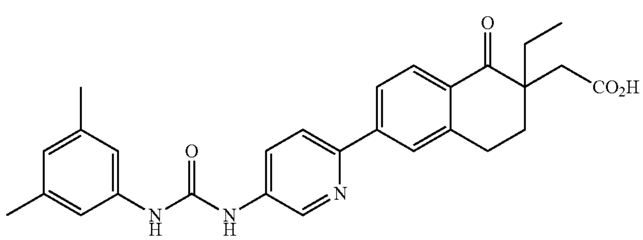 [SMILES: CCC1(CC(=O)O)CCc2cc(-c3ccc(NC(=O)Nc4cc(C)cc(C)c4)cn3)ccc2C1=O] | 1H NMR (300 MHz, DMSO-d6): δ 9.4 (bs, 1H), 9.0 (bs, 1H), 8.74 (s, 1H), 8.15-7.95 (m, 5H), 7.1 (s, 2H), 6.64 (s, 1H), 3.2-2.95 (m, 2H), 2.8 (d, J = 15.9 Hz, 1H), 2.5-2.3 (m, 2H), 2.24 (s, 6H), 2.02-1.98 (m, 1H), 1.70-1.52 (m, 2H), 0.84 (t, J = 7.8 Hz, 3H). | HPLC purity: 94.4%. |
| 153 | 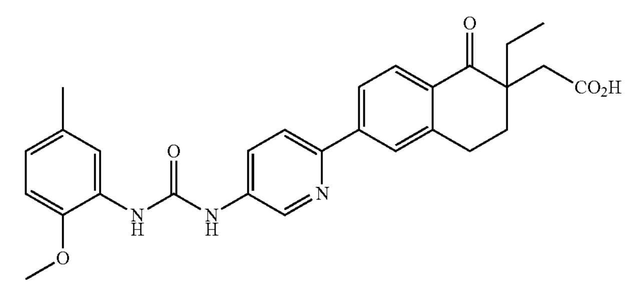 [SMILES: CCC1(CC(=O)O)CCc2cc(-c3ccc(NC(=O)Nc4cc(C)ccc4OC)cn3)ccc2C1=O] | 1H NMR (300 MHz, DMSO-d6): δ 9.78 (bs, 1H), 8.7 (s, 1H), 8.35 (s, 1H), 8.15-7.95 (m, 6H), 6.9 (d, J = 8.1 Hz, 1H), 6.78 (dd, J2 = 8.4 Hz, J1 = 1.5 Hz, 1H), 3.85 (s, 3H), 3.2-2.95 (m, 2H), 2.8 (d, J = 16.8 Hz, 1H), 2.5-2.3 (m, 2H), 2.24 (s, 3H), 2.02-1.98 (m, 1H), 1.70-1.52 (m, 2H), 0.84 (t, J = 7.2 Hz, 3H). | HPLC purity: 98.67% |
| 154 | 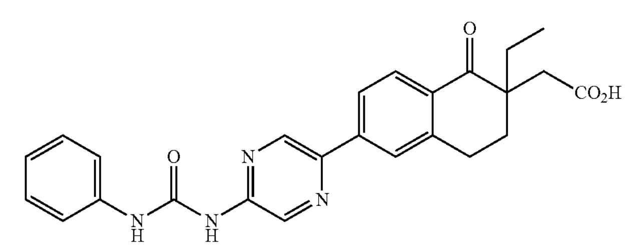 [SMILES: CCC1(CC(=O)O)CCc2cc(-c3cnc(NC(=O)Nc4ccccc4)cn3)ccc2C1=O] | 1H NMR (400 MHz, DMSO-d6): δ 9.83 (bs, 1H), 9.81 (bs, 1H), 9.21 (s, 1H), 9.0 (s, 1H), 8.04-7.96 (m, 3H), 7.52 (d, J = 8.0 Hz, 2H), 7.33 (t, J = 8.0 Hz, 2H), 7.0 (t, J = 7.6 Hz, 1H), 3.2-2.95 (m, 2H), 2.8 (d, J = 16.0 Hz, 1H), 2.5-2.3 (m, 2H), 2.02-1.98 (m, 1H), 1.70-1.52 (m, 2H), 0.84 (t, J = 7.8 Hz, 3H). | ESI-MS m/z = 445 (M + H)+; HPLC purity: 90%. |

-continued

| Ex | Structure | Analytical Data | (M + H)+ |
|---|---|---|---|
| 155 | 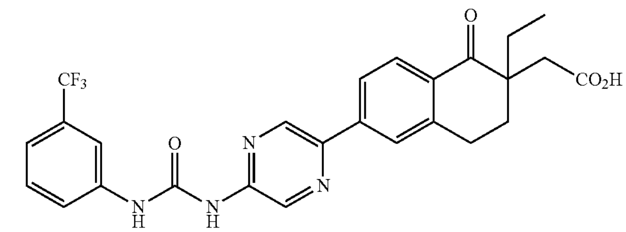 [SMILES: CCC1(CC(=O)O)CCc2cc(-c3cnc(NC(=O)Nc4cccc(C(F)(F)F)c4)cn3)ccc2C1=O] | ¹H NMR (300 MHz, DMSO-d₆): δ 12.1 (s, 1H), 9.95 (bs, 1H), 9.87 (bs, 1H), 9.17 (s, 1H), 9.03 (s, 1H), 8.05-7.9 (m, 4H), 7.67 (d, J = 8.4 Hz, 1H), 7.58 (t, J = 8.4 Hz, 1H), 7.4 (d, J = 7.8 Hz, 1H), 3.2-2.95 (m, 2H), 2.8 (d, J = 16.2 Hz, 1H), 2.5-2.3 (m, 2H), 2.02-1.98 (m, 1H), 1.70-1.52 (m, 2H), 0.84 (t, J = 7.8 Hz, 3H). | ESI-MS m/z = 513 (M + H)+; HPLC purity: 91.59%. |
| 156 | 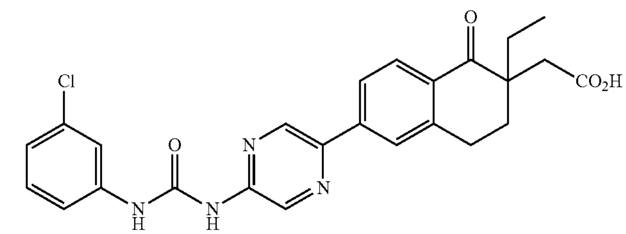 [SMILES: CCC1(CC(=O)O)CCc2cc(-c3cnc(NC(=O)Nc4cccc(Cl)c4)cn3)ccc2C1=O] | ¹H NMR (300 MHz, DMSO-d₆): δ 12.1 (s, 1H), 9.8 (bs, 1H), 9.7 (bs, 1H), 9.16 (s, 1H), 9.01 (s, 1H), 8.04-7.89 (m, 3H), 7.76 (m, 1H), 7.36-7.28 (m, 2H), 7.11 (m, 1H), 3.2-2.95 (m, 2H), 2.8 (d, J = 16.8 Hz, 1H), 2.5-2.3 (m, 2H), 2.02-1.98 (m, 1H), 1.70-1.52 (m, 2H), 0.84 (t, J = 6.9 Hz, 3H). | ESI-MS m/z = 479 (M + H)+; HPLC purity: 91.12%. |
| 157 | 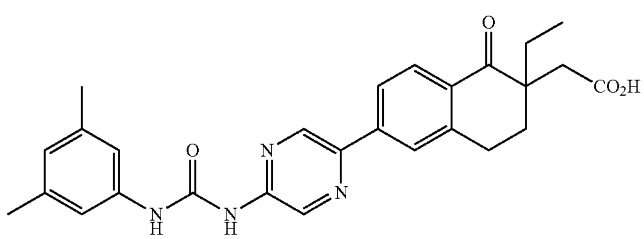 | ¹H NMR (300 MHz, DMSO-d₆): δ 12.05 (s, 1), 9.79 (bs, 1H), 9.62 (bs, 1H), 9.16 (s, 1H), 9.0 (s, 1H), 8.04-7.98 (m, 3H), 7.15 (s, 2H), 6.69 (s, 1H), 3.2-2.95 (m, 2H), 2.8 (d, J = 16.8 Hz, 1H), 2.5-2.3 (m, 2H), 2.26 (s, 6H), 2.02-1.98 (m, 1H), 1.70-1.52 (m, 2H), 0.84 (m, 3H). | HPLC purity: 91.88%. |
| 158 | 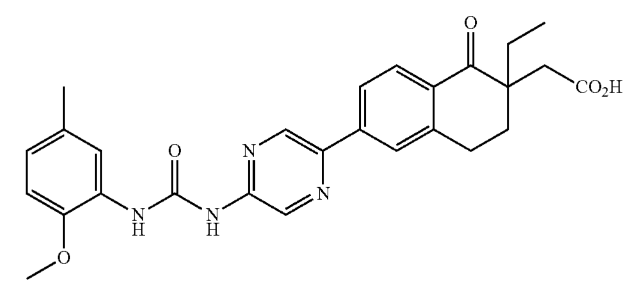 [SMILES: CCC1(CC(=O)O)CCc2cc(-c3cnc(NC(=O)Nc4cc(C)ccc4OC)cn3)ccc2C1=O] | ¹H NMR (300 MHz, DMSO-d₆): δ 12.05 (s, 1H), 10.29 (bs, 1H), 9.94 (bs, 1H) 9.0 (s, 2H), 8.04-7.98 (m, 4H), 6.93 (d, J = 7.8 Hz, 1H), 6.82 (d, J = 7.8 Hz, 1H), 3.89 (s, 3H), 3.2-2.95 (m, 2H), 2.8 (d, J = 16.2 Hz, 1H), 2.5-2.3 (m, 2H), 2.24 (s, 3H), 2.02-1.98 (m, 1H), 1.70-1.52 (m, 2H), 0.84 (t, J = 7.5 Hz, 3H). | HPLC purity: 95.39%. |
| 159 | 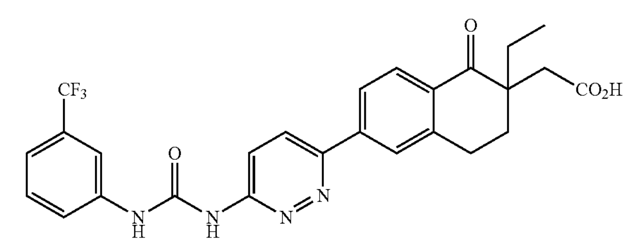 [SMILES: CCC1(CC(=O)O)CCc2cc(-c3ccc(NC(=O)Nc4cccc(C(F)(F)F)c4)nn3)ccc2C1=O] | ¹H NMR (300 MHz, DMSO-d₆): δ 12.05 (bs, 1H), 10.29 (m, 2H), 8.32 (d, J = 7.2 Hz, 1H), 8.25 (s, 1H), 8.07-7.98 (m, 4H), 7.64-7.57 (m, 2H), 7.40 (d, J = 7.8 Hz, 1H), 3.2-2.95 (m, 2H), 2.8 (d, J = 15.9 Hz, 1H), 2.5-2.3 (m, 2H), 2.02-1.98 (m, 1H), 1.70-1.52 (m, 2H), 0.84 (t, J = 7.8 Hz, 3H). | ESI-MS m/z = 513 (M + H)+; purity: 98.83%. |
| 160 | 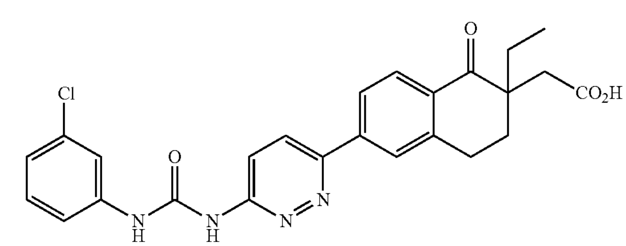 [SMILES: CCC1(CC(=O)O)CCc2cc(-c3ccc(NC(=O)Nc4cccc(Cl)c4)nn3)ccc2C1=O] | ¹H NMR (400 MHz, DMSO-d₆): δ 12.1 (bs, 1H), 10.29 (s, 1H), 9.95 (bs, 1H), 8.38-8.20 (m, 2H), 8.18-8.0 (m, 3H), 7.78 (s, 1H), 7.38 (m, 2H), 7.15 (s, 1H), 3.2-2.95 (m, 2H), 2.8 (d, J = 15.9 Hz, 1H), 2.5-2.3 (m, 2H), 2.0 (m, 1H), 1.70-1.52 (m, 2H), 0.84 (t, J = 7.8 Hz, 3H). | ESI-MS m/z = 479 (M + H)+; HPLC purity: 93.4% |

-continued

| Ex | Structure | Analytical Data | (M + H)+ |
|---|---|---|---|
| 161 | (3-CF3-phenyl)-NH-C(O)-NH-(pyridin-2-yl, 5-linked)-tetrahydronaphthalenone with ethyl and CH2CO2H at 2-position | 1H NMR (300 MHz, DMSO-d6): δ 12.1 (bs, 1H), 10.7 (s, 1H), 9.73 (s, 1H), 8.73 (s, 1H), 8.18 (d, J = 8.4 Hz, 1H), 8.08 (s, 1H), 7.96 (d, J = 8.4 Hz, 1H) 7.68-7.53 (m, 4H), 7.56 (t, J = 8.4 Hz, 1H), 7.38 (d, J = 6.9 Hz, 1H), 3.1-2.9 (m, 2H), 2.8 (d, J = 16.2 Hz, 1H), 2.50-2.36 (m, 2H), 2.0 (m, 1H), 1.75-1.45 (m, 2H), 0.84 (m, 3H). | ESI-MS m/z = 512 (M + H)+. HPLC purity: 95.8%. |
| 162 | (3-Cl-phenyl)-NH-C(O)-NH-(pyridin-2-yl, 5-linked)-tetrahydronaphthalenone with ethyl and CH2CO2H at 2-position | 1H NMR (400 MHz, DMSO-d6): δ 12.0 (bs, 1H), 11.45 (s, 1H), 8.35 (s, 1H), 7.91 (d, J = 7.8 Hz, 1H), 7.88-7.8 (m, 2H), 7.65-7.5 (m, 4H), 7.25 (t, J = 8.0 Hz, 1H), 6.95 (d, J = 7.8 Hz, 1H), 3.15-2.75 (m, 4H), 2.1 (d, J = 15.6 Hz, 1H), 1.84 (m, 1H), 1.7-1.45 (m, 2H), 0.88 (t, J = 7.8 Hz, 3H). | ESI-MS m/z = 478 (M + H)+. HPLC purity: 96.3%. |
| 163 | (phenyl)-NH-C(O)-NH-(pyridin-2-yl, 5-linked)-tetrahydronaphthalenone with ethyl and CH2CO2H at 2-position | 1H NMR (300 MHz, DMSO-d6): δ 10.4 (s, 1H), 9.9 (s, 1H), 8.7 (s, 1H), 8.19 (d, J = 8.4 Hz, 1H), 7.96 (d, J = 8.4 Hz, 1H), 7.8-7.65 (m, 3H), 7.5 (d, J = 7.8 Hz, 2H), 7.33 (t, J = 7.8 Hz, 2H), 7.03 (t, J = 6.9 Hz, 1H), 3.2-2.9 (m, 2H), 2.76 (d, J = 16.8 Hz, 1H), 2.50-2.35 (m, 2H), 2.0 (m, 1H), 1.75-1.45 (m, 2H), 0.84 (t, J = 7.8 Hz, 3H). | ESI-MS m/z = 444 (M + H)+. HPLC purity: 92.7%. |
| 164 | (3-Cl-phenyl)-NH-C(O)-NH-(pyridin-5-yl, 2-linked)-tetrahydronaphthalenone with ethyl and CH2CO2H at 2-position. Chiral | 1H NMR (400 MHz, DMSO-d6): δ 9.26 (bs, 1H), 9.20 (bs, 1H), 8.75 (s, 1H), 8.15 (m, 1H), 8.03 (m, 4H), 7.74 (s, 1H), 7.34 (m, 2H), 7.07 (m, 1H), 3.13-3.02 (m, 2H), 2.8 (d, J = 16.4 Hz, 1H), 2.5-2.35 (m, 2H), 2.03 (m, 1H), 1.71-1.58 (m, 2H), 0.86 (t, J = 6.8 Hz, 3H). | ESI-MS m/z = 478 (M + H)+. HPLC purity: 96.32%. |
| 165 | (3-Cl-phenyl)-NH-C(O)-NH-(pyridin-5-yl, 2-linked)-tetrahydronaphthalenone with ethyl and CH2CO2H at 2-position. Chiral | 1H NMR (400 MHz, DMSO-d6): δ 9.26 (bs, 1H), 9.20 (bs, 1H), 8.75 (s, 1H), 8.15 (m, 1H), 8.03 (m, 4H), 7.74 (s, 1H), 7.34 (m, 2H), 7.07 (m, 1H), 3.13-3.02 (m, 2H), 2.8 (d, J = 16.4 Hz, 1H), 2.5-2.35 (m, 2H), 2.03 (m, 1H), 1.71-1.58 (m, 2H), 0.86 (t, J = 6.8 Hz, 3H). | ESI-MS m/z = 478 (M + H)+. HPLC purity: 99.17%. |
| 166 | (3-CF3-phenyl)-NH-C(O)-NH-(pyrazin-2-yl, 5-linked)-tetrahydronaphthalenone with ethyl and CH2CO2H at 2-position. Chiral: enantiomer-1 | 1H NMR (300 MHz, DMSO-d6): δ 12.08 (s, 1H), 10.0 (bs, 1H), 9.93 (bs, 1H), 9.17 (s, 1H), 9.02 (s, 1H), 8.1-7.9 (m, 4H), 7.68 (d, J = 7.5 Hz, 1H), 7.57 (t, J = 7.5 Hz, 1H), 7.4 (d, J = 6.3 Hz, 1H), 3.2-3.0 (m, 2H), 2.8 (d, J = 15.9 Hz, 1H), 2.5-2.3 (m, 2H), 2.02-1.98 (m, 1H), 1.68-1.55 (m, 2H), 0.84 (m, 3H). | ESI-MS m/z = 513 (M + H)+; HPLC purity: 98%. |

| Ex | Structure | Analytical Data | (M + H)+ |
| --- | --- | --- | --- |
| 167 | Chiral: enantiomer-2 | ¹H NMR (300 MHz, DMSO-d₆): δ 12.08 (s, 1H), 10.0 (bs, 1H), 9.93 (bs, 1H), 9.17 (s, 1H), 9.02 (s, 1H), 8.1-7.9 (m, 4H), 7.68 (d, J = 7.5 Hz, 1H), 7.57 (t, J = 7.5 Hz, 1H), 7.4 (d, J = 6.3 Hz, 1H), 3.2-3.0 (m, 2H), 2.8 (d, J = 15.9 Hz, 1H), 2.5-2.3 (m, 2H), 2.02-1.98 (m, 1H), 1.68-1.55 (m, 2H), 0.84 (m, 3H). | ESI-MS m/z = 513 (M + H)+; HPLC purity: 97.5%. |
| 168 | 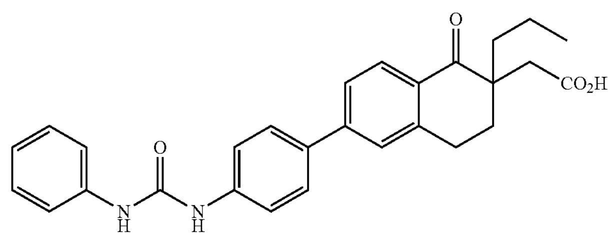 [SMILES: CCCC1(CC(=O)O)CCc2cc(-c3ccc(NC(=O)Nc4ccccc4)cc3)ccc2C1=O] | ¹H NMR (300 MHz, DMSO-d₆): δ 12.07 (bs, 1H), 9.1-8.9 (s, 2H), 7.92 (d, J = 8.4 Hz, 1H), 7.68-7.56 (m, 6H), 7.48-7.46 (d, J = 8.0 Hz, 2H), 7.28 (t, J = 7.6 Hz, 2H), 6.97 (t, J = 7.6 Hz, 1H), 3.08-2.92 (m, 2H), 2.80 (d, J = 16.4 Hz, 1H), 2.40 (m, 1H), 1.96 (m, 1H), 1.61 (m, 1H), 1.45-1.15 (m, 4H), 0.84 (m, 3H). | ESI-LCMS m/z: 457 (98%); HPLC purity: 98%. |
| 169 | 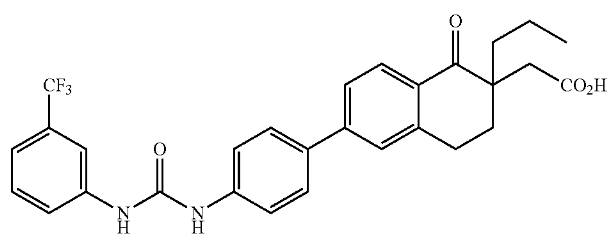 [SMILES: CCCC1(CC(=O)O)CCc2cc(-c3ccc(NC(=O)Nc4cccc(C(F)(F)F)c4)cc3)ccc2C1=O] | ¹H NMR (300 MHz, DMSO-d₆): δ 12.1 (s, 1H), 9.8 (bs, 2H), 8.05 (s, 1H), 7.95 (d, J = 8.2 Hz, 1H), 7.6 (m, 8H), 7.3 (d, J = 7.5 Hz, 1H), 3.1 (m, 1H), 2.8 (m, 2H), 2.35 (d, J = 15.9 Hz, 1H), 2.0 (d, J = 12.6 Hz, 1H), 1.6 (m, 1H), 1.4 (m, 4H), 0.8 (t, J = 6.9 Hz, 3H). | ESI-LCMS m/z: 523 (purity 96%); HPLC purity: 94%. |
| 170 | 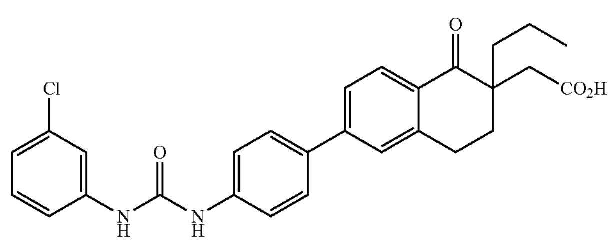 [SMILES: CCCC1(CC(=O)O)CCc2cc(-c3ccc(NC(=O)Nc4cccc(Cl)c4)cc3)ccc2C1=O] | ¹H NMR (300 MHz, DMSO-d₆): δ 12.1 (s, 1H), 9.35 (bs, 2H), 7.9 (d, J = 8.4 Hz, 1H), 7.75 (s, 1H), 7.6 (m, 6H), 7.3 (m, 2H), 7.0 (d, J = 5.7 Hz, 1H), 3.0 (m, 2H), 2.8 (m, 1H), 2.4 (d, J = 16.2 Hz, 1H), 2.0 (d, J = 13.2 Hz, 1H), 1.6 (m, 1H), 1.5-1.2 (m, 4H), 0.8 (m, 3H). | ESI-LCMS m/z: 491 (purity 95%); HPLC purity: 96%. |
| 171 | 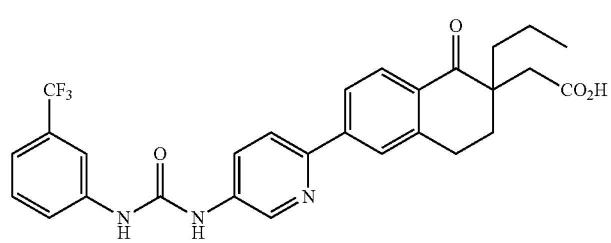 [SMILES: CCCC1(CC(=O)O)CCc2cc(-c3ccc(NC(=O)Nc4cccc(C(F)(F)F)c4)cn3)ccc2C1=O] | ¹H NMR (400 MHz, DMSO-d₆): δ 9.5 (bs, 2H), 8.8 (s, 1H), 8.15 (d, J = 7.8 Hz, 1H), 8 (m, 5H), 7.65 (d, J = 8.4 Hz, 1H), 7.5 (t, J = 7.2 Hz, 1H), 7.35 (d, J = 6.9 Hz, 1H), 3.1-3.0 (m, 2H), 2.8 (m, 1H), 2.4 (m, 2H), 2.0 (m, 1H), 1.6 (m, 1H), 1.4 (m, 3H), 0.8 (m, 3H). | ESI-LCMS m/z: 526 (purity 92%); HPLC purity: 92.5%. |
| 172 | 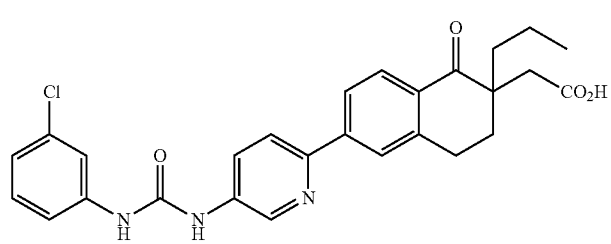 [SMILES: CCCC1(CC(=O)O)CCc2cc(-c3ccc(NC(=O)Nc4cccc(Cl)c4)cn3)ccc2C1=O] | ¹H NMR (400 MHz, DMSO-d₆); δ 12.1 (bs, 1H), 9.4 (s, 2H), 8.75 (s, 1H), 8.1 (d, J = 6.8 Hz, 1H), 8.0 (m, 4H), 7.7 (s, 1H), 7.3 (m, 2H), 7.0 (m, 1H), 3.1-2.9 (m, 3H), 2.8 (d, J = 16.4 Hz, 1H), 2.4 (m, 2H), 2.0 (d, J = 13.2 Hz, 1H), 1.6 (m, 1H), 1.4 (m, 2H), 0.8 (t, J = 7.2 Hz, 3H). | ESI-LCMS m/z: 492 (Purity 97%); HPLC purity: 98%. |

Example-173

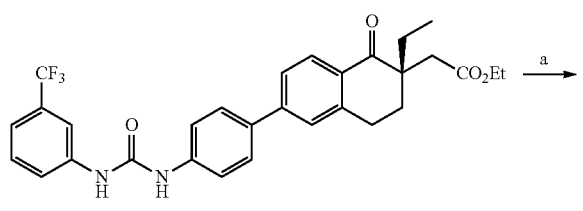

115G1

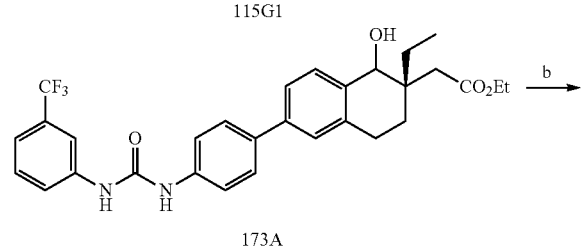

173A

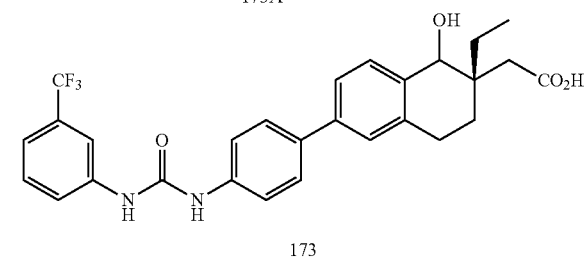

173

Reagents and conditions: a) NaBH₄, EtOH, RT, 5 h; b) LiOH, Dioxane-H₂O, RT, 8 h.

Procedures 2-((2S)-2-Ethyl-1-hydroxy-6-(4-(3-(3-(trifluoromethyl)phenyl)ureido)phenyl)-1,2,3,4-tetrahydronaphthalen-2-yl)acetic acid Ethyl 2-((2S)-2-ethyl-1-hydroxy-6-(4-(3-(3-(trifluoromethyl)phenyl)ureido)phenyl)-1,2,3,4-tetrahydronaphthalen-2-yl)acetate (173A)

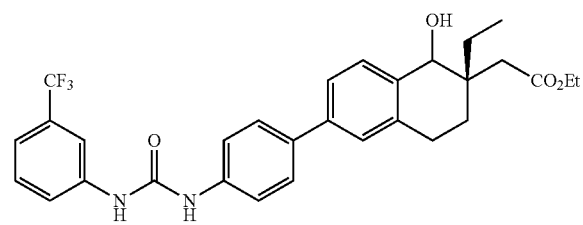
173A

Sodium borohydride (0.197 g, 5.18 mmol) was added portion wise to an ice cold solution of product of Example 115G1 (0.4 g, 0.74 mmol) in ethanol (10 mL), and the mixture was stirred at room temperature for 5 h. Ethanol was concentrated under reduced pressure and diluted with water. The resulting solids were filtered, and crude product was purified by flash chromatography to afford title compound (0.22 g, 55%) as solid. $^1$H NMR (300 MHz, CDCl$_3$): δ 7.68 (bs, 1H), 7.57 (m, 1H), 7.5 (d, J=6.0 Hz, 1H), 7.4 (s, 1H), 7.32-7.27 (m, 2H), 7.23 (m, 2H), 7.09-7.02 (m, 3H), 4.67 (s, 1H), 4.15 (q, J=6.9 Hz, 2H), 3.8 (bs, 1H), 2.78 (t, J=6.3 Hz, 2H), 2.36 (q, J=14.4 Hz, 2H), 1.8 (m, 1H), 1.67-1.6 (m, 2H), 1.45 (m, 1H), 1.29 (m, 3H), 0.92 (t, J=7.2 Hz, 3H).

2-((2S)-2-Ethyl-1-hydroxy-6-(4-(3-(3-(trifluoromethyl)phenyl)ureido)phenyl)-1,2,3,4-tetrahydronaphthalen-2-yl)acetic acid (173)

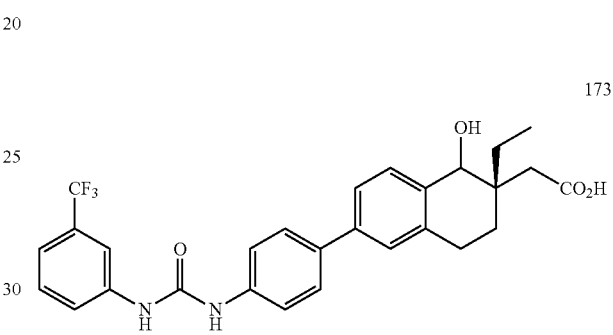
173

Lithium hydroxide (0.046 g, 1.09 mmol) was added to a solution of product of Example 173A (0.15 g, 0.27 mmol) in 4 mL of dioxane-water (3:1) mixture, and the reaction mixture was stirred at room temperature for 8 h. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.05 g, 36%) as white solid. $^1$H NMR (300 MHz, DMSO-d$_6$): δ 9.7 (bs, 1H), 9.46 (bs, 1H), 8.05 (s, 1H), 7.63 (m, 3H), 7.54-7.4 (m, 4H), 7.36-7.26 (m, 3H), 4.5 (s, 1H), 2.6 (m, 2H), 2.2 (m, 2H), 1.8-1.55 (m, 3H), 1.3 (m, 1H), 1.0-0.8 (m, 3H). HPLC purity: 98%.

Examples 174 was prepared by the procedures analogous to those described in Example 173 using appropriate starting materials.

| Ex | Structure | Analytical Data | (M + H)⁺ |
|----|-----------|-----------------|----------|
| 174 | (structure shown) | $^1$H NMR (300 MHz, DMSO-d$_6$): δ 9.7 (bs, 1H), 9.46 (bs, 1H), 8.05 (s, 1H), 7.63 (m, 3H). 7.54-7.4 (m, 4H), 7.36-7.26 (m, 3H), 4.5 (s, 1H), 2.6 (m, 2H), 2.2 (m, 2H), 1.8-1.55 (m, 3H), 1.3 (m, 1H), 1.0-0.8 (m, 3H). | HPLC purity: 99.8% |

Example-175

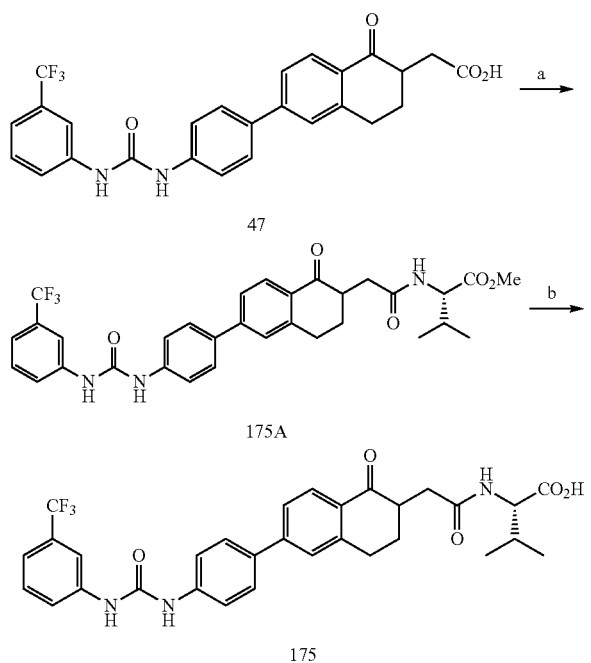

Reagents and conditions: a) HATU, THF, Valine methyl ester, RT, 8 h; b) LiOH, THF—H$_2$O, RT, 12 h.

Procedures (2S)-3-Methyl-2-(2-(1-oxo-6-(4-(3-(3-(trifluoromethyl)phenyl)ureido)phenyl)-1,2,3,4-tetrahydronaphthalen-2-yl)acetamido)butanoic acid (2S)-Methyl 3-methyl-2-(2-(1-oxo-6-(4-(3-(3-(trifluoromethyl)phenyl)ureido)phenyl)-1,2,3,4-tetrahydronaphthalen-2-yl)acetamido) butanoate (175A)

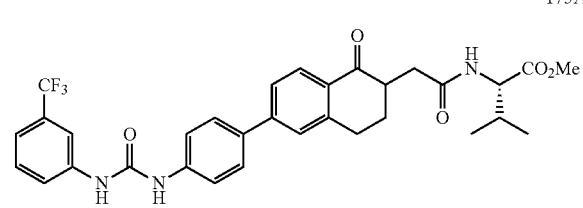

HATU (0.19 g, 0.497 mmol) was added to a solution of product of Example 47A (0.2 g, 0.414 mmol) and N-ethyl diisopropylamine (0.16 g, 1.24 mmol) in THF (10 mL) followed by valine methyl ester (0.07 g, 0.413 mmol). The reaction mixture was stirred at room temperature for 8 h. The reaction mixture was then partitioned between ethyl acetate and water. The organic layer was separated, washed with saturated solution of NaCl, dried over sodium sulphate, filtered and concentrated. The residue obtained was purified by column chromatography using 25% ethyl acetate in hexane as eluent to afford title compound (0.12 g, 49%) as solid. $^1$H NMR (400 MHz, DMSO-d$_6$): δ 9.09 (bs, 1H), 8.97 (bs, 1H), 8.22 (m, 1H), 8.03 (bs, 1H), 7.91 (d, J=8.4 Hz, 1H), 7.71 (d, J=8.0 Hz, 2H), 7.65-7.58 (m, 5H), 7.5 (t, J=7.6 Hz, 1H), 7.32 (d, J=7.6 Hz, 1H), 4.21 (m, 1H), 3.63 (s, 3H), 3.05-2.8 (m, 2H), 2.4-2.3 (m, 2H), 2.2-1.8 (m, 4H), 0.9 (s, 6H).

(2S)-3-Methyl-2-(2-(1-oxo-6-(4-(3-(3-(trifluoromethyl)phenylureido)phenyl-1,2,3,4-tetrahydronaphthalen-2-yl)acetamido)butanoic acid (175)

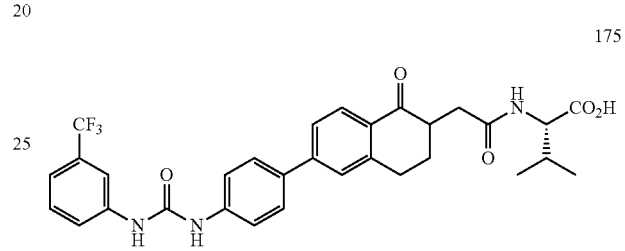

Lithium hydroxide (0.02 g, 0.5 mmol) was added to a solution of product of Example 175A (0.1 g, 0.16 mmol) in 4 mL of THF-water (3:1) mixture, and the reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.05 g, 51%) as solid. $^1$H NMR (400 MHz, DMSO-d$_6$): δ 12.5 (bs, 1H), 9.18 (bs, 1H), 9.04 (bs, 1H), 8.07 (d, J=8.4 Hz, 1H), 8.03 (s, 1H), 7.9 (d, J=7.6 Hz, 1H), 7.7 (d, J=8.4 Hz, 2H), 7.66-7.5 (m, 6H), 7.32 (d, J=8.4 Hz, 1H), 4.2 (m, 1H), 3.1-2.9 (m, 2H), 2.8 (m, 1H), 2.4 (m, 2H), 2.2-2.0 (m, 2H), 1.9 (m, 1H), 0.9 (m, 6H); HPLC purity: 94.8%.

Examples 176-181 were prepared by the procedures analogous to those described in Example 175 or routine variations thereof, starting from the requisite tetralone-2-acetic acid (e.g., Example 47) and amino acid, or appropriately functional-group protected versions thereof, followed by deprotection by procedures well-known to those skilled in the art.

| Ex | Structure | Analytical Data | (M + H)$^+$ |
|---|---|---|---|
| 176 | ![structure] | $^1$H NMR (400 MHz, DMSO-d$_6$): δ 12.5 (bs, 1H), 8.17 (s, 1H), 8.11 (m, 1H), 7.94 (d, J = 8.0 Hz, 1H), 7.86-7.76 (m, 4H), 7.74-7.64 (m, 3H), 7.46 (t, J = 7.6 Hz, 1H), 7.24 (d, J = 7.6 Hz, 1H), 3.85 (m, 2H), 3.4 (m, 1H), 3.1-2.8 (m, 2H), 2.65 (m, 2H), 2.2 (m, 1H), 2.0 (m, 1H). | HPLC purity: 96.06%. |

| Ex | Structure | Analytical Data | (M + H)+ |
|---|---|---|---|
| 177 | 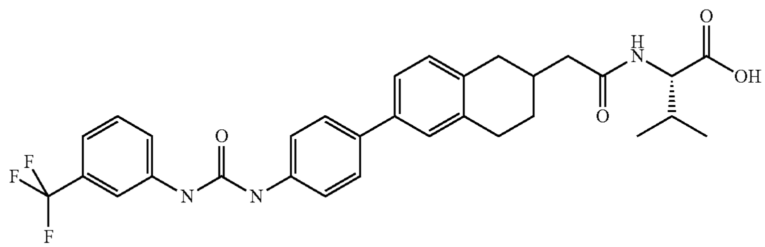 [SMILES: CC(C)[C@H](NC(=O)CC1CCc2cc(-c3ccc(NC(=O)Nc4cccc(C(F)(F)F)c4)cc3)ccc2C1)C(=O)O] | ¹H NMR (400 MHz, DMSO-d₆): δ 12.51 (bs, 1H), 9.31 (bs, 1H), 9.10 (bs, 1H), 8.04 (s, 1H), 7.97 (d, J = 8.1 Hz, 1H), 7.62-7.47 (m, 6H), 7.30 (m, 3H), 7.07 (d, J = 8.4 Hz, 1H), 4.18 (t, J = 6.3 Hz, 1H), 2.85-2.71 (m, 3H), 2.43 (m, 1H), 2.26 (d, J = 7.2 Hz, 2H), 2.08 (m, 2H), 1.90 (m, 1H), 1.45 (m, 1H), 0.9 (m, 6H). | ESI-MS m/z = 567 (M + H)+; HPLC purity: 92%. |
| 178 | 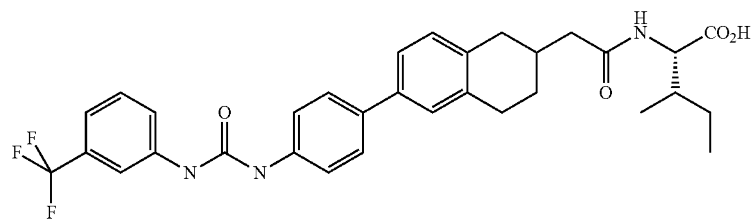 [SMILES: CCC(C)[C@H](NC(=O)CC1CCc2cc(-c3ccc(NC(=O)Nc4cccc(C(F)(F)F)c4)cc3)ccc2C1)C(=O)O] | ¹H NMR (400 MHz, DMSO-d₆): δ 12.40 (bs, 1H), 9.06 (bs, 1H), 8.87 (bs, 1H), 8.02 (m, 2H), 7.59-7.49 (m, 6H), 7.33 (t, J = 7.6 Hz, 3H), 7.07 (d, J = 7.6 Hz, 1H), 4.22 (m, 1H), 2.88-2.79 (m, 3H), 2.45 (m, 1H), 2.25 (d, J = 6.4 Hz, 2H), 2.15 (m, 1H), 1.90-1.79 (m, 2H), 1.41 (m, 2H), 1.23 (m, 1H), 0.89 (m, 6H). | ESI-MS m/z = 582 (M + H)+; HPLC purity: 90%. |
| 179 | 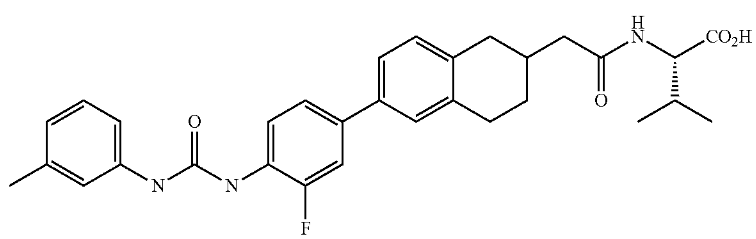 [SMILES: Cc1cccc(NC(=O)Nc2ccc(-c3ccc4c(c3)CCC(CC(=O)N[C@H](C(=O)O)C(C)C)C4)cc2F)c1] | ¹H NMR (400 MHz, DMSO-d₆): δ 12.40 (bs, 1H), 9.07 (bs, 1H), 8.64 (bs, 1H), 8.20 (t, J = 8.4 Hz, 1H), 7.96 (m, 1H), 7.52 (d, J = 12.8 Hz, 1H), 7.43 (d, J = 8.8 Hz, 1H), 7.37 (m, 2H), 7.31 (s, 1H), 7.25-7.15 (m, 2H), 7.08 (d, J = 8.4 Hz, 1H), 6.81 (d, J = 7.2 Hz, 1H), 4.16 (t, J = 6.4 Hz, 1H), 2.89-2.77 (m, 3H), 2.32 (s, 3H), 2.28 (d, J = 7.2 Hz 2H), 2.14-2.05 (m, 3H), 1.89 (m, 1H), 1.40 (m, 1H), 0.85 (m, 6H). | ESI-MS m/z = 532 (M + H)+; HPLC purity: 95%. |
| 180 | 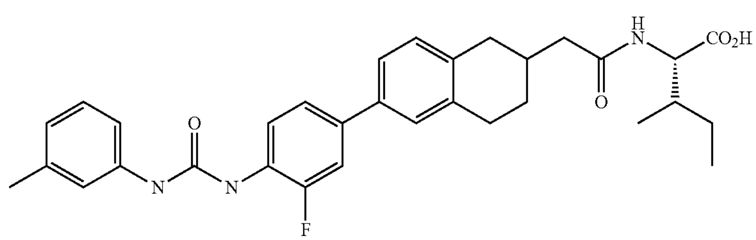 [SMILES: CCC(C)[C@H](NC(=O)CC1CCc2cc(-c3ccc(NC(=O)Nc4cccc(C)c4)c(F)c3)ccc2C1)C(=O)O] | ¹H NMR (400 MHz, DMSO-d₆): δ 12.40 (bs, 1H), 9.06 (bs, 1H), 8.63 (bs, 1H), 8.20 (t, J = 8.4 Hz, 1H), 7.98 (bs, 1H), 7.52 (d, J = 13.2 Hz, 1H), 7.43 (m, 3H), 7.31-7.15 (m, 3H) 7.08 (d, J = 8.0 Hz, 1H), 6.81 (d, J = 7.6 Hz, 1H), 4.20 (m, 1H), 2.98-2.79 (m, 3H), 2.28 (s, 3H), 2.24 (d, J = 6.8 Hz, 2H), 2.14 (m, 2H), 1.99-1.79 (m, 2H), 1.41 (m, 1H), 1.16 (m, 2H), 0.86 (m, 6H). | ESI-MS m/z = 546 (M + H)+; HPLC purity: 91%. |
| 181 | 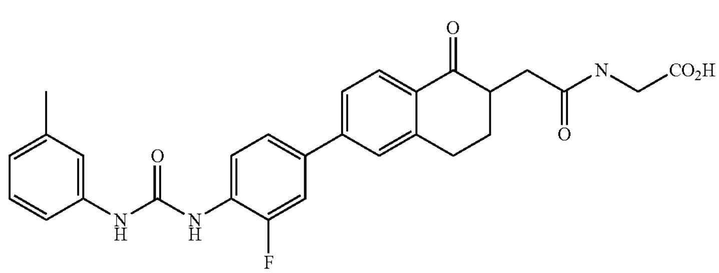 [SMILES: Cc1cccc(NC(=O)Nc2ccc(-c3ccc4c(c3)CCC(CC(=O)NCC(=O)O)C4=O)cc2F)c1] | ¹H NMR (300 MHz, DMSO-d₆): δ 12.4 (bs, 1H), 9.03 (bs, 1H), 8.70 (bs, 1H), 8.34-8.24 (m, 2H), 7.91 (d, J = 9.0 Hz, 1H), 7.73-7.66 (m, 3H), 7.59 (d, J = 8.7 Hz, 1H), 7.31 (bs, 1H), 7.26-7.15 (m, 2H), 6.82 (d, J = 7.2 Hz, 1H), 3.77 (m, 2H), 3.1-2.9 (m, 3H), 2.84-2.71 (m, 1H), 2.4 (m, 1H), 2.29 (s, 3H), 2.0 (m, 1H), 1.87 (m, 1H). | HPLC purity: 94% |

Example-182

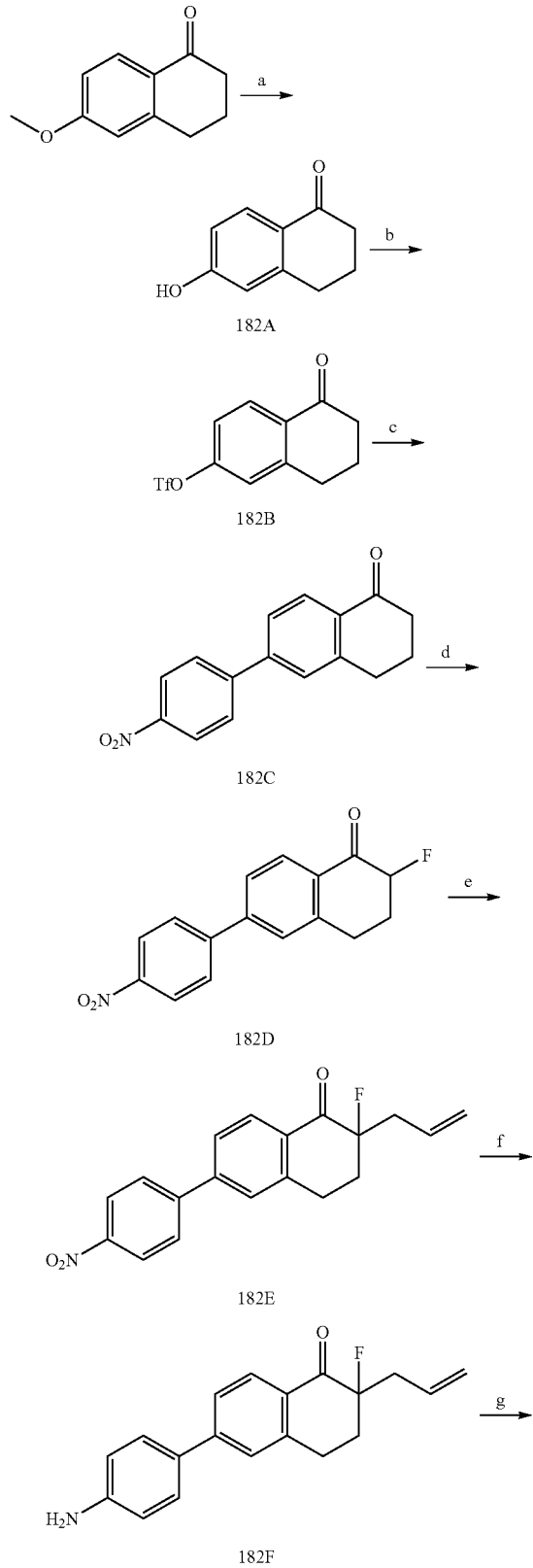

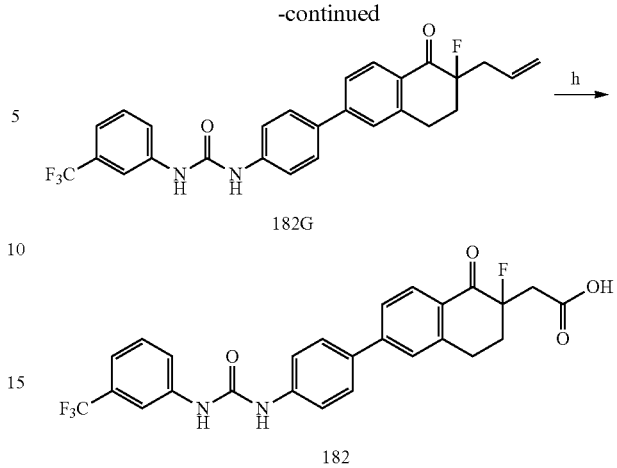

Reagents and conditions: a) Aq HBr Reflux, 12 h; b) Tf₂O, DMAP, Py, RT, 1 h; c) 4-NO₂ phenyl boronic acid, Pd(PPh₃)₄, Cs₂CO₃, Dioxane-H₂O, 80° C., 5 h; d) select Fluor, MeOH, 80° C., 4 h; e) Allyl bromide, TBAI, KOH, RT, 18 h; f) Fe/NH₄Cl, EtOH, H₂O, Reflux, 2 h; g) 3-CF₃-PhNCO, Et₃N, THF, RT, 12 h; h) LiOH, THF—H₂O, RT, 12 h.

Procedures 2-(2-Fluoro-1-oxo-6-(4-(3-(3-(trifluoromethyl)phenyl)ureido)phenyl)-1,2,3,4-tetrahydronaphthalen-2-yl)acetic acid 6-Hydroxy-3,4-dihydronaphthalen-1(2H)-one (182A)

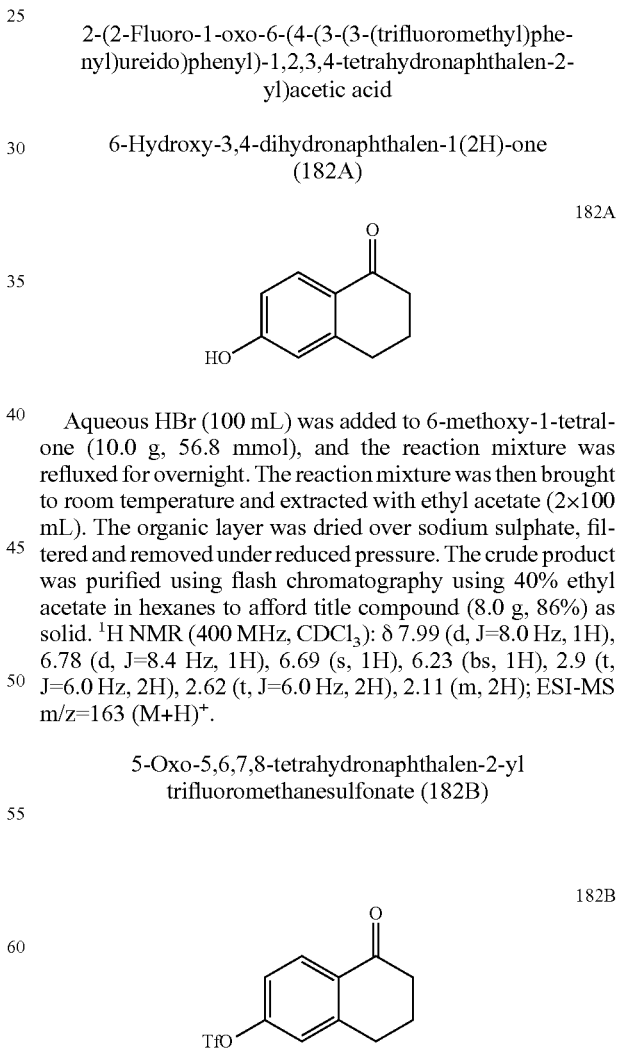

Aqueous HBr (100 mL) was added to 6-methoxy-1-tetralone (10.0 g, 56.8 mmol), and the reaction mixture was refluxed for overnight. The reaction mixture was then brought to room temperature and extracted with ethyl acetate (2×100 mL). The organic layer was dried over sodium sulphate, filtered and removed under reduced pressure. The crude product was purified using flash chromatography using 40% ethyl acetate in hexanes to afford title compound (8.0 g, 86%) as solid. ¹H NMR (400 MHz, CDCl₃): δ 7.99 (d, J=8.0 Hz, 1H), 6.78 (d, J=8.4 Hz, 1H), 6.69 (s, 1H), 6.23 (bs, 1H), 2.9 (t, J=6.0 Hz, 2H), 2.62 (t, J=6.0 Hz, 2H), 2.11 (m, 2H); ESI-MS m/z=163 (M+H)⁺.

5-Oxo-5,6,7,8-tetrahydronaphthalen-2-yl trifluoromethanesulfonate (182B)

Triflic anhydride (16.7 g, 59.2 mmol) was added to an ice cold solution of product of Example 182A (8.0 g, 49.3 mmol), DMAP (1.20 g, 9.83 mmol) and 2,6-lutidine (5.20 g, 49.3 mmol) in dichloromethane (15 mL). The reaction mixture was stirred at room temperature for 1 h. The reaction mixture was then diluted with dichloromethane (50 mL) and washed with saturated aqueous solution of NaCl (50 mL). The organic layer was dried over sodium sulphate, filtered and removed under reduced pressure. The product was purified by flash chromatography using 5% ethyl acetate in hexanes to give title compound (12 g, 85%) as solid. $^1$H NMR (400 MHz, CDCl$_3$): δ 8.14 (d, J=8.4 Hz, 1H), 7.2 (m, 2H), 3.01 (t, J=6.4 Hz, 2H), 2.68 (t, J=6.0 Hz, 2H), 2.18 (m, 2H); ESI-MS m/z=295 (M+H)$^+$.

6-(4-Nitrophenyl)-3,4-dihydronaphthalen-1(2H)-one (182C)

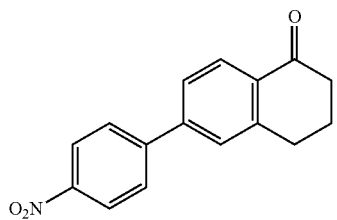

182C

Pd(PPh$_3$)$_4$ (0.023 g, 0.19 mmol) was added to a solution of product of Example 182B (5.0 g, 16.8 mmol) in 60 mL of 1,4 dioxane-H$_2$O (3:1) mixture under argon atmosphere, followed by cesium carbonate (13.7 g, 42.0 mmol) and 4-nitro phenyl boronic acid (2.81 g, 16.8 mmol). The reaction mixture was degassed for 5 min. The reaction mixture was then refluxed for 5 h, and solvent was removed under reduced pressure. The residue was partitioned between ethyl acetate and water. The separated organic layer was dried over sodium sulphate, filtered and removed under reduced pressure. The product was purified by flash chromatography to afford title compound (3.5 g, 77%) as solid. $^1$H NMR (300 MHz, CDCl$_3$): δ 8.34-8.30 (m, 2H), 8.15 (d, J=8.4 Hz, 1H), 7.78-7.75 (m, 2H), 7.57-7.51 (m, 2H), 3.06 (t, J=6.0 Hz, 2H), 2.71 (t, J=6.0 Hz, 2H), 2.23-2.17 (m, 2H); ESI-MS m/z=268 (M+H)$^+$.

2-Fluoro-6-(4-nitrophenyl)-3,4-dihydronaphthalen-1(2H)-one (182D)

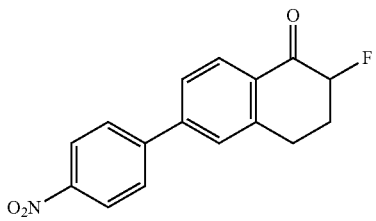

182D

Selectfluor (1.27 g, 3.58 mmol) was added to product of Example 182C (0.8 g, 2.99 mmol) in 20 mL of methanol. The reaction mixture was refluxed for 4 h, and the solvent was then removed under vacuum to obtain the residue. The residue was dissolved in dichloromethane. Insoluble materials were filtered, and filtrate was washed with water followed by brine solution. The organic layer was dried over sodium sulphate, filtered and concentrated to afford title compound (0.6 g, 70%) as solid. $^1$H NMR (300 MHz, CDCl$_3$): δ 8.35 (m, 2H), 8.20 (d, J=Hz, 1H), 7.75 (m, 2H), 7.65 (m, 1H), 7.52 (s, 1H), 5.30-5.10 (m, 1H), 3.30 (m, 2H), 2.65 (m, 1H), 2.40 (m, 1H); ESI-MS m/z=286 (M+H)$^+$.

2-Allyl-2-fluoro-6-(4-nitrophenyl)-3,4-dihydronaphthalen-1(2H)-one (182E)

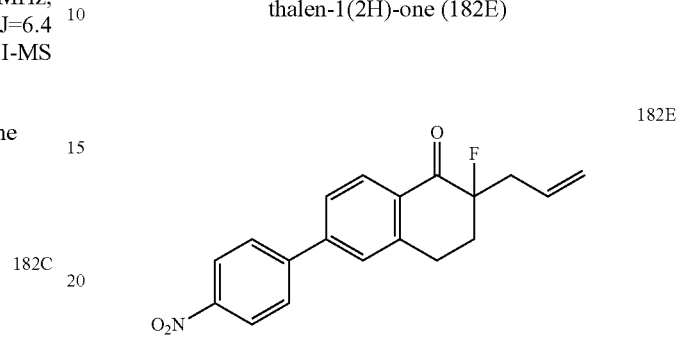

182E

Allyl bromide (1.89 g, 15.7 mmol) was added to a solution of product of Example 182D (3.0 g, 10.5 mmol), KOH (1.17 g, 21.0 mmol) and TBAI (0.77 g, 2.00 mmol) in Toluene (120 mL) at 0° C. The reaction mixture was stirred at room temperature for 18 h. The reaction mixture was then diluted with water and ethyl acetate. The separated organic layer was washed with water, brine solution, dried over sodium sulphate, filtered and concentrated under reduced pressure. The product was purified by flash chromatography using 10% ethyl acetate in hexanes to afford title compound (2.5 g, 73%) as solid. $^1$H NMR (300 MHz, CDCl$_3$): δ 8.38-8.32 (m, 2H), 8.18 (d, J=8.4 Hz, 1H), 7.80-7.75 (m, 2H), 7.61 (m, 1H), 7.50 (s, 1H), 5.86 (m, 1H), 5.23 (d, J=8.4 Hz, 2H), 3.25-3.09 (m, 2H), 2.77-2.25 (m, 4H); ESI-MS m/z=326 (M+H)$^+$.

2-Allyl-6-(4-aminophenyl)-2-fluoro-3,4-dihydronaphthalen-1(2H)-one (182F)

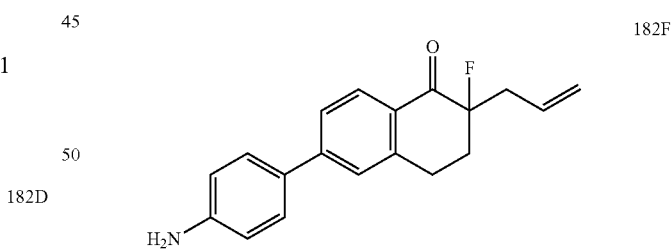

182F

Iron powder (0.214 g, 3.86 mmol) and NH$_4$Cl (0.040 g, 0.74 mmol) was added to a solution of product of Example 182E (0.51 g, 1.53 mmol) in 25 mL of ethanol-water (2:1) mixture. The reaction mixture was refluxed for 2 h, and solvent was removed under reduced pressure. The crude product was purified by flash chromatography using 2% methanol in chloroform to afford title compound (0.3 g, 66%) as solid. $^1$H NMR (300 MHz, CDCl$_3$): δ 8.07 (d, J=7.5 Hz, 1H), 7.53 (dd, J$_1$=1.2 Hz, J$_2$=8.1 Hz, 1H), 7.45 (d, J=8.4 Hz, 2H), 7.39 (s, 1H), 6.75 (d, J=8.4 Hz, 2H), 5.98-5.84 (m, 1H), 5.29-5.20 (m, 2H), 3.84 (bs, 2H), 3.16-2.97 (m, 2H), 2.80-2.54 (m, 2H), 2.46-2.33 (m, 2H); ESI-MS m/z=296 (M+H)$^+$.

159

1-(4-(6-Allyl-6-fluoro-5-oxo-5,6,7,8-tetrahydronaphthalen-2-yl)phenyl)-3-((trifluoromethyl)phenyl)urea (182G)

160

2-(2-Fluoro-1-oxo-6-(4-(3-(3-(trifluoromethyl)phenyl)ureido)phenyl)-1,2,3,4-tetrahydronaphthalen-2-yl)acetic acid (182)

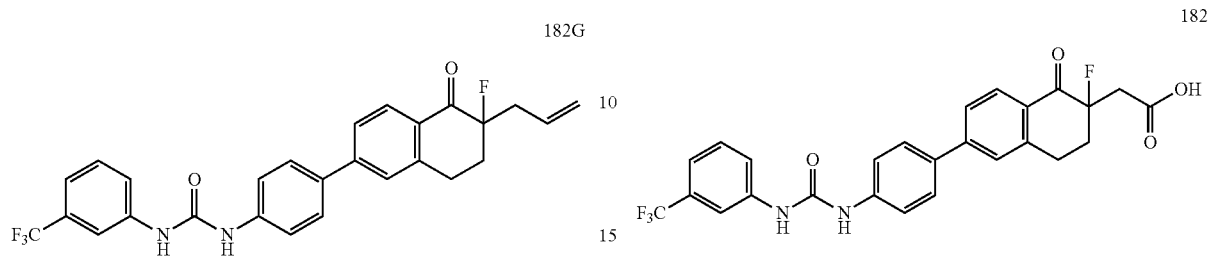

3(Trifluoromethyl)phenyl isocyanate (0.158 g, 0.84 mmol) was added to a solution of product of Example 182F (0.25 g, 0.84 mmol) and triethylamine (0.128 g, 1.26 mmol) in THF (15 mL). The reaction mixture was stirred at room temperature overnight. The solvent was then removed under reduced pressure, and crude product was purified by flash chromatography using 20% ethyl acetate in hexanes to afford title compound (0.2 g, 50%) as solid. $^1$H NMR (300 MHz, CDCl$_3$): δ 8.07 (d, J=7.5 Hz, 1H), 7.67 (s, 1H), 7.62 (d, J=7.8 Hz, 2H), 7.54-7.44 (m, 5H), 7.40-7.28 (m, 4H), 5.90-5.80 (m, 1H), 5.29-5.20 (m, 2H), 3.40-2.98 (m, 2H), 2.60-2.50 (m, 2H), 2.48-2.30 (m, 2H); ESI-MS m/z=483 (M+H)$^+$.

KMnO$_4$ (0.196 g, 1.24 mmol) was added to a solution of product of Example 182G (0.30 g, 0.62 mmol) and NaIO$_4$ (1.33 g, 6.2 mmol) in 30 mL of acetone-water (2:1) mixture. The reaction mixture was stirred at room temperature overnight. After the solvent was removed in vacuo, the residue was dissolved in water and extracted with ethyl acetate. The organic layer was dried over sodium sulphate, filtered and removed under reduced pressure to obtain the crude product which was purified by the preparative HPLC to afford title compound (0.075 g, 25%) as solid. $^1$H NMR (400 MHz, DMSO-d$_6$): δ 12.5 (bs, 1H), 9.11 (bs, 1H), 9.01 (bs, 1H), 7.96 (m, 2H), 7.72 (t, J=8.4 Hz, 4H), 7.62-7.50 (m, 4H), 7.32 (d, J=7.6 Hz, 1H), 3.20-3.05 (m, 4H), 2.90 (m, 1H), 2.66 (m, 1H); ESI-MS m/z=501 (M+H)$^+$; HPLC purity: 96%.

Examples 183-184 were prepared by the analogous procedures as described above in Example 182 using appropriate starting materials.

| Ex | Structure | $^1$H NMR Data | Mass/purity |
|---|---|---|---|
| 183 | ![structure] | $^1$H NMR (400 MHz, DMSO-d$_6$): δ 12.50 (bs, 1H), 8.96 (2s, 2H), 7.95 (d, J = 8.4 Hz, 1H), 7.72 (t, J = 8.8 Hz, 5H), 7.62 (d, J = 8.4 Hz, 2H), 7.33-7.27 (m, 2H), 7.03 (m, 1H), 3.20-3.02 (m, 4H), 2.90 (m, 1H), 2.67 (m, 1H). | MS m/z = 467 (M + H)$^+$; HPLC purity: 98%. |
| 184 | ![structure] | $^1$H NMR (400 MHz, DMSO-d$_6$): δ 12.60 (bs, 1H), 8.88 (bs, 1H), 8.73 (bs, 1H), 7.95 (d, J = 8.4 Hz, 1H), 7.71 (t, J = 8.8 Hz, 4H), 7.59 (d, J = 8.4 Hz, 2H), 7.47 (d, J = 8.0 Hz, 2H), 7.29 (t, J = 8.0 Hz, 2H), 6.98 (t, J = 7.2 Hz, 1H), 3.17 (m, 2H), 3.16-3.04 (m, 2H), 2.93 (m, 1H), 2.89 (m, 1H). | ESI-MS m/z = 432 (M + H)$^+$; HPLC purity: 93%. |

Example-185

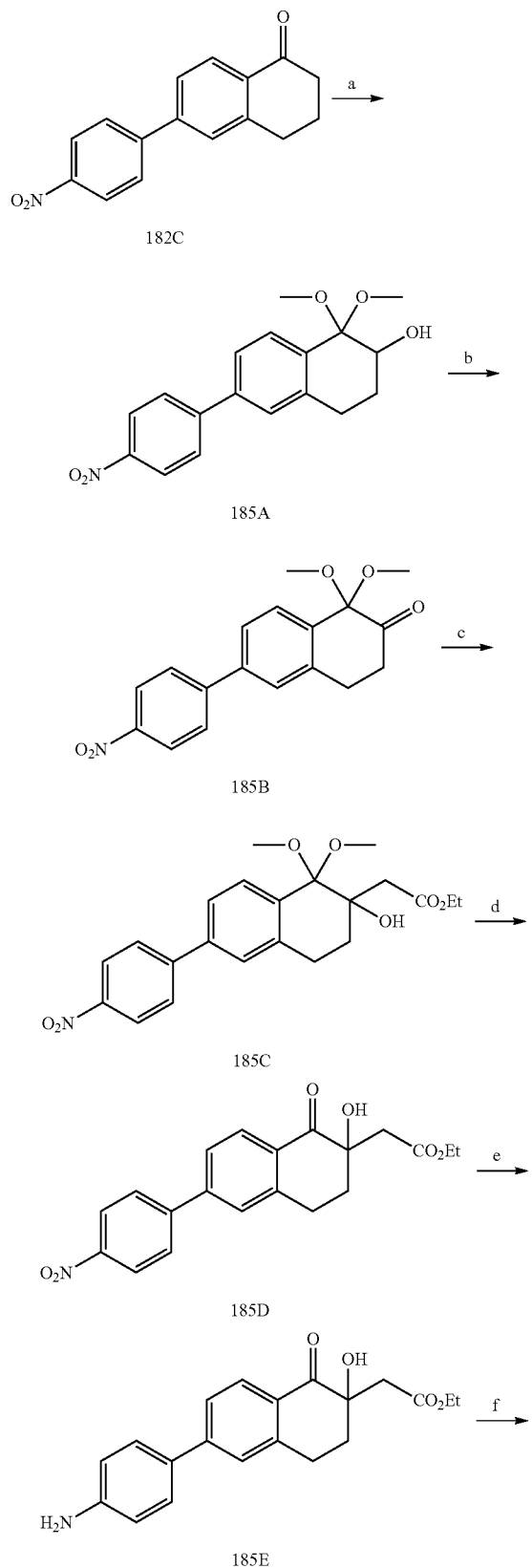
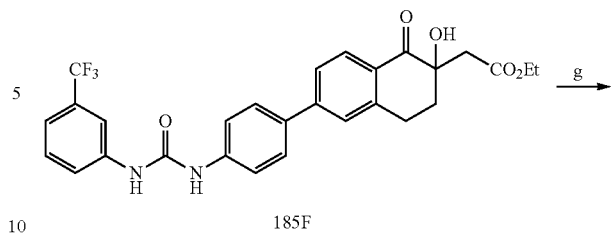

Reagents and conditions: a) PhI(OAc)₂, AcOH, RT, 16 h; b) Pyridinium dichromate, Acetone, RT, 18 h; c) LiHMDS, EtOAc, THF, 0° C. to RT, 4 h; d) 3N HCl, MeOH, RT, 18 h; e) Pd/C, H₂, EtOH, RT, 3 h; f) 3-CF₃PhNCO, Et₃N, THF, RT, 12 h; g) NaOH, MeOH—THF—H₂O, RT, 18 h.

Procedure 2-(2-Hydroxy-1-oxo-6-(4-(3-(3-(trifluoromethyl) phenyl)ureido)phenyl)-1,2,3,4-tetrahydronaphthalen-2-yl)acetic acid 1,1-Dimethoxy-6-(4-nitrophenyl)-1,2,3,4-tetrahydronaphthalen-2-ol (185A)

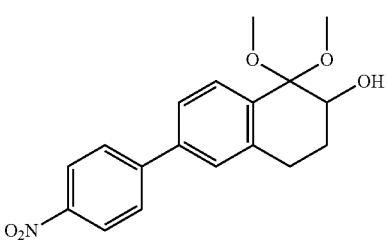

KOH (4.40 g, 78.6 mmol) was added to an ice cold solution of product of Example 182C (7.0 g, 26.2 mmol) and PhI (OAc)₂ (8.44 g, 26.2 mmol) in methanol (180 ml). The reaction mixture was stirred at room temperature for 16 h. The reaction solvent was removed under vacuum, and residue was partitioned between ethyl acetate and water. The separated organic layer was dried over sodium sulphate, filtered and concentrated. The product was washed with pentane to give title compound (7.0 g, 81%) as solid. $^1$H NMR (400 MHz, CDCl₃): δ 8.28 (m, 2H), 7.78 (d, J=8.0 Hz, 1H), 7.75-7.71 (m, 2H), 7.45 (dd, J₁=2.0 Hz, J₂=8.4 Hz, 1H), 7.41 (s, 1H), 4.29 (t, J=4.0 Hz, 1H), 3.45 (s, 3H), 3.12 (s, 3H), 3.0 (m, 1H), 2.83 (m, 1H), 2.27-2.22 (m, 1H), 2.16-2.10 (m, 1H), 1.56 (m, 1H); ESI-MS m/z=330 (M+H)⁺.

1,1-Dimethoxy-6-(4-nitrophenyl)-3,4-dihydronaphthalen-2(1H)-one (185B)

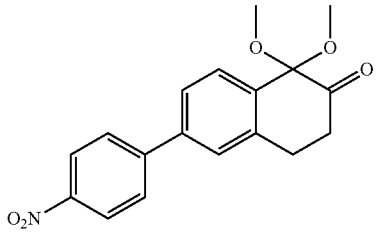

Pyridinium dichromate (0.36 g, 0.97 mmol) was added to a solution of product of Example 185A (0.2 g, 0.6 mmol) and molecular sieves (3A, 0.5 g) in 10 mL dichloromethane under argon atmosphere, followed by acetic anhydride (0.1 mL). The reaction mixture was stirred for 18 h at room temperature. The reaction mixture was then filtered, and the filtrate was washed with water. The separated organic layer was dried over sodium sulphate, filtered and removed under reduced pressure. The product was purified by flash chromatography using 20% ethyl acetate in hexane to afford title compound (0.12 g, 63%) as solid. $^1$H NMR (300 MHz, CDCl$_3$): δ 8.31 (d, J=9.0 Hz, 2H), 7.82 (d, J=8.1 Hz, 1H), 7.75 (d, J=9.0 Hz, 2H), 7.54 (dd, J$_1$=1.5 Hz, J$_2$=8.4 Hz, 1H), 7.46 (s, 1H), 3.38 (s, 6H), 3.25 (t, J=6.0 Hz, 2H), 2.75 (t, J=6.9 Hz, 2H). ESI-MS m/z=328 (M+H)$^+$.

Ethyl-2-(2-hydroxy-1,1-dimethoxy-6-(4-nitrophenyl)-1,2,3,4-tetrahydronaphthalen-2-yl)acetate (185C)

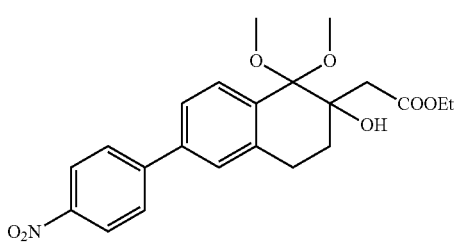

Ethyl acetate (0.2 g, 2.29 mmol) was added to a solution of LiHMDS (0.63 g, 3.82 mmol) in 10 mL of THF at −78° C., and the mixture was stirred for 15 min. The product of Example 185B (0.25 g, 0.76 mmol) was then added. The reaction mixture was performed at −78° C. to room temperature for 4 h and then quenched with 1N HCl. The reaction mixture was partitioned between ethyl acetate and water. The separated organic layer was dried over sodium sulphate, filtered and removed under reduced pressure. The product was purified by flash chromatography using 20% ethyl acetate in hexane to afford title compound (0.15 g, 48%) as off white solid. $^1$H NMR (300 MHz, CDCl$_3$): δ 8.31 (d, J=9.0 Hz, 2H), 7.82-7.72 (m, 3H), 7.46 (d, J=8.4 Hz, 1H), 7.4 (s, 1H), 4.2 (q, J=6.9 Hz, 2H), 3.6 (s, 3H), 3.2 (s, 3H), 3.0 (m, 2H), 2.75 (d, J=14.7 Hz, 1H), 2.4 (d, J=14.7 Hz, 1H), 2.3-2.1 (m, 2H), 1.3 (m, 3H). ESI-MS m/z=416 (M+H)$^+$.

Ethyl 2-(2-hydroxy-6-(4-nitrophenyl)-1-oxo-1,2,3,4-tetrahydronaphthalen-2-yl) acetate (185D)

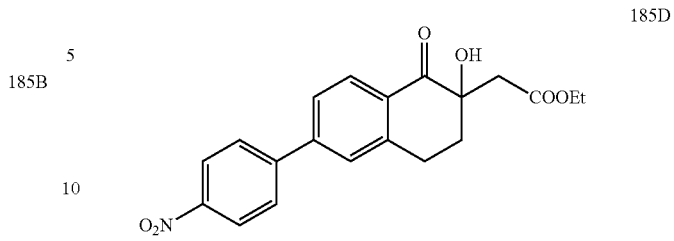

3N HCl (2 mL) was added to a solution of product of Example 185C (0.15 g, 0.36 mmol) in 5 mL of ethanol at 0° C. and stirred for 18 h at RT. The reaction mixture was quenched with water, and solid was collected by filtration to afford title compound (0.08 g, 61%) as white solid. $^1$H NMR (300 MHz, CDCl$_3$): δ 8.34 (d, J=9.3 Hz, 2H), 8.04 (d, J=9.3 Hz, 2H), 7.98 (s, 1H), 7.78 (m, 2H), 5.76 (bs, 1H), 4.02 (q, J=7.8 Hz, 2H), 3.2 (m, 1H), 3.0-2.95 (m, 2H), 2.65 (d, J=15.3 Hz, 1H), 2.39 (m, 1H), 2.16 (m, 1H), 1.15 (t, J=6.9 Hz, 3H); ESI-MS m/z=370 (M+H)$^+$.

Ethyl 2-(6-(4-aminophenyl)-2-hydroxy-1-oxo-1,2,3,4-tetrahydronaphthalen-2-yl) acetate (185E)

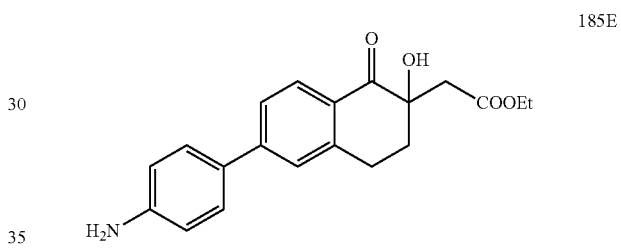

Excess 10% Pd/C (0.04 g) was added to a solution of product of Example 185D (0.08 g, 0.21 mmol) in 5 mL of ethanol, and the reaction mixture was stirred at room temperature for 3 h. The reaction mixture was filtered over celite bed, and filtrate was removed under reduced pressure. The residue was partitioned between ethyl acetate and water. The separated organic layer was dried over sodium sulphate, filtered and removed in vacuum. The crude product was washed with Et$_2$O and pentane to afford title compound (0.05 g, 68%) as off white solid. $^1$H NMR (300 MHz, CDCl$_3$): δ 8.03 (d, J=7.5 Hz, 2H), 7.55-7.35 (m, 4H), 6.75 (m, 1H), 4.53 (bs, 1H), 4.2 (m, 2H), 3.83 (bs, 2H), 3.18 (m, 2H), 2.67 (m, 2H), 2.40 (m, 1H), 2.25 (m, 1H), 1.28 (t, J=6.9 Hz, 3H); ESI-MS m/z=340 (M+H)$^+$.

Ethyl-2-(2-hydroxy-1-oxo-6-(4-(3-(3-(trifluoromethyl)phenyl)ureido)phenyl)-1,2,3,4-tetrahydronaphthalen-2-yl) acetate (185F)

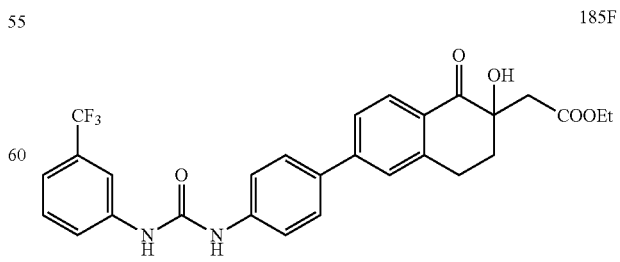

3-(Trifluoromethyl)phenyl isocyanate (0.12 g, 0.64 mmol) was added to a solution of product of Example 185E (0.2 g, 0.58 mmol) and triethylamine (0.17 g, 1.76 mmol) in THF (10 mL). The reaction mixture was stirred at room temperature overnight. The solvent was removed under reduced pressure, and product was purified by flash chromatography using 1% methanol in chloroform to afford title compound (0.14 g, 45%) as white solid. $^1$H NMR (300 MHz, DMSO-d$_6$): δ 9.2 (bs, 1H), 9.0 (bs, 1H), 8.05 (s, 1H), 7.95 (d, J=7.8 Hz, 1H), 7.75-7.45 (m, 8H), 7.35 (d, J=7.8 Hz, 1H), 5.7 (s, 1H), 4.0 (q, J=7.2 Hz, 2H), 3.2 (m, 1H), 2.95 (m, 2H), 2.7 (d, J=15.3 Hz, 1H), 2.4 (m, 1H), 2.2 (m, 1H), 1.2 (t, J=7.2 Hz, 3H); ESI-MS m/z=527 (M+H)$^+$.

2-(2-Hydroxy-1-oxo-6-(4-(3-(3-(trifluoromethyl)phenyl)ureido)phenyl)-1,2,3,4-tetrahydronaphthalen-2-yl)acetic acid (185)

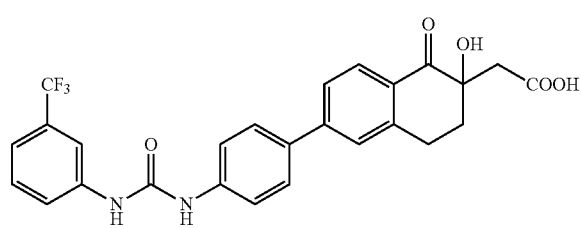

2N NaOH (0.031 g, 0.79 mmol) was added to a solution of product of Example 185F (0.14 g, 0.26 mmol) in 15 mL of THF-methanol (2:1) mixture, and the reaction mixture was stirred at room temperature for 18 h. After the solvent was removed under vacuum, the residue was dissolved in water and washed with ethyl acetate. The aqueous layer was neutralized with 2N aq. HCl. The resulting solution was cooled to 0° C., and solids were collected by filtration and dried under vacuum to afford title compound (0.09 g, 69%) as white-solid. $^1$H NMR (400 MHz, DMSO-d$_6$): δ 11.4 (bs, 2H), 8.13 (s, 1H), 7.94 (d, J=8.0 Hz, 1H), 7.75 (d, J=6.0 Hz, 1H), 7.62 (d, J=6.4 Hz, 1H), 7.5-7.35 (m, 6H), 7.22 (d, J=7.2 Hz, 1H), 6.0 (bs, 1H), 3.15 (m, 1H), 3.03 (d, J=15.6 Hz, 1H), 2.85 (m, 1H), 2.5 (m, 1H), 2.35 (d, J=15.6 Hz, 1H), 2.0 (m, 1H); ESI-MS m/z=449 (M+H)$^+$. HPLC purity: 96.49%.

Examples 186-189 were prepared by the procedures analogous to those described in Example 185 using appropriate starting materials.

| Ex | Structure | $^1$H NMR Data | Mass/purity |
|---|---|---|---|
| 186 | 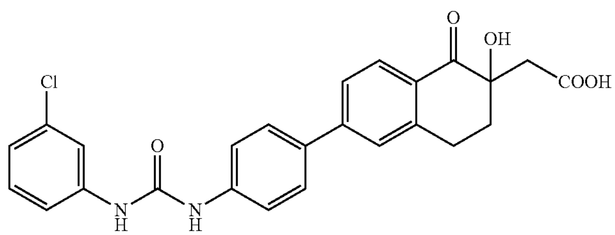 [SMILES: O=C(O)CC1(O)CCc2cc(-c3ccc(NC(=O)Nc4cccc(Cl)c4)cc3)ccc2C1=O] | $^1$H NMR (400 MHz, DMSO-d$_6$): δ 12.2 (bs, 1H), 9.04 (s, 2H), 7.92 (d, J = 8.0 Hz, 1H), 7.75-7.55 (m, 7H), 7.31 (m, 2H), 7.03 (d, J = 6.8 Hz, 1H), 5.63 (bs, 1H), 3.2 (m, 1H), 2.93 (m, 2H), 2.6-2.4 (m, 2H), 2.1 (m, 1H). | ESI-MS m/z = 465 (M + H)$^+$. HPLC purity: 97.5%. |
| 187 | 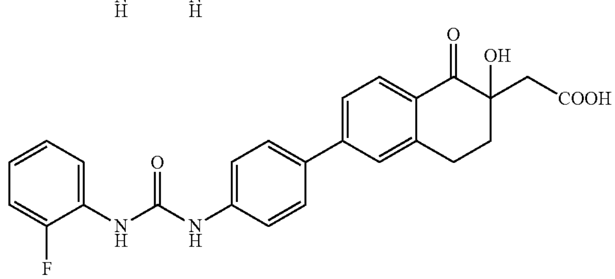 | $^1$H NMR (300 MHz, DMSO-d$_6$): δ 9.36 (bs, 1H), 8.68 (bs, 1H), 8.15 (t, J = 7.5 Hz, 1H), 7.92 (d, J = 8.4 Hz, 1H), 7.75-7.55 (m, 6H), 7.25 (m, 1H), 7.15 (t, J = 7.5 Hz, 1H), 7.03 (m, 1H), 3.2 (m, 1H), 2.95-2.8 (m, 2H), 2.5-2.35 (m, 2H), 2.1 (m, 1H). | ESI-MS m/z = 449 (M + H)$^+$; HPLC purity: 93.3%. |
| 188 | 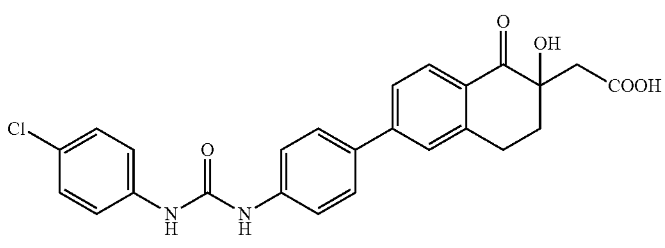 [SMILES: O=C(O)CC1(O)CCc2cc(-c3ccc(NC(=O)Nc4ccc(Cl)cc4)cc3)ccc2C1=O] | $^1$H NMR (300 MHz, DMSO-d$_6$): δ 9.49 (bs, 2H), 7.92 (d, J = 8.4 Hz, 1H), 7.7-7.45 (m, 8H), 7.32 (d, J = 8.4 Hz, 2H), 3.2 (m, 1H), 2.95-2.8 (m, 2H), 2.5-2.4 (m, 2H), 2.1 (m, 1H). | ESI-MS m/z = 465 (M + H)$^+$. LCMS purity: 92%. |
| 189 | 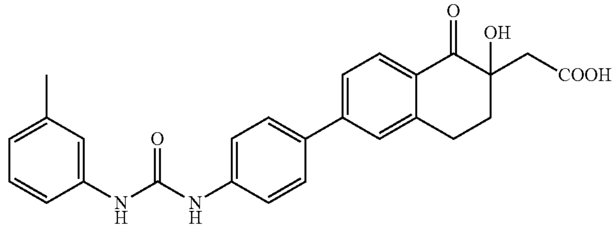 [SMILES: Cc1cccc(NC(=O)Nc2ccc(-c3ccc4c(c3)CCC(O)(CC(=O)O)C4=O)cc2)c1] | $^1$H NMR (300 MHz, DMSO-d$_6$): δ 12.1 (bs, 1H), 9.16 (bs, 1H), 8.94 (bs, 1H), 7.92 (d, J = 7.8 Hz, 1H), 7.75-7.55 (m, 6H), 7.35-7.25 (m, 2H), 7.16 (t, J = 7.5 Hz, 1H), 6.8 (d, J = 6.9 Hz, 1H), 3.39 (m, 1H), 3.21 (m, 1H), 2.92 (d, J = 15.3 Hz, 2H), 2.55 (m, 1H), 2.28 (s, 3H), 2.12 (m, 1H). | ESI-MS m/z = 445 (M + H)$^+$. LCMS purity: 91.88%. |

167

Example 190

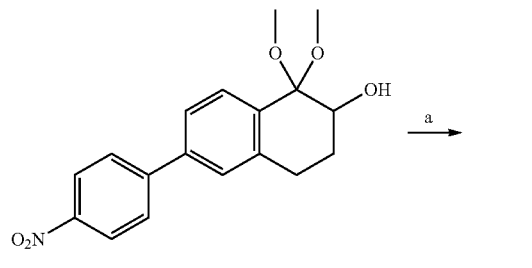

185A

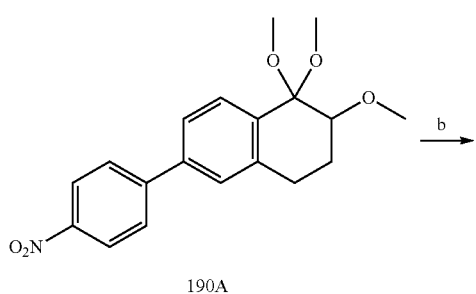

190A

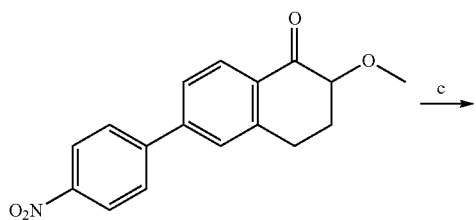

190B

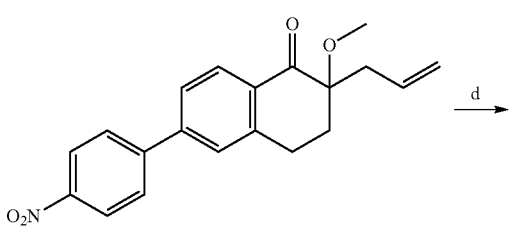

190C

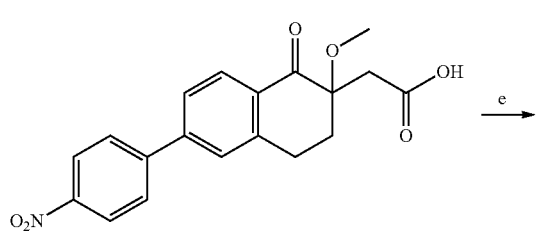

190D

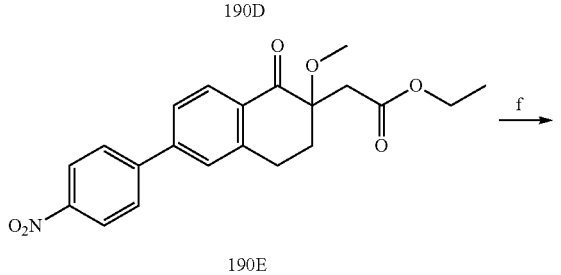

190E

168

-continued

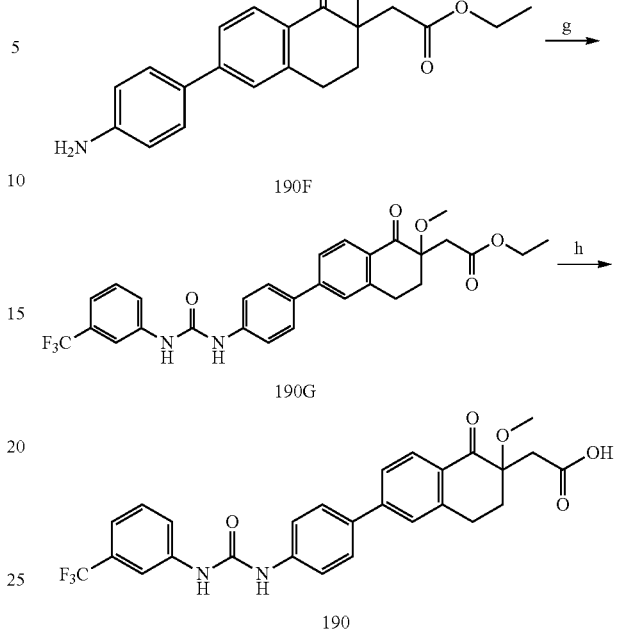

190F

190G

190

Reagents and conditions: a) NaH, MeI, THF, RT, 16 h; b) 3N HCl, EtOH, RT, 3 h; c) Allyl bromide, TBAI, KOH, toluene, RT, 16 h; d) KMnO$_4$, NaIO$_4$, RT, 16 h; e) MeSO$_3$H, EtOH, RT, 12 h; f) Fe—NH$_4$Cl, EtOH—H$_2$O, 90° C., 2 h; g) 3-CF$_3$PhNCO, Et$_3$N, THF, RT, 12 h; h) LiOH, THF—H$_2$O, RT, 12 h.

Procedures 2-(2-Methoxy-1-oxo-6-(4-(3-phenylureido)phenyl)-1,2,3,4-tetrahydronaphthalen-2-yl)acetic acid 1,1,2-Trimethoxy-6-(4-nitrophenyl)-1,2,3,4-tetrahydronaphthalene (190A)

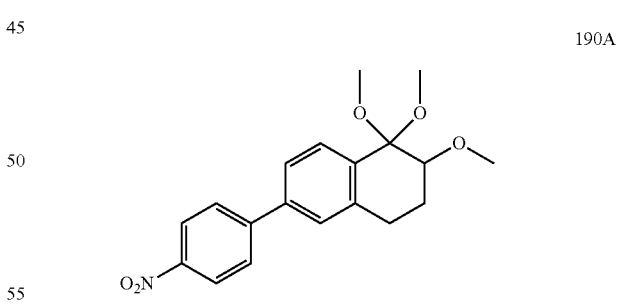

190A

Methyl iodide (15.1 g, 106.1 mmol) was added to an ice cold solution of product of Example 185A (2.0 g, 6.1 mmol) and NaH (0.76 g, 31.91 mmol) in THF (120 mL)). The reaction mixture was stirred at room temperature for 16 h. The reaction mixture was then quenched with ice cold water and extracted with ethyl acetate. The separated organic layer was dried over Na$_2$SO$_4$, filtered and removed under reduced pressure to give title compound (6.0 g, 83%) as solid. $^1$H NMR (400 MHz, CDCl$_3$): δ 8.29-8.25 (m, 2H), 7.80 (d, J=8.0 Hz, 1H), 7.73-7.69 (m, 2H), 7.45 (dd, J$_1$=2.0 Hz, J$_2$=8.4 Hz, 1H), 7.37 (s, 1H), 3.87 (m, 1H), 3.42 (s, 6H), 3.07 (s, 3H), 2.95 (m, 1H), 2.83-2.77 (m, 1H), 2.28-2.19 (m, 2H)); ESI-MS m/z=344 (M+H)⁺.

2-Methoxy-6-(4-nitrophenyl)-3,4-dihydronaphthalen-1(2H)-one (190B)

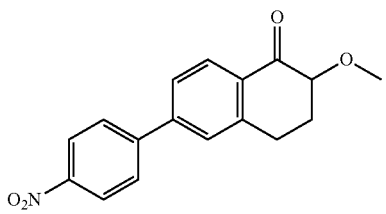

190B

3N HCl (60 mL) was added to an ice cold solution of product of Example 190A (6.0 g, 17.4 mmol) in ethanol (150 mL), and the reaction mixture was stirred at room temperature for 3 h. The residue was partitioned between ethyl acetate and water. The solvent was removed under reduced pressure, and water added until the compound was precipitated out. Solid was collected by filtration and dried. The product was washed with pentane to give title compound (5.0 g, 96%) as solid. ¹H NMR (300 MHz, CDCl₃): δ 8.35 (m, 2H), 8.15 (d, J=8.4 Hz, 1H), 7.75 (m, 2H), 7.55 (m, 1H), 7.50 (s, 1H), 4.00 (m, 1H), 3.60 (s, 3H), 3.25 (s, 1H), 3.10 (m, 1H), 2.40 (m, 1H), 2.30 (m, 1H); ESI-MS m/z=298 (M+H)⁺

2-Allyl-2-methoxy-6-(4-nitrophenyl)-3,4-dihydronaphthalen-1(2H)-one (190C)

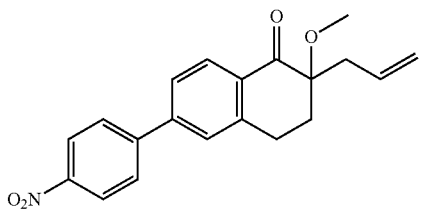

190C

Allyl bromide (3.63 g, 30.6 mmol) was added to an ice cold solution of product of Example 190B (6.0 g, 20.2 mmol) KOH (2.82 g, 50.5 mmol) and TBAI (2.98 g, 8.0 mmol) in toluene (120 mL), and the reaction mixture was stirred at room temperature for 16 h. The residue was partitioned between ethyl acetate and water. The separated organic layer was dried over Na₂SO₄, filtered and removed under reduced pressure. The product was purified by flash chromatography using 10% ethyl acetate in hexanes to afford to give title compound (4.46 g, 64%) as solid. ¹H NMR (300 MHz, CDCl₃): δ 8.35 (m, 2H), 8.16 (d, J=8.4 Hz, 1H), 7.75 (m, 2H), 7.55 (dd, J₁=2.0 Hz, J₂=8.4 Hz, 1H), 7.5 (s, 1H), 5.83 (m, 1H), 5.16 (d, J=12.0 Hz, 2H), 3.32 (m, 1H), 3.24 (s, 3H), 2.95-2.79 (m, 1H), 2.75 (m, 1H), 2.52-2.42 (m, 2H), 2.35-2.06 (m, 1H); ESI-MS m/z=338 (M+H)⁺

2-(2-Methoxy-6-(4-nitrophenyl)-1-oxo-1,2,3,4-tetrahydronaphthalen-2-yl)acetic acid (190D)

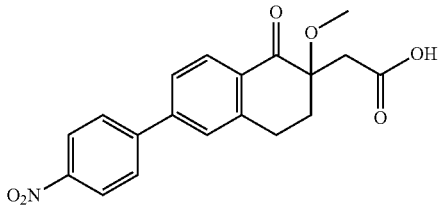

190D

KMnO₄ (0.187 g, 1.18 mmol) was added to an ice cold solution of product of Example 190C (0.20 g, 0.59 mmol) and NaIO₄ (1.26 g, 5.90 mmol) in acetone-water (2:1) mixture. The reaction mixture was stirred at room temperature for 16 h. The residue was partitioned between ethyl acetate and water. The separated organic layer was dried over Na₂SO₄, filtered and removed under reduced pressure to afford title compound (0.14 g, 69%) as solid. ¹H NMR (300 MHz, DMSO-d₆): δ 12.10 (bs, 1H), 8.35-8.31 (m, 3H), 8-16-7.99 (m, 3H), 7.77 (d, J=7.2 Hz, 1H), 3.35 (m, 1H), 3.25 (m, 1H), 3.19 (s, 3H), 2.92 (m, 1H), 2.73 (d, J=16.8 Hz, 1H), 2.45 (m, 2H); ESI-MS m/z=356 (M+H)⁺.

Ethyl 2-(2-methoxy-6-(4-nitrophenyl)-1-oxo-1,2,3,4-tetrahydronaphthalen-2-yl) acetate (190E)

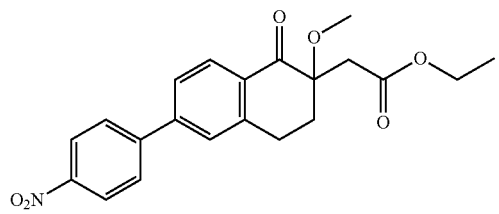

190E

Methane sulphonic acid (0.5 ml) was added to a solution of product of Example 190D (0.26 g, 0.18 mmol) in ethanol (15 mL), and the reaction mixture was stirred at room temperature overnight. The solvent was removed under reduced pressure, and product was purified by flash chromatography using 10% ethyl acetate in hexanes to afford title compound (0.07 g, 46%) as solid. ¹H NMR (300 MHz, DMSO-d₆): δ 8.38-8.31 (m, 2H), 8.16 (d, J=8.4 Hz, 1H), 7.80-7.75 (m, 2H), 7.56 (m, 1H), 7.48 (s, 1H), 4.2 (q, J=7.5 Hz, 2H), 3.45 (m, 1H), 3.25 (s, 3H), 2.95-2.73 (m, 3H), 2.5 (m, 2H), 1.25 (t, J=6.9 Hz, 3H); ESI-MS m/z=384 (M+H)⁺

Ethyl 2-(6-(4-aminophenyl)-2-methoxy-1-oxo-1,2,3,4-tetrahydronaphthalen-2-yl) acetate (190F)

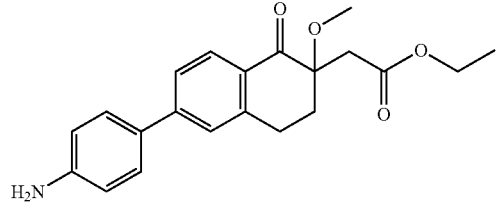

190F

Iron powder (0.182 g, 3.26 mmol) and NH₄Cl (0.034 g, 0.65 mmol) was added to a solution of product of Example 190E (0.5 g, 1.30 mmol) in 30 mL of ethanol-water (2:1)

mixture. The reaction mixture was refluxed for 2 h. Solvent was removed under reduced pressure, and product was purified by flash chromatography using 2% methanol in chloroform to afford title compound (0.4 g, 86%) as solid. $^1$H NMR (300 MHz, CDCl$_3$): δ 8.06 (d, J=8.1 Hz, 1H), 7.47-7.43 (m, 3H), 7.38 (s, 1H), 6.73 (m, 2H), 4.15 (q, J=7.5 Hz, 2H), 3.80 (bs, 2H), 3.42-3.35 (m, 1H), 3.3 (s, 3H), 2.94-2.79 (m, 3H), 2.53-2.36 (m, 2H), 1.2 (t, J=6.9 Hz, 3H); ESI-MS m/z=354 (M+H)$^+$.

Ethyl2-(2-methoxy-1-oxo-6-(4-(3-phenylureido)phenyl)-1,2,3,4-tetrahydronaphthalen-2-yl) acetate (190G)

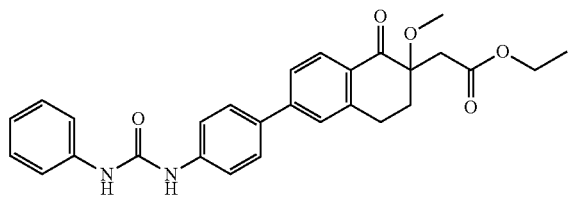

190G

Phenyl isocyanate (0.067 g, 0.56 mmol) was added to a solution of product of Example 190F (0.200 g, 0.56 mmol) and triethylamine (0.178 g, 1.68 mmol) in THF (10 mL). The reaction mixture was stirred at room temperature overnight. The solvent was removed under reduced pressure, and product was purified by flash chromatography using 10% in hexane to afford title compound (0.2 g, 76%) as solid. $^1$H NMR (400 MHz, DMSO-d$_6$): δ 8.86 (bs, 1H), 8.72 (bs, 1H), 7.95 (d, J=8.4 Hz, 1H), 7.69 (m, 2H), 7.64-7.57 (m, 4H), 7.46 (d, J=8.4 Hz, 2H), 7.29 (t, J=6.9 Hz, 2H), 6.98 (t, J=7.5 Hz, 1H), 4.07 (q, J=6.9 Hz, 2H), 3.23 (m, 1H), 3.13 (s, 3H), 2.93 (m, 1H), 2.86 (d, J=15.3 Hz, 2H), 2.43 (m, 2H), 1.18 (t, J=7.8 Hz, 3H); ESI-MS m/z=473 (M+H)$^+$.

2-(2-Methoxy-1-oxo-6-(4-(3-phenylureido)phenyl)-1,2,3,4-tetrahydronaphthalen-2-yl)acetic acid (190)

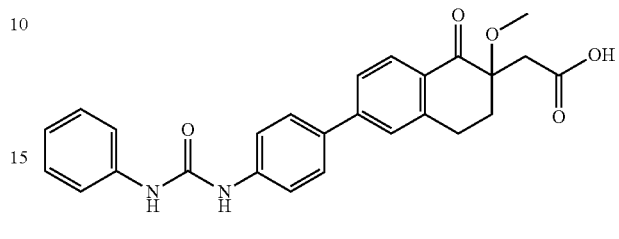

190

Lithium hydroxide (0.088 g, 2.11 mmol) was added to a solution of product of Example 190G (0.2 g, 0.42 mmol) in 12 mL of THF-water (3:1) mixture. The reaction mixture was stirred at room temperature overnight. After the solvent was removed in vacuum, the residue was dissolved in water and washed with ethyl acetate. The aqueous layer was acidified with addition of 2N aqueous solution of HCl until pH 2 was attained. The resulting solution was cooled to 0° C. and solids were collected by filtration and dried under vacuum to afford title compound (0.05 g, 26%) as white solid. $^1$H NMR (400 MHz, CDCl$_3$): δ 12.0 (bs, 1H), 8.87 (bs, 1H), 8.74 (bs, 1H), 7.94 (d, J=8.4 Hz, 1H), 7.70 (d, J=8.4 Hz, 2H), 7.65 (d, J=8.4 Hz, 1H), 7.59 (m, 3H), 7.47 (d, J=8.0 Hz, 2H), 7.29 (t, J=8.0 Hz, 2H), 6.98 (t, J=7.2 Hz, 1H), 3.23-3.15 (m, 1H), 3.12 (s, 3H), 2.90 (d, J=15.2 Hz, 2H), 2.68 (m, 1H), 2.46 (m, 2H); ESI-MS m/z=445 (M+H)$^+$; HPLC purity: 90%.

Examples-191-196 were prepared by the procedures analogous to those described in Example 190 using appropriate starting materials. Enantiomers were separated from racemic mixtures using similar procedures as described in Example 129.

| Ex | Structure | $^1$H NMR Data | Mass/purity |
| --- | --- | --- | --- |
| 191 | 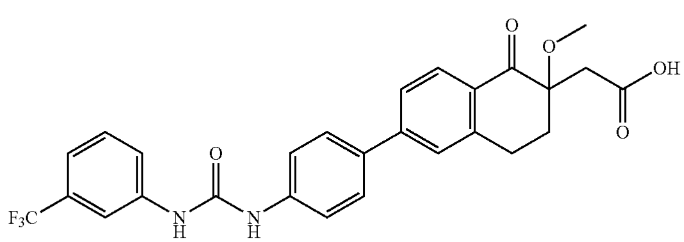 [SMILES: COC1(CC(=O)O)CCc2cc(-c3ccc(NC(=O)Nc4cccc(C(F)(F)F)c4)cc3)ccc2C1=O] | $^1$H NMR (400 MHz, DMSO-d$_6$): δ 12.20 (bs, 1H), 9.10 (bs, 1H), 8.99 (bs, 1H), 8.03 (s, 1H), 7.95 (d, J = 8.0 Hz, 1H), 7.71 (d, J = 8.8 Hz, 2H), 7.65 (d, J = 8.0 Hz, 1H), 7.60 (m, 4H), 7.52 (t, J = 7.6 Hz, 1H), 7.32 (d, J = 8.0 Hz, 1H), 3.24-3.15 (m, 1H), 3.13 (s, 3H), 2.91 (m, 2H), 2.69 (m, 1H), 2.50-2.39 (m, 2H). | ESI-MS m/z = 513 (M + H)$^+$; HPLC purity: 98%. |
| 192 | 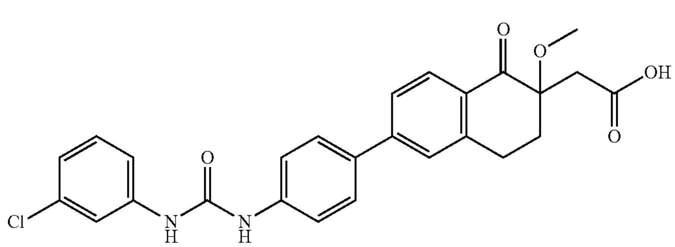 [SMILES: COC1(CC(=O)O)CCc2cc(-c3ccc(NC(=O)Nc4cccc(Cl)c4)cc3)ccc2C1=O] | $^1$H NMR (400 MHz, DMSO-d$_6$): δ 12.20 (bs, 1H), 8.94 (bs, 2H), 7.94 (d, J = 11.2 Hz, 1H), 7.70 (d, J = 11.3 Hz, 3H), 7.66-7.57 (m, 4H), 7.34-7.26 (m, 2H), 7.05-7.01 (m, 1H), 3.23 (m, 1H), 3.12 (s, 3H), 2.90 (m, 2H), 2.72 (m, 1H), 2.44 (m, 2H). | ESI-MS m/z = 479 (M + H)$^+$; HPLC purity: 98%. |

-continued

| Ex | Structure | ¹H NMR Data | Mass/purity |
|---|---|---|---|
| 193 | 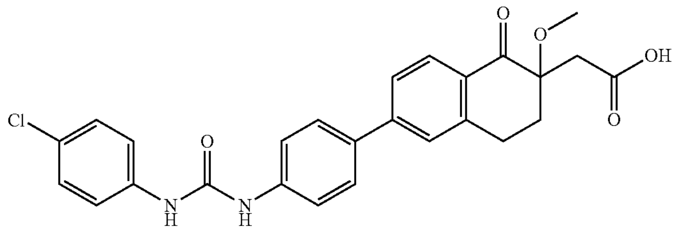 [SMILES: COC1(CC(=O)O)CCc2cc(-c3ccc(NC(=O)Nc4ccc(Cl)cc4)cc3)ccc2C1=O] | ¹H NMR (400 MHz, DMSO-d₆): δ 12.20 (bs, 1H), 8.92 (2s, 2H), 7.94 (d, J = 7.8 Hz, 1H), 7.72-7.66 (m, 2H), 7.63-7.57 (m, 4H), 7.50 (d, J = 9.0 Hz, 2H), 7.33 (d, J = 8.4 Hz, 2H), 3.23 (m, 1H), 3.13 (s, 3H), 2.90 (d, J = 15.3 Hz, 2H), 2.74 (m, 1H), 2.43 (m, 2H). | ESI-MS m/z = 479 (M + H)⁺; HPLC purity: 90%. |
| 194 | Chiral: enantiomer-2 | ¹H NMR (300 MHz, DMSO-d₆): δ 12.10 (bs, 1H), 8.90 (2s, 2H), 7.94 (d, J = 8.4 Hz, 1H), 7.72-7.56 (m, 6H), 7.50 (d, J = 9.0 Hz, 2H), 7.33 (d, J = 9.0 Hz, 2H), 3.23 (m, 1H), 3.12 (s, 3H), 2.90 (d, J = 10.5 Hz, 2H), 2.70 (s, 1H), 2.44 (m, 2H). | ESI-MS m/z = 479 (M + H)⁺; HPLC purity: 96%. |
| 195 | Chiral: enantiomer-1 | ¹H NMR (300 MHz, DMSO-d₆): δ 12.20 (bs, 1H), 8.90 (2s, 2H), 7.94 (d, J = 8.4 Hz, 1H), 7.72-7.56 (m, 6H), 7.50 (d, J = 9.0 Hz, 2H), 7.33 (d, J = 9.0 Hz, 2H), 3.23 (m, 1H), 3.12 (s, 3H), 2.90 (d, J = 10.5 Hz, 2H), 2.70 (m, 1H), 2.44 (m, 2H). | ESI-MS m/z = 479 (M + H)⁺; HPLC purity: 96% |
| 196 | 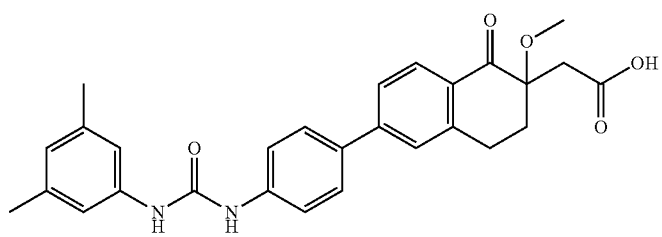 [SMILES: COC1(CC(=O)O)CCc2cc(-c3ccc(NC(=O)Nc4cc(C)cc(C)c4)cc3)ccc2C1=O] | ¹H NMR (300 MHz, DMSO-d₆): δ 12.10 (bs, 1H), 8.68 (bs, 1H), 8.60 (bs, 1H), 7.90 (d, J = 7.5 Hz, 1H), 7.70-7.56 (m, 6H), 7.09 (s, 2H), 6.62 (s, 1H), 3.18 (m, 1H), 3.12 (s, 3H), 2.90 (d, J = 15.6 Hz, 2H), 2.73 (m, 1H), 2.43 (m, 2H), 2.24 (s, 6H). | ESI-MS m/z = 473 (M + H)⁺; HPLC purity: 96% |

Example-197

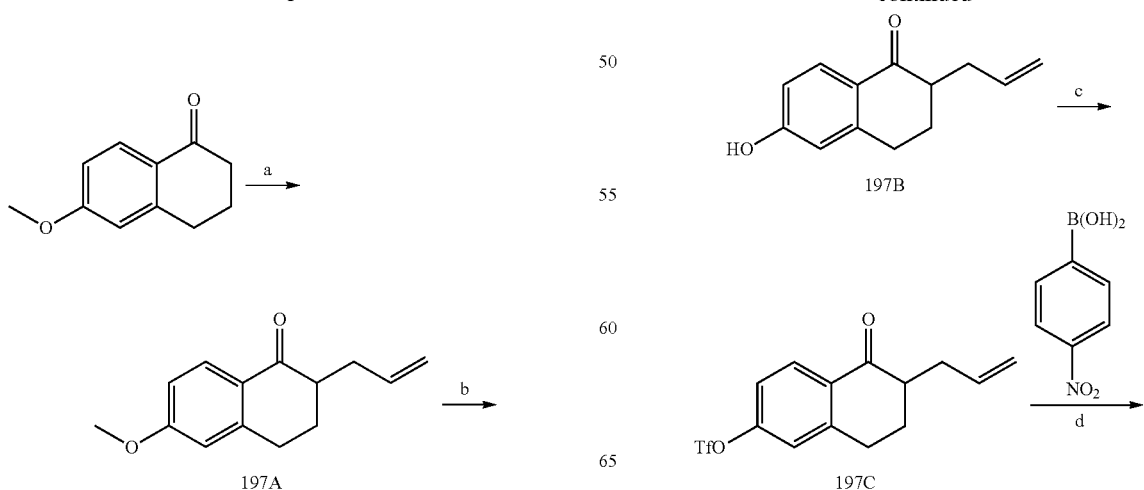

175
-continued

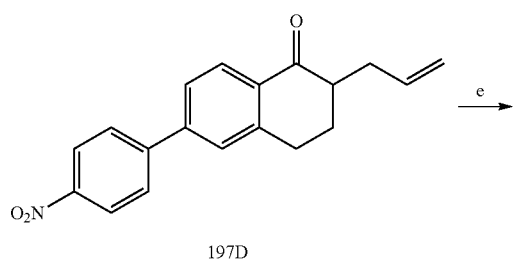
197D

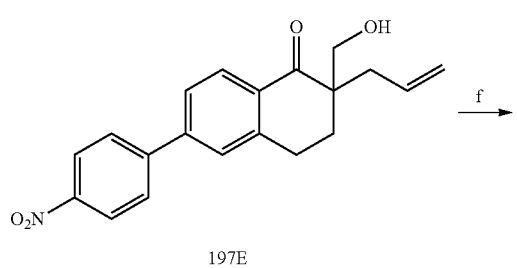
197E

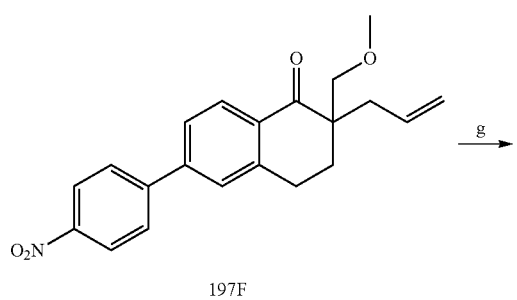
197F

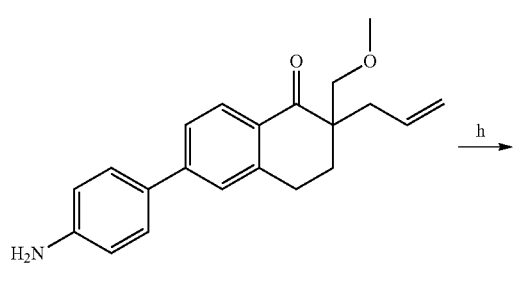
197G

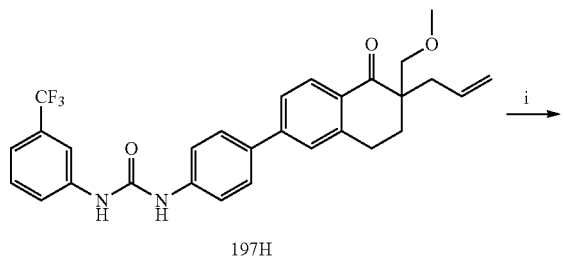
197H

176
-continued

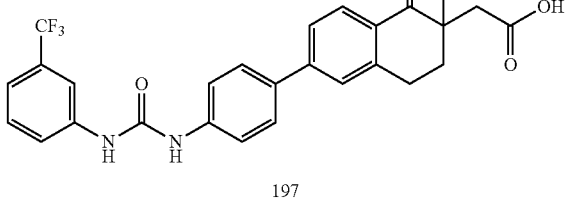
197

Reagents and conditions: 1) Allyl bromide, KOtBu, THF, RT, 18 h; b) BBr₃, CH₂Cl₂, RT, 12 h; c) Tf₂O, Py, CH₂Cl₂, RT, 3 h; d) Pd(PPh₃)₄, Cs₂CO₃, Dioxane-H₂O, 80° C., 3 h; e) HCHO, 2N NaOH, THF, RT, 3 h; f) NaH, MeI, THF, RT, 18 h; g) Fe—NH₄Cl, EtOH—H₂O, 90° C., 2 h; h) 3-CF₃PhNCO, Et₃N, THF, RT, 12 h; i) KMnO₄, NaIO₄, Acetone-H₂O, RT, 18 h.

Procedures 2-(2-(Methoxymethyl)-1-oxo-6-(4-(3-(3-(trifluoromethyl)phenyl)ureido)phenyl)-1,2,3,4-tetrahydronaphthalen-2-yl)acetic acid 2-Allyl-6-methoxy-3,4-dihydronaphthalen-1(2H)-one (197A)

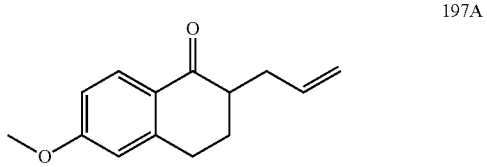 [SMILES: C=CCC1CCc2cc(OC)ccc2C1=O]

Allyl bromide (5.4 g, 45.0 mmol) was added to a solution of 6-methoxy-1-tetralone (10.0 g, 56.0 mmol) and potassium tert-butoxide in THF (50 mL), and the reaction mixture was stirred at room temperature for 18 h. The reaction mixture was then diluted with ethyl acetate. The separated organic layer was washed with water, brine solution, dried over sodium sulphate, filtered and removed under reduced pressure. The product was purified by flash chromatography using 4% ethyl acetate in hexanes to afford title compound (2.0 g, 15%) as solid. ¹H NMR (400 MHz, CDCl₃): δ 8.01 (d, J=8.4 Hz, 1H), 6.80 (dd, J₁=2.8 Hz, J₂=8.8 Hz, 1H), 6.68 (m, 1H), 5.89-5.79 (m, 1H), 5.12 (t, J=17.2 Hz, 2H) 3.85 (s, 3H), 2.95 (m, 2H), 2.93-2.72 (m, 1H), 2.53-2.46 (m, 1H), 2.29-2.17 (m, 2H), 1.89-1.79 (m, 1H).

2-Allyl-6-hydroxy-3,4-dihydronaphthalen-1(2H)-one (197B)

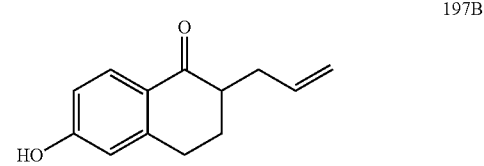

BBr₃ was added slowly drop wise to product of Example 197A (2.0 g, 9.00 mmol) at −78° C. in dichloromethane (75 mL), and the reaction mixture was stirred for overnight. The reaction mixture was then quenched with ice cold water and extracted with dichloromethane (2×100 mL). The organic layer was dried over sodium sulphate, filtered and removed under vacuum. The residue was purified by flash chromatography using 15% ethyl acetate in hexanes to afford title compound (0.9 g, 60%) as liquid. $^1$H NMR (300 MHz, CDCl$_3$): δ 7.98 (d, J=8.4 Hz, 1H), 6.76 (dd, J$_1$=2.1 Hz, J$_2$=8.4 Hz, 1H), 6.66 (m, 1H), 5.90-5.77 (m, 1H), 5.12-5.04 (m, 2H), 2.92 (m, 2H), 2.78-2.70 (m, 1H), 2.56-2.46 (m, 1H), 2.31-2.15 (m, 2H), 1.91-1.78 (m, 1H).

6-Allyl-5-oxo-5,6,7,8-tetrahydronaphthalen-2-yl trifluoromethanesulfonate (197C)

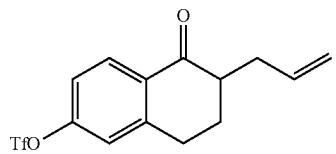

197C

Triflic anhydride (1.5 g, 5.34 mmol) was added to an ice cold solution of product of Example 197B (0.9 g, 4.45 mmol) and pyridine (0.421 g, 5.34 mmol) in dichloromethane (20 mL), and the reaction mixture was stirred at room temperature for 3 h. The reaction mixture was then diluted with dichloromethane (50 mL) and washed with saturated aqueous solution of NaCl (50 mL). The organic layer was dried over sodium sulphate, filtered and removed under vacuum. The residue was purified by flash chromatography using 10% ethyl acetate in hexanes to give title compound (1.1 g, 61%) as solid. $^1$H NMR (300 MHz, CDCl$_3$): δ 8.12 (d, J=8.1 Hz, 1H), 7.21-7.16 (m, 2H), 5.90-5.75 (m, 1H), 5.14-5.07 (m, 2H), 3.04 (m, 2H), 2.79-2.70 (m, 1H), 2.62-2.52 (m, 1H), 2.32-2.22 (m, 2H), 1.96-1.82 (m, 1H).

2-Allyl-6-(4-nitrophenyl)-3,4-dihydronaphthalen-1 (2H)-one (197D)

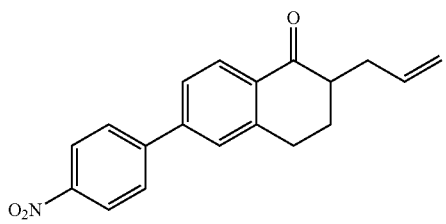

197D

Pd(PPh$_3$)$_4$ (0.04 g, 0.035 mmol) was added to a solution of product of Example 197C (1.0 g, 2.99 mmol) in 20 mL of 1,4 dioxane-H$_2$O (4:1) mixture under Argon atmosphere, followed by cesium carbonate (2.42 g, 7.48 mmol) and 4-nitrophenyl boronic acid (0.6 g, 3.59 mmol). The reaction mixture was degassed for 5 min. The reaction mixture was then refluxed for 3 h, and solvent was removed under reduced pressure. The residue was partitioned between ethyl acetate and water. The separated organic layer was dried over sodium sulphate, filtered and removed under reduced pressure. The product was purified by flash chromatography using 10% ethyl acetate in hexanes to give title compound (0.9 g, 61%) as solid. $^1$H NMR (400 MHz, CDCl$_3$): δ 8.32 (m, 2H), 8.14 (d, J=8.0 Hz, 1H), 7.77 (m, 2H), 7.55 (dd, J$_1$=1.6 Hz, J$_2$=8.4 Hz, 1H), 7.49 (s, 1H), 5.91-5.80 (m, 1H), 5.10 (t, J=16.0 Hz, 2H), 3.07 (m, 2H), 2.80-2.75 (m, 1H), 2.63-2.56 (m, 1H), 2.34-2.26 (m, 2H), 1.97-1.86 (m, 1H).

2-Allyl-2-(hydroxymethyl)-6-(4-nitrophenyl)-3,4-dihydronaphthalen-1(2H)-one (197E)

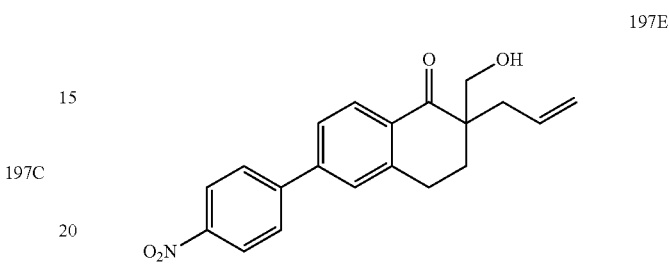

37% Formaldehyde solution (5 mL) was added to a solution of product of Example 197D (0.9 g, 2.92 mmol) in 7 mL of THF under argon atmosphere, followed by 2N NaOH solution (2 mL) at RT. The reaction mixture was stirred for 3 h, and solvent removed under reduced pressure. The residue was acidified with 2N HCl and partitioned between ethyl acetate and water. The separated organic layer was dried over sodium sulphate, filtered and removed under vacuum to give crude product was purified by flash chromatography using 15% ethyl acetate in hexanes to give title compound (0.62 g, 61%) as solid. $^1$H NMR (300 MHz, DMSO-d$_6$): δ 8.33 (d, J=8.4 Hz, 2H), 8.06-7.93 (m, 3H), 7.76-7.73 (m, 2H), 5.79-5.65 (m, 1H), 5.05 (m, 2H), 3.77 (d, J=5.7 Hz, 1H), 3.50 (d, J=9.6 Hz, 1H), 3.11-3.01 (m, 2H), 2.44 (m, 1H), 2.30-2.14 (m, 2H), 2.03-1.94 (m, 1H).

2-Allyl-2-(methoxymethyl)-6-(4-nitrophenyl)-3,4-dihydronaphthalen-1(2H)-one (197F)

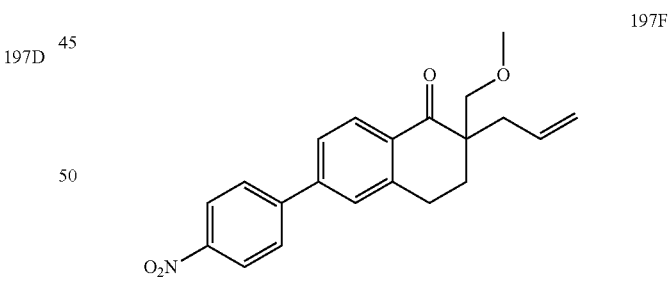

Methyl iodide (1.29 g, 9.15 mmol) was added to an ice cold solution of product of Example 197E (0.6 g, 1.83 mmol) and NaH (0.146 g, 3.67 mmol) in THF (20 mL), and the reaction mixture was stirred at room temperature for 18 h. The reaction mixture was then diluted with water and extracted with ethyl acetate (60 mL). The organic layer was dried over sodium sulphate, filtered and removed under reduced pressure. The product was purified by flash chromatography using 10% ethyl acetate in hexanes to give title compound (0.3 g, %) as white solid. $^1$H NMR (400 MHz, CDCl$_3$): δ 8.32 (d, J=8.8 Hz, 2H), 8.15 (d, J=5.2 Hz, 1H), 7.76 (d, J=8.4 Hz, 2H), 7.55 (dd, J$_1$=1.2 Hz, J$_2$=8.0 Hz, 1H), 7.47 (s, 1H), 5.80-5.71 (m, 1H), 5.13-5.07 (m, 2H), 3.74 (d, J=9.2 Hz, 1H), 3.42 (d, J=9.6 Hz, 1H), 3.33 (s, 3H), 3.11-3.05 (m, 2H), 2.53-2.48 (m, 1H), 2.38 (m, 2H), 2.16-2.10 (m, 1H).

2-Allyl-6-(4-aminophenyl)-2-(methoxymethyl)-3,4-dihydronaphthalen-1(2H)-one (197G)

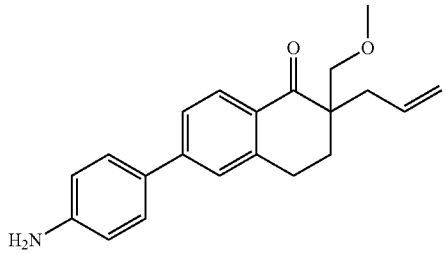

Iron powder (0.09 g, 1.7 mmol) and NH$_4$Cl (0.023 g, 0.427 mmol) was added to a solution of 197F (0.3 g, 0.847 mmol) in 25 mL of ethanol-water (2:1) mixture. The reaction mixture was refluxed for 2 h, and solvent was removed under reduced pressure and extracted with ethyl acetate (40 mL). The organic layer was washed with water, dried over sodium sulphate, filtered and removed under reduced pressure to give title compound (0.22 g, %) as yellow solid. $^1$H NMR (300 MHz, DMSO-d$_6$): δ 7.83 (d, J=8.4 Hz, 1H), 7.53-7.44 (m, 4H), 6.64 (d, J=9.0 Hz, 2H), 5.75-5.65 (m, 1H), 5.42 (s, 2H), 5.09-5.03 (m, 2H), 3.62 (d, J=9.0 Hz, 1H), 3.21 (s, 3H), 2.99-2.5 (m, 2H), 2.44-2.27 (m, 1H), 2.25-2.12 (m, 2H), 2.00-1.94 (m, 2H).

1-(4-(6-allyl-6-(methoxymethyl)-5-oxo-5,6,7,8-tetrahydronaphthalen-2-yl)phenyl)-3-(3-(trifluoromethyl)phenyl)urea (197H)

3-(Trifluoromethyl)phenyl isocyanate (0.256 g, 1.37 mmol) was added to a solution of product of Example 197G (0.26 g, 1.21 mmol) and triethylamine (0.138 g, 1.37 mmol) in THF (5 mL), and the reaction mixture was stirred at room temperature overnight. The solvent was removed under reduced pressure, and product was purified by flash chromatography using 1% methanol in chloroform to give title compound (0.46 g, 31%) as solid. $^1$H NMR (300 MHz, DMSO-d$_6$): δ 9.10 (s, 1H), 8.98 (s, 1H), 8.03 (s, 1H), 7.91 (d, J=7.5 Hz, 1H), 7.72-7.69 (m, 2H), 7.64-7.43 (m, 6H), 7.32 (d, J=7.8 Hz, 1H), 5.77-5.68 (m, 1H), 5.09-5.04 (m, 2H), 3.63 (d, J=9.0 Hz, 1H), 3.33 (m, 1H), 3.21 (s, 3H), 2.5 (m, 2H), 2.45-2.38 (m, 1H), 2.3-2.15 (m, 2H), 2.04-1.95 (m, 1H).

2-(2-(Methoxymethyl)-1-oxo-6-(4-(3-(3-(trifluoromethyl)phenyl)ureido)phenyl)-1,2,3,4-tetrahydronaphthalen-2-yl)acetic acid (197)

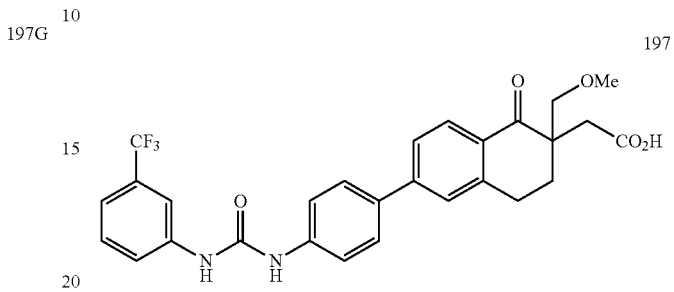

KMnO$_4$ (0.015 g, 0.35 mmol) was added to a solution of product of Example 197H (0.45 g, 0.11 mmol) and NaIO$_4$ in 15 mL of acetone-water (3:1) mixture. The reaction mixture was stirred at room temperature for 18 h. After the solvent was removed in vacuo, the residue was dissolved in water and extracted with ethyl acetate. The organic layer was dried over sodium sulphate, filtered and removed under reduced pressure. The residue was purified by the preparative HPLC to afford title compound (30 mg). $^1$H NMR (300 MHz, DMSO-d$_6$): δ 12.0 (bs, 1H), 9.12 (s, 1H), 9.00 (s, 1H), 8.03 (s, 1H), 7.90 (d, J=8.4 Hz, 1H), 7.72-7.68 (m, 2H), 7.61-7.49 (m, 6H), 7.32 (d, J=7.8 Hz, 1H), 3.61 (d, J=9.0 Hz, 1H), 3.36 (d, J=9.0 Hz, 1H), 3.22 (s, 3H), 3.11 (m, 1H), 2.99 (m, 1H), 2.88-2.82 (m, 1H), 2.44 (m, 2H), 2.27-2.18 (m, 1H); ESI-MS m/z=527 (M+H)$^+$; HPLC purity: 98.63%.

Example 198

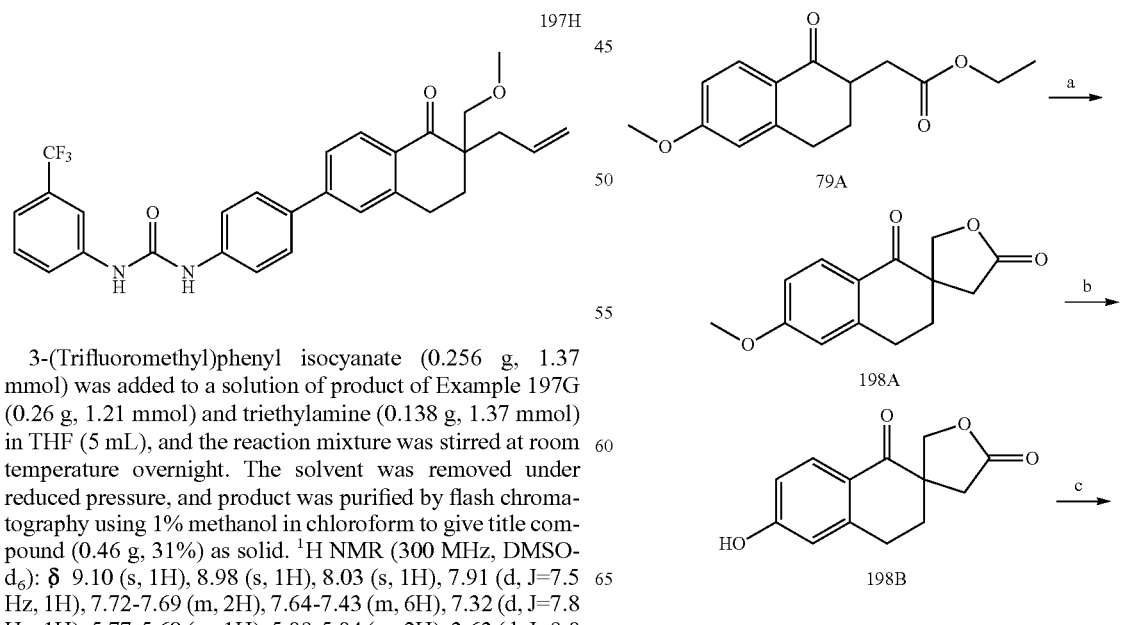

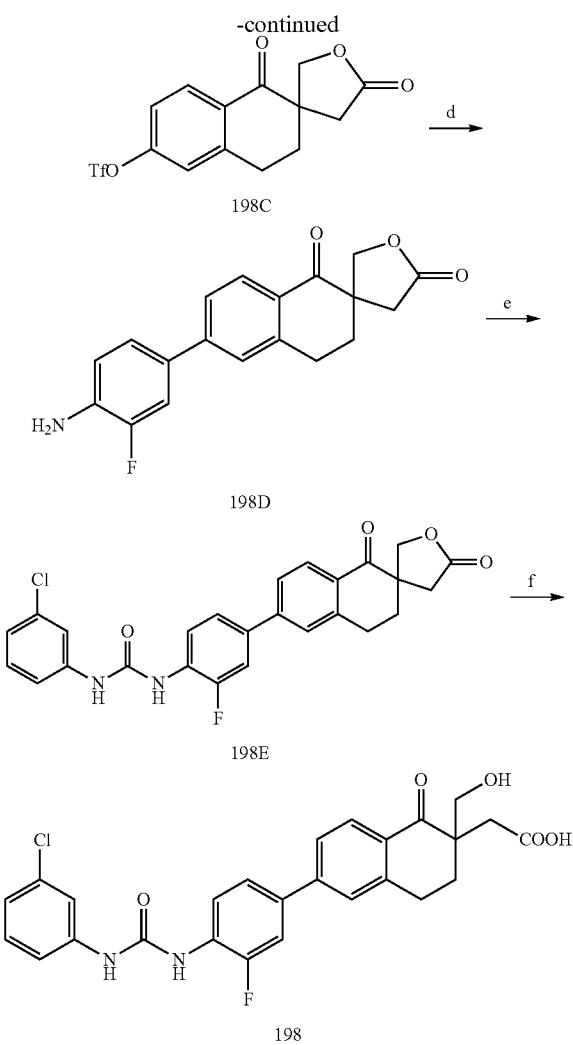

Reagents and conditions: a) HCHO, 2N NaOH, THF, RT, 3 h; b) Aq HBr, 100° C., 1 h; c) Tf₂O, Py, CH₂Cl₂, RT, 3 h; d) Pd(PPh₃)₄, Cs₂CO₃, Dioxane-H₂O, 80° C., 3 h; e) 3-ClPhNCO, Et₃N, THF, RT, 4 h; f) LiOH, THF—H₂O, RT, 4 h.

2-(6-(4-(3-(3-Chlorophenyl)ureido)-3-fluorophenyl)-2-(hydroxymethyl)-1-oxo-1,2,3,4-tetrahydro naphthalen-2-yl)acetic acid 6'-Methoxy-3',4'-dihydro-1'H,2H-spiro[furan-3,2'-naphthalene]-1',5(4H)-dione (198A)

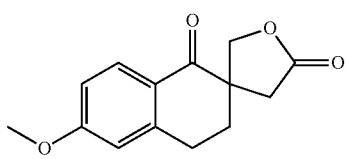

37% Formaldehyde solution (15 mL) was added to a solution of product of Example 79A (2.0 g, 7.0 mmol) in 20 mL of THF under argon atmosphere, followed by 2N aqueous solution of NaOH (0.06 g, 15.0 mmol) at room temperature. The reaction mixture was stirred for 3 h, solvent was removed under vacuum, and residue was acidified with 2N HCl. Aqueous layer was extracted with ethyl acetate and separated organic layer was dried over sodium sulphate, filtered and concentrated to afford the crude title compound (0.6 g, 31%) as gummy material. $^1$H NMR (400 MHz, DMSO-d₆): δ 7.87 (d, J=8.4 Hz, 1H), 6.93 (d, J=8.8 Hz, 1H), 6.89 (s, 1H), 4.45 (d, J=8.8 Hz, 1H), 4.25 (d, J=8.8 Hz, 1H), 3.83 (s, 3H), 2.98-2.91 (m, 2H), 2.70 (m, 2H), 2.22 (m, 2H).

6'-Hydroxy-3',4'-dihydro-1'H,2H-spiro[furan-3,2'-naphthalene]-1',5(4H)-dione (198B)

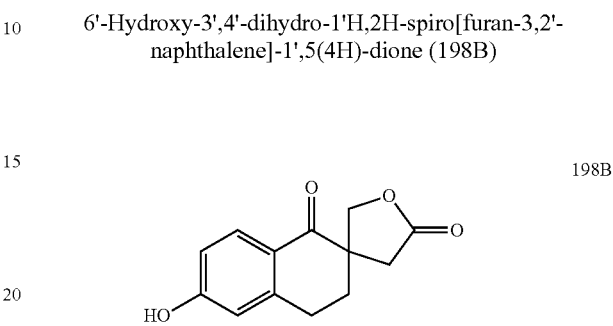

Aqueous HBr (20 mL) was added to product of Example 198A (0.6 g, 2.43 mmol), and the reaction mixture was refluxed for 1 h. The reaction mixture was then brought to room temperature and extracted with ethyl acetate (2×100 mL). The separated organic layer dried over sodium sulphate, filtered and removed under reduced pressure to afford title compound (0.37 g, 65%) as solid. $^1$H NMR (400 MHz, CDCl₃): δ 8.01 (d, J=8.4 Hz, 1H), 6.79 (d, J=8.8 Hz, 1H), 6.67 (s, 1H), 5.51 (s, 1H), 4.58 (d, J=8.8 Hz, 1H), 4.22 (d, J=8.0 Hz, 1H), 3.1-2.98 (m, 3H), 2.50-2.46 (m, 1H), 2.26 (t, J=6.4 Hz, 2H).

1',5-Dioxo-3',4',4',5-tetrahydro-1'H,2H-spiro[furan-3,2'-naphthalene]-6'-yl trifluoromethanesulfonate (198C)

Triflic anhydride (0.493 g, 1.75 mmol) was added to an ice cold solution of product of Example 198B (0.37 g, 1.59 mmol) and pyridine (0.138 g, 1.75 mmol) in dichloromethane (15 mL), and the mixture was stirred at room temperature for 3 h. The reaction mixture was diluted with dichloromethane (50 mL) and extracted with saturated aqueous solution of NaCl (50 mL). The organic layer was dried over sodium sulphate, filtered and removed under reduced pressure. The product was purified by flash chromatography using 20% ethyl acetate in hexanes to give title compound (0.46 g, 79%) as solid. $^1$H NMR (400 MHz, DMSO-d₆): δ 8.08 (d, J=9.6 Hz, 1H), 7.59 (s, 1H), 7.51 (d, J=8.8 Hz, 1H), 4.53 (d, J=8.8 Hz, 1H), 4.25 (d, J=9.2 Hz, 1H), 3.05 (t, J=6.0 Hz, 2H), 2.75 (d, J=7.6 Hz, 2H), 2.29 (m, 2H).

6'-(4-Amino-3-fluorophenyl)-3',4'-dihydro-1'H,2H-spiro[furan-3,2'-naphthalene]-1',5(4H)-dione (198D)

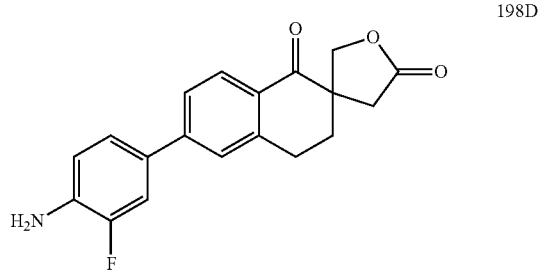 [SMILES: Nc1ccc(-c2ccc3c(c2)CCC2(COC(=O)C2)C3=O)cc1F]

Pd(PPh₃)₄ (0.011 g, 0.009 mmol) was added to a solution of product of Example 198C (0.3 g, 0.824 mmol) in 12 mL of 1,4 dioxane-H₂O (4:1) mixture under Argon atmosphere, followed by cesium carbonate (0.67 g, 2.06 mmol) and 4-amino 2-fluoro phenyl boronic acid (0.234 g, 0.989 mmol). The reaction mixture was degassed for 15 min. The reaction mixture was then refluxed for 3 h, and solvent was removed under vacuum. The residue was partitioned between ethyl acetate and water. The separated organic layer was dried over sodium sulphate, filtered and removed under reduced pressure. The crude product was purified by flash chromatography using 20% ethyl acetate in hexane to afford title compound (1.3 g, 72%) as solid. ¹H NMR (400 MHz, DMSO-d₆): δ 7.92 (d, J=8.4 Hz, 1H), 7.48-7.43 (m, 2H), 7.27 (t, J=8.8 Hz, 1H), 6.48 (dd, J₁=2.4 Hz, J₂=8.4 Hz, 1H), 6.42 (dd, J₁=2.4 Hz, J₂=16.4 Hz, 1H), 5.74 (s, 2H), 4.50 (d, J=9.2 Hz, 1H), 4.28 (d, J=9.2 Hz, 1H), 3.05 (m, 2H), 2.73 (d, J=9.6 Hz, 2H), 2.26 (m, 2H).

3-Chloro-N-(4-(1',5-dioxo-3',4,4',5-tetrahydro-1'H,2H-spiro[furan-3,2'-naphthalene]-6'-yl)-2-fluoro phenyl)benzamide (198E)

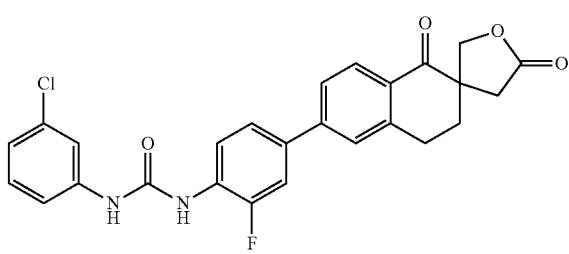

3-Chlorophenyl isocyanate (0.052 g, 0.338 mmol) was added to a solution of product of Example 198D (0.1 g, 0.307 mmol) and triethylamine (0.034 g, 0.338 mmol) in THF (5 mL), and the reaction mixture was stirred at room temperature for 4 h. The solvent was removed under reduced pressure, and product was purified by flash chromatography using 40% ethyl acetate in hexanes to afford title compound (0.09 g, 31%) as solid. ¹H NMR (300 MHz, DMSO-d₆): δ 9.31 (s, 1H), 8.78 (m, 1H), 8.28 (t, J=8.4 Hz, 1H), 7.98 (d, J=5.7 Hz, 1H), 7.75-7.71 (m, 4H), 7.63-7.60 (m, 1H), 7.36-7.23 (m, 2H), 7.07-7.04 (m, 1H), 4.51 (d, J=9.0 Hz, 1H), 4.3 (d, J=9.3 Hz, 1H), 3.16 (d, J=4.8 Hz, 1H), 3.06 (m, 1H), 2.75 (d, J=4.2 Hz, 2H), 2.28 (t, J=5.7 Hz, 2H).

2-(6-(4-(3-(3-Chlorophenyl)ureido)-3-fluorophenyl)-2-(hydroxymethyl)-1-oxo-1,2,3,4-tetrahydro naphthalen-2-yl)acetic acid (198)

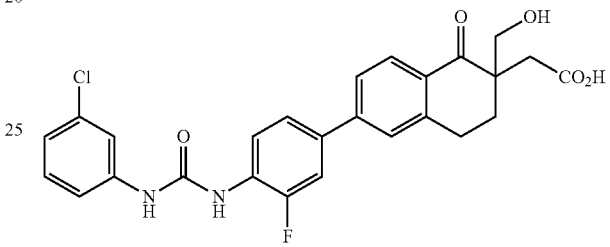

Lithium hydroxide (0.023 g, 0.564 mmol) was added to a solution of product of Example 198E (0.09 g, 0.188 mmol) in 15 mL of THF-water (2:1) mixture, and the reaction mixture was stirred at room temperature for 4 h. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., solids were collected by filtration and dried under vacuum to afford title compound (0.05 g, 53%) as white solid. ¹H NMR (300 MHz, DMSO-d₆): δ 12.0 (bs, 1H), 9.70 (bs, 1H), 9.11 (bs, 1H), 8.20 (t, J=8.1 Hz, 1H), 7.91 (d, J=8.4 Hz, 1H) 7.76 (s, 1H), 7.68-7.64 (m, 3H), 7.57 (d, J=9.0 Hz, 1H) 7.32-7.28 (m, 2H), 7.03 (m, 1H), 3.15-2.90 (m, 4H), 2.74-2.67 (m, 1H), 2.44-2.34 (m, 1H), 2.28-2.16 (m, 1H), 2.00 (m, 1H); ESI-MS m/z=466 (M-CH₂OH).

Examples 199-200 were prepared by the procedures analogous to those described in Example 198 using appropriate starting materials.

| Ex | Structure | ¹H NMR Data | Mass/Purity |
|---|---|---|---|
| 199 | ![structure] | ¹H NMR (300 MHz, DMSO-d₆): δ 12.0 (bs, 2H), 8,14 (s, 1H), 7.96 (m, 1H), 7.80 (m, 1H), 7.66 (m, 1H) 7.47-7.40 (m, 2H), 7.33 (m, 4H), 7.20 (d, J = 7.6 Hz, 1H), 3.09 (m, 1H), 2.94 (m, 3H), 2.33 (m, 2H), 2.02 (m, 2H). | ESI-MS m/z = 481 (M − CH₂OH); HPLC purity: 95.09%. |

| Ex | Structure | ¹H NMR Data | Mass/Purity |
|---|---|---|---|
| 200 | 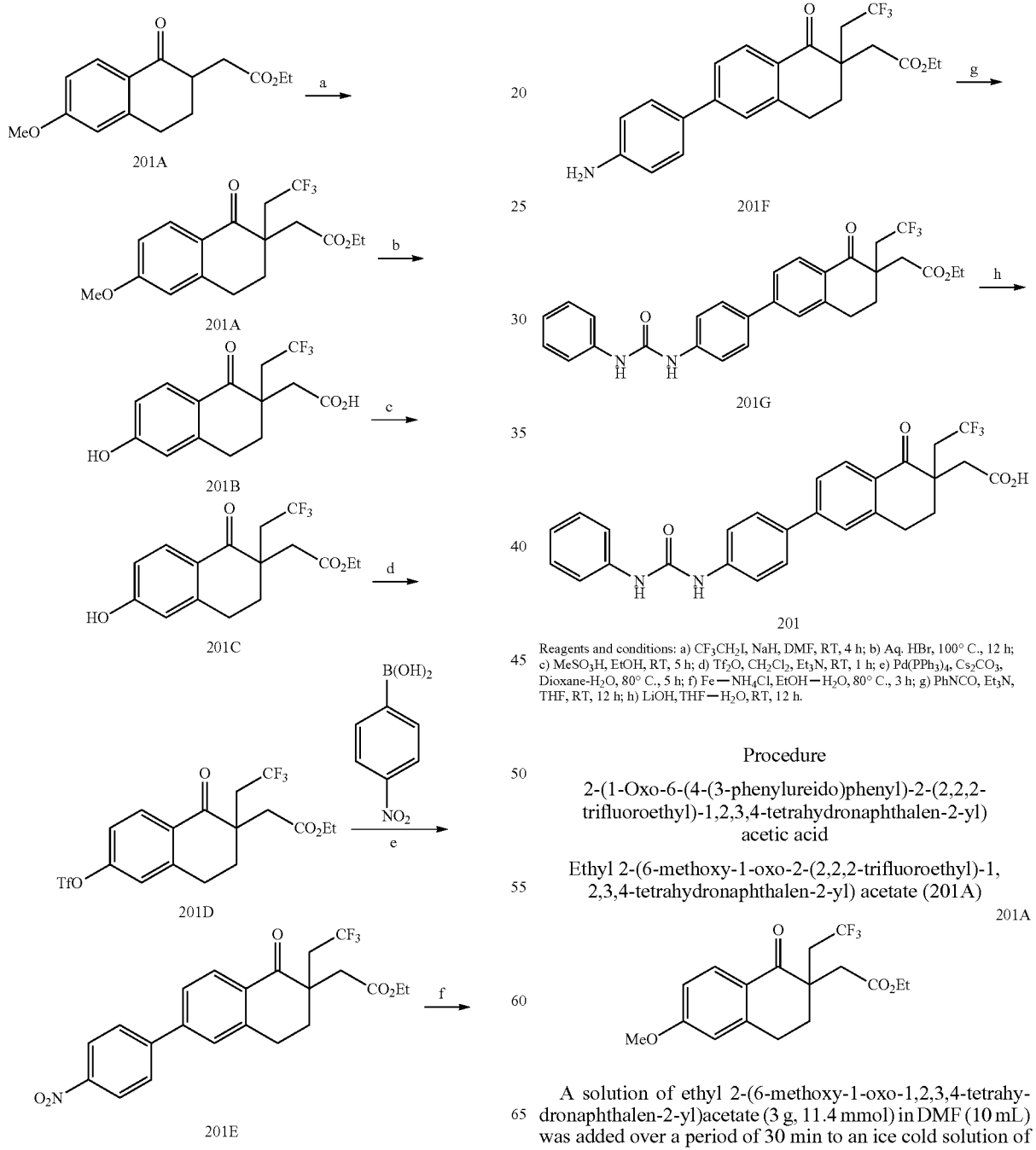 | ¹H NMR (300 MHz, DMSO-d₆): δ 12.0 (bs, 1H), 9.12 (bs, 2H), 7.90 (d, J = 8.1 Hz, 1H), 7.70-7.55 (m, 6H), 7.35 (s, 1H), 7.25 (m, 1H), 7.16 (t, J = 7.8 Hz, 1H), 6.80 (d, J = 6.9 Hz, 1H), 3.20-3.02 (m, 2H), 2.97-2.86 (m, 2H), 2.70 (m, 2H) 2.30 (s, 3H), 2.20-2.12 (m, 1H), 2.08-1.90 (m, 1H). | ESI-MS m/z = 429 (M − CH₂OH); HPLC purity: 95.33%. |

Example-201

Reagents and conditions: a) CF₃CH₂I, NaH, DMF, RT, 4 h; b) Aq. HBr, 100° C., 12 h; c) MeSO₃H, EtOH, RT, 5 h; d) Tf₂O, CH₂Cl₂, Et₃N, RT, 1 h; e) Pd(PPh₃)₄, Cs₂CO₃, Dioxane-H₂O, 80° C., 5 h; f) Fe—NH₄Cl, EtOH—H₂O, 80° C., 3 h; g) PhNCO, Et₃N, THF, RT, 12 h; h) LiOH, THF—H₂O, RT, 12 h.

Procedure 2-(1-Oxo-6-(4-(3-phenylureido)phenyl)-2-(2,2,2-trifluoroethyl)-1,2,3,4-tetrahydronaphthalen-2-yl) acetic acid Ethyl 2-(6-methoxy-1-oxo-2-(2,2,2-trifluoroethyl)-1,2,3,4-tetrahydronaphthalen-2-yl) acetate (201A)

A solution of ethyl 2-(6-methoxy-1-oxo-1,2,3,4-tetrahydronaphthalen-2-yl)acetate (3 g, 11.4 mmol) in DMF (10 mL) was added over a period of 30 min to an ice cold solution of NaH (1.14 g, 28.5 mmol) in DMF (20 mL), and the reaction mixture was stirred for 10 min. Trifluoroethyl iodide (5.9 g, 28.22 mmol) was then added, and the mixture was stirred for 2 h at room temperature. The reaction was then brought to 0° C., excess NaH was quenched with ice water and extracted with ethyl acetate (2×50 mL). The combined organic layers were dried over sodium sulphate, filtered and removed under vacuum to give title compound (1.5 g, 38%) as solid. $^1$H NMR (300 MHz, CDCl$_3$): δ 8.02 (d, J=9.3 Hz, 1H), 6.85 (dd, J$_1$=2.7 Hz, J$_2$=9.0 Hz, 1H), 6.68 (d, J=2.7 Hz, 1H), 4.1 (q, J=6.9 Hz, 2H), 3.86 (s, 3H), 3.05-2.9 (m, 4H), 2.6-2.4 (m, 4H), 1.23 (t, J=6.9 Hz, 3H); ESI-MS m/z: 345 (M+H)$^+$ 2-(6-Hydroxy-1-oxo-2-(2,2,2-trifluoroethyl)-1,2,3,4-tetrahydronaphthalen-2-yl)acetic acid (201B)

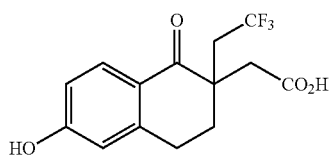

201B

Aqueous HBr (15 mL) was added to product of Example 201A (1.5 g, 4.36 mmol), and the reaction mixture was refluxed for overnight. The reaction mixture was then brought to room temperature and extracted with ethyl acetate (2×100 mL). The organic layer was dried over sodium sulphate, filtered and removed under reduced pressure to afford crude compound (1.2 g) as solid, which was carried on to the next step without further purification.

Ethyl 2-(6-hydroxy-1-oxo-2-(2,2,2-trifluoroethyl)-1,2,3,4-tetrahydronaphthalen-2-yl) acetate (201C)

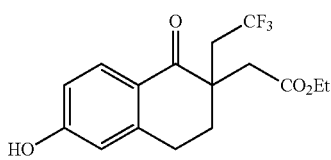

201C

Methane sulphonic acid (2 mL) was added to a solution of product of Example 201B (1.2 g, 3.97 mmol) in ethanol (15 mL), and the reaction mixture was stirred at room temperature for 12 h. Ethanol was removed from reaction mixture under reduced pressure, and residue was diluted with ethyl acetate and washed with brine solution. The organic layer was dried over sodium sulphate, filtered, and solvent was removed under reduced pressure. The crude product was purified by flash chromatography using 20% ethyl acetate in hexanes to give title compound (0.9 g, 62%) as syrup. $^1$H NMR (400 MHz, CDCl$_3$): δ 7.97 (d, J=9.2 Hz, 1H), 6.75 (dd, J$_1$=2.4 Hz, J$_2$=8.8 Hz, 1H), 6.64 (d, J=2.4 Hz, 1H), 4.1 (q, J=6.8 Hz, 2H), 3.0-2.8 (m, 4H), 2.62-2.5 (m, 2H), 2.4 (m, 1H), 2.3 (m, 1H), 1.23 (t, J=7.2 Hz, 3H); ESI-MS m/z: 329 (M−H)$^−$ Ethyl 2-(1-oxo-2-(2,2,2-trifluoroethyl)-6-(trifluoromethylsulfonyloxy)-1,2,3,4-tetrahydronaphthalen-2-yl) acetate (201D)

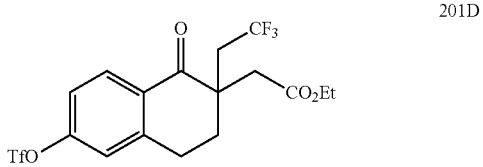 [SMILES: CCOC(=O)CC1(CC(F)(F)F)CCc2cc(OS(=O)(=O)C(F)(F)F)ccc2C1=O]

201D

Triflic anhydride (1.33 g, 4.71 mmol) was added to an ice cold solution of product of Example 201C (1.3 g, 3.93 mmol) and pyridine (0.34 g, 4.72 mmol) in dichloromethane (15 mL), and the reaction mixture was stirred at room temperature for 2 h. The reaction mixture was diluted with dichloromethane (100 mL) and washed with saturated aqueous solution of NaCl (25 mL). The organic layer was dried over sodium sulphate, filtered and removed under reduced pressure. The product was purified by flash chromatography using 5% ethyl acetate in hexanes to give title compound (1.1 g, 61%) as syrup. $^1$H NMR (300 MHz, CDCl$_3$): δ 8.16 (d, J=9.0 Hz, 1H), 7.28-7.18 (m, 2H), 4.12 (q, J=7.2 Hz, 2H), 3.09 (t, J=6.3 Hz, 2H), 2.95-2.8 (m, 2H), 2.66-2.45 (m, 3H), 2.34 (m, 1H), 1.24 (t, J=6.9 Hz, 3H).

Ethyl 2-(6-(4-nitrophenyl)-1-oxo-2-(2,2,2-trifluoroethyl)-1,2,3,4-tetrahydronaphthalen-2-yl) acetate (201E)

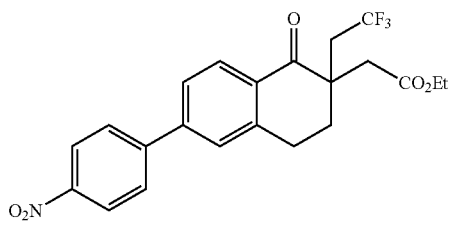

201E

Pd(PPh$_3$)$_4$ (0.022 g, 0.02 mmol) was added to a solution of product of Example 201D (0.9 g, 1.94 mmol) in 13 mL of 1,4 dioxane-H$_2$O (3:1) mixture under argon atmosphere, followed by cesium carbonate (1.9 g, 5.8 mmol) and 4-nitro phenyl boronic acid (0.35 g, 2.09 mmol). The reaction mixture was degassed for 5 min. The reaction mixture was refluxed for 4 h, and solvent was then removed under reduced pressure. The residue was partitioned between ethyl acetate and water. The separated organic layer was dried over sodium sulphate, filtered and removed under reduced pressure. The product was purified by flash chromatography to afford title compound (0.4 g, 47%) as solid. $^1$H NMR (400 MHz, CDCl$_3$): δ 8.33 (d, J=8.8 Hz, 2H), 8.17 (d, J=8.4 Hz, 1H), 7.76 (d, J=8.8 Hz, 2H), 7.6 (m, 1H), 7.5 (s, 1H), 4.14 (q, J=6.8 Hz, 2H), 3.13 (t, J=6.0 Hz, 2H), 2.95-2.85 (m, 2H), 2.7-2.58 (m, 2H), 2.5 (m, 1H), 2.4 (m, 1H), 1.25 (t, J=6.8 Hz, 3H). ESI-MS m/z: 436 (M+H)$^+$ Ethyl 2-(6-(4-aminophenyl)-1-oxo-2-(2,2,2-trifluoroethyl)-1,2,3,4-tetrahydronaphthalen-2-yl) acetate (201F)

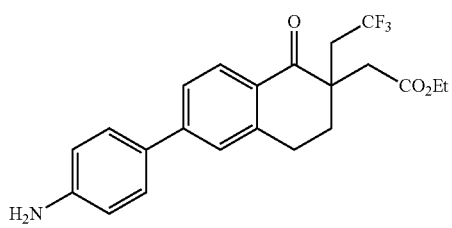

201F

Iron powder (0.12 g, 2.3 mmol) was added to a solution of product of Example 201E (0.4 g, 0.9 mmol) in 15 mL of ethanol-water mixture (2:1) followed by $NH_4Cl$ (0.024 g, 0.45 mmol), and the reaction mixture was refluxed for 4 h. The solvent was removed under reduced pressure, and residue was partitioned between ethyl acetate and water. The separated organic layer was dried over sodium sulphate, filtered and removed in vacuo to give title compound (0.2 g, 50%). $^1$H NMR (300 MHz, DMSO-$d_6$): δ 7.86 (d, J=8.4 Hz, 1H), 7.6-7.45 (m, 4H), 6.65 (d, J=9.0 Hz, 2H), 5.44 (bs, 2H), 4.03 (q, J=7.2 Hz, 2H), 3.1-2.8 (m, 4H), 2.75-2.6 (m, 2H), 2.38 (m, 1H), 2.15 (m, 1H), 1.14 (t, J=7.2 Hz, 3H). ESI-MS m/z: 406 (M+H)$^+$ Ethyl 2-(1-oxo-6-(4-(3-phenylureido)phenyl)-2-(2,2,2-trifluoroethyl)-1,2,3,4-tetrahydronaphthalen-2-yl) acetate (201G)

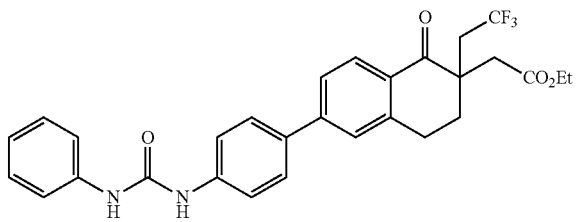

201G

Phenyl isocyanate (0.035 g, 0.3 mmol) was added to a solution of product of Example 201F (0.12 g, 0.3 mmol) and triethylamine (0.06 g, 0.6 mmol) in THF (5 mL), and the reaction mixture was stirred at room temperature overnight. The solvent was removed under reduced pressure, and product was purified by flash chromatography using 20% ethyl acetate in hexanes to afford title compound (0.08 g, 66%) as solid. $^1$H NMR (400 MHz, CDCl$_3$): δ 8.1 (d, 8.4 Hz, 1H), 7.6-7.45 (m, 5H), 7.42-7.35 (m, 5H), 7.19 (m, 1H), 6.6 (s, 1H), 6.5 (s, 1H), 4.1 (q, J=7.2 Hz, 2H), 3.1 (m, 2H), 2.9 (m, 2H), 2.63 (m, 2H), 2.5-2.3 (m, 2H), 1.25 (t, J=7.2 Hz, 3H); ESI-MS m/z: 526 (M+H)$^+$ 2-(1-Oxo-6-(4-(3-phenylureido)phenyl)-2-(2,2,2-trifluoroethyl)-1,2,3,4-tetrahydronaphthalen-2-yl) acetic acid (201)

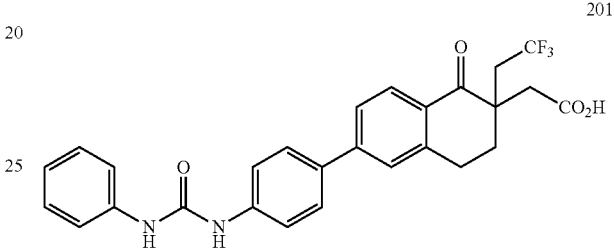

201

Lithium hydroxide (0.025 g, 0.61 mmol) was added to a solution of product of Example 201G (0.08 g, 0.15 mmol) in 4 mL of THF-water (3:1) mixture, and the reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., solids were collected by filtration and dried under vacuum to afford title compound (0.05 g, 66%) as white solid. $^1$H NMR (400 MHz, DMSO-$d_6$): δ 12.4 (bs, 1H), 9.15 (bs, 1H), 8.95 (bs, 1H), 7.93 (d, J=8.4 Hz, 1H), 7.7-7.62 (m, 4H), 7.57 (d, J=8.8 Hz, 2H), 7.48 (d, J=8.0 Hz, 2H), 7.28 (t, J=8.0 Hz, 2H), 6.97 (t, J=7.2 Hz, 1H), 3.2-2.9 (m, 3H), 2.83-2.67 (m, 2H), 2.6-2.45 (m, 2H), 2.15 (m, 1H); ESI-MS m/z: 495 (M−H)$^−$; HPLC purity: 95%.

Examples 202-211 were prepared by the procedures analogous to those described in Examples 173, 197 and 201 using appropriate starting materials.

| Exp | Structure | Analytical Data | (M + H)$^+$ |
|---|---|---|---|
| 202 | ![structure] | $^1$H NMR (300 MHz, DMSO-$d_6$): δ 12.2 (bs, 1H), 8.78 (s, 1H), 8.7 (s, 1H), 7.6-7.52 (m, 4H), 7.5-7.4 (m, 3H), 7.38-7.26 (m, 4H), 6.97 (t, J = 7.5 Hz, 1H), 5.5 (d, J = 6.3 Hz, 1H), 4.5 (d, J = 5.4 Hz, 1H), 2.9-2.55 (m, 4H), 2.4-2.2 (m, 2H), 1.94 (m, 2H). | ESI-MS m/z: 499 (M + H)$^+$; HPLC purity: 99%. |

-continued

| Exp | Structure | Analytical Data | (M + H)+ |
|---|---|---|---|
| 203 | (3,5-dimethylphenyl urea linked to phenyl-tetrahydronaphthalenone with CF3 and CH2CO2H substituents) | $^1$H NMR (400 MHz, DMSO-$d_6$): δ 12.1 (bs, 1H), 9.16 (bs, 1H), 8.9 (bs, 1H), 7.93 (d, J = 8.4 Hz, 1H), 7.7-7.55 (m, 6H), 7.1 (s, 2H), 6.6 (s, 1H), 3.2-2.9 (m 3H), 2.84-2.7 (m, 2H), 2.55 (m, 1H), 2.45 (m, 1H), 2.24 (s, 6H), 2.16 (m, 1H). | ESI-MS m/z: 525 (M + H)+; HPLC purity: 97%. |
| 204 | (3-methoxyphenyl urea linked to phenyl-tetrahydronaphthalenone with CF3 and CH2CO2H substituents) | $^1$H NMR (300 MHz, DMSO-$d_6$): δ 12.2 (bs, 1H), 8.9 (bs, 1H), 8.8 (bs, 1H), 7.93 (d, J = 7.5 Hz, 1H), 7.72-7.55 (m, 6H), 7.24-7.16 (m, 2H), 6.95 (d, J = 7.8 Hz, 1H), 6.56 (d, J = 6.3 Hz, 1H), 3.74 (s, 3H), 3.2-2.9 (m, 3H), 2.85-2.65 (m, 3H), 2.55 (m, 1H), 2.17 (m, 1H). | ESI-MS m/z: 525 (M − H)−; HPLC purity: 98%. |
| 205 | (3-chlorophenyl urea linked to phenyl-tetrahydronaphthalenone with CF3 and CH2CO2H substituents) | $^1$H NMR (400 MHz, DMSO-$d_6$): δ 12.4 (bs, 1H), 9.2 (bs, 2H), 7.93 (d, J = 8.4 Hz, 1H), 7.74-7.64 (m, 5H), 7.59 (d, J = 8.0 Hz, 2H), 7.32-7.28 (m, 2H), 7.02 (m, 1H), 3.2-2.9 (m, 3H), 2.82 (d, J = 16.4 Hz, 1H), 2.7 (m, 1H), 2.56 (m, 1H), 2.45 (m, 1H), 2.18 (m, 1H). | ESI-MS m/z: 529 (M − H)−; LCMS purity: 98%. |
| 206 | (3-chlorophenyl urea linked to phenyl-tetrahydronaphthalene with OH, CF3 and CH2CO2H substituents) | $^1$H NMR (400 MHz, DMSO-$d_6$): δ 9.32 (bs, 1H), 9.24 (bs, 1H), 7.74 (s, 1H), 7.65-7.52 (m, 4H), 7.5-7.35 (m, 3H), 7.3 (m, 2H), 7.0 (m, 1H), 4.54 (s, 1H), 2.95-2.8 (m, 4H), 2.5-2.2 (m, 2H), 1.9 (m, 2H). | ESI-MS m/z: 531 (M − H)−; LCMS purity: 93%. |
| 207 | (2-methoxy-5-methylphenyl urea linked to phenyl-tetrahydronaphthalenone with CF3 and CH2CO2H substituents) | $^1$H NMR (400 MHz, DMSO-$d_6$): δ 12.2 (bs, 1H), 9.51 (s, 1H), 8.23 (s, 1H), 8.0 (s, 1H), 7.93 (d, J = 8.4 Hz, 1H), 7.75-7.55 (m, 6H), 6.90 (d, J = 8.4 Hz, 2H), 6.75 (d, J = 7.6 Hz, 1H), 3.85 (s, 3H), 3.2-2.9 (m 3H), 2.84-2.65 (m, 2H), 2.55 (m, 1H), 2.45 (m, 1H), 2.24 (s, 3H), 2.18 (m, 1H). | ESI-MS m/z: 541 (M + H)+; LCMS purity: 93%. |
| 208 | (3-trifluoromethylphenyl urea linked to pyridyl-tetrahydronaphthalene with OH, Et and CH2CO2H substituents) | $^1$H NMR (400 MHz, DMSO-$d_6$): δ 9.39 (bs, 1H), 9.31 (bs, 1H), 8.73 (bs, 1H), 8.1 (d, J = 8.4 Hz, 1H), 8.0 (s, 1H), 7.95 (d, J = 8.4 Hz, 1H), 7.81 (d, J = 7.6 Hz, 1H), 7.76 (s, 1H), 7.62 (d, J = 7.6 Hz, 1H), 7.54 (t, J = 8.0 Hz, 1H), 7.43 (d, J = 8.0 Hz, 1H), 7.34 (d, J = 7.2 Hz, 1H), 4.42 (s, 1H), 2.81 (m, 2H), 2.13 (m, 2H), 1.84 (m, 1H), 1.7 (m, 1H), 1.56 (m, 1H), 1.4 (m, 1H), 0.9 (t, J = 6.8 Hz, 3H). | ESI-MS m/z: 512 (M + H)+; LCMS purity: 96%. |

-continued

| Exp | Structure | Analytical Data | (M + H)+ |
|---|---|---|---|
| 209 | 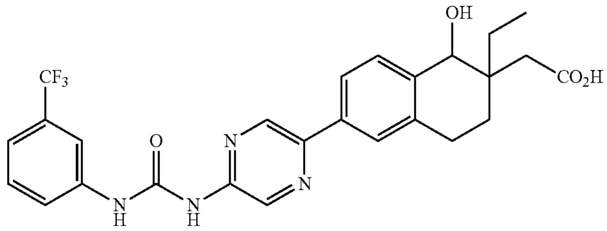 [SMILES: CCC1(CC(=O)O)CCc2cc(-c3cnc(NC(=O)Nc4cccc(C(F)(F)F)c4)cn3)ccc2C1O] | $^1$H NMR (400 MHz, DMSO-$d_6$): δ 12.0 (bs, 1H), 10.0 (bs, 1H), 9.8 (bs, 1H), 9.1 (s, 1H), 8.9 (s, 1H), 8.05 (s, 1H), 7.84 (d, J = 7.6 Hz, 1H), 7.8 (s, 1H), 7.67 (d, J = 8 Hz, 1H), 7.54 (t, J = 7.6 Hz, 1H), 7.45 (d, J = 8.0 Hz, 1H), 7.39 (d, J = 7.2 Hz, 1H), 4.5 (s, 1H), 2.81 (m, 2H), 2.26 (m, 2H), 1.85 (m, 1H), 1.7 (m, 1H), 1.6 (m, 1H), 1.45 (m, 1H), 0.9 (t, J = 7.2 Hz, 3H). | ESI-MS m/z: 513 (M + H)+; LCMS purity: 90%. |
| 210 | 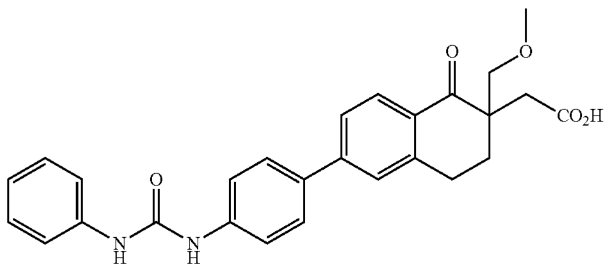 [SMILES: COCC1(CC(=O)O)CCc2cc(-c3ccc(NC(=O)Nc4ccccc4)cc3)ccc2C1=O] | $^1$H NMR (300 MHz, DMSO-$d_6$): δ 12.05 (bs, 1H), 8.85 (s, 1H), 8.7 (s, 1H), 7.9 (d, J = 7.5 Hz, 1H), 7.7 (d, J = 8.4 Hz, 2H), 7.65-7.55 (m, 4H), 7.45 (d, J = 7.8 Hz, 2H), 7.3 (t, J = 7.5 Hz, 2H), 7.0 (m, 1H), 3.6 (d, J = 9.3 Hz, 1H), 3.36 (d, J = 9.9 Hz, 1H), 3.22 (s, 3H), 3.12-2.89 (m, 2H), 2.85 (m, 1H), 2.42 (m, 2H), 2.18 (m, 1H). | HPLC purity: 92%. |
| 211 | 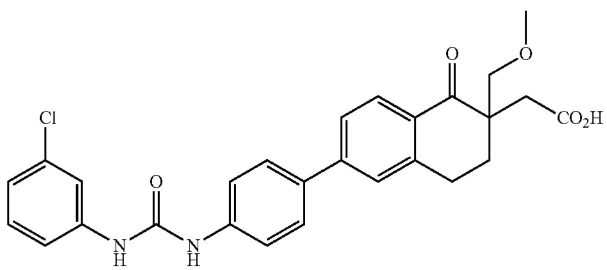 [SMILES: COCC1(CC(=O)O)CCc2cc(-c3ccc(NC(=O)Nc4cccc(Cl)c4)cc3)ccc2C1=O] | $^1$H NMR (300 MHz, DMSO-$d_6$): δ 12.05 (bs, 1H), 8.95 (s, 2H), 7.9 (d, J = 7.5 Hz, 1H), 7.7 (d, J = 9.0 Hz, 2H), 7.63-7.57 (m, 4H), 7.34-7.29 (m, 2H), 7.03 (m, 1H), 3.6 (d, J = 9.3 Hz, 1H), 3.36 (d, J = 9.9 Hz, 1H), 3.22 (s, 3H), 3.18-2.9 (m, 2H), 2.85 (m, 1H), 2.42 (m, 2H), 2.15 (m, 1H). | ESI-MS m/z: 491 (M − H)−; HPLC purity: 91%. |

Example-212

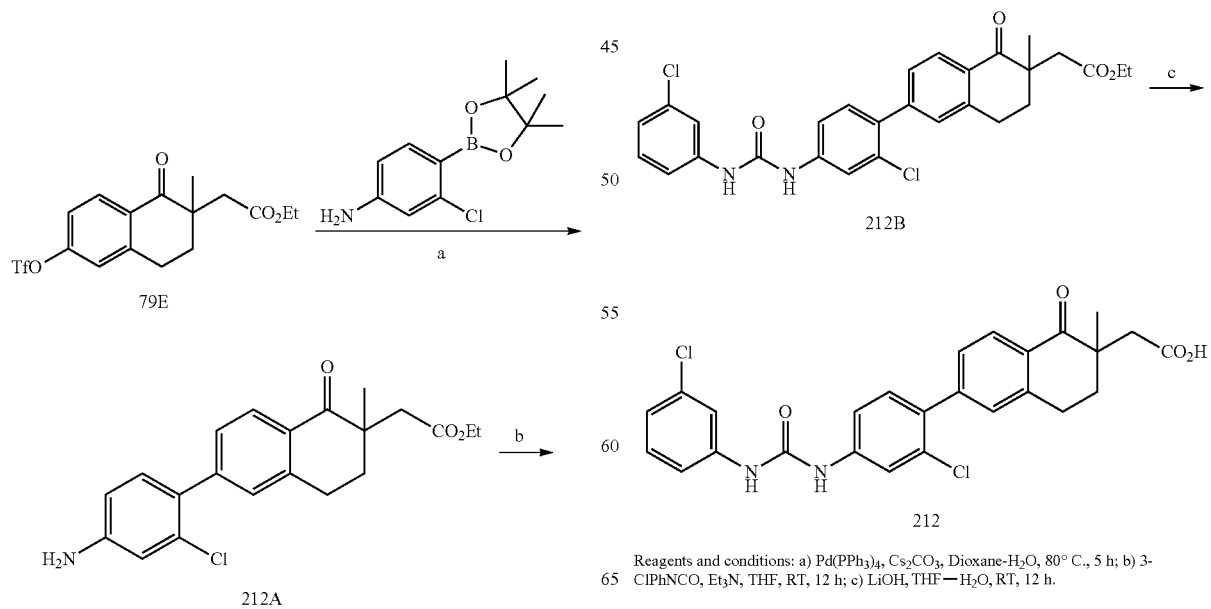

Reagents and conditions: a) Pd(PPh$_3$)$_4$, Cs$_2$CO$_3$, Dioxane-H$_2$O, 80° C., 5 h; b) 3-ClPhNCO, Et$_3$N, THF, RT, 12 h; c) LiOH, THF—H$_2$O, RT, 12 h.

Procedures

2-(6-(2-Chloro-4-(3-(3-chlorophenyl)ureido)phenyl)-2-methyl-1-oxo-1,2,3,4-tetrahydronaphthalen-2-yl) acetic acid

Ethyl 2-(6-(4-amino-2-chlorophenyl)-2-methyl-1-oxo-1,2,3,4-tetrahydronaphthalen-2-yl)acetate (212A)

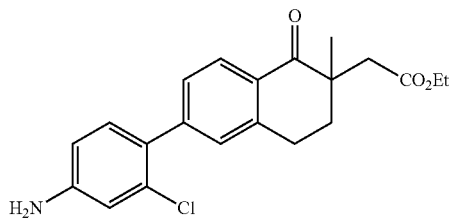

212A

Pd(PPh$_3$)$_4$ (0.088 g, 0.076 mmol) was added to a solution of product of Example 79E (2.5 g, 6.34 mmol) in 35 mL of 1,4 dioxane-H$_2$O (5:1) mixture under Argon atmosphere, followed by cesium carbonate (6.2 g, 19.02 mmol) and 4-Amino-2-chlorophenylboronic acid, pinacol ester (1.607 g, 6.34 mmol). The reaction mixture was degassed for 5 min. The reaction mixture was refluxed for 5 h, and solvent was removed under reduced pressure. The residue was partitioned between ethyl acetate and water. The separated organic layer was dried over sodium sulphate, filtered and removed under reduced pressure. The product was purified by flash chromatography to afford title compound (2 g, 85%) as solid. $^1$H NMR (400 MHz, CDCl$_3$): δ 8.07 (d, J=8.4 Hz, 1H), 7.38-7.36 (dd, J$_1$=1.6 Hz, J$_2$=8.0 Hz, 1H), 7.28 (s, 1H), 7.11 (d, J=8.4 Hz, 1H), 6.78 (d, J=2.4 Hz, 1H), 6.64-6.61 (dd, J$_1$=2.0 Hz, J$_2$=8.0 Hz, 1H), 4.1 (q, J=6.8 Hz, 2H), 3.8 (bs, 2H), 3.1 (m, 1H), 2.95 (m, 2H), 2.5 (m, 2H), 1.95 (m, 1H), 1.3 (s, 3H), 1.25 (m, 3H).

Ethyl 2-(6-(2-chloro-4-(3-(3-chlorophenyl)ureido)phenyl)-2-methyl-1-oxo-1,2,3,4-tetrahydronaphthalen-2-yl)acetate (212B)

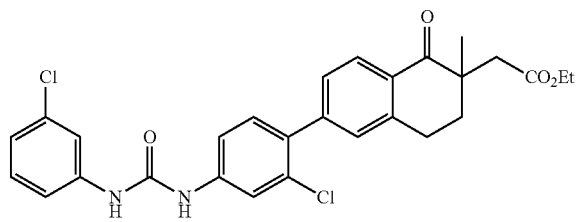

212B

1-Chloro-3-isocyanatobenzene (0.892 g, 5.81 mmol) was added to a solution of product of Example 212A (1.8 g, 4.84 mmol) and triethylamine (2.024 g, 14.52 mmol) in THF (25 mL), and the reaction mixture was stirred at room temperature overnight. The solvent was removed under reduced pressure, and product was purified by flash chromatography using 12% ethyl acetate in hexanes to afford title compound (1.2 g, 47.2%) as solid. $^1$H NMR (300 MHz, CDCl$_3$): δ 8.05 (s, 1H), 8.02 (s, 1H), 7.48 (m, 2H), 7.36 (m, 1H), 7.29 (m, 1H), 7.21 (m, 1H), 7.11-7.03 (m, 5H), 4.11 (q, J=7.5 Hz, 2H), 3.12-2.89 (m, 3H), 2.44 (m, 2H), 1.95 (m, 1H), 1.3 (s, 3H), 1.2 (t, J=7.2 Hz, 3H).

Compound 212B (0.88 g) was racemic mixture with 1:1 enantiomeric ratio and was separated on chiral column to obtain single enantiomers of 212B1 (Rt 17.32 min) and 212B2 (Rt 19.06 min) using following conditions:

Column: CHIRAL PAK IA 4.6×250 mm, 5μ

Column ID: ANL_CHIRAL IA__141

Mobile Phase: A=n-HEXANE, C=Ethanol; ISOCRATIC: 90:10; Flow rate: 1.0 mL/min

2-(6-(2-chloro-4-(3-(3-chlorophenyl)ureido)phenyl)-2-methyl-1-oxo-1,2,3,4-tetrahydronaphthalen-2-yl) acetic acid (212)

Chiral: enantiomer-1

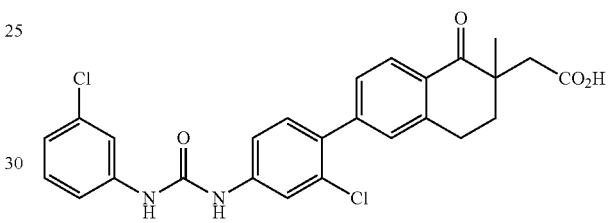

Lithium hydroxide (0.08 g, 1.903 mmol) was added to a solution of product of Example 212B1 (0.25 g, 0.476 mmol) in 10 mL of dioxane-water (4:1) mixture, and the reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.19 g, 80%) as white solid. $^1$H NMR (400 MHz, DMSO-d$_6$): δ 12.1 (bs, 1H), 9.1 (bs, 1H), 9.03 (bs, 1H), 7.94 (d, J=9.0 Hz, 1H), 7.8 (d, J=1.8 Hz, 1H), 7.7 (m, 1H), 7.43-7.39 (m, 4H), 7.32-7.3 (m, 2H), 7.06-7.03 (m, 1H), 3.11-2.98 (m, 2H), 2.87 (d, J=15.6 Hz, 1H), 2.5 (m, 1H), 2.4 (d, J=16.5 Hz, 1H), 1.87 (m, 1H), 1.2 (s, 3H); ESI-MS m/z=495 (M−H)$^−$; HPLC Purity: 95%.

Example 213

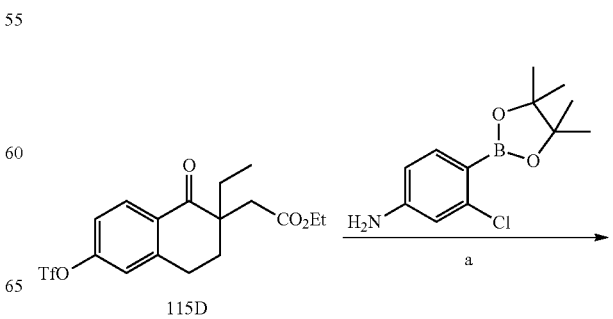

115D

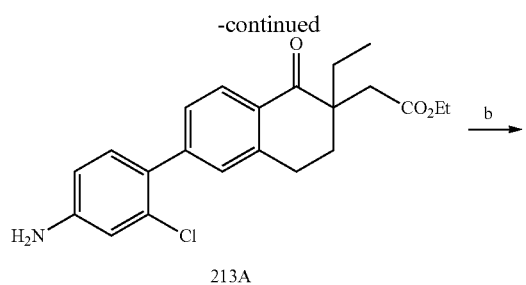

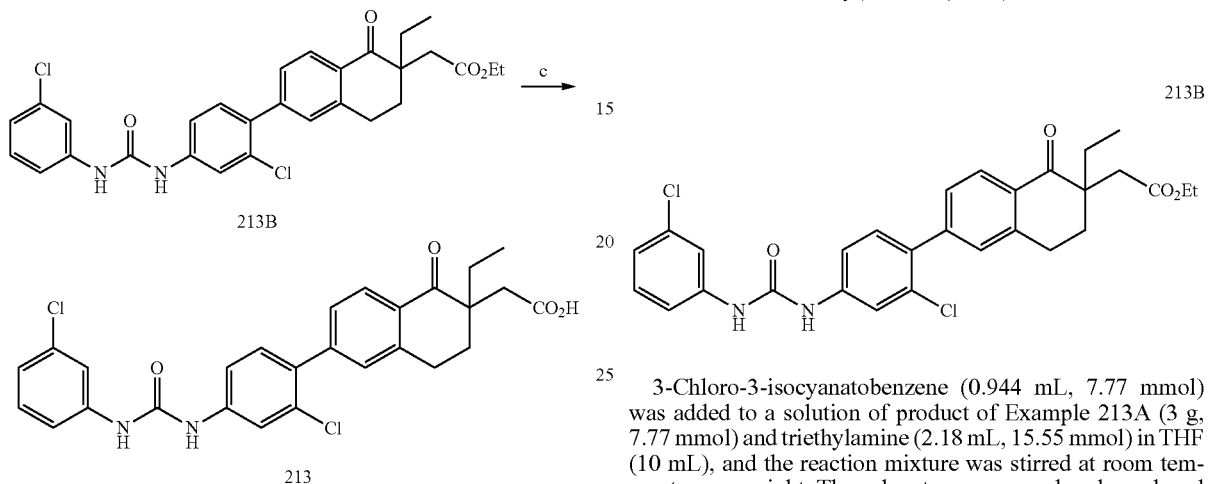

Reagents and conditions: a) Pd(PPh₃)₄, Cs₂CO₃, Dioxane-H₂O, 80° C., 5 h; b) 3-ClPhNCO, Et₃N, THF, RT, 12 h; c) LiOH, THF—H₂O, RT, 12 h.

Procedures 2-(6-(2-chloro-4-(3-(3-chlorophenyl)ureido)phenyl)-2-ethyl-1-oxo-1,2,3,4-tetrahydronaphthalen-2-yl)acetic acid Ethyl 2-(6-(4-amino-2-chlorophenyl)-2-ethyl-1-oxo-1,2,3,4-tetrahydronaphthalen-2-yl)acetate (213A)

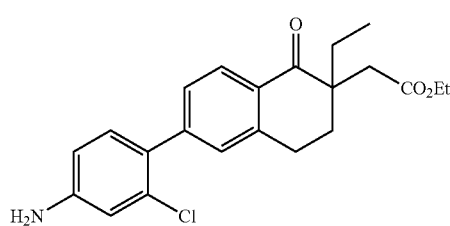

Pd(PPh₃)₄ (0.085 g, 0.073 mmol) was added to a solution of product of Example 115D (3 g, 7.35 mmol) in 40 mL of 1,4 dioxane-H₂O (3:1) mixture under argon atmosphere, followed by cesium carbonate (7.18 g, 22.04 mmol) and 3-chloro-4-(4,4,5,5-tetramethyl-1,3,2-dioxaborolan-2-yl) aniline (1.862 g, 7.35 mmol). The reaction mixture was degassed for 5 min. The reaction mixture was refluxed for 3 h, and solvent was removed under reduced pressure. The residue was partitioned between ethyl acetate and water. The separated organic layer was dried over sodium sulphate, filtered and concentrated under reduced pressure to give curde product which was purified by flash chromatography to afford title compound (3 g, 58%) as solid. ¹H NMR (400 MHz, DMSO-d₆): δ 8.07 (d, J=7.6 Hz, 1H), 7.36 (dd, J₁=1.6 Hz, J₂=8.4 Hz, 1H), 7.26 (m, 1H), 7.11 (d, J=8.4 Hz, 1H), 6.79 (d, J=2 Hz, 1H), 6.62 (dd, J₁=2 Hz, J₂=8.4 Hz, 1H), 4.12 (q, J=7.2 Hz, 2H), 3.13-3.07 (m, 1H), 3.00-2.88 (m, 2H), 2.52-2.38 (m, 2H), 2.09-2.03 (m, 1H), 1.82-1.6 (m, 2H), 1.23 (t, J=7.2 Hz, 3H), 0.92 (t, J=7.8 Hz, 3H).

Ethyl 2-(6-(2-chloro-4-(3-(3-chlorophenyl)ureido)phenyl)-2-ethyl-1-oxo-1,2,3,4-tetrahydronaphthalen-2-yl)acetate (213B)

3-Chloro-3-isocyanatobenzene (0.944 mL, 7.77 mmol) was added to a solution of product of Example 213A (3 g, 7.77 mmol) and triethylamine (2.18 mL, 15.55 mmol) in THF (10 mL), and the reaction mixture was stirred at room temperature overnight. The solvent was removed under reduced pressure, and product was purified by flash chromatography using 20% ethyl acetate in hexanes to afford title compound (1 g, 14%) as yellow solid. ¹H NMR (300 MHz, DMSO-d₆): δ 9.13 (s, 1H), 9.06 (s, 1H), 7.93 (d, J=8.1 Hz, 1H), 7.84 (d, J=2.1 Hz, 1H), 7.72 (s, 1H), 7.46-7.28 (m, 6H), 7.06-7.02 (m, 1H), 4.02 (q, J=7.2 Hz, 2H), 3.31-2.8 (m, 3H), 2.5-2.34 (m, 2H), 2.03-1.99 (m, 1H), 1.73-1.53 (m, 2H), 1.14 (t, J=7.2 Hz, 3H), 0.84 (t, J=7.5 Hz, 3H).

Compound 213B (1 g) was racemic mixture with 1:1 enantiomeric ratio and was separated on chiral column to obtain single enantiomers of 213B1 (Rt 15.15 min) and 213B2 (Rt 16.97 min) using following conditions:
Column: CHIRAL PAK IA 4.6×250 mm, 5µ
Colunm ID: ANL_CHIRAL IA_141
Mobile Phase: D=n-HEXANE (0.1% DEA), C=Ethanol; ISOCRATIC: 90:10; Flow rate: 1.0 mL/min.

2-(6-(2-Chloro-4-(3-(3-chlorophenyl)ureido)phenyl)-2-ethyl-1-oxo-1,2,3,4-tetrahydronaphthalen-2-yl)acetic acid (213)

Chiral: enantiomer-1

Lithium hydroxide (0.136 g, 3.24 mmol) was added to a solution of product of Example 213B1 (0.35 g, 0.649 mmol) in 12 mL of THF-water (5:1) mixture, and the reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., solids were collected by filtration and dried under vacuum to afford title compound (0.24 g, 71%) as white solid. $^1$H NMR (300 MHz, DMSO-d$_6$): δ 12.16 (bs, 1H), 9.21 (bs, 2H), 7.93 (d, J=8.1 Hz, 1H), 7.87 (s, 1H), 7.72 (s, 1H), 7.41-7.27 (m, 6H), 7.08-7.0 (m, 1H), 3.07-3.03 (m, 1H), 2.94-2.79 (m, 2H), 2.50-2.34 (m, 2H), 2.00-1.95 (m, 1H), 1.72-1.49 (m, 2H), 0.85 (t, J=7.5 Hz, 3H); LCMS: 98.6% m/z=511 (M+H)$^+$; HPLC purity: 94%.

Example-214

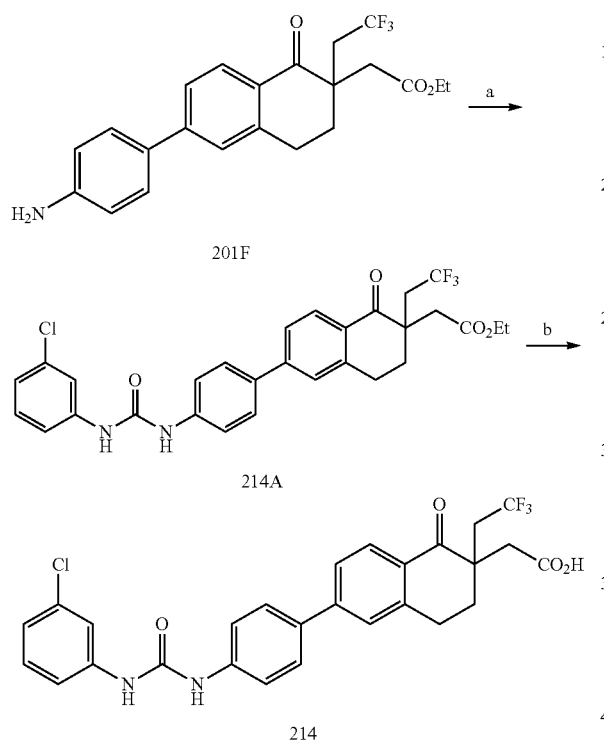

Reagents and conditions: a) 3-ClPhNCO, Et$_3$N, THF, RT, 12 h; b) LiOH, THF—H$_2$O, RT, 12 h.

Procedures 2-(6-(4-(3-(3-Chlorophenyl)ureido)phenyl)-1-oxo-2-(2,2,2-trifluoroethyl)-1,2,3,4-tetrahydronaphthalen-2-yl)acetic acid Ethyl 2-(6-(4-(3-(3-chlorophenyl)ureido)phenyl)-1-oxo-2-(2,2,2-trifluoroethyl)-1,2,3,4-tetrahydronaphthalen-2-yl)acetate (214A)

3-Chlorophenyl isocyanate (0.604 g, 3.95 mmol) was added to a solution of product of Example 201F (1.6 g, 3.95 mmol) and triethylamine (0.79 g, 7.89 mmol) in THF (10 mL), and the reaction mixture was stirred at room temperature overnight. The solvent was removed under reduced pressure, and product was purified by flash chromatography using 20% ethyl acetate in hexanes to afford title compound (1.6 g, 64.5%) as solid. $^1$H NMR (300 MHz, DMSO-d$_6$): δ 8.95 (bs, 2H), 7.93 (d, J=8.1 Hz, 1H), 7.73-7.57 (m, 7H), 7.31-7.29 (m, 2H), 7.05-7.02 (m, 1H), 4.04 (q, J=7.3 Hz, 2H), 2.91-2.85 (m, 4H), 2.72-2.64 (m, 2H), 2.39 (m, 2H), 1.15 (t, J=7.2 Hz, 3H). Yield=64.5%.

Compound 214A was racemic mixture with 1:1 enantiomeric ratio and was separated on chiral column to obtain single enantiomers of 214A1 (Rt 5.832 min) and 214A2 (Rt 6.469 min) using following prep conditions:

Column: CHIRAL PAK IA 4.6×250 mm,

Colunm ID: ANL_CHIRAL IA_110

Mobile Phase: A=n-HEXANE, C=Ethanol; ISOCRATIC: 60:40; Flow rate: 1.0 mL/min 2-(6-(4-(3-(3-Chlorophenyl)ureido)phenyl)-1-oxo-2-(2,2,2-trifluoroethyl)-1,2,3,4-tetrahydronaphthalen-2-yl)acetic acid (214)

Chiral: enantiomer-1

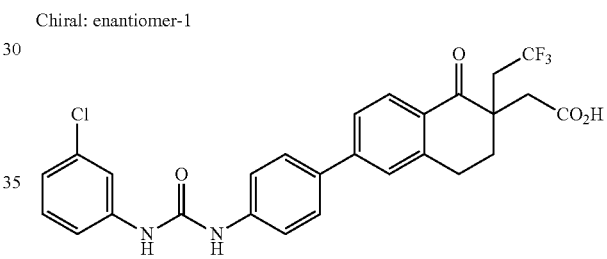

Lithium hydroxide (0.131 g, 3.13 mmol) was added to a solution of product of Example 214A1 (0.35 g, 0.626 mmol) in 10 mL of THF-water (4:1) mixture, and the reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., solids were collected by filtration and dried under vacuum to afford title compound (0.22 g, 65%) as white solid. $^1$H NMR (400 MHz, DMSO-d$_6$): δ 11.8 (bs, 1H), 9.8 (bs, 2H), 7.95 (d, J=8 Hz, 1H), 7.75 (m, 1H), 7.7-7.5 (m, 6H), 7.36-7.26 (m, 2H), 7.0 (d, J=7.2 Hz, 1H), 3.16-2.96 (m, 3H), 2.95-2.78 (m, 2H), 2.54 (m, 1H), 2.46 (m, 1H), 2.16-2.12 (m, 1H); ESI-MS m/z: 495 (M–H)$^−$; HPLC purity: 95%.

Alternative Synthesis of Example 214

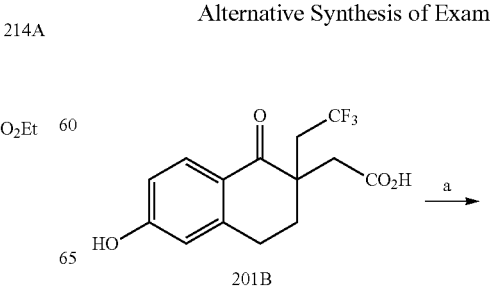

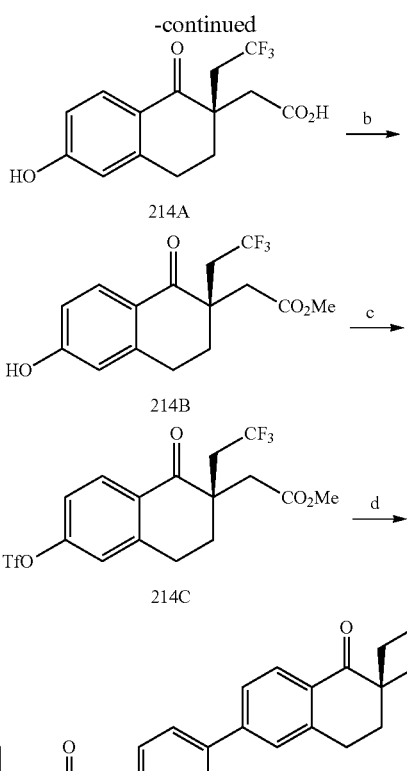

Reagents and conditions: a) Cinchonidine, IPA-H₂O, 80° C. - RT, 24 h then 5N HCl, RT; b) H₂SO₄, MeOH, 70° C., 12 h; c) Tf₂O, CH₂Cl₂, Et₃N, RT, 1 h.

Procedures (S)-2-(6-hydroxy-1-oxo-2-(2,2,2-trifluoroethyl)-1,2,3,4-tetrahydronaphthalen-2-yl)acetic acid

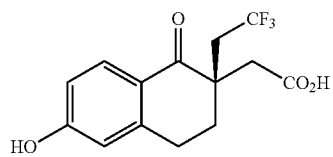

Cinchonidine (0.97 g, 3.31 mmol) was added to a solution of product of Example 201B (1 g, 3.31 mmol), in isopropyl alcohol (9 mL) and water (3 mL), and the reaction mixture was heated to 80° C. 4 h. The resulting solution was stirred at room temperature for 16 h, and the salt was filtered and washed with a mixture of isopropyl alcohol (2 mL) and water (2 mL). The salt was dissolved in 5N HCl (5 mL), extracted with ethyl acetate (25 mL), dried and concentrated to afford the title compound (0.18 g, 18%) as white solid. $^1$H NMR (300 MHz, DMSO-$d_6$): δ 12.2 (bs, 1H), 10.4 (s, 1H), 7.75 (d, J=8.1 Hz, 1H), 6.74 (dd, $J_1$=2.1 Hz, $J_2$=8.1 Hz, 1H), 6.64 (s, 1H), 3.05-2.80 (m, 3H), 2.75-2.60 (m, 2H), 2.45 (m, 1H), 2.35 (m, 1H), 2.15-2.0 (m, 1H).

Compounds 214B, 214C and 214 may be synthesized from chiral 214A compound using the procedures analogous to those described for Example-201 and 214.

Example-215

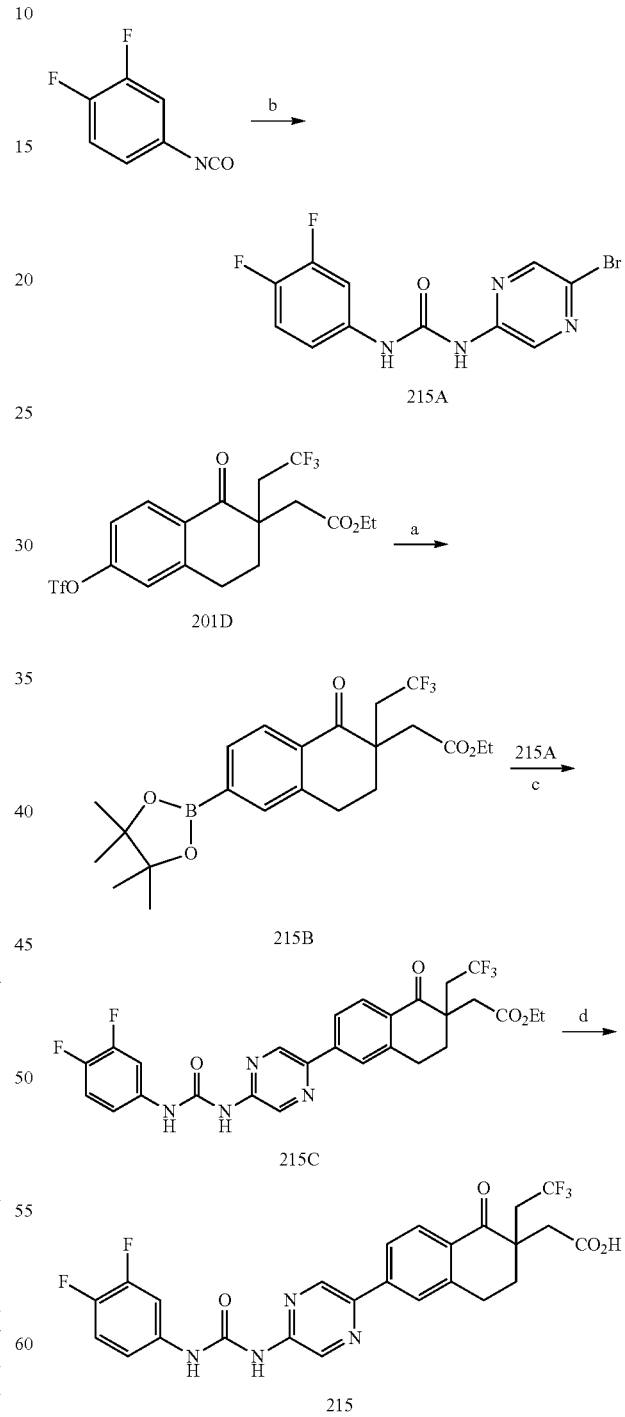

Reagents and conditions: e) PdCl₂(dppf), KOAc, Dioxane, 100° C., 5 h; b) 2-amino-4-bromo pyrazine, Et₃N, Toluene, 120° C., 12 h; c) Pd(PPh₃)₄, Cs₂CO₃, Dioxane-H₂O, 80° C., 5 h; d) LiOH,EtOH—H₂O, RT, 12 h.

Procedures

2-(6-(5-(3-(3,4-Difluorophenyl)ureido)pyrazin-2-yl)-1-oxo-2-(2,2,2-trifluoroethyl)-1,2,3,4-tetrahydronaphthalen-2-yl)acetic acid

1-(5-Bromopyrazin-2-yl)-3-(3,4-difluorophenyl)urea (215A)

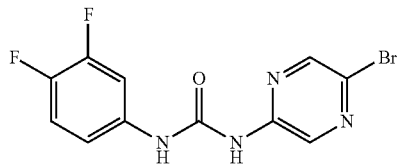

3,4-Difluorophenyl isocyanate (8.8 g, 56.9 mmol) was added to a solution of 2-amino-4-bromo pyrazine (9 g, 51.72 mmol) and triethyl amine (3.98 mL, 28.4 mmol) in toluene (100 mL), and the reaction mixture was stirred at 120° C. for 12 hr. The solvent was removed under reduced pressure, and the residue was purified by flash chromatography eluting with 20% ethyl acetate in hexane to afford title compound (10 g, 59%) as solid. $^{1}$H NMR (300 MHz, DMSO-$d_6$): δ 9.69 (s, 1H), 9.46 (s, 1H), 8.93 (d, J=1.2 Hz, 1H), 8.52 (d, J=1.8 Hz, 1H), 7.74-7.64 (m, 1H), 7.46-7.32 (m, 1H), 7.22-7.14 (m, 1H).

Ethyl 2-(1-oxo-6-(4,4,5,5-tetramethyl-1,3,2-dioxaborolan-2-yl)-2-(2,2,2-trifluoroethyl)-1,2,3,4-tetrahydronaphthalen-2-yl)acetate (215B)

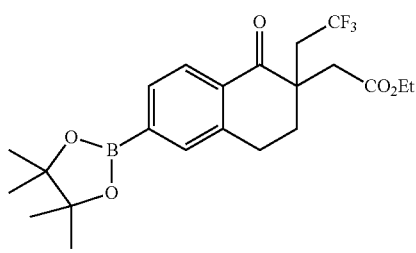

PdCl$_2$(dppf)-CH$_2$Cl$_2$ adduct (0.58 g, 0.71 mmol) was added to a solution of Example 201D (6.6 g, 14.27 mmol) in 50 mL of 1,4 dioxane in argon atmosphere, followed by potassium acetate (4.19 g, 42.85 mmol) and 4,4,4',4',5,5,5',5'-octamethyl-2,2'-bi(1,3,2-dioxaborolane) (3.62 g, 14.27 mmol). The reaction mixture was degassed for 5 min. The reaction mixture was refluxed for 5 hr, cooled to room temperature and filtered over celite bed. The filtrate was concentrated under reduced pressure, and the residue was purified by flash chromatography using 10% ethyl acetate in hexane to afford title compound (5.6 g, 89%) as viscous liquid.: $^{1}$HNMR (400 MHz, CDCl$_3$): δ 8.02 (d, J=7.6 Hz, 1H), 7.75 (d, J=7.6 Hz, 1H), 7.70 (s, 1H), 4.14-4.09 (q, J=7.2 Hz, 2H), 3.06-3.03 (m, 2H), 2.89-2.82 (m, 2H), 2.63-2.56 (m, 2H), 2.42-2.29 (m, 2H), 1.35-1.31 (m, 3H), 1.24-1.19 (m, 12H).

Ethyl 2-(6-(5-(3-(3,4-difluorophenyl)ureido)pyrazin-2-yl)-1-oxo-2-(2,2,2-trifluoroethyl)-1,2,3,4-tetrahydronaphthalen-2-yl)acetate (215C)

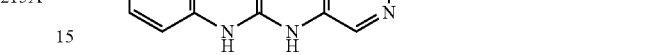

Pd(PPh$_3$)$_4$ (0.3 g, 0.26 mmol) was added to a solution of Example 215B (2.3 g, 3.22 mmol) in 60 mL of 1,4 dioxane-H$_2$O (5:1) mixture under argon atmosphere, followed by cesium carbonate (5.11 g, 15.67 mmol) and compound 215A (2.063 g, 6.27 mmol). The reaction mixture was degassed for 30 min. The reaction mixture was refluxed for 16 h, and solvent was removed under reduced pressure. The residue was partitioned between ethyl acetate and water, organic layer was separated, dried over Na$_2$SO$_4$, filtered and concentrated under reduced pressure. The product was purified by flash chromatography using 18% ethyl acetate in hexane to afford title compound (1 g, 32%) as solid. $^{1}$H NMR (300 MHz, DMSO-$d_6$): δ 9.82 (s, 1H), 9.75 (s, 1H), 9.16 (d, J=1.5 Hz, 1H), 9.03 (d, J=1.5 Hz, 1H), 8.10-7.95 (m, 3H), 7.78-7.68 (m, 1H), 7.48-7.35 (m, 1H), 7.26-7.18 (m, 1H), 4.08-3.98 (q, J=7.2 Hz, 2H), 3.26-3.10 (m, 2H), 3.08-2.85 (m, 2H), 2.80-2.64 (m, 2H), 2.48-2.36 (m, 2H), 2.28-2.15 (m, 1H), 1.14 (t, J=7.2 Hz, 3H). ESI-MS m/z=563 (M+1).

Compound 215C was racemic mixture with 1:1 enantiomeric ratio and was separated on chiral column to obtain single enantiomers of 215C1 (Rt 9.394 min) and 215C2 (Rt 12.342 min) using following prep conditions:

Column: CHIRAL PAK IA 4.6×250 mm, 5μ

Mobile Phase: A=n-HEXANE, C=isopropanol; ISOCRATIC: 70:30; Flow rate: 1.0 mL/min

2-(6-(5-(3-(3,4-Difluorophenyl)ureido)pyrazin-2-yl)-1-oxo-2-(2,2,2-trifluoroethyl)-1,2,3,4-tetrahydronaphthalen-2-yl)acetic acid (215)

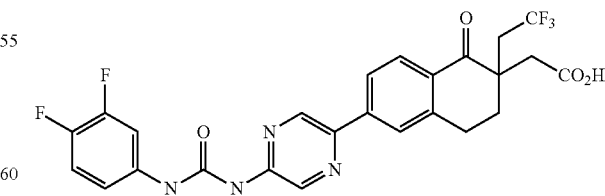

Chiral: enantiomer-1

Lithium hydroxide (0.075 g, 3.11 mmol) was added to a solution of product of Example 215C (0.35 g, 0.62 mmol) in 30 mL of ethanol-water (5:1) mixture, and the reaction mixture was stirred at room temperature overnight. After the solvent was removed in vacuo, the residue was dissolved in water and washed with ethyl acetate. The aqueous layer was acidified with addition of 2N aqueous solution of HCl until pH 2 was attained. The resulting solution was cooled to 0° C., and solids were collected by filtration and dried under vacuum to afford title compound (0.255 g, 76%) as white solid. $^1$H NMR (300 MHz, DMSO-$d_6$): δ 12.42 (bs, 1H), 9.83 (s, 1H), 9.77 (s, 1H), 9.16 (d, J=1.2 Hz, 1H), 9.02 (d, J=1.5 Hz, 1H), 8.1-7.94 (m, 3H), 7.78-7.68 (m, 1H), 7.46-7.35 (m, 1H), 7.24 (m, 1H), 3.41-3.35 (m, 1H), 3.20-2.95 (m, 2H), 2.88-2.80 (m, 2H), 2.65-2.55 (m, 1H), 2.50-2.42 (m, 1H), 2.24-2.14 (m, 1H). ESI-MS m/z=535 {(M+H)$^+$}. HPLC purity: 98.87%.

Example-216

Procedures 2-(6-(5-(3-cyclohexylureido)pyrazin-2-yl)-1-oxo-2-(2,2,2-trifluoroethyl)-1,2,3,4-tetrahydronaphthalen-2-yl)acetic acid 1-(5-bromopyrazin-2-yl)-3-cyclohexylurea (216A)

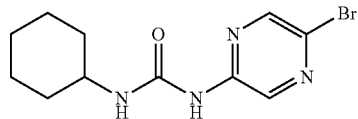

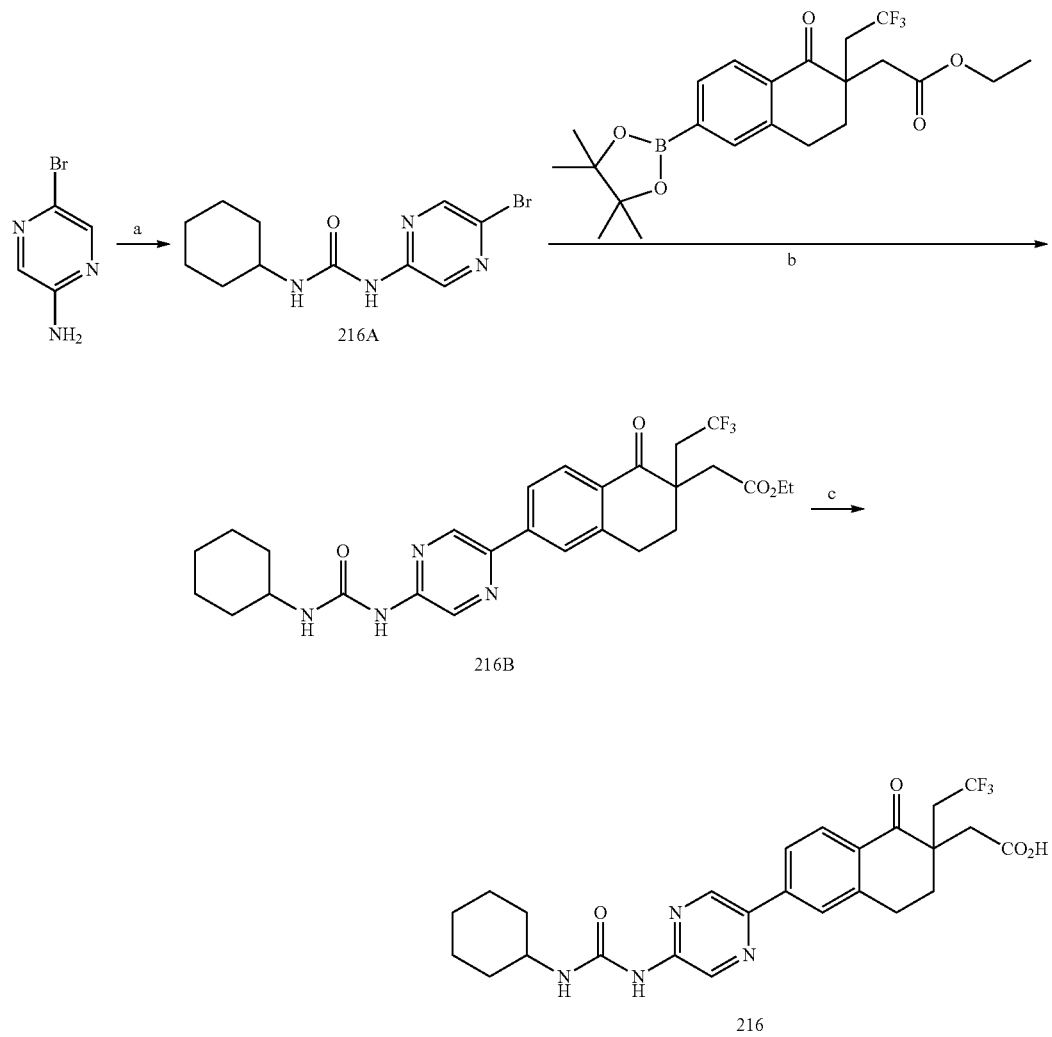

Reagents and conditions: a) cyclohexyl isocyanate, Et$_3$N, Toluene, 120° C., 12 h; b) Pd(PPh$_3$)$_4$, Cs$_2$CO$_3$, Dioxane-H$_2$O, 80° C., 5 h; c) LiOH, Dioxane-H$_2$O, RT, 12 h.

Isocyanatocyclohexane (2.158 g, 17.24 mmol) was added to a solution of 2-amino-4-bromo pyrazine (3 g, 17.24 mmol) and triethylamine (1 mL, 7.17 mmol) in 20 mL toluene and stirred at 120° C. for 5 h. The solvent was evaporated under reduced pressure and the residue was purified by flash chromatography using 15% ethyl acetate in hexane to afford title compound (1.60 g, 31%) as solid. $^1$HNMR (300 MHz, CDCl$_3$): δ 9.6 (bs, 1H), 8.38 (bs, 1H), 8.2 (m, 2H), 3.8 (m, 1H), 2.04-1.95 (m, 2H), 1.75-1.58 (m, 3H), 1.49-1.13 (m, 5H).

Ethyl 2-(6-(5-(3-cyclohexylureido)pyrazin-2-yl)-1-oxo-2-(2,2,2-trifluoroethyl)-1,2,3,4-tetrahydronaphthalen-2-yl)acetate (216B)

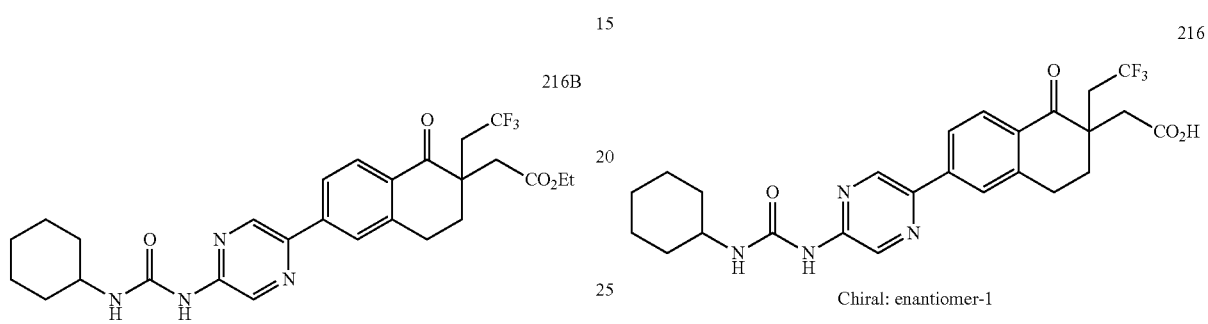

Pd(Ph$_3$P)$_4$ (0.07 g, 0.06 mmol) was added to a solution of Example 216A (1.50 g, 5.01 mmol) in 15 mL of 1,4 dioxane-H$_2$O (3:1) mixture under argon atmosphere, followed by cesium carbonate (4.90 g, 15.04 mmol) and Example 216B (2.2 g, 5.01 mmol). The reaction mixture was degassed for 5 min. The reaction mixture was refluxed for 5 hr, and solvent was removed under reduced pressure. The residue was partitioned between ethyl acetate and water, organic layer was separated, dried over Na$_2$SO$_4$, filtered and concentrated under reduced pressure. The product was purified by flash chromatography using 30% ethyl acetate in hexane to afford title compound (0.88 g, 33%) as solid. $^1$H NMR (300 MHz, CDCl$_3$): δ 8.8 (bs, 2H), 8.6 (s, 1H), 8.39 (bs, 1H), 8.15 (d, J=7.2 Hz, 1H), 7.9-7.85 (m, 2H), 4.13 (q, J=7.2 Hz, 2H), 3.85 (m, 1H), 3.13 (t, J=6.6 Hz, 2H), 2.9-2.85 (m, 2H), 2.67-2.60 (m, 2H), 2.4-2.3 (m, 2H), 2.0 (m, 2H), 1.7-1.6 (m, 3H), 1.4-1.2 (m, 8H).

Compound 216B (0.88 g) was racemic mixture with 1:1 enantiomeric ratio and was separated in chiral column to obtain single enantiomers of 216B1 (Rt 11.1 min) and 216B2 (Rt 15.1 min) using following conditions:
Column: Chiralpak IA (4.6×250 mm) 5μ
Mobile Phase D=n-Hexane (0.1% TFA) B=IPA; Isocratic: D:B=80:20; Flow Rate: 1.0 mL/min 2-(6-(5-(3-cyclohexylureido)pyrazin-2-yl)-1-oxo-2-(2,2,2-trifluoroethyl)-1,2,3,4-tetrahydronaphthalen-2-yl)acetic acid (216)

Chiral: enantiomer-1

LiOH (40.5 mg, 1.69 mmol) was added to a solution of Example 216B1 (300 mg, 0.563 mmol) in 7 mL of 1,4-dioxane-H$_2$O (3:1) mixture, and the reaction mixture was stirred at room temperature for 12 hr. After the solvent was removed in vacuum, the residue was dissolved in water and washed with ethyl acetate. The aqueous layer was acidified with addition of saturated citric acid solution until pH 2 was attained. The resulting solution was cooled to 0° C., solids were collected by filtration and dried under vacuum to afford title compound (0.220 g, 77%) as white solid. $^1$H NMR (400 MHz, DMSO-d$_6$): δ 12.4 (bs, 1H), 9.56 (bs, 1H), 9.04 (s, 1H), 8.9 (s, 1H), 8.06-7.95 (m, 3H), 7.4 (d, J=7.2 Hz, 1H), 3.56 (m, 1H), 3.16-2.69 (m, 5H), 2.5-2.37 (m, 2H), 2.13 (m, 1H), 1.8 (m, 2H), 1.65-1.5 (m, 3H), 1.39-1.2 (m, 5H); LCMS m/z=505 (M+H)$^+$; HPLC PURITY=97.8%.

Example-217

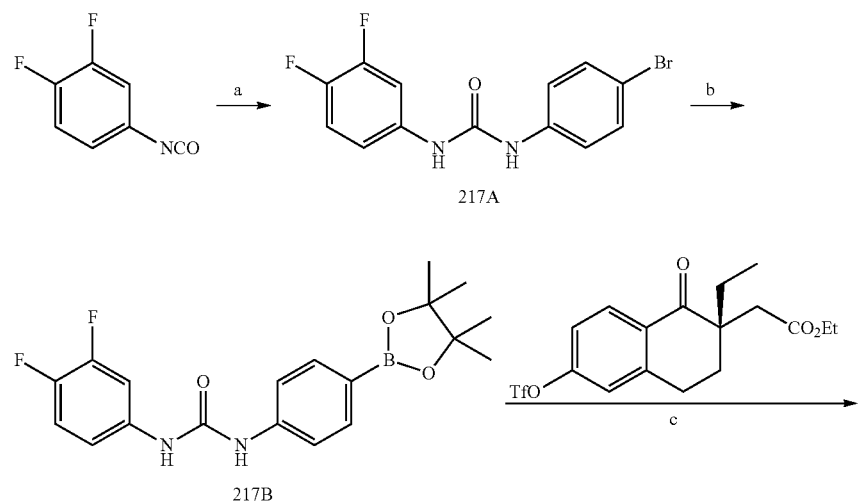

-continued

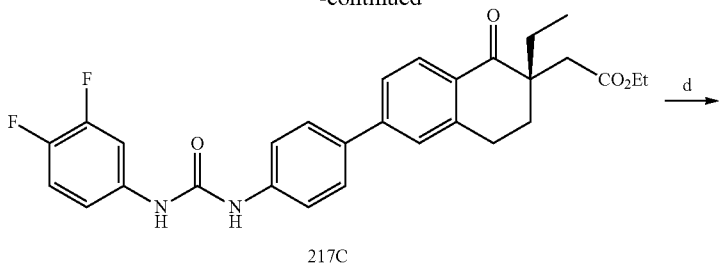

217C

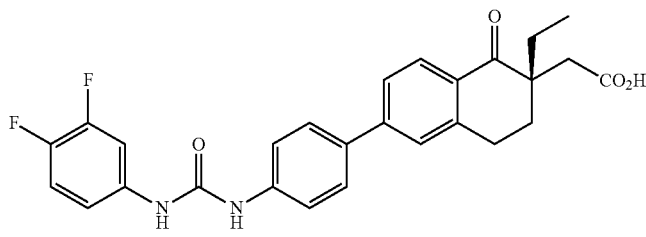

217

Reagents and conditions: a) 4-bromo aniline, THF, RT, 12 h; b) PdCl₂(dppf), bis-pinacolato diborane, KOAc, DMF, 85° C., 6 h; c) Pd(PPh₃)₄, Cs₂CO₃, Dioxane-H₂O, 80° C., 12 h; d) LiOH, Dioxane-H₂O, RT, 12 h.

Procedures (S)-2-(6-(4-(3-(3,4-Difluorophenyl)ureido)phenyl)-2-ethyl-1-oxo-1,2,3,4-tetrahydronaphthalen-2-yl)acetic acid 1-(4-bromophenyl)-3-(3,4-difluorophenyl)urea (217A)

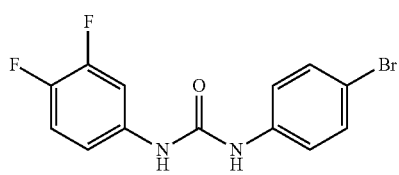

3,4-Difluorophenyl isocyanate (0.74 g, 4.8 mmol) was added to a solution of 4-bromo aniline (0.75 g, 4.36 mmol) in THF (20 mL) and stirred at room temperature for 2 hr. The solvent was removed under reduced pressure and the residue was triturated with chloroform (60 mL) to afford title compound (0.6 g, 42%) as solid. $^1$H NMR (300 MHz, DMSO-d₆): δ 8.9 (s, 1H), 8.87 (s, 1H), 7.64 (m, 1H), 7.47-7.41 (m, 4H), 7.39 (m, 1H), 7.2 (m, 1H).

1-(3,4-difluorophenyl)-3-(4-(4,4,5,5-tetramethyl-1,3,2-dioxaborolan-2-yl)phenyl)urea (217B)

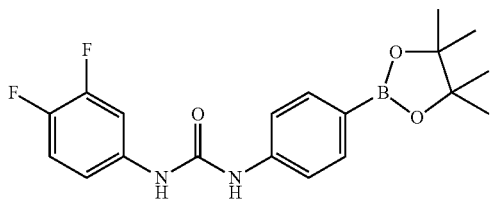

PdCl₂(dppf)CH₂Cl₂ (0.125 g, 0.153 mmol) was added to a solution of Example 217A (1.0 g, 3.06 mmol) in 15 mL of DMF, followed by potassium acetate (0.6 g, 6.11 mmol) and 4,4,4',4',5,5,5',5'-octamethyl-2,2'-bi(1,3,2-dioxaborolane) (0.932 g, 3.67 mmol), and the solution was degassed for 30 min using argon. The reaction mixture was stirred at 85° C. for 6 h and then concentrated under reduced pressure. The residue was partitioned between ethyl acetate and water. The organic layer was separated dried over Na₂SO₄ and concentrated under reduced pressure. The product was purified by flash chromatography using 15% ethyl acetate in DCM to afford title compound (0.6 g, 52%) as solid. $^1$H NMR (400 MHz, DMSO-d₆): δ 8.9 (m, 2H), 7.7 (m, 1H), 7.63-7.59 (m, 2H), 7.5-7.42 (m, 2H), 7.4-7.3 (m, 1H), 7.1 (m, 1H), 1.3 (s, 12H). ESI-MS m/z=375 (M+H)⁺.

(S)-Methyl 2-(6-(4-(3-(3,4-difluorophenyl)ureido)phenyl)-2-ethyl-1-oxo-1,2,3,4-tetrahydronaphthalen-2-yl)acetate (217C)

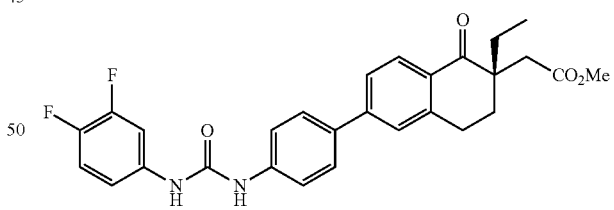

Pd(PPh₃)₄ (0.018 g, 0.015 mmol) was added to a solution of (S)-ethyl 2-(2-ethyl-1-oxo-6-(trifluoromethylsulfonyloxy)-1,2,3,4-tetrahydronaphthalen-2-yl)acetate (129C, 0.3 g, 0.761 mmol) in 10 mL 1,4 dioxane-H₂O (4:1) mixture under argon atmosphere, followed by cesium carbonate (0.74 g, 2.28 mmol) and Example 217B (0.313 g, 0.837 mmol). The reaction mixture was degassed for 30 min. The reaction mixture was refluxed for 12 h, and solvent was removed under reduced pressure. The residue was partitioned between ethyl acetate and water. The organic layer was separated, dried over Na₂SO₄, filtered and concentrated under reduced pressure. The product was purified by flash chromatography using 20% ethyl acetate in hexane to afford title compound (0.15 g, 40%)

as solid. ¹H NMR (400 MHz, CDCl₃): δ 8.05 (s, 1H), 8.03 (s, 1H), 7.44-7.37 (m, 3H), 7.35-7.31 (s, 4H), 7.18 (m, 1H), 7.08-6.97 (m, 2H), 3.67 (s, 3H), 3.14 (m, 1H), 3.04 (d, J=16 Hz, 1H), 2.90 (m, 1H), 2.5 (d, J=16 Hz, 1H), 2.45 (m, 1H), 2.05 (m, 1H), 1.79-1.6 (m, 2H), 0.94 (t, J=7.6 Hz, 3H); ESI-MS m/z=493 (M+H)⁺.

(S)-2-(6-(4-(3-(3,4-Difluorophenyl)ureido)phenyl)-2-ethyl-1-oxo-1,2,3,4-tetrahydronaphthalen-2-yl)acetic acid (217)

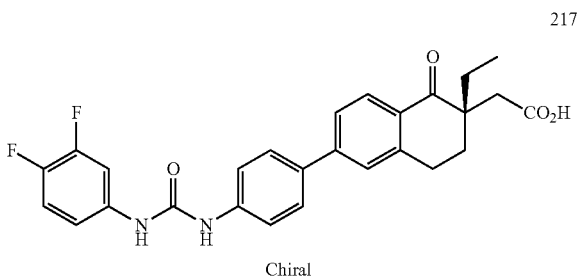 [SMILES: CC[C@@]1(CC(=O)O)CCc2cc(-c3ccc(NC(=O)Nc4ccc(F)c(F)c4)cc3)ccc2C1=O]

LiOH (17.9 mg, 0.426 mmol) was added to a solution of Example 217C (70 mg, 0.142 mmol) in 5 mL of 1,4-dioxane-H₂O (4:1) mixture, and the reaction mixture was stirred at room temperature for 12 hr. After the solvent was removed in vacuum, the residue was dissolved in water and washed with ethyl acetate. The aqueous layer was acidified with addition of saturated citric acid solution until pH 2 was attained. The resulting solution was cooled to 0° C., and solids were collected by filtration and dried under vacuum to afford title compound (0.035 g, 51%) as pale yellow solid. ¹H NMR (400 MHz, DMSO-d₆): δ 12.05 (bs, 1H), 8.95 (s, 1H), 8.9 (s, 1H), 7.92 (d, J=8 Hz, 1H), 7.7-7.65 (m, 3H), 7.63-7.56 (m, 4H), 7.35 (q, J=8 Hz, 1H), 7.15 (m, 1H), 3.07 (m, 1H), 2.96 (m, 1H), 2.8 (d, J=16.8 Hz, 1H), 2.44 (m, 1H), 2.4 (d, J=16 Hz, 1H), 1.9 (m, 1H), 1.68 (m, 1H), 1.54 (m, 1H), 0.84 (t, J=7.2 Hz, 3H); LCMS m/z=479 (M+H)⁺; PURITY=95%.

Examples 218-230 were prepared by procedures analogous to those described in Examples 190, and 212-217 using appropriate starting materials. The requisite boronic acids (and appropriately functional-group-protected versions thereof) utilized herein were purchased if available commercially, were synthesized as described in the literature or by routine modifications thereof known by those skilled in the art, or were synthesized by alternative procedures known by those skilled in the art.

| Exp | Structure | Analytical Data | (M + H)⁺ |
|---|---|---|---|
| 218 | Chiral: enantiomer-1 | ¹H NMR (400 MHz, DMSO-d₆): δ 12.1 (bs, 1H), 9.23 (s, 1H), 9.18 (s, 1H), 8.02 (s, 1H), 7.93 (d, J = 8.4 Hz, 1H), 7.85 (s, 1H), 7.63-7.58 (m, 1H), 7.56-7.51 (m, 1H), 7.46-7.32 (m, 5H), 3.14-3.04 (m, 1H), 2.97-2.89 (m, 1H), 2.84-2.77 (m, 1H), 2.48-2.36 (m, 2H), 2.02-1.96 (m, 1H), 1.74-1.62 (m, 1H), 1.58-1.50 (m, 1H), 0.84 (t, J = 7.2 Hz, 3H). | ESI-MS m/z: 545 (M + H)⁺; HPLC purity: 99%. |
| 219 | Chiral: enantiomer-1 | ¹H NMR (400 MHz, DMSO-d₆): δ 12.4 (bs, 1H), 9.52 (bs, 1H), 9.04 (s, 1H), 8.92 (s, 1H), 8.04-7.95 (m, 3H), 7.23 (d, J = 8.4 Hz, 1H), 3.55 (m, 1H), 3.15-2.96 (m, 3H), 2.75 (m, 2H), 2.50-2.40 (m, 2H), 2.15 (m, 1H), 1.6-1.35 (m, 4H), 0.9 (t, J = 7.6 Hz, 6H). | ESI-MS m/z: 493 (M + H)⁺; HPLC purity: 99%. |
| 220 | Chiral: enantiomer-1 | ¹H NMR (300 MHz, DMSO-d₆): δ 12.4 (bs, 1H), 9.9 (bs, 1H), 9.7 (bs, 1H), 9.18 (d, J = 1.5 Hz, 1H), 8.99 (d, J = 1.2 Hz, 1H), 8.07-7.97 (m, 3H) 7.43 (d, J = 8.4 Hz, 2H), 7.15 (d, J = 8.4 Hz, 2H), 3.2-2.7 (m, 6H), 2.6-2.50 (m, 2H), 2.46 (m, 1H), 2.18 (m, 1H), 1.15 (t, J = 7.5 Hz, 3H). | ESI-MS m/z: 525 (M − H)⁻; HPLC purity: 98%. |

-continued

| Exp | Structure | Analytical Data | (M + H)+ |
|---|---|---|---|
| 221 | Chiral: enantiomer-1 | $^1$H NMR (400 MHz, DMSO-$d_6$): δ 12.4 (bs, 1H), 8.85 (bs, 1H), 7.92 (d, J = 8.4 Hz, 1H), 7.66-7.58 (m, 4H), 7.5 (d, J = 8.8 Hz, 2H), 6.44 (bs, 1H), 3.12-2.9 (m, 5H), 2.85-2.65 (m, 2H), 2.5-2.4 (m, 2H), 2.12 (m, 1H), 1.45-1.25 (m, 4H), 0.9 (t, J = 7.2 Hz, 3H). | ESI-MS m/z: 477 (M + H)+; HPLC purity: 95%. |
| 222 | Chiral: enantiomer-1 | $^1$H NMR (400 MHz, DMSO-$d_6$): δ 12.4 (bs, 1H), 9.22 (bs, 1H), 9.1 (bs, 1H), 8.03 (s, 1H), 7.93 (d, J = 7.6 Hz, 1H), 7.72-7.58 (m, 7H), 7.53 (t, J = 7.6 Hz, 1H), 7.32 (d, J = 7.2 Hz, 1H), 3.2-2.65 (m, 5H), 2.6-2.44 (m, 2H), 2.18 (m, 1H). | ESI-MS m/z: 565 (M + H)+; HPLC purity: 98%. |
| 223 | Chiral: enantiomer-1 | $^1$H NMR (400 MHz, DMSO-$d_6$): δ 12.4 (bs, 1H), 9.87 (s, 1H), 9.83 (s, 1H), 9.17 (s, 1H), 9.02 (s, 1H), 8.12-7.96 (m, 3H), 7.77 (s, 1H), 7.36 (d, J = 4.8 Hz, 2H), 7.1 (m, 1H), 3.24-2.92 (m, 3H), 2.83 (d, J = 16.4 Hz, 1H), 2.8-2.65 (m, 1H), 2.57 (d, J = 16.0 Hz, 1H), 2.50-2.42 (m, 1H), 2.24-2.15 (m, 1H). | ESI-MS m/z: 531 (M − H)−; HPLC purity: 99% |
| 224 | Chiral: enantiomer-1 | $^1$H NMR (300 MHz, DMSO-$d_6$): δ 12.4 (bs, 1H), 9.32 (bs, 1H), 9.26 (bs, 1H), 7.94 (d, J = 7.5 Hz, 1H), 7.75-7.5 (m, 8H), 7.16 (s, 1H), 3.20-2.90 (m, 3H), 2.85-2.64 (m, 2H), 2.6-2.4 (m, 2H), 2.19-2.08 (m, 1H). | ESI-MS m/z: 565 (M + H)+; HPLC purity: 99%. |
| 225 | Chiral: enantiomer-1 | $^1$H NMR (400 MHz, DMSO-$d_6$): δ 12.3 (bs, 1H), 8.85 (s, 1H), 8.65 (s, 1H), 7.93 (d, J = 8 Hz, 1H), 7.71-7.57 (m, 6H), 7.37 (d, J = 8 Hz, 2H), 7.12 (d, J = 7.6 Hz, 2H), 3.2-2.92 (m, 3H), 2.84-2.65 (m, 2H), 2.60-2.40 (m, 4H), 2.21-2.10 (m, 1H), 1.16 (t, J = 7.2 Hz, 3H). | ESI-MS m/z: 525 (M + H)+; HPLC purity: 99%. |

-continued

| Exp | Structure | Analytical Data | (M + H)+ |
|---|---|---|---|
| 226 | Chiral: enantiomer-1 | ¹H NMR (400 MHz, DMSO-d₆): δ 12.4 (bs, 1H), 8.5 (bs, 1H), 7.91 (d, J = 8.4 Hz, 1H), 7.63 (m, 4H), 7.49 (d, J = 8.4 Hz, 2H), 6.14 (d, J = 7.2 Hz, 1H), 3.46 (m, 1H), 3.15-2.9 (m, 3H), 2.85-2.6 (m, 2H), 2.55-2.40 (m, 2H), 2.17-2.10 (m, 1H), 1.88-1.60 (m, 4H), 1.53 (m, 1H), 1.40-1.12 (m, 5H). | ESI-MS m/z: 503 (M + H)+; HPLC purity: 99%. |
| 227 | Chiral: enantiomer-1 | ¹H NMR (400 MHz, DMSO-d₆): δ 12.4 (bs, 1H), 9.12 (bs, 1H), 9.05 (bs, 1H), 7.94 (d, J = 8.4 Hz, 1H), 7.84 (s, 1H), 7.71 (s, 1H), 7.46-7.37 (m, 4H), 7.34-7.30 (m, 2H), 7.05 (m, 1H), 3.2-2.9 (m, 3H), 2.85 (d, J = 16 Hz, 1H), 2.76-2.66 (m, 1H), 2.59 (d, J = 16 Hz, 1H), 2.50-2.44 (m, 1H), 2.17 (m, 1H). | ESI-MS m/z: 565 (M + H)+; HPLC purity: 99%. |
| 228 | Chiral: enantiomer-1 | 1H NMR (300 MHz, DMSO-d₆): δ 12.2 (bs, 1H), 9.13 (s, 1H), 9.01 (s, 1H), 8.03 (s, 1H), 7.95 (d, J = 7.8 Hz, 1H), 7.75-7.48 (m, 8H), 7.32 (d, J = 7.8 Hz, 1H), 3.28-3.15 (m, 1H), 3.13 (s, 3H), 2.90 (d, J = 15.6 Hz, 2H), 2.72 (d, J = 15.3 Hz, 1H), 2.42-2.38 (m, 2H). | ESI-MS m/z: 512 (M + H)+; HPLC purity: 98%. |
| 229 | Chiral: enantiomer-1 | 1H NMR (400 MHz, DMSO-d₆): δ 12.2 (bs, 1H), 8.95 (s, 2H), 7.95 (d, J = 8.0 Hz, 1H), 7.73-7.56 (m, 7H), 7.32-7.28 (m, 2H), 7.05-7.01 (m, 1H), 3.28-3.15 (m, 1H), 3.13 (s, 3H), 2.94-2.86 (m, 2H), 2.71 (d, J = 16 Hz, 1H), 2.48-2.38 (m, 2H). | ESI-MS m/z: 479 (M + H)+; HPLC purity: 99%. |
| 230 | Chiral: enantiomer-1 | ¹H NMR (400 MHz, DMSO-d₆): δ 12.4 (bs, 1H), 9.51 (bs, 1H), 9.04 (d, J = 1.6 Hz, 1H), 8.92 (d, J = 1.2 Hz, 1H), 8.05-7.95 (m, 3H), 7.23 (d, J = 7.6 Hz, 1H), 4.19 (m, 1H), 3.18-2.90 (m, 3H), 2.85-2.6 (m, 2H), 2.50-2.40 (m, 2H), 2.3-2.1 (m, 3H), 1.9 (m, 2H), 1.65 (m, 2H). | ESI-MS m/z: 477 (M + H)+; LCMS purity: 98%. |

Biological Assay

Inhibition of Human DGAT1 Activity In Vitro

Human DGAT1 was expressed in Sf9 insect cells using a baculovirus expression system. Microsomes were prepared and used as enzyme for in vitro inhibition testing in either of two formats measuring production of coenzyme A or tridecanoylglycerol product, respectively. All steps were performed at 21-23° C. All data for DGAT1 inhibition by test compounds were collected under conditions where product formation was linear with reaction time.

For inhibition of CoA product formation, test compounds were prepared in 100% DMSO, diluted 100-fold into assay buffer, and 10 uL added to 96-well half-area plates (Greiner 675076). An equal volume (10 uL) of 3× enzyme in buffer was added and the components incubated for 30 minutes pre-reaction incubation to allow enzyme and test compounds to attain binding equilibrium. The 3× enzyme mixture contained 30 uM {4-[4-(4-amino-7,7-dimethyl-7H-pyrimido[4,5-b][1,4]oxazin-6-yl)phenyl]cyclohexyl}acetic acid for fully inhibited control wells. Some assays were performed with inclusion of didecanoylglycerol in the pre-reaction incubation of test compound and enzyme. DGAT reactions (30 uL) were initiated upon addition of 10 uL of 3× substrate solution. Final reaction conditions consisted of 20 mM HEPES pH 7.5, 2 mM $MgCl_2$, 1 mM CHAPS, 50 uM didecanoylglycerol, 3 uM decanoyl-CoA, 1 ug/mL microsomal protein, and 1% DMSO. Following a 60 minute reaction incubation, reactions were stopped and CoA product derivatized with 30 uL of buffer containing 10 uM {4-[4-(4-amino-7,7-dimethyl-7H-pyrimido[4,5-b][1,4]oxazin-6-yl)phenyl]cyclohexyl}acetic acid and 50 uM 7-diethylamino-3-(4'-maleimidylphenyl)-4-methylcoumarin (CPM). Fluorescence was read using Envision reader at Ex 405 nm/Em 480 nm about 30 minutes after addition of final solution Inhibition was normalized to controls containing DMSO or 10 uM {4-[4-(4-amino-7,7-dimethyl-7H-pyrimido[4,5-b][1,4]oxazin-6-yl)phenyl]cyclohexyl}acetic acid. $IC_{50}$s were fitted using GraphPad Prism to a sigmoidal dose response.

For inhibition of triacylglycerol product formation, 11 uL reactions were run in white Polyplate-384 (PerkinElmer6007300) starting with a 30 minute pre-reaction incubation of 5 uL of 2.2× enzyme and 1 uL of 100% DMSO containing test compound or control compound, {4-[4-(4-amino-7,7-dimethyl-7H-pyrimido[4,5-b][1,4]oxazin-6-yl)phenyl]cyclohexyl}acetic acid. Some assays were performed with inclusion of didecanoylglycerol in the pre-reaction incubation of test compounds and enzyme. Reactions were initiated after 30 minute pre-reaction incubation via addition of 5 uL of 2.2× substrate. Final reaction conditions consisted of 50 mM HEPES pH 7.5, 2 mM $MgCl_2$, 1 mM CHAPS, 25 uM didecanoylglycerol, 0.5 uM decanoyl-CoA, 0.3 nCi/uL [$^{14}$C]-decanoyl-CoA or 0.5 nCi/uL [$^{3}$H]-decanoyl-CoA, 0.05-4 ug/mL microsomal protein, and 1% DMSO. Following 60 minute reaction incubation, reactions were stopped with 40 uL of 45% isopropanol and 50 mM sodium carbonate in water and mixed. Extraction of tridecanoylglycerol product was accomplished via addition of 30 uL Microscint-E (Perkin Elmer) and 2 hours of incubation (sealed). Plates were read on a Microbeta Microplate reader Inhibition was normalized to controls containing DMSO or 10 uM {4-[4-(4-amino-7,7-dimethyl-7H-pyrimido[4,5-b][1,4]oxazin-6-yl)phenyl]cyclohexyl}acetic acid. $IC_{50}$s were fitted using GraphPad Prism to a sigmoidal dose response.

Biological Data

Exemplified compounds of the present invention were tested at one or more DGAT assays described above and were found to be inhibitors of DGAT1 with $IC_{50}$<10 uM or % inhibition >50 at 10 uM. Data for some specific examples tested at the human DGAT1 fluorescene (CPM) assay are listed below.

| Example # | hDGAT $IC_{50}$ (nM) |
|---|---|
| 1 | 1880.0 |
| 20 | 586.0 |
| 40 | 357.0 |
| 42 | 60.0 |
| 47 | 180.5 |
| 68 | 503.0 |
| 69 | 113.6 |
| 76 | 112.0 |
| 79 | 35.4 |
| 81 | 18.8 |
| 90 | 12.0 |
| 109 | 14.2 |
| 115 | 2.9 |
| 116 | 18 |

-continued

| Example # | hDGAT $IC_{50}$ (nM) |
|---|---|
| 129 | 3.1 |
| 130 | 138.3 |
| 131 | 2.5 |
| 139 | 10.8 |
| 140 | 31.8 |
| 141 | 9.4 |
| 143 | 11.2 |
| 144 | 5.8 |
| 154 | 47.8 |
| 164 | 4.5 |
| 173 | 10.8 |
| 182 | 48.0 |
| 185 | 32.0 |
| 190 | 67.6 |
| 192 | 10.6 |
| 197 | 2.3 |
| 198 | 55.0 |
| 201 | 2.6 |
| 202 | 6.5 |
| 205 | 3.5 |
| 212 | 32.8 |
| 213 | 5.9 |
| 214 | 0.6 |
| 215 | 1.8 |
| 216 | 2.7 |
| 218 | 7.4 |
| 219 | 5955.0 |
| 220 | 0.3 |
| 223 | 0.7 |
| 224 | 2.8 |
| 225 | 1.2 |
| 226 | 6.1 |
| 228 | 6.9 |
| 229 | 5.2 |
| 230 | 27.5 |

The invention claimed is:

1. A compound of Formula (I):

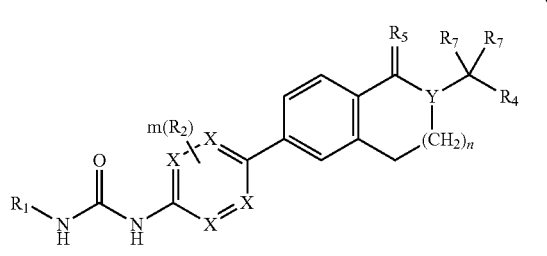

(I)

wherein $R_1$ is $C_1$-$C_6$alkyl, $C_3$-$C_7$cycloalkyl, aryl or heteroaryl, wherein said aryl and heteroaryl may be substituted with one to three groups independently selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;

$R_2$ is selected from the group consisting of H, $C_1$-$C_6$alkyl, alkoxy, cyano, halo, urea, amide, hydroxyl, oxo, and nitro;

$R_4$ is $CH_2COOH$, COOH, ester, or amide;

$R_5$ is hydrogen, hydroxyl, or oxo;

each $R_7$ is independently H or $C_1$-$C_3$alkyl;

each X is independently C or N, provided that at least two X's are C;

Y is N or $CR_3$, wherein $R_3$ is H, $C_1$-$C_6$alkyl, hydroxyl, halo, or alkoxy, wherein said $C_1$-$C_6$alkyl may be further substituted with one to three groups independently selected from halo, hydroxyl, alkoxy, COOH, and ester;
m is 0-3;
n is 0-1, provided that when n is 0, Y is $CR_3$;
or a pharmaceutically acceptable salt thereof.

2. The compound of claim 1, which is represented by Formula (I)(A):

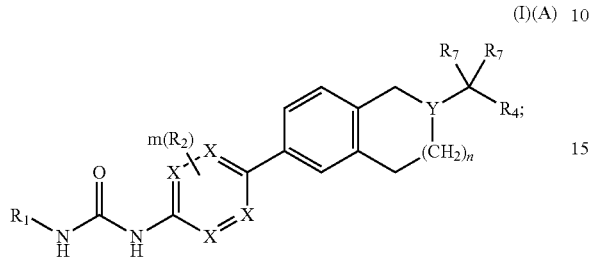

wherein
$R_1$ is $C_1$-$C_6$alkyl, $C_3$-$C_7$cycloalkyl, aryl or heteroaryl, wherein said aryl or heteroaryl may be substituted with one to three groups independently selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;
$R_2$ is selected from the group consisting of H, $C_1$-$C_6$alkyl, alkoxy, cyano, halo, urea, amide, hydroxyl, oxo, and nitro;
$R_4$ is $CH_2COOH$, COOH, ester, or amide;
each $R_7$ is independently H or $C_1$-$C_3$alkyl;
each X is independently C or N, provided that at least two X's are C;
Y is N or $CR_3$, wherein $R_3$ is H, $C_1$-$C_6$alkyl, hydroxyl, halo, or alkoxy, wherein said $C_1$-$C_6$alkyl may be further substituted with one to three groups independently selected from halo, hydroxyl, alkoxy, COOH, and ester;
m is 0-3;
n is 0-1, provided that when n is 0, Y is $CR_3$;
or a pharmaceutically acceptable salt thereof.

3. The compound of claim 1, which is represented by Formula (I)(B):

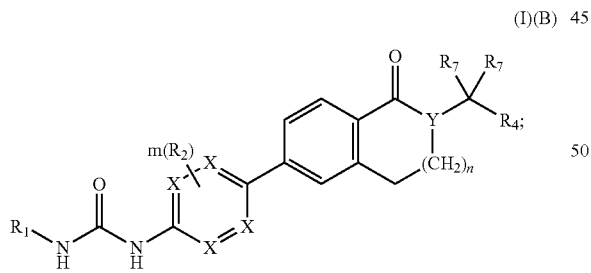

wherein
$R_1$ is $C_1$-$C_6$alkyl, $C_3$-$C_7$cycloalkyl, aryl or heteroaryl, wherein said aryl or heteroaryl may be substituted with one to three groups independently selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;
$R_2$ is selected from the group consisting of H, $C_1$-$C_6$alkyl, alkoxy, cyano, halo, urea, amide, hydroxyl, oxo, and nitro;
$R_4$ is $CH_2COOH$, COOH, ester, or amide;
each $R_7$ is independently H or $C_1$-$C_3$alkyl;

each X is independently C or N, provided that at least two X's are C;
Y is N or $CR_3$, wherein $R_3$ is H, $C_1$-$C_6$alkyl, hydroxyl, halo, or alkoxy, wherein said $C_1$-$C_6$alkyl may be further substituted with one to three groups independently selected from halo, hydroxyl, alkoxy, COOH, and ester;
m is 0-3;
n is 0-1, provided that when n is 0, Y is $CR_3$;
or a pharmaceutically acceptable salt thereof.

4. The compound of claim 1, which is represented by Formula (I)(C):

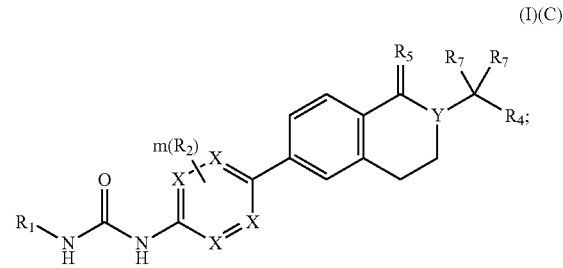

wherein
$R_1$ is $C_1$-$C_6$alkyl, $C_3$-$C_7$cycloalkyl, aryl or heteroaryl, wherein said aryl or heteroaryl may be substituted with one to three groups independently selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;
$R_2$ is selected from the group consisting of H, $C_1$-$C_6$alkyl, alkoxy, cyano, halo, urea, amide, hydroxyl, oxo, and nitro;
$R_4$ is $CH_2COOH$, COOH, ester, or amide;
$R_5$ is hydrogen, hydroxyl, or oxo;
each $R_7$ is independently H or $C_1$-$C_3$alkyl;
each X is independently C or N, provided that at least two X's are C;
Y is N or $CR_3$, wherein $R_3$ is H, $C_1$-$C_6$alkyl, hydroxyl, halo, or alkoxy, wherein said $C_1$-$C_6$alkyl may be further substituted with one to three groups independently selected from halo, hydroxyl, alkoxy, COOH, and ester;
m is 0-3;
or a pharmaceutically acceptable salt thereof.

5. The compound of claim 1, which is represented by Formula (I)(D):

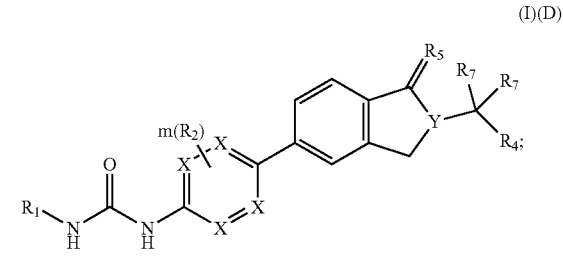

wherein
$R_1$ is $C_1$-$C_6$alkyl, $C_3$-$C_7$cycloalkyl, aryl or heteroaryl, wherein said aryl or heteroaryl may be substituted with one to three groups independently selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;

$R_2$ is selected from the group consisting of H, $C_1$-$C_6$alkyl, alkoxy, cyano, halo, urea, amide, hydroxyl, oxo, and nitro;

$R_4$ is $CH_2COOH$, COOH, ester, or amide;

$R_5$ is hydrogen, hydroxyl, or oxo;

each $R_7$ is independently H or $C_1$-$C_3$alkyl;

each X is independently C or N, provided that at least two X's are C;

Y is $CR_3$, wherein $R_3$ is H, $C_1$-$C_6$alkyl, hydroxyl, halo, or alkoxy, wherein said $C_1$-$C_6$alkyl may be further substituted with one to three groups independently selected from halo, hydroxyl, alkoxy, COOH, and ester;

m is 0-3;

or a pharmaceutically acceptable salt thereof.

6. The compound of claim 1, which is represented by Formula (I)(F):

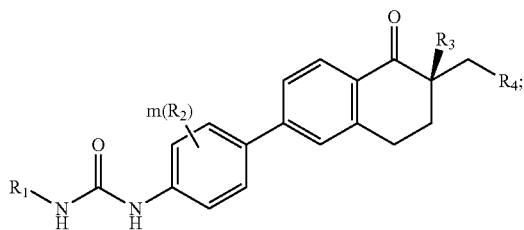

(I)(F)

wherein $R_1$ is $C_1$-$C_6$alkyl, $C_3$-$C_7$cycloalkyl, aryl or heteroaryl, wherein said aryl or heteroaryl may be substituted with one to three groups independently selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;

$R_2$ is selected from the group consisting of H, $C_1$-$C_6$alkyl, alkoxy, cyano, halo, urea, amide, hydroxyl, oxo, and nitro;

$R_4$ is $CH_2COOH$, COOH, ester, or amide;

$R_3$ is $C_1$-$C_6$alkyl, hydroxyl, halo, or alkoxy, wherein said $C_1$-$C_6$alkyl may be further substituted with one to three groups independently selected from halo, hydroxyl, alkoxy, COOH, and ester;

m is 0-3;

or a pharmaceutically acceptable salt thereof.

7. The compound of claim 1, which is represented by Formula (I)(H):

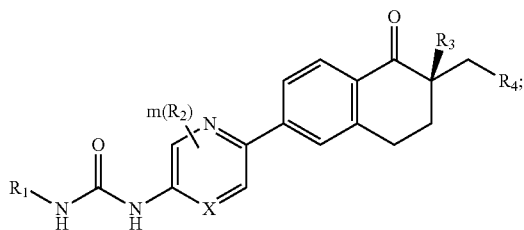

(I)(H)

wherein $R_1$ is $C_1$-$C_6$alkyl, $C_3$-$C_7$cycloalkyl, aryl or heteroaryl, wherein said aryl or heteroaryl may be substituted with one to three groups independently selected from the group consisting of acyl, $C_1$-$C_6$alkyl, alkylsulfonyl, alkoxy, alkoxycarbonyl, cyano, halo, urea, amide, hydroxyl, $SF_5$, oxo, and nitro;

$R_2$ is selected from the group consisting of H, $C_1$-$C_6$alkyl, alkoxy, cyano, halo, urea, amide, hydroxyl, oxo, and nitro;

$R_4$ is $CH_2COOH$, COOH, ester, or amide;

X is in C or N;

$R_3$ is H, $C_1$-$C_6$alkyl, hydroxyl, halo, or alkoxy, wherein said $C_1$-$C_6$alkyl may be further substituted with one to three groups independently selected from halo, hydroxyl, alkoxy, COOH, and ester;

m is 0-2;

or a pharmaceutically acceptable salt thereof.

8. The compound of claim 1, wherein $R_5$ is hydroxyl, or a pharmaceutically acceptable salt thereof.

9. The compound of claim 1, wherein each X is C, or a pharmaceutically acceptable salt thereof.

10. The compound of claim 1, wherein $R_1$ is phenyl which may be substituted with one to three groups independently selected from the group consisting of methyl, ethyl, $OCF_3$, —$OCF_2H$, trifluoromethyl, methoxy, ethoxy, cyano, Cl, or F, or a pharmaceutically acceptable salt thereof.

11. The compound of claim 1, wherein $R_1$ is $C_1$-$C_6$alkyl, or a pharmaceutically acceptable salt thereof.

12. The compound of claim 1, wherein $R_2$ is $C_1$-$C_3$alkyl, F, Cl, or CN, or a pharmaceutically acceptable salt thereof.

13. The compound of claim 1, wherein Y is $CR_3$, wherein $R_3$ is H, $C_1$-$C_6$alkyl, hydroxyl, halo, or alkoxy, wherein said $C_1$-$C_6$alkyl may be further substituted with one to three groups independently selected from halo, hydroxyl, alkoxy, COOH, and ester, or a pharmaceutically acceptable salt thereof.

14. The compound of claim 1, wherein Y is $CR_3$, wherein $R_3$ is methyl, $CH_2CF_3$, $CH_2OCH_3$ or ethyl; or a pharmaceutically acceptable salt thereof.

15. The compound of claim 1, wherein Y is N, or a pharmaceutically acceptable salt thereof.

16. The compound of claim 1, wherein m is or a pharmaceutically acceptable salt thereof.

17. The compound of claim 1, wherein $R_4$ is —$CH_2COOH$ or COOH, or a pharmaceutically acceptable salt thereof.

18. A method of treating obesity comprising administering to a human in need thereof an effective amount of the compound or salt according to claim 1.

19. A pharmaceutical composition comprising the compound or salt according to claim 1, and a pharmaceutically acceptable carrier.

* * * * *